US008877442B2

(12) United States Patent
Quake et al.

(10) Patent No.: US 8,877,442 B2
(45) Date of Patent: Nov. 4, 2014

(54) NON-INVASIVE DETERMINATION OF FETAL INHERITANCE OF PARENTAL HAPLOTYPES AT THE GENOME-WIDE SCALE

(75) Inventors: Stephen R. Quake, Stanford, CA (US); Hei-Mun C. Fan, Fremont, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/313,909

(22) Filed: Dec. 7, 2011

(65) Prior Publication Data

US 2012/0196754 A1 Aug. 2, 2012

Related U.S. Application Data

(60) Provisional application No. 61/420,768, filed on Dec. 7, 2010.

(51) Int. Cl.
*C12Q 1/68* (2006.01)

(52) U.S. Cl.
CPC ............ *C12Q 1/6881* (2013.01); *C12Q 1/6869* (2013.01); *C12Q 1/6806* (2013.01); *C12Q 2537/165* (2013.01); *C12Q 2521/537* (2013.01)
USPC ........................... 435/6.11; 435/6.1; 435/6.12

(58) Field of Classification Search
USPC ................................................. 506/9; 435/6.1
See application file for complete search history.

(56) References Cited

U.S. PATENT DOCUMENTS

2010/0099092 A1* 4/2010 Song et al. .................. 435/6
2011/0105353 A1* 5/2011 Lo et al. ..................... 506/9

FOREIGN PATENT DOCUMENTS

WO        2011057094 A1    5/2011

OTHER PUBLICATIONS

Fan et al., "Detection of Aneuploidy with Digital Polymerase Chain Reaction," Anal. Chem. 2007, 79:7576-7579.*
Ma et al., "Direct determination of molecular haplotypes by chromosome microdissection," Nature Methods 2010, 7:299-301, published online Mar. 21, 2010.*
Sujana Ghanta, et al., "Non-Invasive Prenatal Detection of Trisomy 21 Using Tandem Single Nucleotide Polymorphisms," PloS One, vol. 5, No. 10, Oct. 8, 2010, p. E13184, XP055026992.
Hei-Mun Christina Fan, "Molecular Counting: From Noninvasive Prenatal Diagnostics to Whole-Genome Haplotyping," A dissertation submitted to the Dept. of Bioengineering and the Committee on Graduate Studies of Stanford University, Nov. 30, 2010, XP02675933, Retrieved from the Internet: URL:https://stacks.stanford.edu/file/druid:cw095xw9265/thesisfinal-augmented.pdf. [retrieved on May 8, 2012].

(Continued)

*Primary Examiner* — Samuel Woolwine
*Assistant Examiner* — Kaijiang Zhang
(74) *Attorney, Agent, or Firm* — Rothwell, Figg, Ernst & Manbeck, P.C.

(57) ABSTRACT

The present invention provides a method, device and a computer program for haplotyping single cells, such that a sample taken from a pregnant female, without directly sampling the fetus, provides the ability to non-invasively determine the fetal genome. The method can be performed by determining the parental and inherited haplotypes, or can be performed merely on the basis of the mother's genetic information, obtained preferably in a blood or serum sample. The novel device allows for sequence analysis of single chromosomes from a single cell, preferably by partitioning single chromosomes from a metaphase cell into long, thin channels where a sequence analysis can be performed.

18 Claims, 84 Drawing Sheets

(56) References Cited

OTHER PUBLICATIONS

Jonathan Marchini, et al., "A Comparison of Phasing Algorithms for Trios and Unrelated Individuals," Am. J. Hum. Genet, Jan. 1, 2006, pp. 437-450, XP055026881.

Michael Wirtenberger, et al., "SNP microarray analysis for genome-wide detection of crossover regions," Human Genetics, Springer, Berlin, DE, vol. 117, No. 4, Aug. 1, 2005, pp. 389-397, XP019346161.

Fiona M. F. Lun, et al., " Noninvasive prenatal diagnosis of monogenic diseases by digital size selection and relative mutation dosage on DNA in maternal plasma," Proceedings of the National Academy of Sciences, National Academy of Sciences, vol. 105, No. 50, Dec. 16, 2008, pp. 19920-19925, XP002620453.

Ravinder Dhallan, et al., "A non-invasive test for prenatal diagnosis based on fetal DNA present in maternal blood: a preliminary study," The Lancet, Lancet Limited, London, GB, vol. 369, No. 9560, Feb. 8, 2007, pp. 474-481, XP005879775.

H Christina Fan, et al., "Whole-genome molecular haplotyping of single cells," Nature Biotechnology, vol. 29, No. 1, Dec. 19, 2010, pp. 51-57, XP055026438.

PCT International Search Report, issued in PCT/US2011/063796 on Oct. 15, 2012, 21 pages.

* cited by examiner

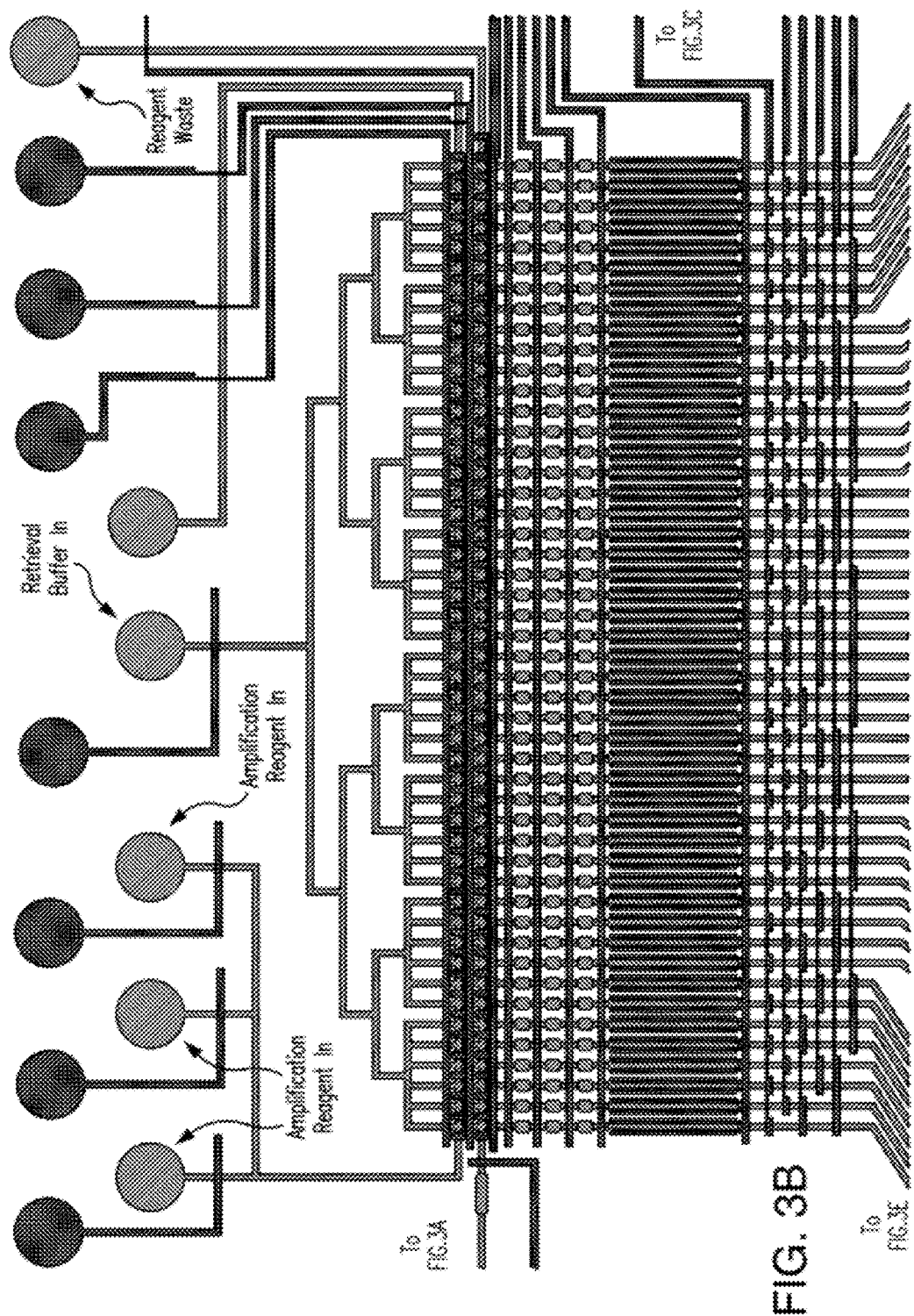

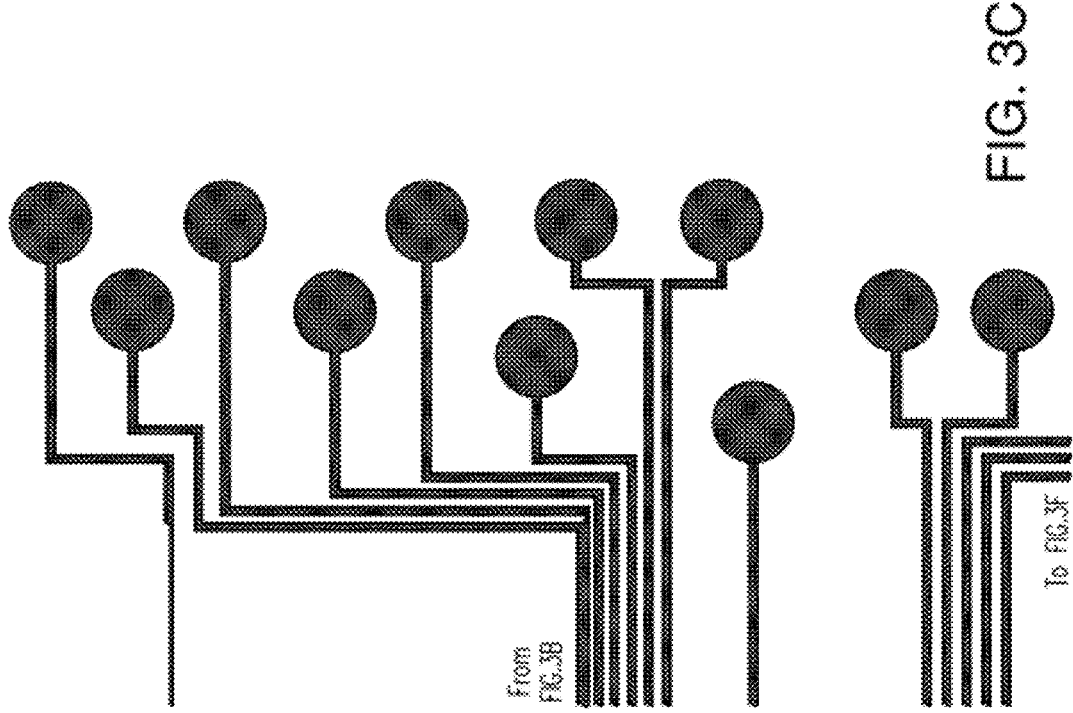

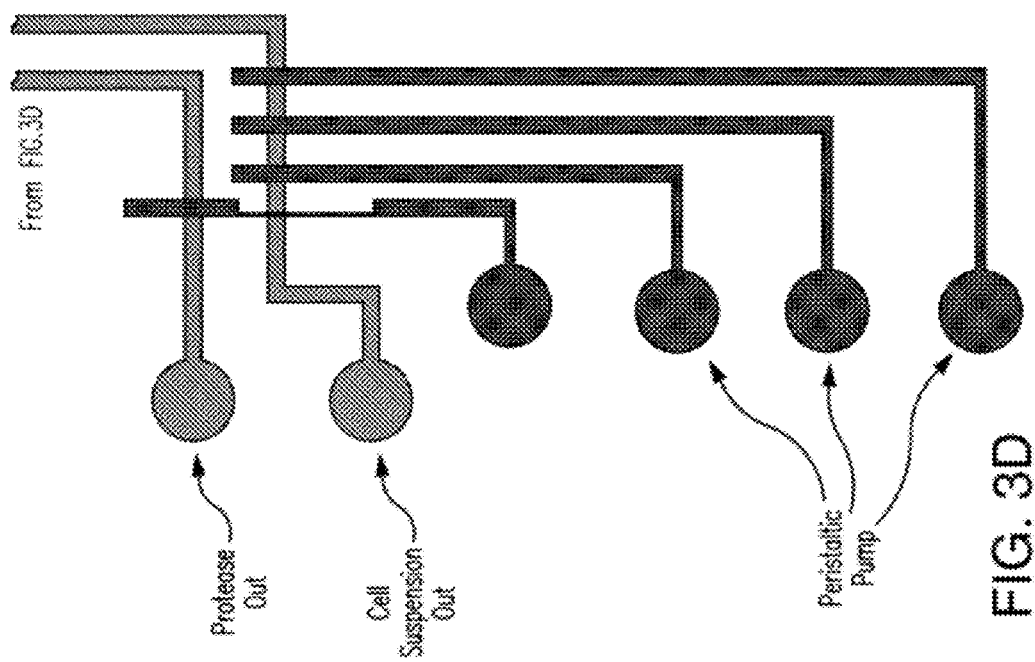

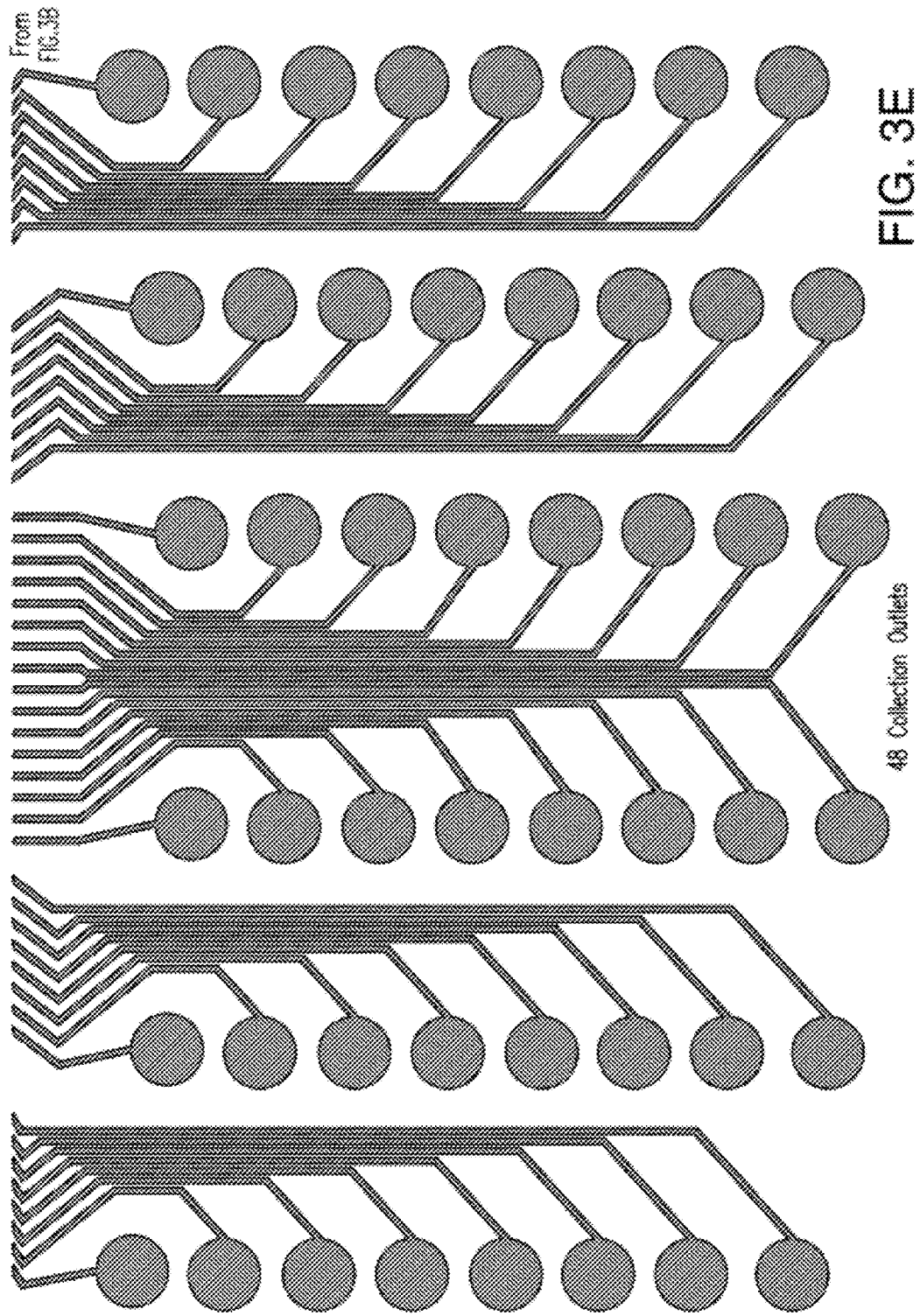

| HapMap CNP ID | Chr | Start | End | Size | HapMap III copy number | | | Paternal | Maternal | 12891 | | 12892 | |
|---|---|---|---|---|---|---|---|---|---|---|---|---|---|
| | | | | | 12878 | 12891 | 12892 | | | Homolog 1 | Homolog 2 | Homolog 1 | Homolog 2 |
| HM3_CNP71 | 2 | 14622400 | 14622543 | 5143 | 1 | 1 | 2 | 0/2³ | 1/1 | 0/3 | 3/3 | 1/1 | 1/1 |
| HM3_CNP116 | 2 | 18379369B | 183798167 | 4369 | 1 | 1 | 2 | 0/2 | 1/1 | 0/3 | 3/3 | 1/1 | 3/3 |
| HM3_CNP201 | 4 | 9819751 | 9844366 | 24615 | 1 | 1 | 0 | 2/4 | 0/4 | 2/2 | 0/2 | 0/3 | 0/3 |
| HM3_CNP319 | 5 | 137833560 | 137844856 | 8936 | 1 | 1 | 2 | 0/4 | 1/4 | 3/3 | 0/3 | 3/3 | 3/3 |
| HM3_CNP371⁴ | 6 | 137261050 | 137264736 | 3686 | 1 | 1 | 2 | 1/3 | 3/3 | 3/3 | 1/3 | 2/2 | 2/1 |
| HM3_CNP593 | 11 | 55124465 | 55209385 | 85120 | 1 | 1 | 2 | 0/2 | 3/3 | 0/3 | 3/3 | 1/1 | 1/1 |
| HM3_CNP768 | 14 | 73311441 | 73315360 | 3919 | 1 | 1 | 2 | 0/2 | 3/3 | 1/1 | 0/1 | 2/2 | 2/3 |

FIG. 8B

1 Number of typed markers/number of markers typed in at least one homolog within the region.
2 At least one homolog did not contain any typed markers.
3 Number of homologs giving positive PCR amplification/number of homologs tested.
4 Both homologs gave positive PCR amplification, although the copy number of this CNV was 1 for the two individuals.

| Single Cell Experiment ID/Library | 1 | | 2 | | 3 | |
|---|---|---|---|---|---|---|
| Content as determined by Initial 46-loci Genotyping | Chr 6 | | Chr 6, 16, 18 | | Chr 6 | |
| Which Homolog of Chr 6 | 1 | | 1 | | 2 | |
| Paired-End Read | Read 1 | Read 2 | Read 1 | Read 2 | Read 1 | Read 2 |
| % Passed Filters | 94.25 | 94.25 | 94.60 | 94.60 | 93.78 | 93.78 |
| Total Number of Reads (1E6) | 27.77 | 27.77 | 24.92 | 24.92 | 17.58 | 17.58 |
| % No Match | 6.06 | 6.29 | 3.57 | 4.55 | 5.91 | 6.47 |
| % Failed QC | 0.01 | 0.19 | 0.02 | 0.21 | 0.02 | 0.23 |
| % Repeated | 15.54 | 15.61 | 16.63 | 16.65 | 14.74 | 14.74 |
| % Chr 6 | 77.70 | 77.17 | 39.69 | 39.04 | 78.95 | 78.13 |
| % Chr 16 | -- | -- | 16.74 | 16.46 | -- | -- |
| % Chr 18 | -- | -- | 23.01 | 22.65 | -- | -- |
| % Other Chr | 0.69 | 0.74 | 0.35 | 0.44 | 0.38 | 0.42 |
| % Paired Chr 6 Reads | 94.06 | | 93.03 | | 94.06 | |
| Median Insert Size (Chr 6) | 75 | | 67 | | 74 | |
| % Chr 6 Sequenced Bases Covered | 37.75 | | 40.34 | | 50.11 | |
| % Unique reads | 42.92 | | 70.25 | | 54.91 | |
| Average Coverage of Chr 6 (considering only unique reads) | 5.81 | | 2.74 | | | |
| % Chr 6 Sequenced Bases Covered for Each Homolog | 59.74 | | 50.11 | | | |
| % Chr 6 Sequenced Bases Covered for Both Homologs | | | 72.37 | | | |

FIG. 13

| ID[1] | Chr | Start | End | Heterozygous Marker[2] | Allele 1[3] | Allele 2[3] |
|---|---|---|---|---|---|---|
| 5-109 | 5 | 109387000 | 109408000 | rs10039735 | C | T |
| 6-10 | 6 | 103844000 | 103869000 | rs6596815 | A | C |
| 6-64 | 6 | 64781000 | 64796000 | rs6596815 | A | C |
| 15-89 | 15 | 89948000 | 89992000 | rs3929062 | C | T |
| 13-63 | 13 | 63123000 | 63135000 | rs2801749 | A | G |
| 1-15 | 1 | 15082000 | 15085000 | rs3131972 | A | G |
| 8-25 | 8 | 25029000 | 25046000 | rs2003497 | A | G |
| 19-56 | 19 | 56825000 | 56840000 | rs2312724 | C | T |

[1] Same labeling as in Supplementary Table 4 of Pushkarev et al. [2009]
[2] A heterozygous SNP chosen to define the two homologous copies of chromosome 6 of P0.
[3] Allele of the chosen SNP on each of the homologous copies.
[4] Number of typed markers/number of markers typed in at least one homolog within the region.
[5] Positive or negative PCR signal.
[6] PCR experiments were done on amplified materials from separated chromosome homologs obtained from 3 single cells; 'C' refers to combined genotyping results from the same homolog in 3 single cells.
[7] Homologous copies were not separated for this particular single cell experiment.

FIG. 16A

| Method | Single Cell ID[6] | Homolog 1 | Homolog 2 |
|---|---|---|---|
| SNP Array | C | 17/17[4] | 0/17 |
| PCR[5] | 1 | + | − |
| | 2 | + | − |
| | 3 | + | − |
| SNP Array | C | − | − |
| PCR | 1 | + | − |
| | 2 | − | − |
| | 3 | + | − |
| SNP Array | C | 0/3 | 3/3 |
| PCR | 1 | − | + |
| | 2 | − | + |
| | 3 | − | + |
| SNP Array | C | 0/16 | 16/16 |
| PCR | 1 | No data[7] | No data[7] |
| | 2 | − | + |
| | 3 | − | + |
| SNP Array | C | 1/1 | 0/1 |
| PCR | 1 | + | − |
| | 2 | + | − |
| | 3 | + | − |
| SNP Array | C | 0/0 | 0/0 |
| PCR | 1 | − | + |
| | 2 | − | + |
| | 3 | − | + |
| SNP Array | C | 0/0 | 0/0 |
| PCR | 1 | − | + |
| | 2 | − | + |
| | 3 | − | + |
| SNP Array | C | 0/0 | 0/0 |
| PCR | 1 | − | + |
| | 2 | No data[7] | No data[7] |
| | 3 | − | + |

FIG. 16B

| | HLA-A | HLA-B | HLA-C | HLA-DRB1 | HLA-DQA1 | HLA-DQB1 |
|---|---|---|---|---|---|---|
| HLA alleles by direct typing: genomic DNA | 0101/2301 | 0801/5107 | 0701/1402 | 0301/0101 | -- | 0201/0501 |
| HLA haplotypes by phylogenetic analysis: Haplotype 1 | 2301 | ? | ? | 0101 | 0101 | 0501 |
| Haplotype 2 | 0101 | 0801 | 0701 | 0301 | 0501 | 0201 |
| HLA haplotypes by combining results from phylogenetic analysis and direct typing: Haplotype 1 | 2301 | 5107 | 1402 | 0101 | 0101 | 0501 |
| Haplotype 2 | 0101 | 0801 | 0701 | 0301 | 0501 | 0201 |

FIG. 17G

| Chromosome | Position (build 36.3) | ABI Taqman Genotyping Assay ID | rs number |
|---|---|---|---|
| 1 | 24281001 | C___234618_10 | rs4513343 |
| 1 | 203578903 | C___9114654_10 | rs7549293 |
| 2 | 44679217 | C___1116650_10 | rs1703420 |
| 2 | 182121504 | C___1276208_10 | rs1799745 |
| 3 | 11528669 | C___1190749_1_ | rs1872575 |
| 3 | 194690074 | C___2574928_10 | rs6444724 |
| 4 | 76644920 | C___1880371_10 | rs13134862 |
| 4 | 157709356 | C___742840_10 | rs154472 |
| 5 | 136661237 | C___2556113_10 | rs13182883 |
| 5 | 159420531 | C___1995608_10 | rs7704770 |
| 6 | 12167940 | C___9371416_10 | rs1321840 |
| 6 | 152739399 | C___2515225_10 | rs214955 |
| 7 | 9910771 | C___3020950_10 | rs10264272 |
| 7 | 99108475 | C___26201809_30 | rs776746 |
| 8 | 28466991 | C___2049946_10 | rs10092491 |
| 8 | 42168525 | C___2533651_10 | rs732812 |
| 9 | 3582942 | C___305619_10 | rs2236291 |
| 9 | 9767866 | C___665481_10 | rs689697 |
| 10 | 9673104.5 | C___27104892_10 | rs1057910 |
| 10 | 97162585 | C___7538108_10 | rs1410059 |
| 11 | 5665604 | C___145217.5_10 | rs1498553 |
| 11 | 105418194 | C___1636106_10 | rs6591147 |
| 12 | 4800621 | C___488643_10 | rs12423234 |
| 12 | 6816175 | C___2184724_1_ | rs2269355 |
| 13 | 22963424 | C___176074_7_10 | rs4770456 |
| 13 | 98836234 | C___1619935_1_ | rs1058083 |
| 14 | 24920672 | C___2120263_10 | rs1454361 |
| 14 | 90577236 | C___1310541_10 | rs11847557 |
| 15 | 37100694 | C___1167373.5_10 | rs1821380 |
| 15 | 51404201 | C___29375514_10 | rs8037429 |
| 16 | 746255 | C___3149546_10 | rs7205345 |
| 16 | 71730706 | C___2605375_10 | rs6499616 |
| 17 | 38540348 | C___1163118.5_10 | rs2175957 |
| 17 | 44761912 | C___1121246_10 | rs747039 |
| 18 | 27565032 | C___745990.5_10 | rs985492 |
| 18 | 53376775 | C___328537_1_ | rs1736442 |
| 19 | 356407 | C___2576338_10 | rs768963 |
| 19 | 38159197 | C___8582892_1_ | rs2304102 |
| 20 | 16189416 | C___1274718_10 | rs12480506 |
| 20 | 27965082 | C___3206279_10 | rs2567608 |
| 21 | 33078504 | C___1135480.6_10 | rs1267142 |
| 21 | 41478755 | C___31891795 | rs8130833 |
| 22 | 40853887 | C___2710242.5_10 | rs16947 |
| 22 | 40856638 | C___11484460_40 | rs1065852 |
| X | 140537528 | C___3057669_20 | rs636416 |
| Y | SRY | Custom (non-genotyping)[1] | SRY gene |

FIG. 18A

| Y | SRY[1] | Yp11.3 | CGCTTAACATAGCAGAAGCA | AGTTCGAACTCTGGCACCT | TGTCGCACTCTCCTTGTTTTGACA | FAM |

[1]Ultraconserved element: Annotation follows the online supplement of Bejerano, G. et al. Ultraconserved elements in the human genome. *Science* 304, 1321-5 (2004). (http://www.soe.ucsc.edu/jill/ultra.html)

FIG. 18B

| HapMap III CNP ID | Chr | Forward primer | Reverse primer | Probe |
|---|---|---|---|---|
| HM3 CNP71 | 2 | AAGGCTTCCTTAGTGCTCCT | TGAAAGAAACTCATGGCTCA | TTGCTTTCTGATAGTTCTTGGCCTG |
| HM3 CNP116 | 2 | GCCTCAGTTTCAGGCATTAT | CTCCTGCCTCATAGAAGTGA | CCACCCTTACCTTCTCTTTCTGC |
| HM3 CNP201 | 4 | TCCACTGACCAGATACATGC | ACCATCAGACCAAGACATCC | TCCGTGGTTATAGGCATGCC |
| HM3 CNP309 | 5 | ATTCATAATAGGCGGAGTGG | AGGCCTATTTCATTGTTTGG | AATCCAAATGTCTATTCAACCAGTGCA |
| HM3 CNP371 | 6 | CTCAAATGGCTGTGTATGGAA | AATTCAACCTGCAGAAGCAT | TCCCATGTCCTATGTCTGCAATT |
| HM3 CNP593 | 11 | TAAAATGCAGACCATGACTGA | GTCCAACTCTCGAAGTTTGC | TCAAGAAGTGTCCTACTTGCCTGAGA |
| HM3 CNP708 | 14 | CTGTGGTTGTGAGTCCTGAG | TGTTACGGTTCTGAAGAGCA | TCCACTCTGGTGGGGAAGGCT |

FIG. 19

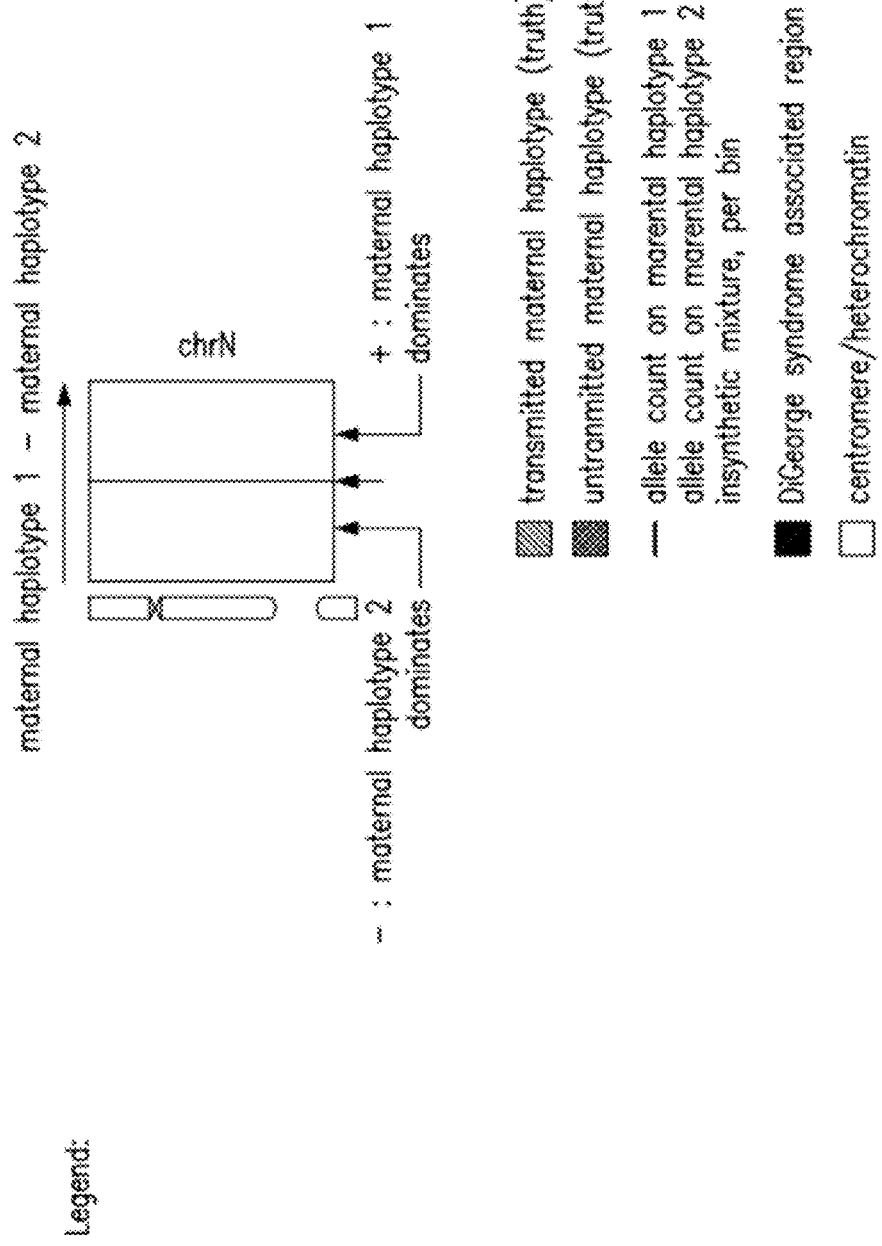

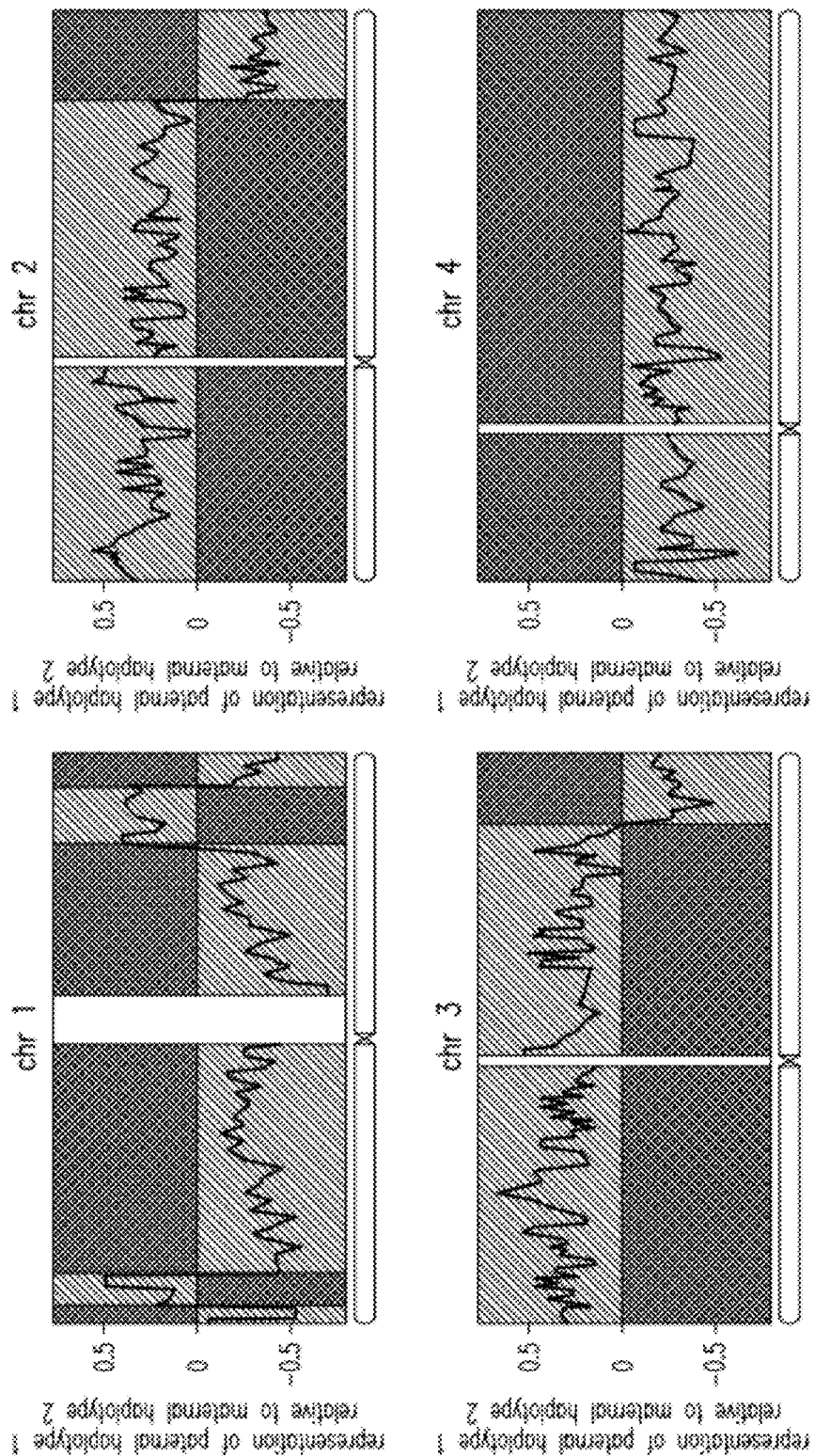

NON-INVASIVE DETERMINATION OF FETAL INHERITANCE OF PARENTAL HAPLOTYPES AT THE GENOME-WIDE SCALE

CROSS-REFERENCE TO RELATED APPLICATIONS

This application claims priority from U.S. Provisional Application Ser. No. 61/420,768, filed Dec. 7, 2010, which is hereby incorporated by reference in its entirety.

STATEMENT OF GOVERNMENTAL SUPPORT

This invention was made with Government support under contracts CA143907 and OD000251 awarded by the National Institutes of Health. The Government has certain rights in this invention.

REFERENCE TO SEQUENCE LISTING, COMPUTER PROGRAM, OR COMPACT DISK

Applicants assert that the text copy of the Sequence Listing is identical to the Sequence Listing in computer readable form found on the accompanying computer file. Applicants incorporate the contents of the sequence listing by reference in its entirety.

BACKGROUND OF THE INVENTION

Field of the Invention

The passage of nucleated cells from fetal to maternal circulation was first noted by Walknowska et al in 1969, and potential applications and limitations of fetal cells for prenatal testing have since been well characterized. Although the genetic material derived from these cells theoretically provides a noninvasive means for prenatal testing, circulating fetal cells are scarce, and thus costly and time-consuming to isolate from a sample of maternal blood. (Simpson and Elias, 1994; Bianchi, 1995; Steele et al., 1996). Universal cell markers that would allow separation and enrichment of nucleated fetal cells have yet to be discovered, precluding the use of these methods to obtain robust, reproducible results. (Bischoff et al., 2002).

In 1997, the discovery of fragmented, cell-free fetal DNA circulating in maternal plasma and serum afforded a potential alternative to isolation of rare fetal cells for noninvasive testing. (Lo et al., 1997). Originating in trophoblast cells lining the placental intervillous space, fetal DNA fragments are released into maternal circulation after trophoblast degradation; apoptosis of fetal cells circulating in maternal blood may provide a minor source of cell-free fetal DNA. (Alberry et al., 2007; Sekizawa et al., 2003b; Wataganara et al., 2005). Soon after this finding, the presence of placenta-derived mRNA in maternal blood was also observed as a third source of fetal genetic material in maternal circulation. (Poon et al., 2000). Cell-free fetal DNA can be detected in maternal circulation as early as 5 weeks of gestational age and persists throughout pregnancy. (Birch et al., 2005). The transfer of cellfree fetal DNA to maternal blood is detectable in all pregnancies. (Lo et al., 2000). Due to its mean half-life of 16.3 minutes, cell-free fetal DNA is cleared from circulation within a matter of hours after delivery, and thus previous pregnancies do not confound identification and analysis of fetal DNA from a current pregnancy. (Lo et al., 1999c). As expected, cell-free DNA in maternal circulation can be of either maternal or fetal origin, and the concentration of cellfree fetal DNA relative to total DNA ranges from 3.4% to 6.2%, or 25.4 to 292.2 genome equivalents per milliliter of maternal blood. (Lo et al., 1998). Potentially due to its instability or variable transcription throughout development, cell-free fetal mRNA can only be identified in 22% of first- and second-trimester pregnancies and 63% of third-trimester pregnancies. (Poon et al., 2000).

Despite these qualities of cell-free fetal nucleic acids and particularly cell-free fetal DNA, their application in noninvasive prenatal testing has been hindered by the significant challenge of differentiating genetic material of the fetus from maternal genetic material. Namely, as the fetus has inherited one-half of its genetic information from its mother, the isolation of DNA or RNA fragments of fetal origin requires pinpointing information or features of these nucleic acids that distinguish them from their maternal counterparts.

The usefulness of fetal-specific sequences in maternal blood, including paternally inherited alleles or de novo mutations, is being explored with respect to sex determination, blood group and human leukocyte antigen (HLA) typing, and detection or exclusion of single-gene disorders or inheritance of other polymorphisms. For the purpose of aneuploidy detection, the ratio of concentrations of heterozygous alleles or sequences specific to particular chromosomes may be utilized. Epigenetic signatures of the fetus or mRNA species originating exclusively from the placenta may serve as alternative diagnostic tools by differentiating between fetal and maternal genetic material. (Poon et al., 2002; Lo et al., 2007b).

For pregnancies medically indicated for prenatal sex testing, currently recommended invasive diagnostic procedures include chorionic villus sampling between 10 and 12 gestational weeks or amniocentesis between 15 and 20 weeks, each of which is followed by karyotyping resulting in essentially 100% accuracy in sex determination. (Nicolaides et al., 1994). Medical indications for prenatal sex testing include prevention or management of sex-linked disorders. (Hyett et al., 2005). A male is at 50% risk of inheriting a recessive X-linked condition, such as hemophilia or Duchenne muscular dystrophy, if his mother is a carrier of one affected allele. Currently, recommendations for pregnant carriers of genes for these disorders include invasive testing for the presence of the specific genetic mutation on the X chromosome. (Sherman et al., 2005). Through early noninvasive sex determination using cell-free nucleic acids, women bearing female fetuses can be spared the risks of undergoing further invasive testing and can receive results sooner in pregnancy. (Wald et al., 2003; Sherman et al., 2005; Santacroce et al., 2006).

The initial discovery of cell-free fetal DNA in maternal plasma relied on polymerase chain reaction (PCR) amplification and electrophoresis of DSY14, a gene located on the Y chromosome. (Lo et al., 1997). By this method, fetal DNA is necessarily detected only in blood samples of women bearing male fetuses; however, not all of these women had a detectable concentration of DSY14 and sensitivity in this original research was limited to 80% detection of male-bearing pregnancies. More recently, prenatal sex determination has relied on the detection of SRY, the sex-determining region on the Y chromosome, which may provide more reliable diagnostic capability than DYS14. (Honda et al., 2002). Laboratory techniques for sex detection have also been improved from combined PCR-electrophoresis to quantitative real-time PCR, which increases throughput and improves accuracy to 97% to 100% in the first trimester of pregnancy. (Lo et al., 1998; Costa et al., 2001; Hromanikova et al., 2003; Sekizawa et al., 2001).

Fetal sex determination demonstrated that cell-free DNA sequences exclusive to the fetus circulating in maternal blood could provide significant prenatal diagnostic information. Within a year of this finding, comparable techniques were applied to RhD blood group genotyping. RhD blood group incompatibility between a fetus and pregnant woman may result in isoimmunization, hemolytic disease and miscarriage, but with modern perinatal care including administration of prophylactic anti-RhD immune globulin, negative outcomes are effectively preventable. Using a combined PCR-electrophoresis protocol or quantitative real-time PCR technology, similarly as for fetal sex detection, cell-free RhD sequences from an RhD-positive fetus can be detected in the blood of RhD-negative pregnant women. (Faas et al., 1998; Bischoff et al., 1999) A meta-analysis demonstrates that fetal RhD blood type tests offer overall 95% accuracy and can be performed as early as a gestational age of 8 weeks. (Geifman-Holtzman et al., 2006).

Cell-free fetal DNA tests are also being developed to detect maternal-fetal incompatibilities for other blood types, including RhC, RhE, and Kell (K). Similarly to RhD testing, high accuracy for blood group typing has been achieved using either real-time PCR or PCR-MS, particularly when testing is enhanced by locked nucleic acids. (Li et al., 2008; Finning et al., 2007).

Using principles similar to those for fetal sex and blood type detection, the presence of a sequence in a mother's blood that is not part of the maternal genome may indicate that either the fetus has inherited an allele solely from the father or a de novo mutation has occurred. Detection or absence of such alleles and mutations can aid in the diagnosis or exclusion of single-gene disorders and the identification of HLA haplotypes.

In 2000, scientists first used cell-free fetal DNA to detect the inheritance of a paternal mutation for a dominant single-gene disorder in a fetus at risk for myotonic dystrophy. (Amicucci et al., 2000). Successful identification of this known mutation, given that it did not exist in the maternal DNA, utilized PCR followed by electrophoresis. Follow-up studies using restriction fragment length polymorphism analysis or touchdown or nested PCR demonstrated improved detection of known mutations, such as those for achondroplasia and hemoglobinopathy, by reducing mispriming. (Li et al., 2004; Fucharoen et al., 2003; Saito et al., 2000). Soon after, allele-specific PCR followed by electrophoresis was applied to the diagnosis and exclusion of Hb Lepore disease and Huntington disease; identification of Huntington disease status was demonstrated to be highly accurate as early as 10 weeks of gestational age, although test sensitivity was reduced with greater expansion of CAG trinucleotide repeats (which correspond to greater disease penetrance and earlier age of onset). (Amicucci et al., 2000; Gonzalez-Gonzalez et al., 2003a; Gonzalez-Gonzalez et al., 2003b; Bustamante-Aragones et al., 2008; Lazaros et al., 2006) Similarly, allele-specific real-time PCR has been demonstrated for HLA typing, which may be useful if HLA matching is desired in a fetus for the purpose of hematopoietic stem cell transplantation to an ailing sibling. (Reed et al., 2002). In addition to detecting disease-causing mutations, real-time PCR for paternally inherited short tandem repeats has also been applied to noninvasive paternity testing. (Wagner al., 2009).

Recessive disorders pose a greater challenge to prenatal diagnosis using cell-free fetal nucleic acids, due to the inability to distinguish between maternal and fetal sequences and thus the uncertainty of fetal inheritance of maternal alleles. Absence of a paternally inherited or de novo mutation in maternal blood permits definitive exclusion of recessive traits. Meanwhile, detection of a mutation demonstrates that the fetus is either a heterozygous carrier or an affected compound heterozygote or homozygote, depending on whether the maternal mutation is identical to paternal mutation. Allele-specific PCR followed by electrophoresis allows detection or exclusion of paternal mutations for recessive conditions, such as CAH and cystic fibrosis, between 11 and 17 weeks of gestational age. (Gonzalez-Gonzalez et al., 2002; Chiu et al., 2002a). Similarly, allele specific real-time PCR can be applied to mutations for cystic fibrosis and β-thalassemia with 100% sensitivity and near-perfect specificity. (Chiu et al., 2002b; Lun et al., 2008).

A unique approach to the diagnosis of recessive diseases in which the mother and father carry the same mutation entails examination of the relative mutation dosage, or the ratio of mutated to wild-type alleles in DNA from maternal blood. (Lun et al., 2008). Given the equal contribution of wild-type and mutated alleles from a heterozygous mother, the status of fetal inheritance will be dictated by an overrepresentation in maternal blood of the wild-type allele (fetus is unaffected) or mutation (fetus is affected), or a balance of representation of wild-type and mutated alleles (fetus is heterozygous carrier). Similarly, if the mother carries a dominant mutation, predominance of wild-type alleles in maternal blood would imply noninheritance of the condition, whereas balanced wild-type and mutated alleles would represent inheritance of the dominant condition. Specifically, digital real-time PCR, which is more precise than conventional PCR due to individual partitioning of reactions, has been used in this manner to detect inheritance of maternal mutations for thalassemia, hemoglobinopathy, and hemophilia. (Lun et al., 2008; Tsui et al., 2011). Theoretically, such analysis could be applied to diagnosis (and not merely exclusion) of recessive diseases with multiple disease-causing alleles, provided the paternal genotype is known, and in cases of unique paternal mutations, the paternal mutation is also tested in maternal blood.

Like with the detection of SRY and RHD, PCR followed by MS provides greater specificity in detection of known, recessive and dominant paternal mutations, including those for β-thalassemia and achondroplasia. (Ding, 2008; Ding et al., 2004; Li et al., 2009; Li et al., 2007) Again, there may be significant practical barriers to clinical implementation of MS analysis for single-gene disorders, as most laboratories do not possess the expensive equipment required for MS. (Wright and Burton, 2009).

One mechanism for bringing single-gene and other types of noninvasive tests closer to clinical application is enrichment of fetal DNA or RNA despite predominantly maternal circulating nucleic acids. Because of the discrepancy between the fragment lengths of cell-free fetal and maternal DNA (less than 300 bp and more than 1000 bp, respectively), size fractionation presents one avenue for increasing the fetal-to-maternal DNA ratio. (Li et al., 2004). Isolation of shorter fragments and thus concentration of fetal DNA using electrophoresis has improved detection of paternally inherited single-nucleotide polymorphisms (SNPs), paternally inherited and de novo mutations, and fetal microsatellite markers; methods using digital PCR for selective amplification of shorter fragments are also being explored. (Li et al., 2004; Li et al., 2007; Li et al., 2009; Li et al., 2005; Chan et al., 2004). Whole genome amplification may be a secondary means of counteracting low levels of fetal DNA. (Jorgez and Bischoff, 2009). Alternatively, suppression of wild-type alleles, either in fetal or maternal DNA, and thus improved enrichment of mutated alleles can be achieved by using peptide nucleic acid-mediated PCR to hinder amplification of wild-type sequences. (Li et al., 2005; Galbiati et al., 2006).

Prenatal aneuploidy testing is another potential realm for the application of cell-free fetal DNA technology. Aneuploidy, defined as any abnormal number of chromosomes, affects 1 in 300 newborns and is the most common cause of mental retardation; aneuploidies are also responsible for at least 35% of miscarriages. (Hassold et al., 1996). The most common aneuploidies in live births include trisomy 21 (Down syndrome), trisomy 13, trisomy 18, and monosomy or trisomy of the sex chromosomes, including Turner syndrome and Klinefelter syndrome. Several commercial cell-free fetal DNA and RNA technologies are under development to test a pregnancy for aneuploidy, mostly focusing on Down syndrome testing. These include either directly comparing the total concentration of the chromosome in question with that which is expected based on the concentration of an unaffected chromosome, or by determining the ratio of maternally inherited to paternally inherited alleles on the affected chromosome. By the first method, one would expect a fetus with trisomy to have a 3:2 relative chromosome dosage of affected to unaffected chromosomes. By the second, a trisomic fetus would have a 2:1 allelic imbalance favoring either maternally or paternally inherited alleles. The advantage of using a chromosome dosage method over an allelic balance method is due to its polymorphism-independent nature. With the latter, the presence of an allele inherited from the father, but not the mother, or vice versa, is necessary to determine allelic balance, and the identification of such an allele is not always possible or convenient. (Wright, 2009.) Thus, these methods of allelic ratio determination have been ineffective in instances of fetal homozygosity. Moreover, as fetal DNA exists in reduced concentration relative to maternal DNA, analysis using specific alleles makes use of only a small subset of DNA; a significant problem confronting this research entails the development of effective analytic methods despite low fetal DNA concentrations.

Proof of concept for differential epigenetic signatures of fetal and maternal DNA was demonstrated in the unique methylation patterns of some fetal SNPs and led to the first use of allelic ratio for aneuploidy detection. Specifically, the placental maspin gene promoter on chromosome 18 is hypomethylated relative to the densely methylated maternal promoter. (Poon et al., 2002). These differences in methylation can be exploited to assess fetal DNA concentration; shortly after this discovery, researchers demonstrated proof of principle for diagnosis of trisomy 18 via maspin allelic ratio using methylation-specific PCR. (Chim et al., 2005; tong et al., 2006). As different alleles are necessary to determine allelic ratio, this method could not be applied in cases of fetal homozygosity. More recent studies have continued to search for other fetal DNA markers based on epigenetic modification. (Chan et al., 2006; Old et al., 2007; Nygren et al., 2010).

Evidence for successful determination of allelic balance for chromosome 18 gene led to analysis of chromosome 21 SNPs, including those on PLAC4 mRNA, which is expressed exclusively in the placenta, to detect Down syndrome. (Lo et al., 2007b; Oudejans et al., 2003). For fetuses heterozygous for a specific PLAC4 SNP, identification of trisomy 21 by allelic imbalance using reverse transcription PCR and MS attained 90% sensitivity and 97% specificity. A similar technique was applied to a set of 5 SNP loci on PLAC4, attaining 92% sensitivity and 100% specificity, and may represent a higher-throughput, more widely applicable use of PLAC4 SNP analysis. (Deng et al., 2011). In both instances, fetal homozygosity precluded aneuploidy detection. However, more generally, this success in using mRNA to detect aneuploidy stimulated the proliferation of research on placenta-originating mRNA in attempts to discover novel universal fetal genetic markers for broader prenatal diagnostic purposes. (Tsui et al., 2004).

Aneuploidy detection by allelic imbalance was next explored using digital PCR, chosen to improve quantification sensitivity and based on earlier proof of principle using amniocyte samples. (Zimmermann et al., 2002; Lo et al., 2007a). Using an SNP on PLAC4 to determine allelic balance for chromosome 21, classification of aneuploid and euploid fetuses reached 100% accuracy, although with a small sample size. One of these samples required further testing beyond the initial plate; due to the predominance of maternal DNA in real samples, calculations suggest approximately 3% of cases will require such follow-up analysis for a conclusive diagnosis to be made.

This same study also demonstrated the first use of relative chromosomal dosage to detect aneuploidy. (Zimmermann et al., 2002; Lo et al., 2007a). By examining the ratio of concentrations of nonpolymorphic loci on chromosomes 1 and 21, this polymorphism-independent method proved 100% accurate. However, between 1 and 7 plates were required for each conclusive diagnosis, thus making digital PCR in this form labor-intensive. The precision of digital PCR in relative chromosomal dosage and thus aneuploidy detection was confirmed, while highlighting the need for extensive analyses in light of low ratios of fetal DNA to maternal DNA. (Fan and Quake, 2007a).

Massively parallel genomic sequencing was introduced to address previous concerns of the preponderance of maternal DNA over fetal DNA while achieving the desired precision of digital PCR. (Chiu et al., 2008; Fan et al., 2008). Although PCR depends on select loci only present on some DNA fragments, massively parallel sequencing can be used in both a polymorphism-independent and loci-independent manner to take advantage of all DNA fragments in a sample. By simultaneously sequencing all or even targeted fragments, aligning the sequences to their respective chromosomes, and quantifying each chromosomal dosage, issues surrounding predominance of maternal DNA can be resolved even with markedly smaller sample sizes. (Liao et al., 2011). Proof of principle studies demonstrated 100% accurate detection of chromosomal overrepresentation in instances of trisomies 13, 18, and 21. (Chiu et al., 2008; Fan et al., 2008). Follow-up studies indicate that sensitivity to aneuploidy or mosaicism is constrained only by sequencing depth: that is, the greater the number of sample reads, the greater the detection of over- or under-representation of any complete or partial chromosomal anomaly. (Fan and Quake, 2010b). Massively parallel genomic sequencing may also provide a means to detect trisomy caused by other cytogenetic anomalies, such as Robertsonian translocations. (Lun et al., 2011).

An alternative strategy for aneuploidy detection uses tandem SNPs to bypass concerns of maternal DNA predominance while avoiding high costs associated with sequencing methods. (Ghanta et al., 2010). Tandem SNPs are 2 highly heterozygous, neighboring polymorphisms that allow for 4 possible haplotype permutations. If a mother expresses 2 different haplotypes and the father carries at least 1 additional distinct haplotype, the dosage of each haplotype in maternal plasma will be informative for the fetal haplotype. In cases of trisomy, a fetus will have either 3 haplotypes or an imbalance of 2 haplotypes, depending on when nondisjunction occurred. In addition to a preliminary specificity and sensitivity of 100%, this technique of PCR or sequencing platforms and applicability to a range of chromosomal aberrations; however, a significant proportion of cases will not be informative for a given tandem SNP. (Ghanta et al., 2010).

Until recently, certain genetic conditions have presented methodological complications intractable to existing analytic methods. Because of the fragmented state of cell-free fetal DNA, any disease-causing sequences longer than 300 base pairs have not been detectable with these methods. (Chan et al., 2004; Norbury and Norbury, 2008). Additionally, by virtue of the difficulties in distinguishing between identical maternally and paternally inherited alleles in fetal DNA, efforts at prenatal detection of recessive disorders caused by a single mutation, such as sickle cell anemia, have been minimal.

Previously reported MS analysis of admixed maternal-fetal DNA despite identical maternal and paternal disease-causing mutations suggested a means to avoid this limitation; by analyzing the maternal and paternal haplotypes and seeking informative paternal SNPs linked to the mutation, fetal inheritance of the paternal SNP and thus haplotype allowed deduction of fetal β-thalassemia status. (Ding et al., 2004).

Cell-free fetal nucleic acids may also serve an important role in perinatal care, as the concentration of circulating DNA has predictive capabilities for pregnancy complications. Most notably, the severity of proteinuria and hypertension, the 2 major symptoms of preeclampsia, is associated with increased concentrations of cell-free fetal DNA. (Sekizawa et al., 2004b; Lo et al., 1999b). This elevation of cell-free fetal DNA levels typically precedes the onset of preeclampsia, offering potential identification of at-risk pregnancies. (Zhong et al., 2002; Farina et al., 2004). Elevated cell-free fetal DNA levels have also been noted in pregnant women with invasive placenta, hyperemesis gravidarum, and preterm labor. (Sekizawa et al., 2002; Sekizawa et al., 2001; Leung et al., 1998). This type of quantitative analysis is typically accomplished by determining concentrations of Y-specific sequences circulating in the blood of women bearing male fetuses divided by concentrations of a marker of total cell-free DNA, like β-globin or GAPDH, to calculate the amount of DNA derived specifically from the fetus. (Zhong et al., 2001a; Sekizawa et al., 2003a). Alternative methods include measuring concentrations of other fetal genetic markers, such as PLAC1, CRH, and selectin-P mRNA, for femalebearing pregnancies. (Maron et al., 2007; Purwosunu et al., 2007; Farina et al., 2006; Ng et al., 2003) As researchers continue to search for fetal DNA or RNA indicators for pregnancy complications, it is plausible that new universal markers for fetal-specific genetic sequences in maternal blood will be discovered that will be valuable for use in other applications of noninvasive prenatal testing.

Hurdles to the clinical implementation of prenatal genome mapping include high cost and low throughput of sequencing platforms, requirement of complex statistical methods, and currently limited knowledge of haplotype information. For diagnosis of disease in at-risk populations, these barriers may be avoided through targeted searches for known disease-causing regions.

The discovery of cell-free fetal DNA and RNA circulating in the maternal bloodstream has opened the door to noninvasive genome-wide prenatal testing with novel clinical implications. Moreover, the range of fetal genetic traits that can be identified using this technology seems to be constrained only by our knowledge of genomics. As scientific research and development of cell-free fetal DNA and RNA technology is advanced, this testing may gradually supersede or supplement existing screening and diagnostic procedures. This technology has demonstrated potential to significantly change prenatal genetic testing because of its noninvasiveness, broad indications, and earlier timing for use.

The above-described state of the art of cell-free fetal nucleic acid testing has been reviewed in exquisite detail by Sayres and Cho, 2011, which is incorporated herein by reference in its entirety.

SUMMARY OF THE INVENTION

The following brief summary is not intended to include all features and aspects of the present invention, nor does it imply that the invention must include all features and aspects discussed in this summary.

Conventional experimental methods of studying the human genome are limited by the inability to independently study each of the homologous copies of the chromosomes. These haplotypes are important features of the genome but in general cannot be easily determined. Determination of whole genome haplotypes would have applications in personal genomics, single-cell genomics and statistical genetics.

In an effort to overcome the aforementioned deficiencies in prior art methods of non-invasively determining fetal inheritance of parental haplotypes, particularly at the genome-wide scale, the inventors have surprisingly found that by diluting a mixture containing multiple homologous copies of a region to single-molecule density and performing genetic analysis on individual molecules, one can measure haplotypes. In particular, the present inventors have developed methods of globally amplifying a single, intact chromosome molecule within a single cell, such that the high-throughput genetic analyses of the amplified materials provide genome-wide haplotypes of an individual.

The present invention relates to devices and methods for non-invasively determining parental haplotypes that are inherited by fetus. Because fetal genetic material is present in maternal blood, a sample from a female pregnant with at least one fetus is sufficient to identify the parental haplotypes, as well as the genetic information of the fetus without the need to invasively sample the fetus, and thus avoid possible risks to the fetus during pregnancy.

Thus, the present invention comprises, in certain aspects a method of non-invasively determining parental haplotypes which are inherited by a fetus, including (a) obtaining a maternal sample from a female pregnant with at least one fetus, wherein said sample contains DNA from both the pregnant female and the fetus; (b) determining a paternally inherited haplotype by the steps of: (i) determining a set of single nucleotide polymorphisms (SNPs) in the DNA of the fetus's father; (ii) determining a set of SNPs in the DNA of the fetus's mother; (iii) determining all SNPs that are heterozygous in the father and homozygous in the mother to identify at various loci alleles present in the father and absent in the mother, thereby defining each of the father's haplotypes; and (iv) counting a number of representative alleles on each paternal haplotype to determine a representation of the two haplotypes; (v) comparing the representation of the two haplotypes to obtain a relative representation; (vi) determining an over-representation $\epsilon$ of one of the two haplotypes; and (vii) correlating the over-representation $\epsilon$ with a paternally inherited haplotype; and (c) determining a maternally inherited haplotype by the steps of: (i) determining all SNPs that are heterozygous in the fetus's mother; (ii) identifying alleles present in the mother but absent in the paternally inherited haplotype at each SNP locus to define the mother's haplotypes; (iii) counting a number of representative alleles on each maternal haplotype to determine a representation of the two haplotypes; (iv) comparing the representation of the two haplotypes to obtain a relative representation; (v) determining an over-representation ∈ of one of the two haplotypes; and (vi) correlating the over-representations with a maternally inherited haplotype.

The invention also relates to a method of non-invasively determining maternal haplotypes which are inherited by a fetus, including: (a) obtaining a maternal sample from a female pregnant with at least one fetus, wherein said sample contains DNA from both the pregnant female and the fetus; (b) counting markers in the sample that define each of two maternal haplotypes to determine a representation of the two haplotypes; (c) comparing the representation of the two haplotypes to obtain a relative representation; (d) determining an over-representations of one of the two haplotypes; and (e) correlating the over-representation ∈ with a transmitted maternal haplotype.

Also included in the invention is a method of determining an appropriate set of markers that define a maternal haplotype, comprising determining alleles that are present at polymorphic loci in a first maternal haplotype but not at corresponding loci on a second maternal haplotype.

Another aspect of the invention is to provide a method of determining a minimum amount of digital sampling to achieve a desired confidence level as to which parental haplotypes are over-represented, including: (a) estimating a fraction of fetal DNA present in the sample; and (b) estimating density of available markers.

Yet another aspect of the invention is to provide a method of estimating fetal DNA fraction in a maternal sample, including measuring relative representation of parental haplotypes by examining the over-representation of one of the maternal haplotype or by the presence of paternally inherited haplotype.

Still another aspect of the invention is to provide a microfluidic device for performing the method of the invention, wherein the device includes (a) a chromosome partitioning region; (b) an amplification region; and (c) a product retrieval region, and optionally, (d) a cell sorting region; and (e) a chromosome release region.

The invention also includes a computer program for controlling the microfluidic device, and for analyzing the sample data.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

The application file contains at least one drawing executed in color. Copies of any patent or patent application publication from this application containing color drawing(s) will be provided by the Office upon request and payment of the necessary fee.

FIG. 1A. In the case when blood or other genetic materials from both parents are available, genome-wide, chromosome length haplotypes of the parents are obtained, for instance, using direct deterministic phasing in this study. The four parental haplotypes are differentiated by the alleles specific to each of them. Molecular counting of parental haplotypes is achieved by shotgun sequencing maternal plasma. The inheritance of maternal haplotypes is revealed by counting the alleles on each maternal haplotype and determining the relative representation of the two maternal haplotypes. The inheritance of paternal haplotypes is determined by counting the number of alleles specific to each of the paternal haplotypes. FIG. 1B. In the case when blood is only available from the pregnant mother, the inheritance of maternal haplotypes is determined in the same manner, but the paternally inherited haplotype is reconstructed by imputation based on the paternal specific alleles detected in the maternal plasma.

FIG. 5A. Bar graph showing the fraction of SNPs present on the array phased for each chromosome of each individual (GM12891, GM12892, GM12878 and a European individual P0) is shown as a colored bar. FIG. 5B. Bar graph showing the number of replicates of phasing per SNP for each individual.

FIG. 7A-B. Table showing cross-over regions in paternal (GM12891) and maternal (GM12892) chromosomes leading to CM12878's genome.

FIG. 8. A. Phasing of heterozygous deletions in the CEU family trio using data from SNP arrays. In FIG. 8, 'Homolog 1' is the plotted on the right, and 'Homolog 2' is plotted on the left. The homolog carrying a copy of the region is boldfaced. B. Phasing of heterozygous deletions in, the CEU family trio using real-time PCR. The homolog carrying a copy of the region is boldfaced. [1]Number of typed markers / number of markers typed in at least one homolog within the region; [2]At least one homolog did not contain any typed markers; [3]Number of homologs giving positive PCR amplification / number of homologs tested; [4]Both homologs gave positive PCR amplification, although the copy number of this CNV was 1 for the two individuals.

FIG. 13. Table showing Statistics of high-throughput sequencing of the two homologous copies of P0's chromosome 6. Reads were mapped to NCBI Build 36.

FIG. 14. Distribution of 32 bp reads across chromosome 6 for three different homologous copies of chromosome 6 sequenced, labeled as libraries 1, 2, and 3, and represented as bars.

FIG. 15A shows the average switch error and single site error per region in statistical haplotype inference for an individual without family information. FIG. 15B shows the distribution of switch error and single site error per region.

FIG. 16A-B. Phasing of heterozygous deletions of P0. The homolog carrying the target region is boldfaced. [1]Same labeling as in Supplementary Table 4 of Pushkarev et al., 2009; [2]A heterozygous SNP chosen to define the two homologous copies of chromosome 6 of P0; [3]Allele of the chosen SNP on each of the homologous copies; [4]Number of typed markers / number of markers typed in at least on homolog within the region; [5]Positive or negative PCR signal; [6]PCR experiments were done on amplified materials from separated chromosome homologs obtained from 3 single cells ('C' refers to combined genotyping results from the same homolog in 3 single cells); [7]Homologous copies were not separated for this particular single cell experiment.

FIG. 17A-G. HLA haplotypes of P0 determined using DDP. At each of the 6 classical HLA loci, the experimentally phased SNP haplotypes of P0 and 176 phased SNP haplotypes of CEU trios available from HapMap phase III were placed on a neighbor-joining tree. FIG. 17A is a tree for HLA-A. FIG. 17A is a tree for HLA-C. FIG. 17C is a tree for HLA-DQA1. FIG. 17D is a tree for HLA-B. FIG. 17C is a tree for HLA-DRB1. FIG. 17F is a tree for HLA-DQB1. The two haplotypes of P0 are labeled as Haplotype 1 and Haplotype 2. For haplotypes in the CEU panel with HLA typing data, the four-digit HLA allele is presented next to the sample label. Most part of a tree is compressed. Each compressed subtree is labeled with the HLA allele associated with members inside the subtree, if HLA allele information is available. FIG. 17G lists the results of direct HLA typing of genomic DNA. The allelic identities of HLA-B and HLA-C on haplotype 1 were not determined with DDP since CEU individuals with similar SNP haplotypes as P0's SNP haplotypes did not have HLA typing data at these loci, but could be inferred from the results of direct HLA typing of genomic DNA (first row FIG. 17G). HLA-DQAI was not directly typed.

FIG. 18A. List of 46 genotyping assays used for whole-genome haplotyping. FIG. 18B Sequences of primers and Taqman probes for ChrY. The Forward primer, Reverse primer, and Probe sequences for ChrY are recited in SEQ ID NO: 22, SEQ ID NO: 23, and SEQ ID NO: 24, respectively.

FIG. 19. Sequences of primers and Taqman probes used for the phasing of the heterozygous deletions within the family trio.

The Forward primer, Reverse primer, and Probe sequences for HM3 CNP71 are recited in SEQ ID NO: 1, SEQ ID NO: 8, and SEQ ID NO: 15, respectively.

The Forward primer, Reverse primer, and Probe sequences for HM3 CNP116 are recited in SEQ ID NO: 2, SEQ ID NO: 9, and SEQ ID NO: 16, respectively.

The Forward primer, Reverse primer, and Probe sequences for HM3 CNP201 are recited in SEQ ID NO: 3, SEQ ID NO: 10, and SEQ ID NO: 17, respectively.

The Forward primer, Reverse primer, and Probe sequences for HM3 CNP309 are recited in SEQ ID NO: 4, SEQ ID NO: 11, and SEQ ID NO: 18, respectively.

The Forward primer, Reverse primer, and Probe sequences for HM3 CNP371 are recited in SEQ ID NO: 5, SEQ ID NO: 12, and SEQ ID NO: 19, respectively.

The Forward primer, Reverse primer, and Probe sequences for HM3 CNP593 are recited in SEQ ID NO: 6, SEQ ID NO: 13, and SEQ ID NO: 20, respectively.

The Forward primer, Reverse primer, and Probe sequences for HM3 CNP708 are recited in SEQ ID NO: 7, SEQ ID NO: 14, and SEQ ID NO: 21, respectively.

Figure 20:
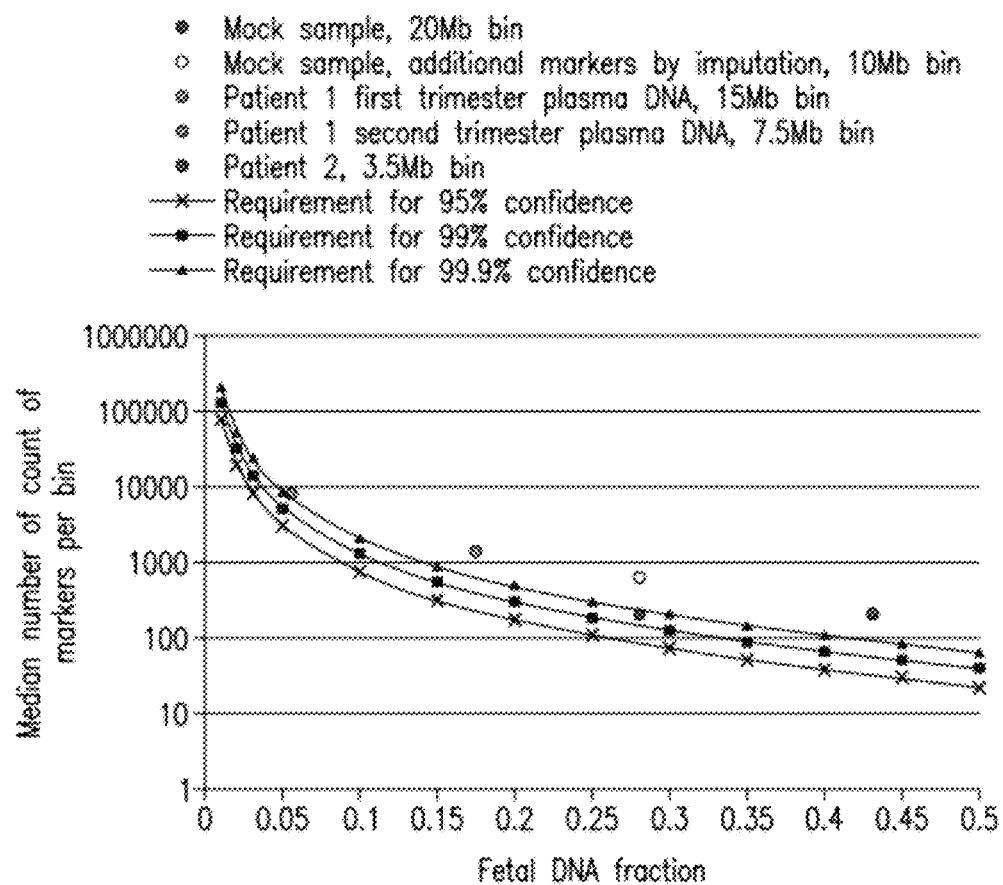

FIG. 20. Relationship between fetal DNA fraction in maternal plasma and the required sampling depth for deducing fetal inheritance of maternal haplotypes. The measure of sampling depth is the median number of occurrences of the markers per bin on the transmitted maternal haplotype. The predicted sampling requirements for a given fetal DNA fraction at different confidence level are plotted as solid lines.

Figure 21A:
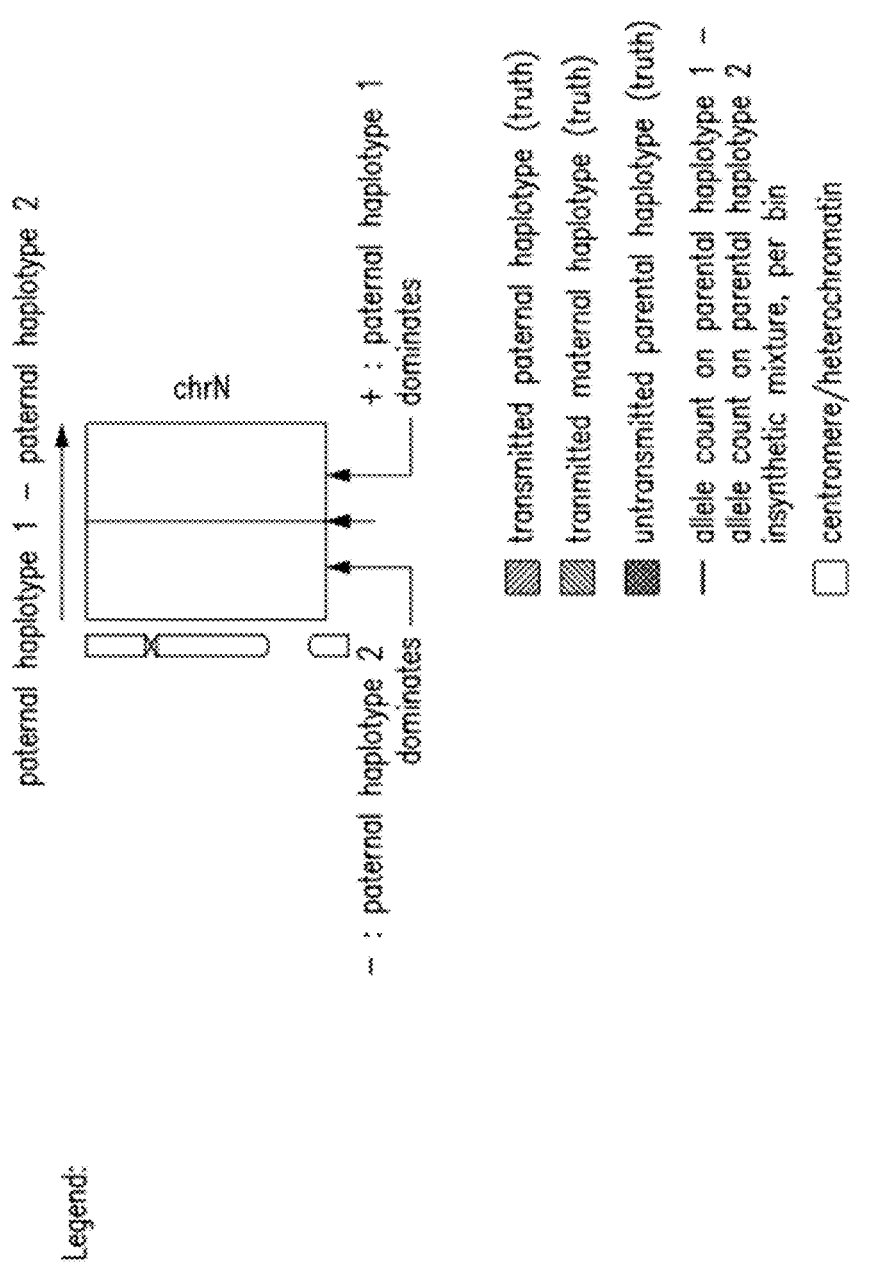
Figures 1, 21A:
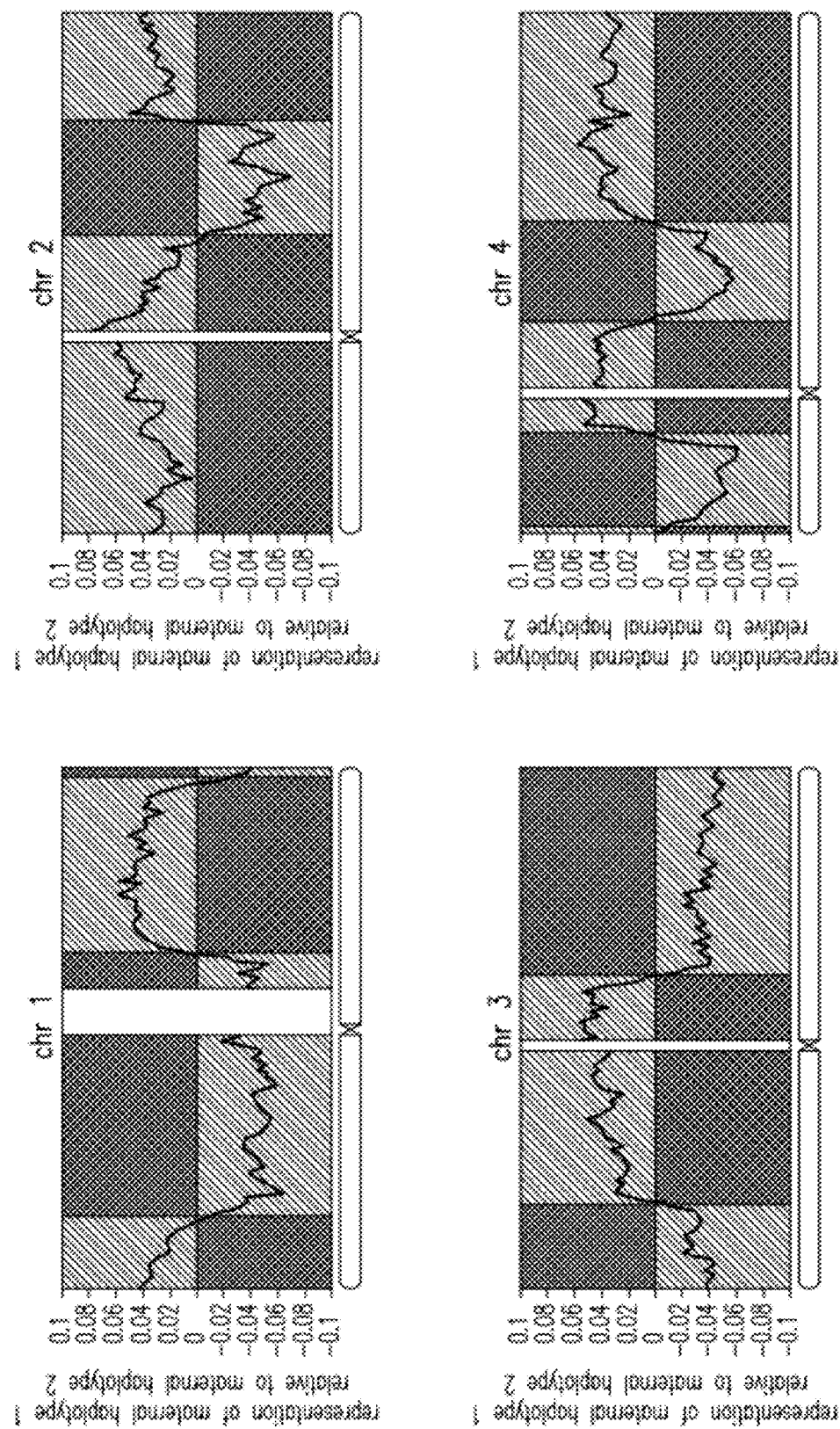
Figures 2, 21A:
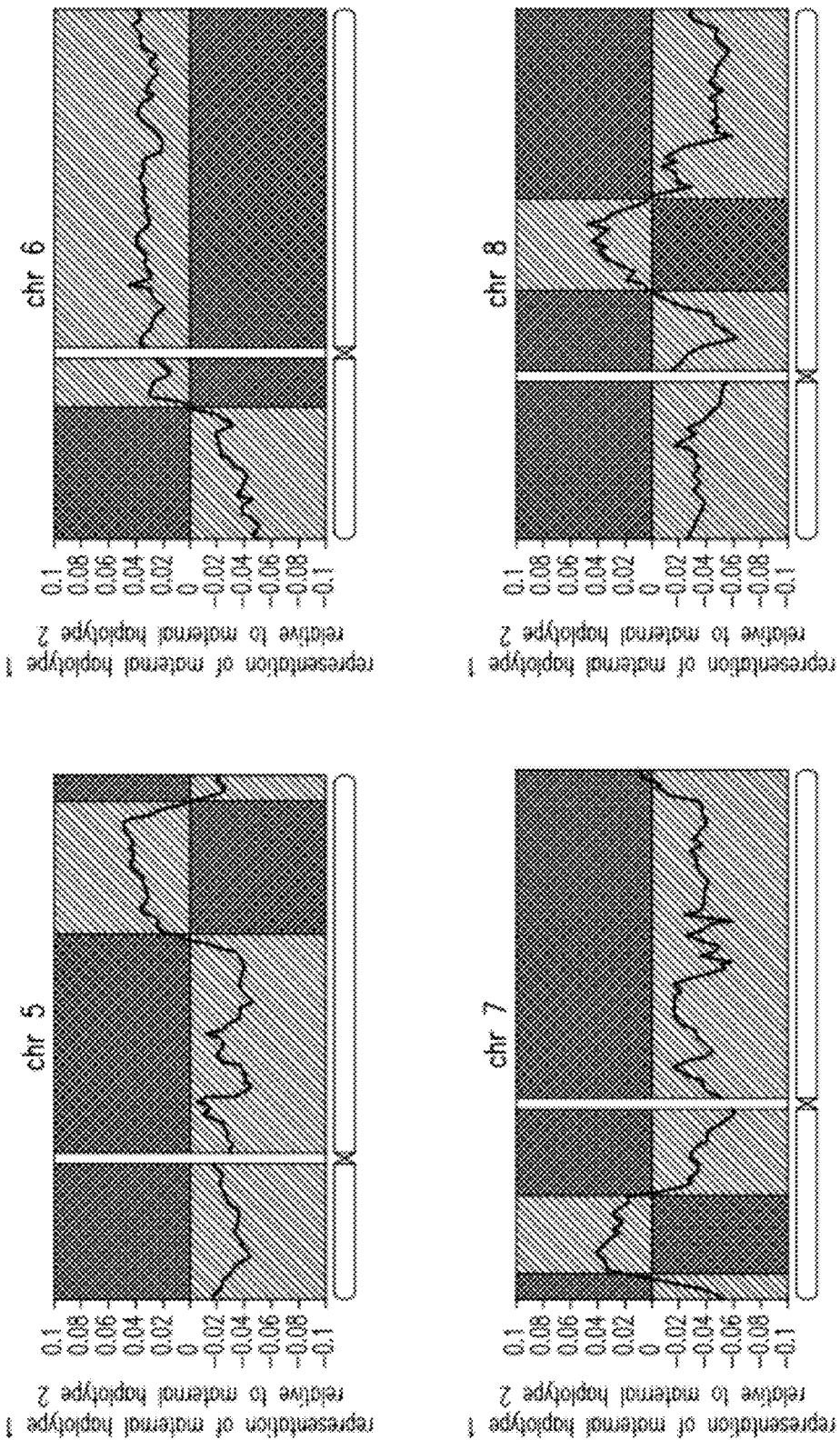
Figures 3, 21A:
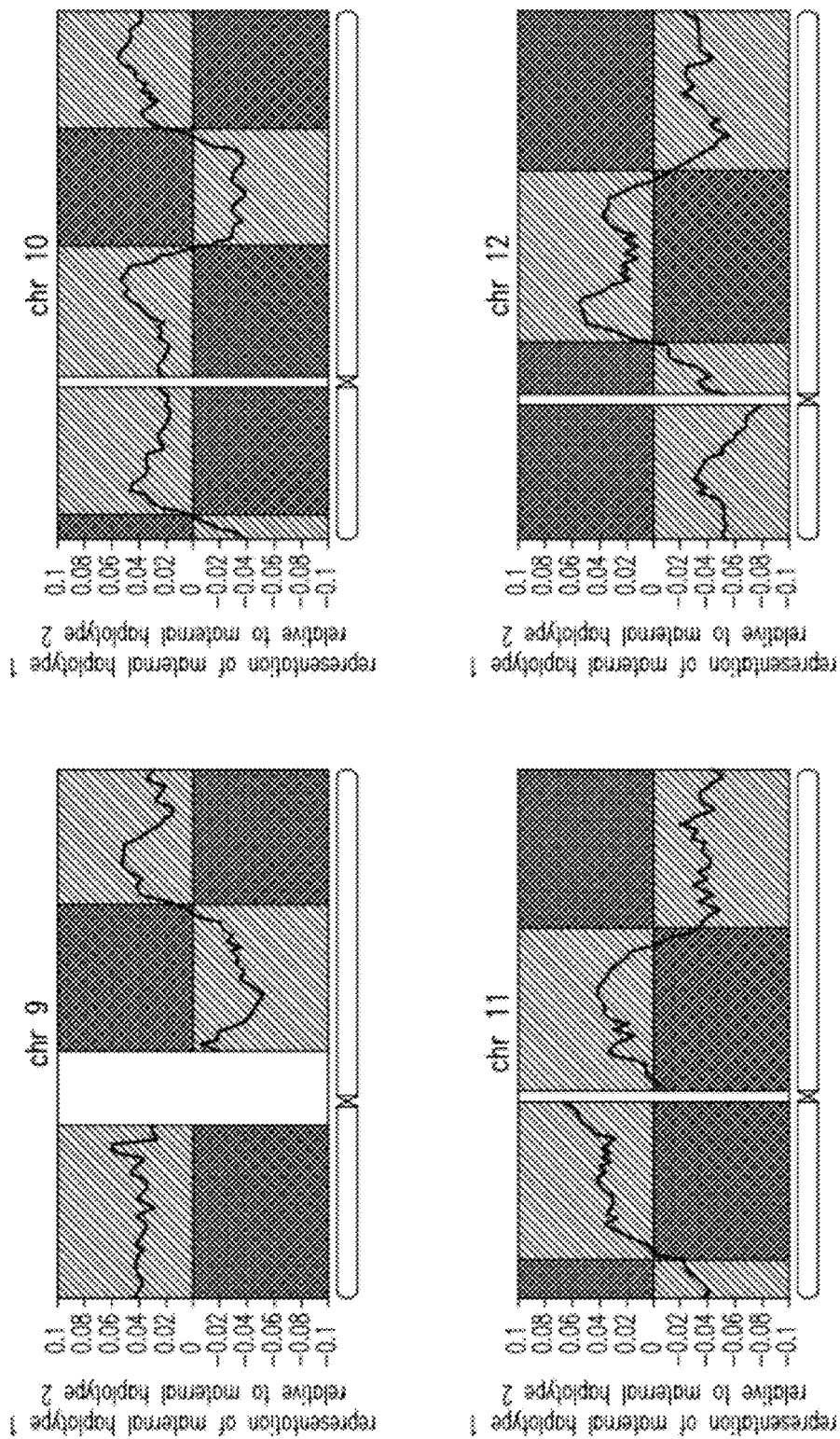
Figures 4, 21A:
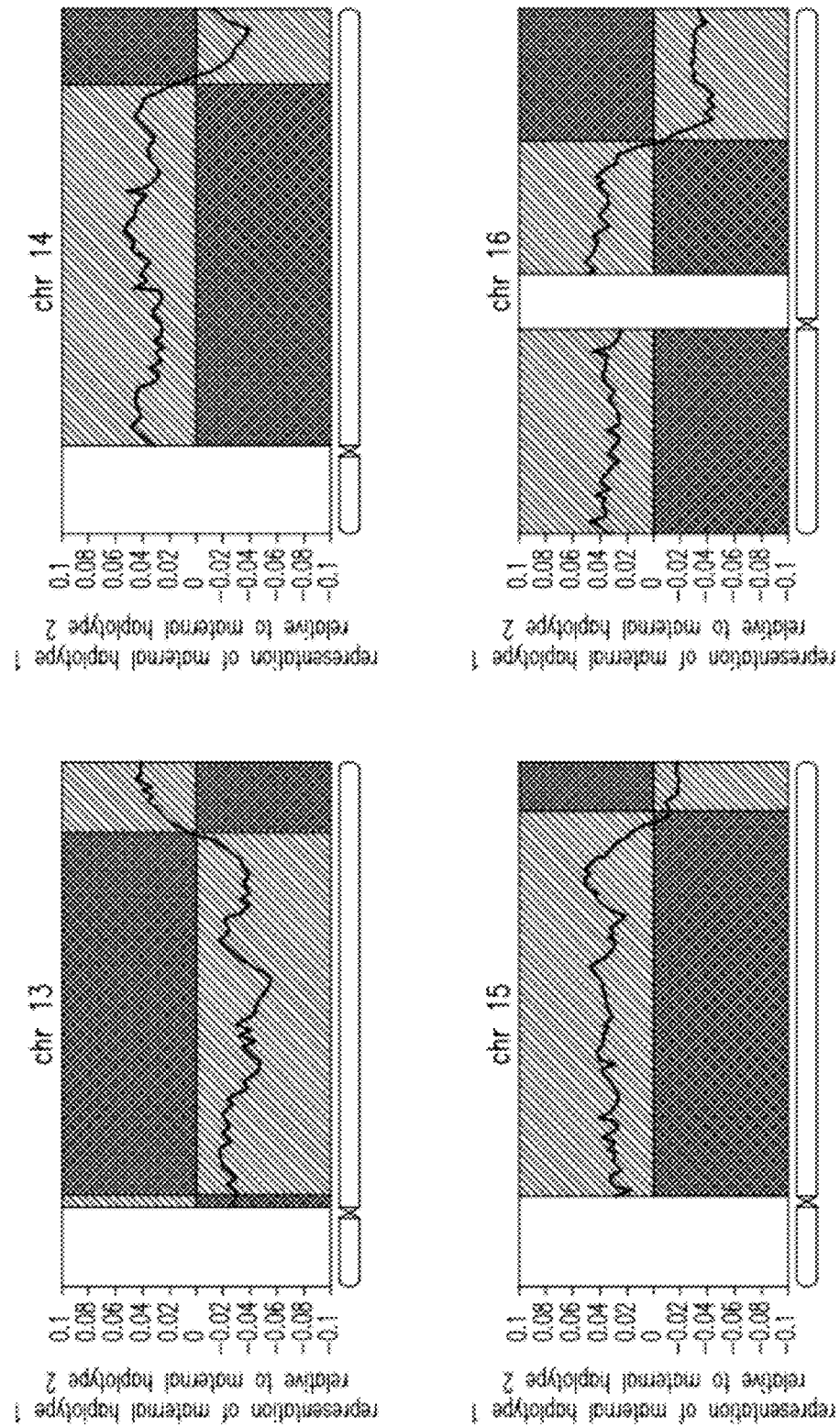
Figures 5, 21A:
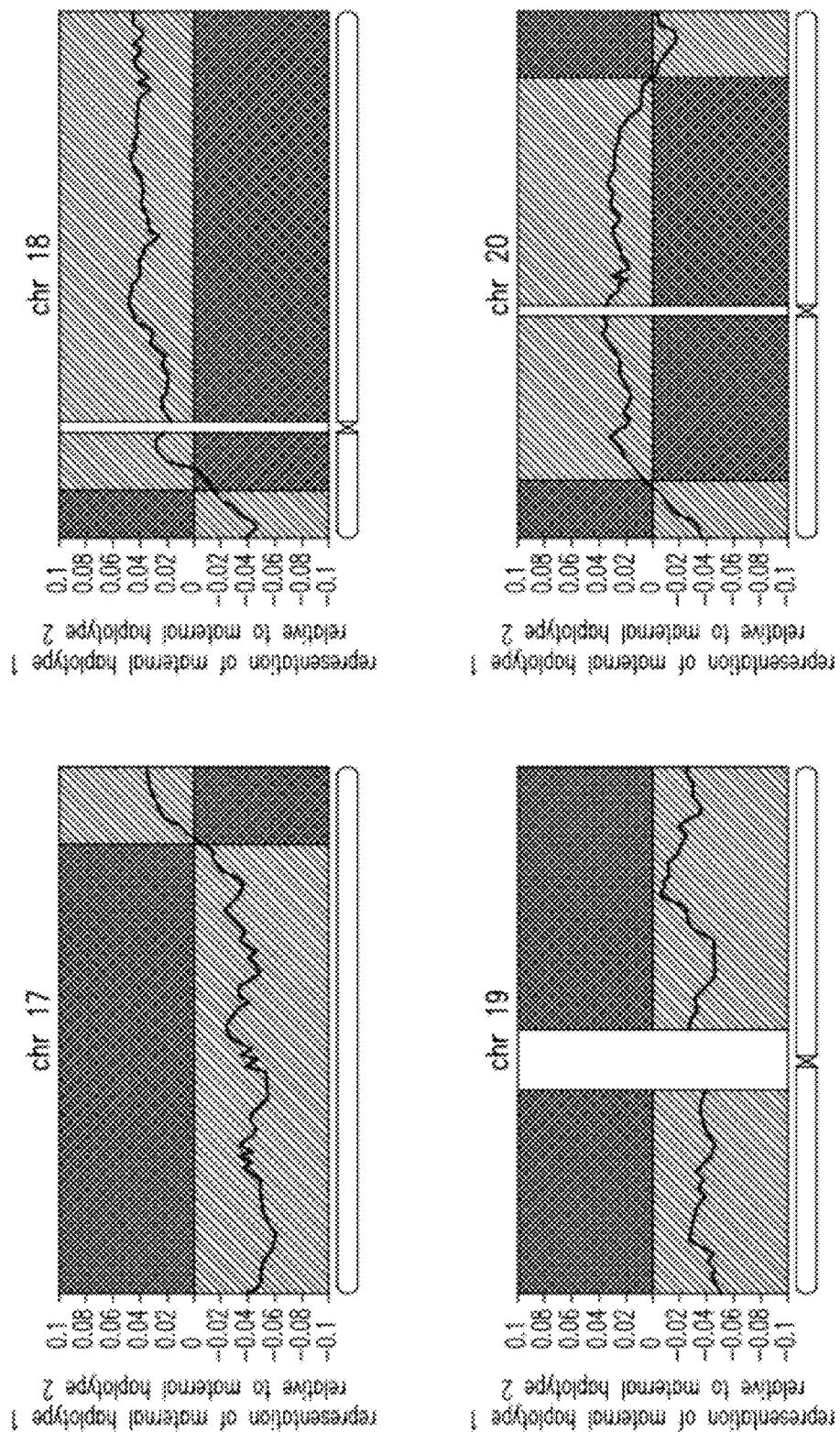
Figures 6, 21A:
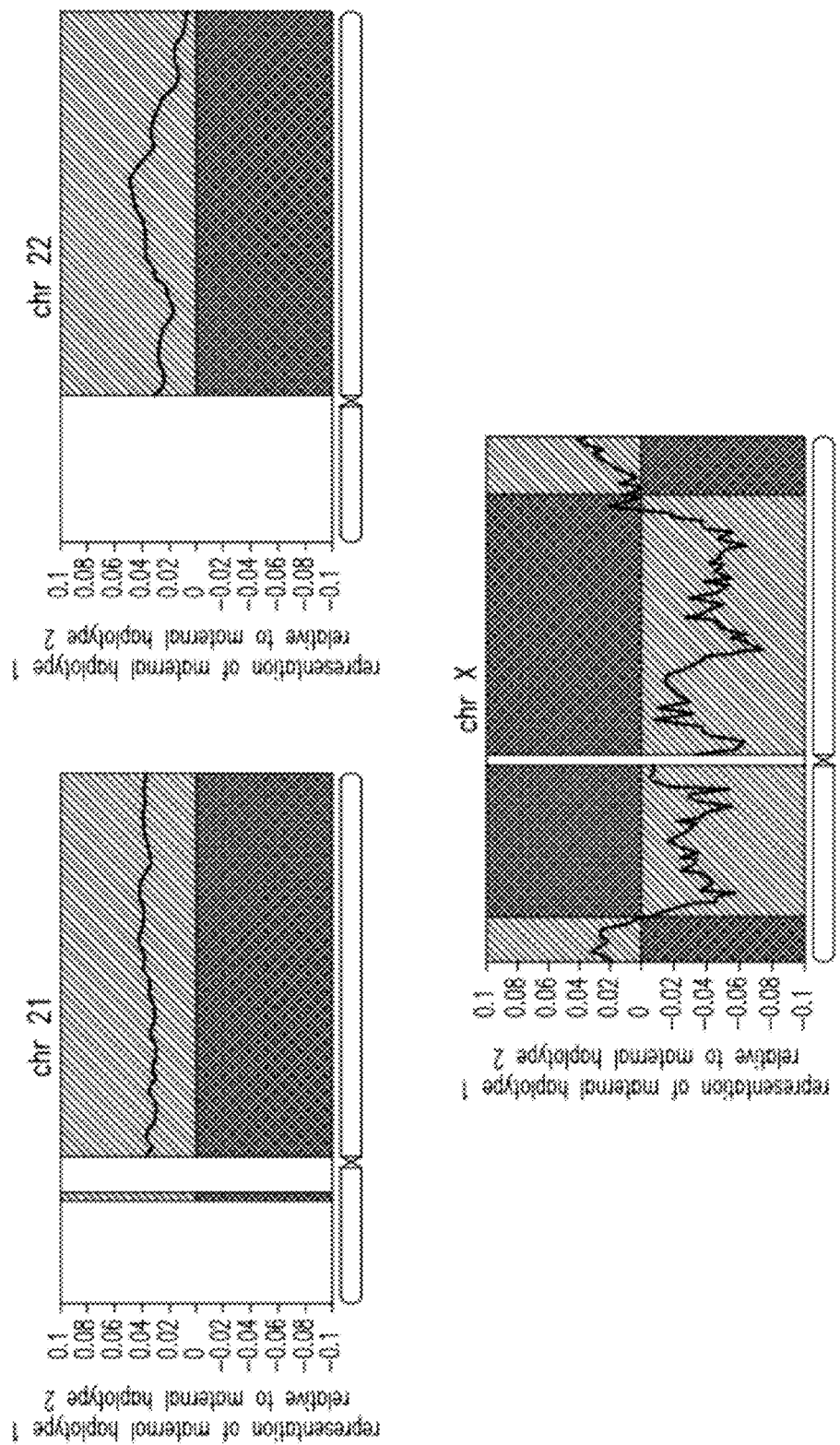
Figure 21B:
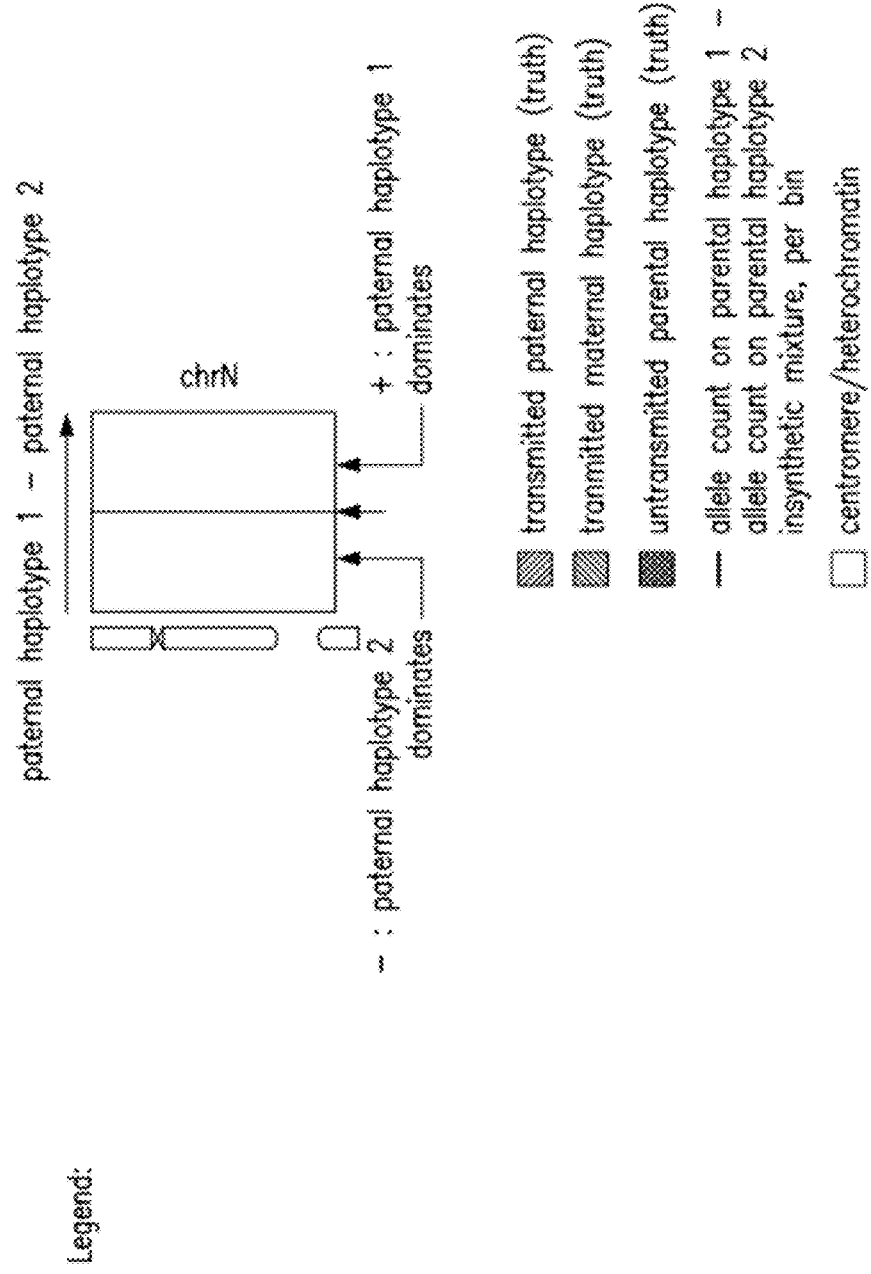
Figures 1, 21B:
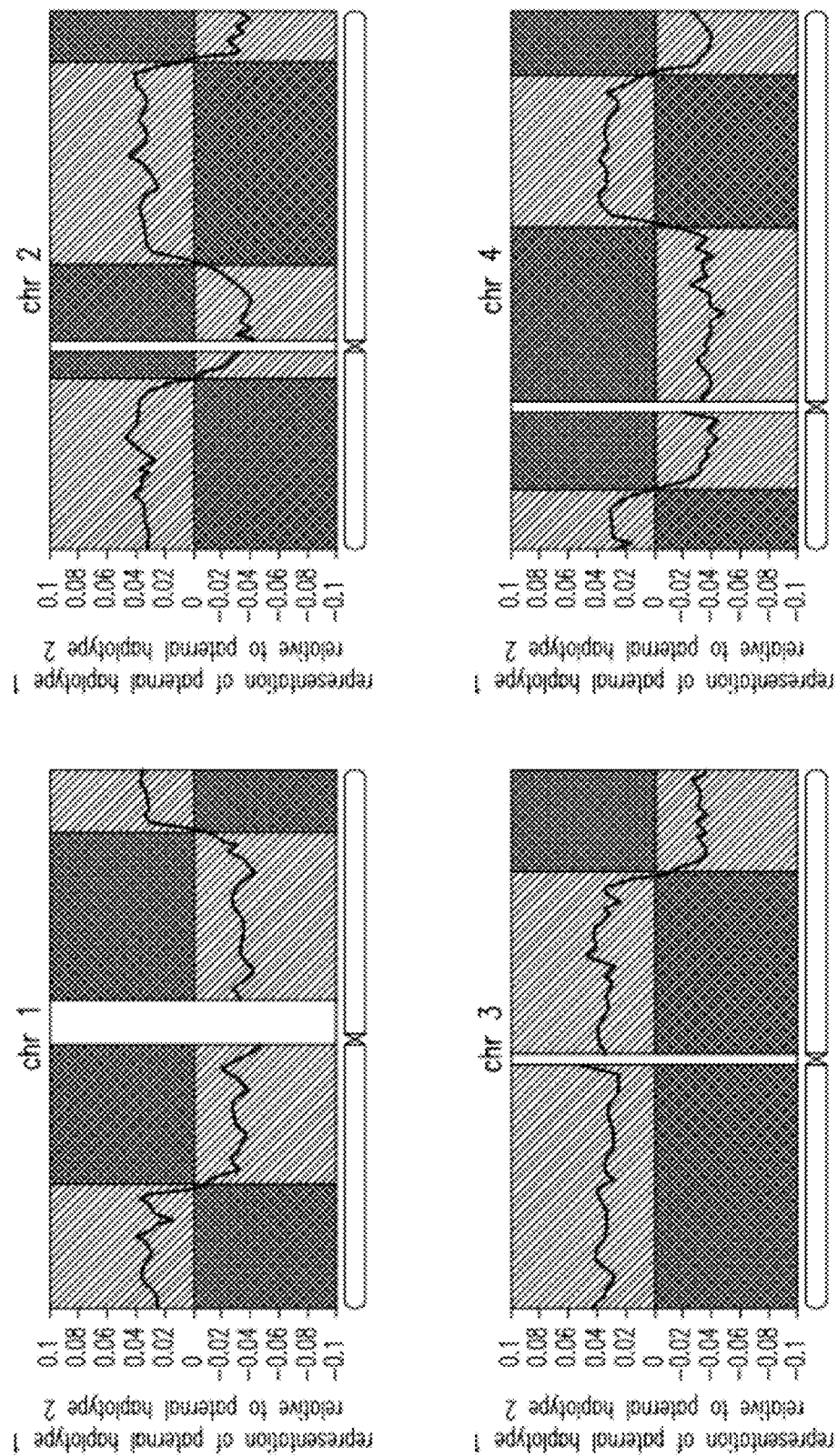
Figures 2, 21B:
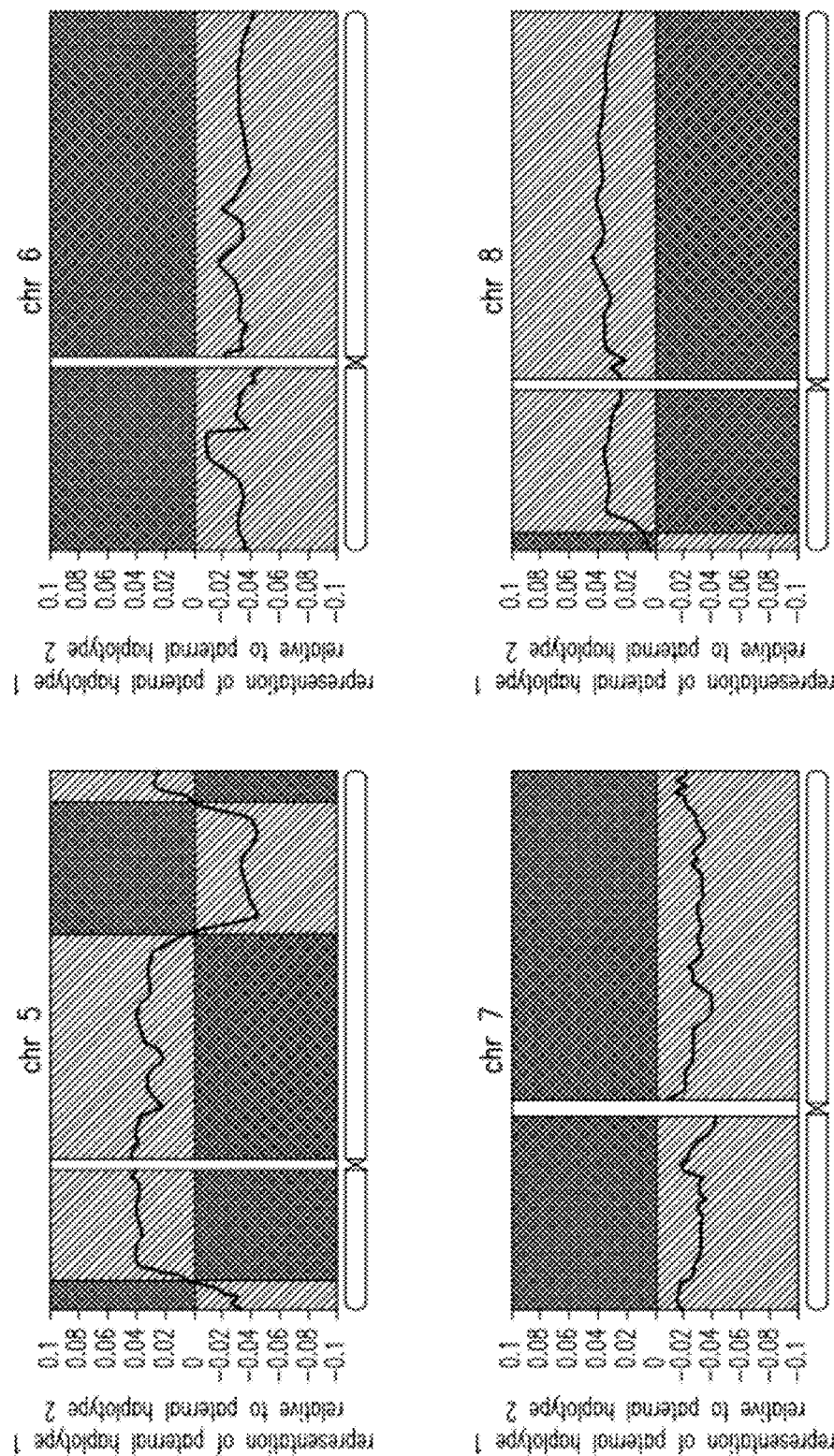
Figures 3, 21B:
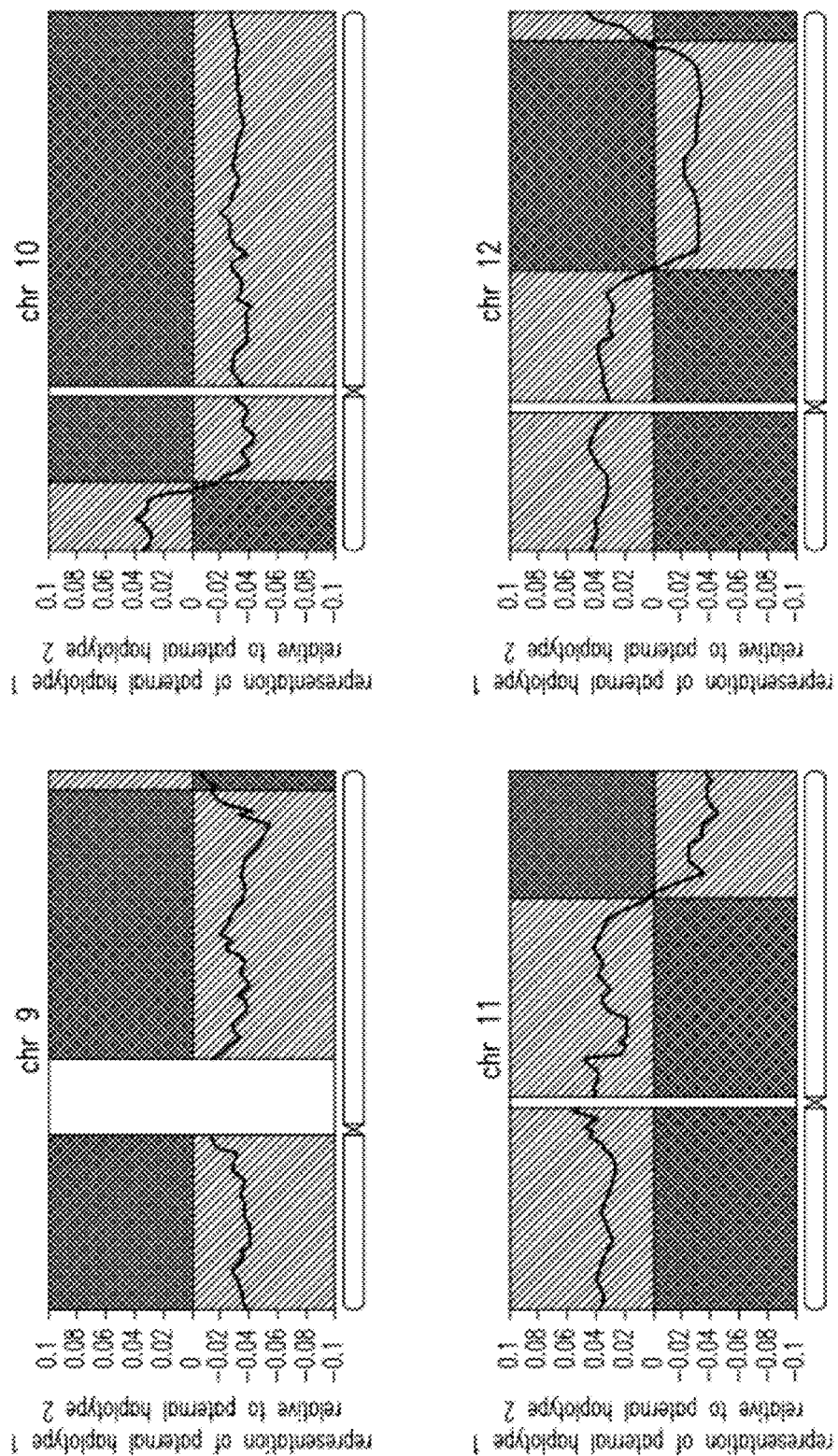
Figures 4, 21B:
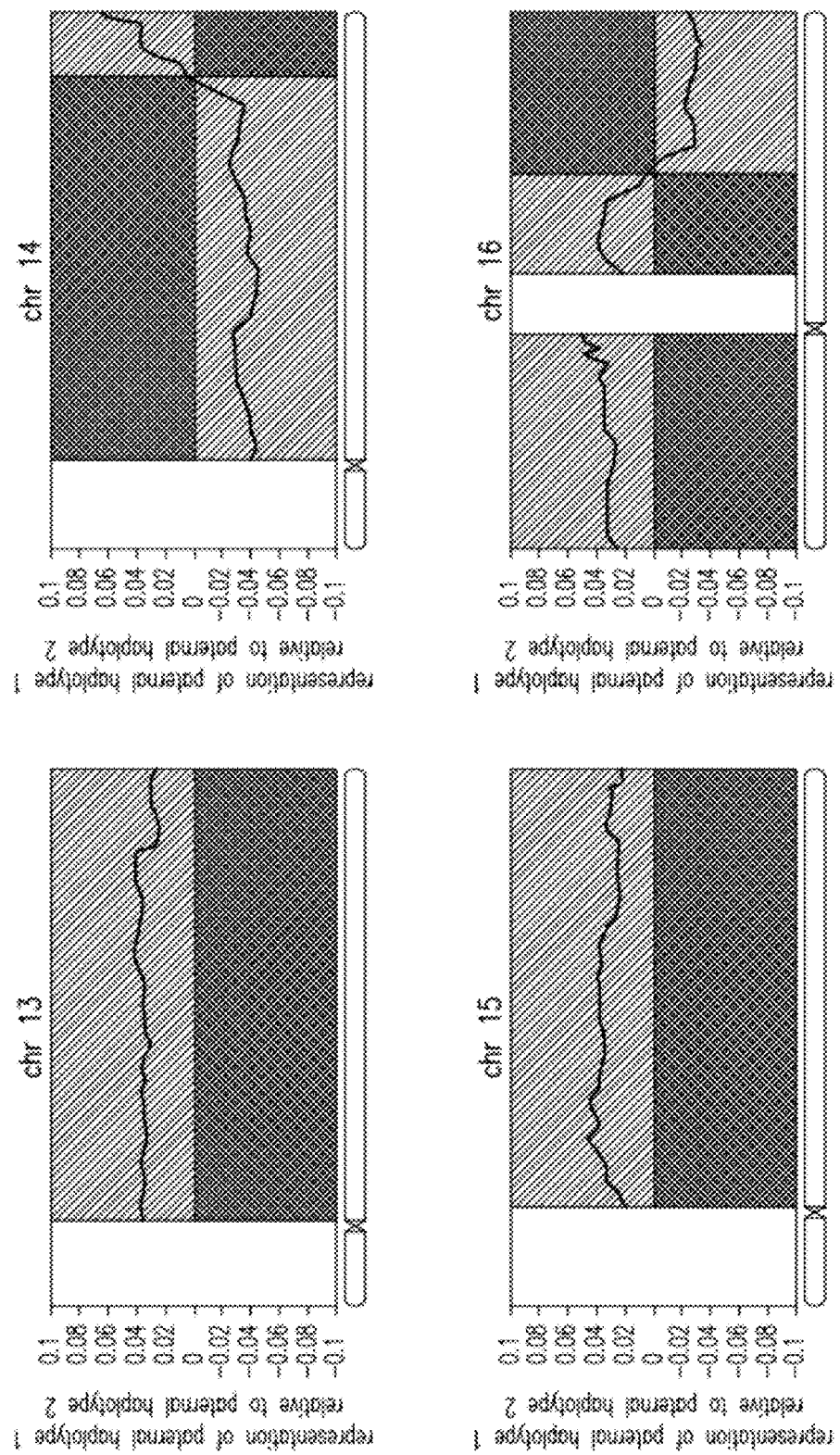
Figures 5, 21B:
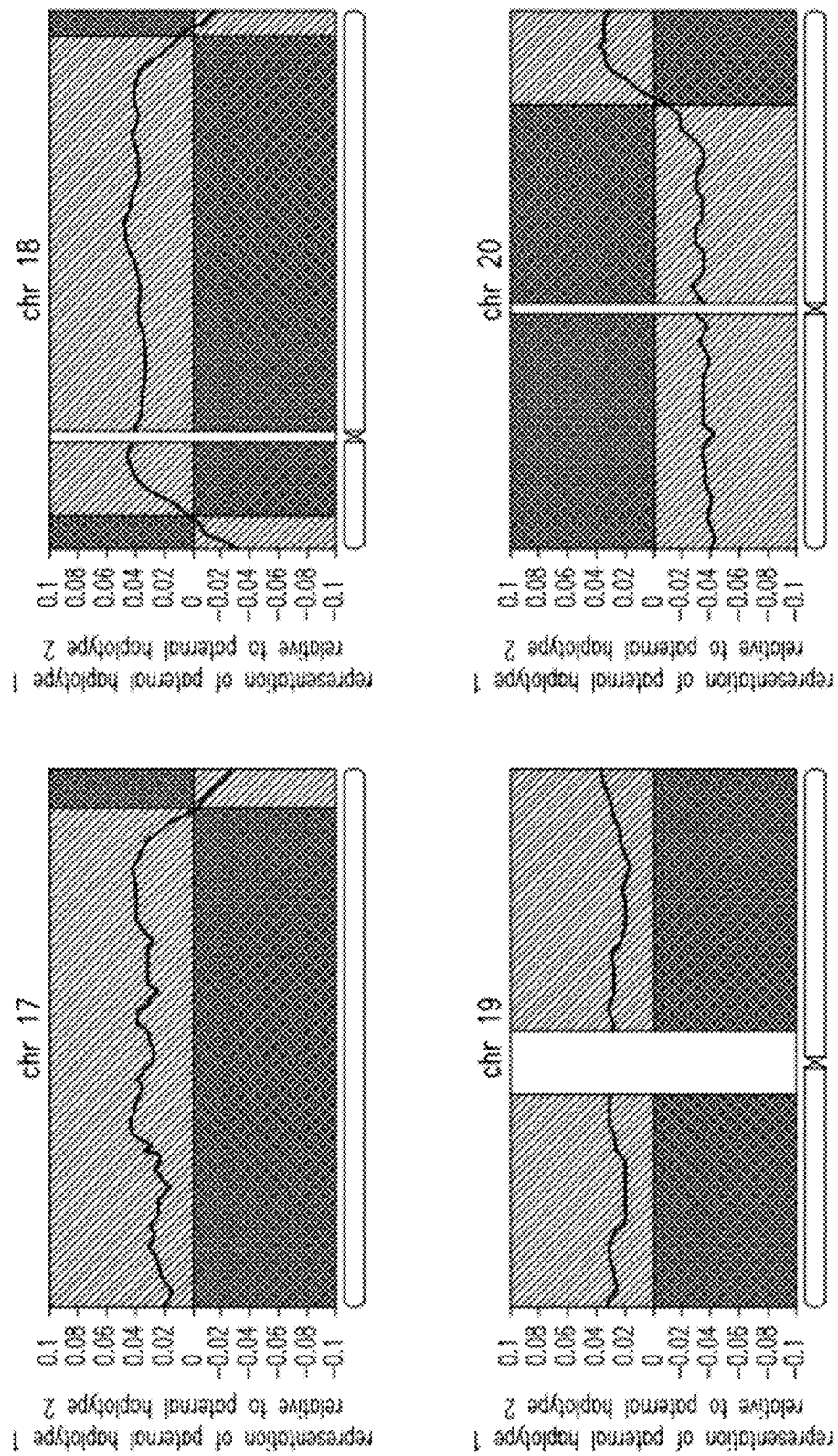
Figures 6, 21B:
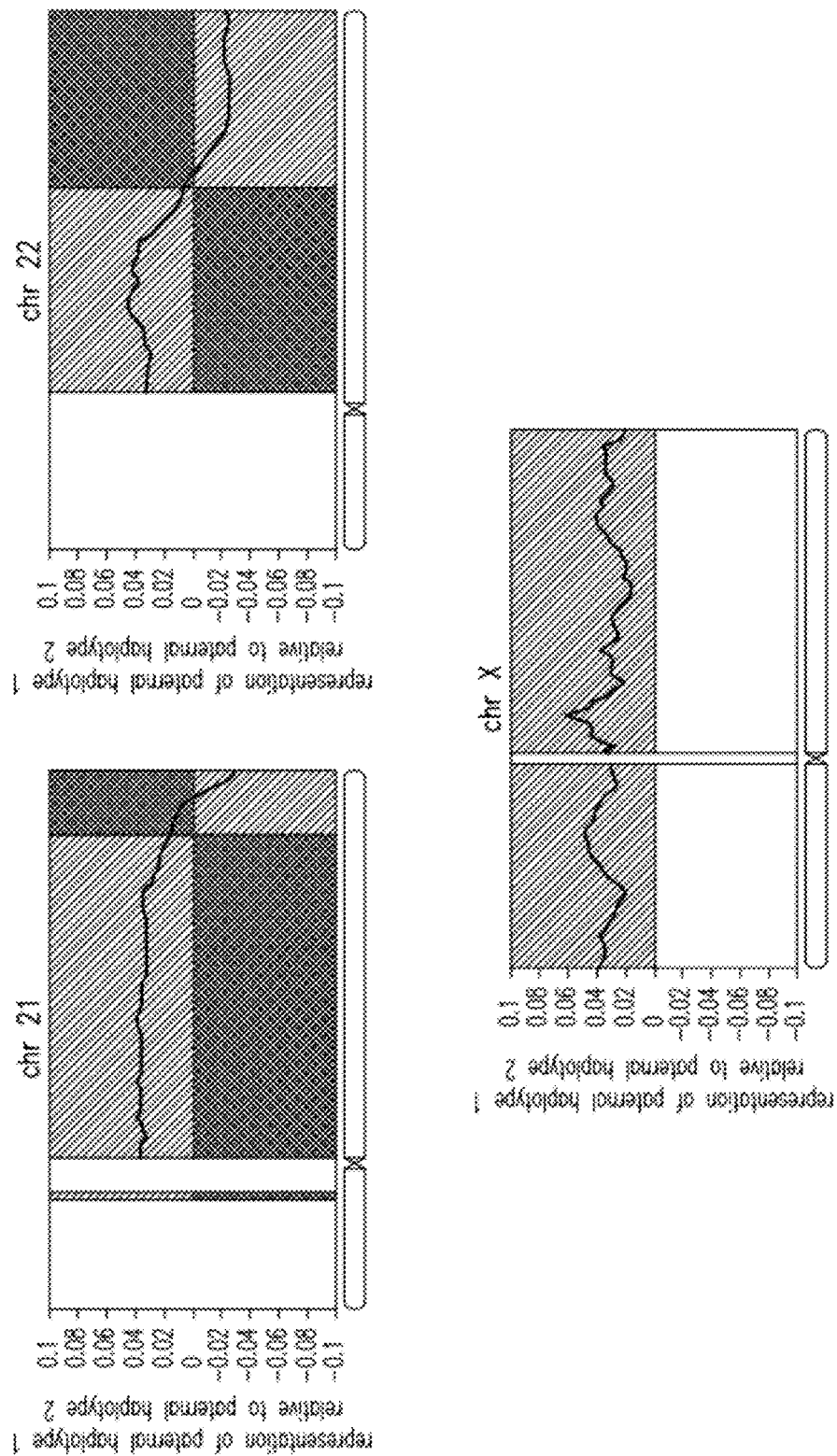
Figure 21C:
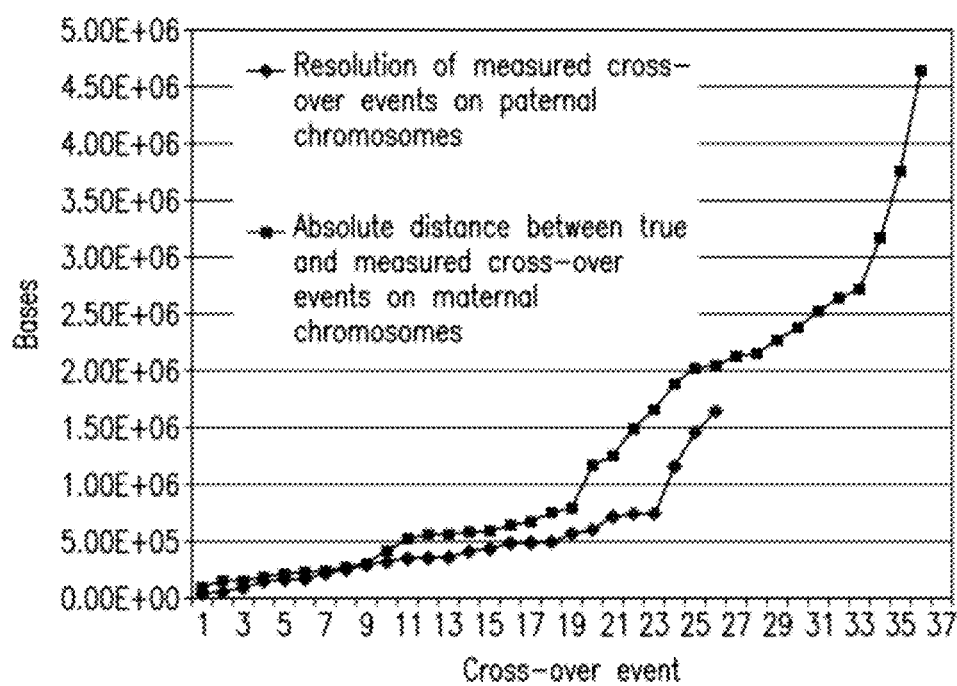

FIG. 21A-C. Determining the child's inheritance of parental haplotypes in a mixture containing maternal and child's genomic DNA. FIG. 21A is a legend for FIG. 21A-1 to A-6. FIG. 21A-1 to A-6. Maternal haplotypes. Each black circle corresponds to the relative representation of the two maternal haplotypes evaluated using the markers lying within a 10 Mb region centered at the circle. Each black circle is accompanied by an error bar that corresponds to the 95% confidence interval for each measurement, estimated by simulating the distribution of reads assuming the count of each maternal haplotype was the mean of a Poisson random variable. Relative representation was calculated with a sliding window of 100 kb. The true inheritance of maternal haplotypes, as determined by previous whole-genome haplotyping experiments of the trio, are shown as the background left hatching: transmitted from mother to daughter; crosshatching: untransmitted; white: heterochromatin/centromere). All chromosomes are plotted with the same length. FIG. 21B is a legend for FIG. 21B-1 to B-6. FIGS. 21B-1 to B-6. Paternal haplotypes. White crosses represent the paternal alleles on each of the two paternal haplotypes observed in the sequencing data. Each black circle corresponds to the relative representation of the two paternal haplotypes evaluated using the markers lying within a 10 Mb region centered at the position of the circle. Relative representation was calculated with a sliding window of 100 kb. The true inheritance of paternal haplotypes, as determined by previous whole-genome haplotyping experiments of the trio, are shown as the background right hatching: transmitted from father to daughter; crosshatching: untransmitted; white: heterochromatin/centromere). All chromosomes are plotted with the same length. FIG. 21C. Resolution of measuring cross-over events. For cross-over events on the maternal chromosomes, the distance between each measured cross-over and the corresponding true cross-over is plotted. For cross-over events on the paternal chromosomes, the width of each measured cross-over event is plotted. The cross-over events are sorted by resolution.

Figures 1, 22A:
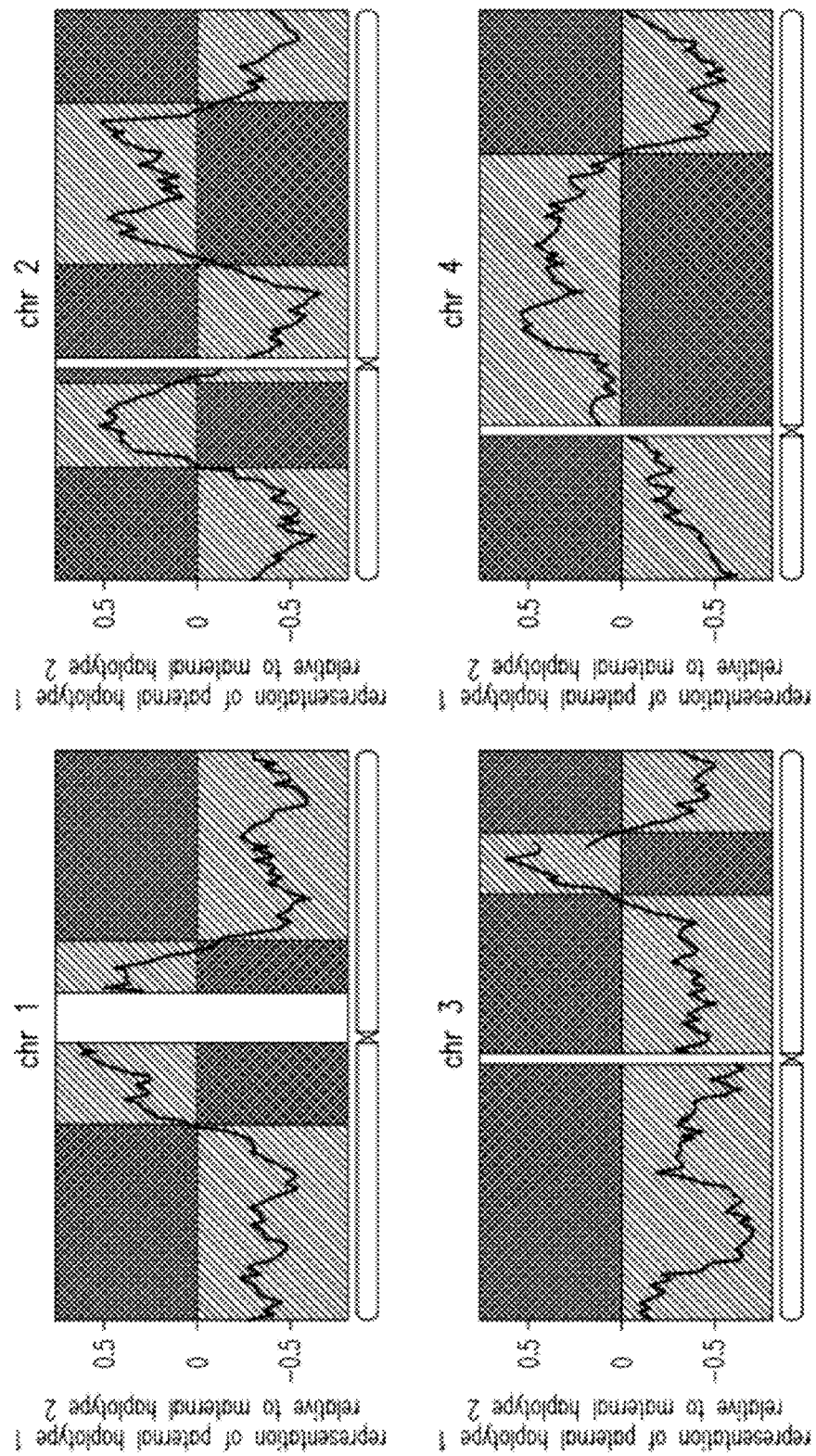
Figures 2, 22A:
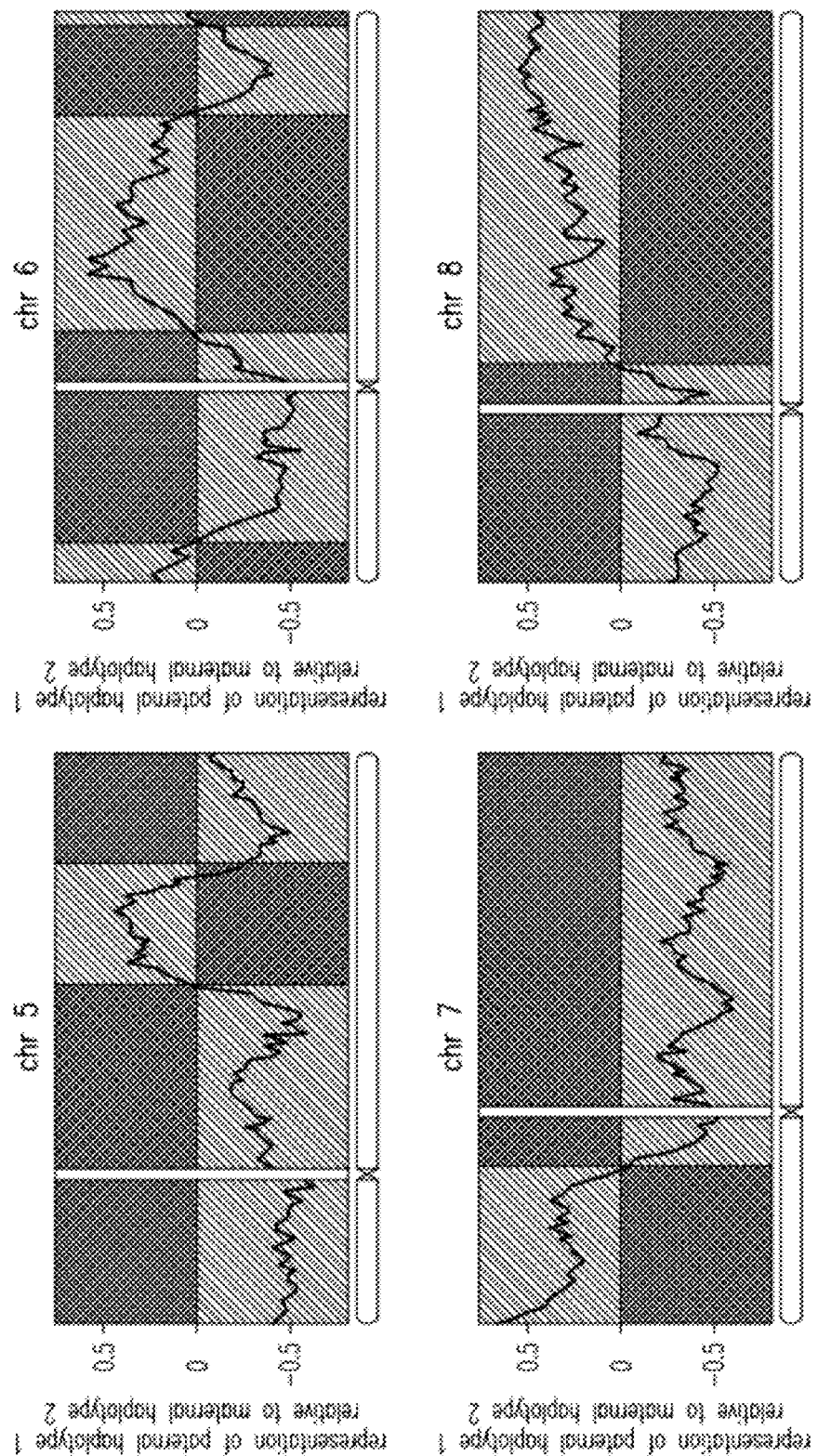
Figures 3, 22A:
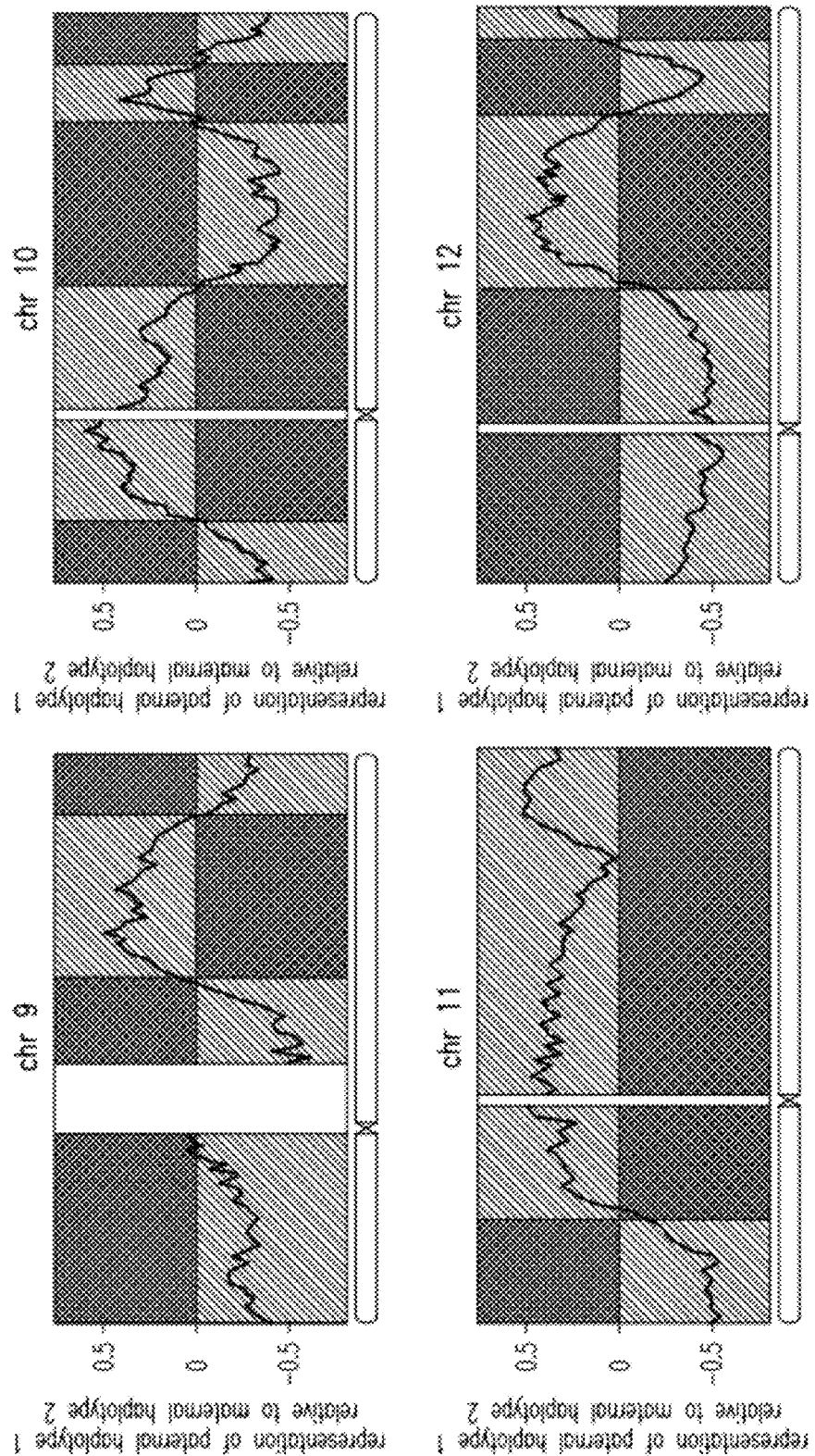
Figures 4, 22A:
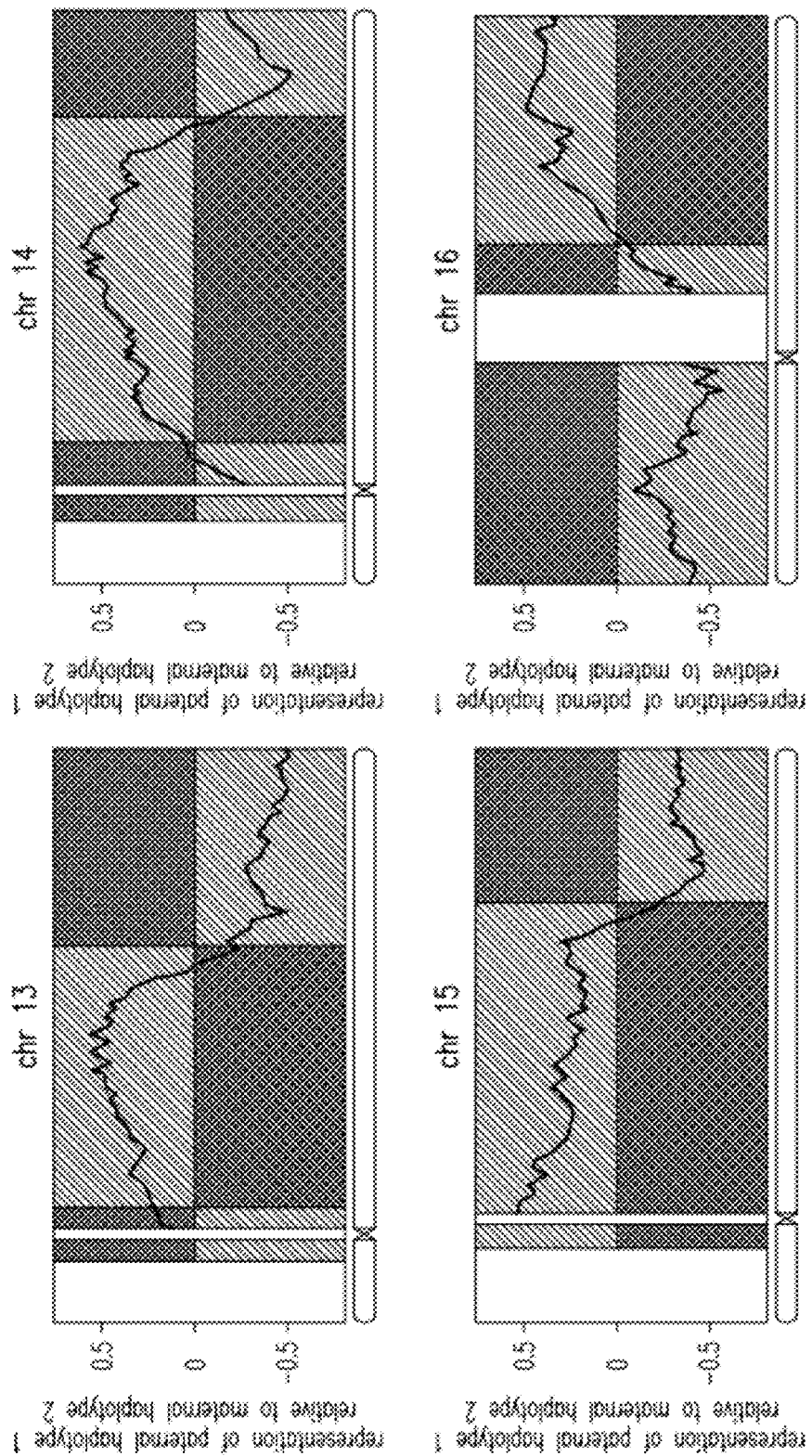
Figures 5, 22A:
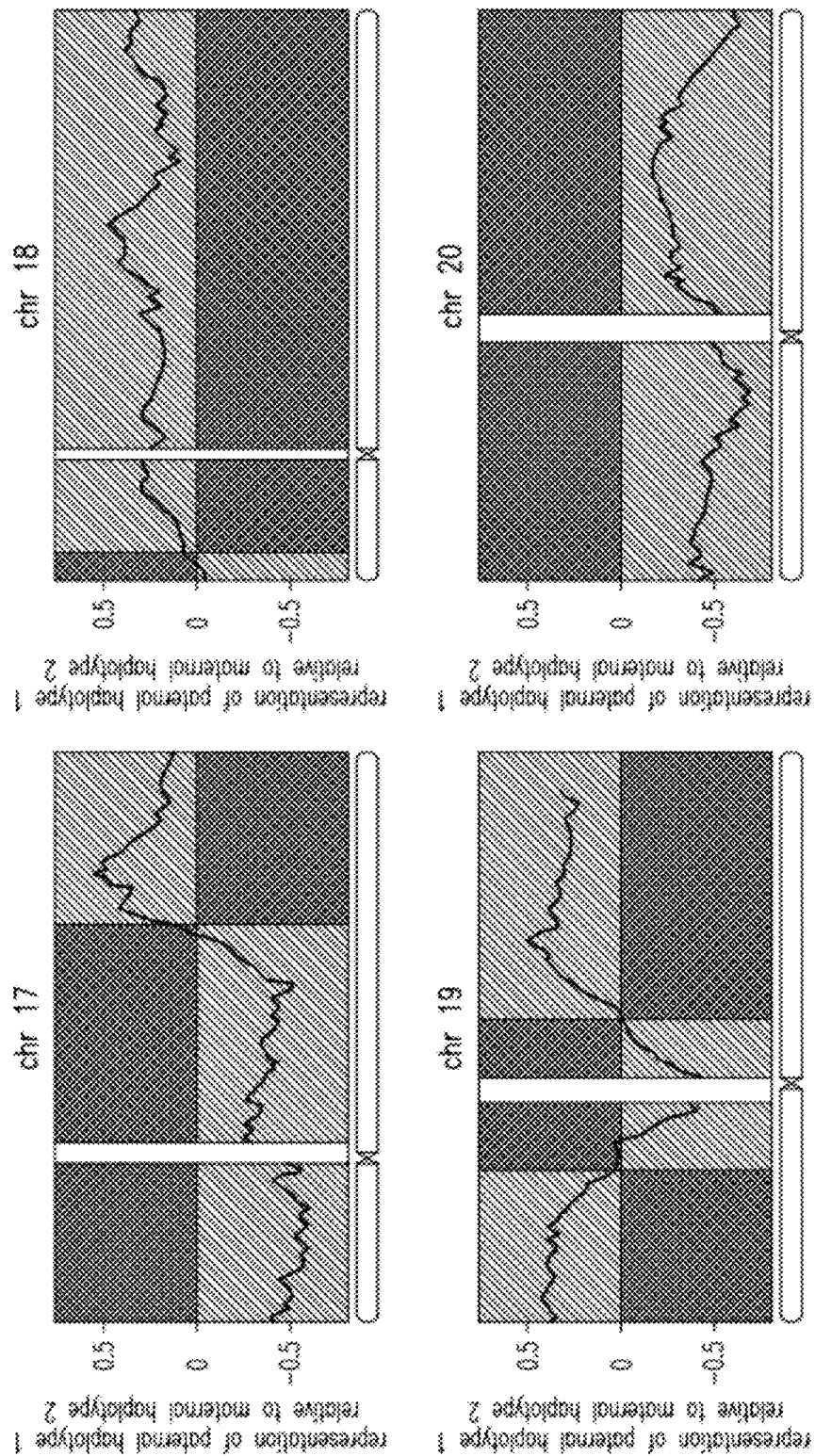
Figures 6, 22A:
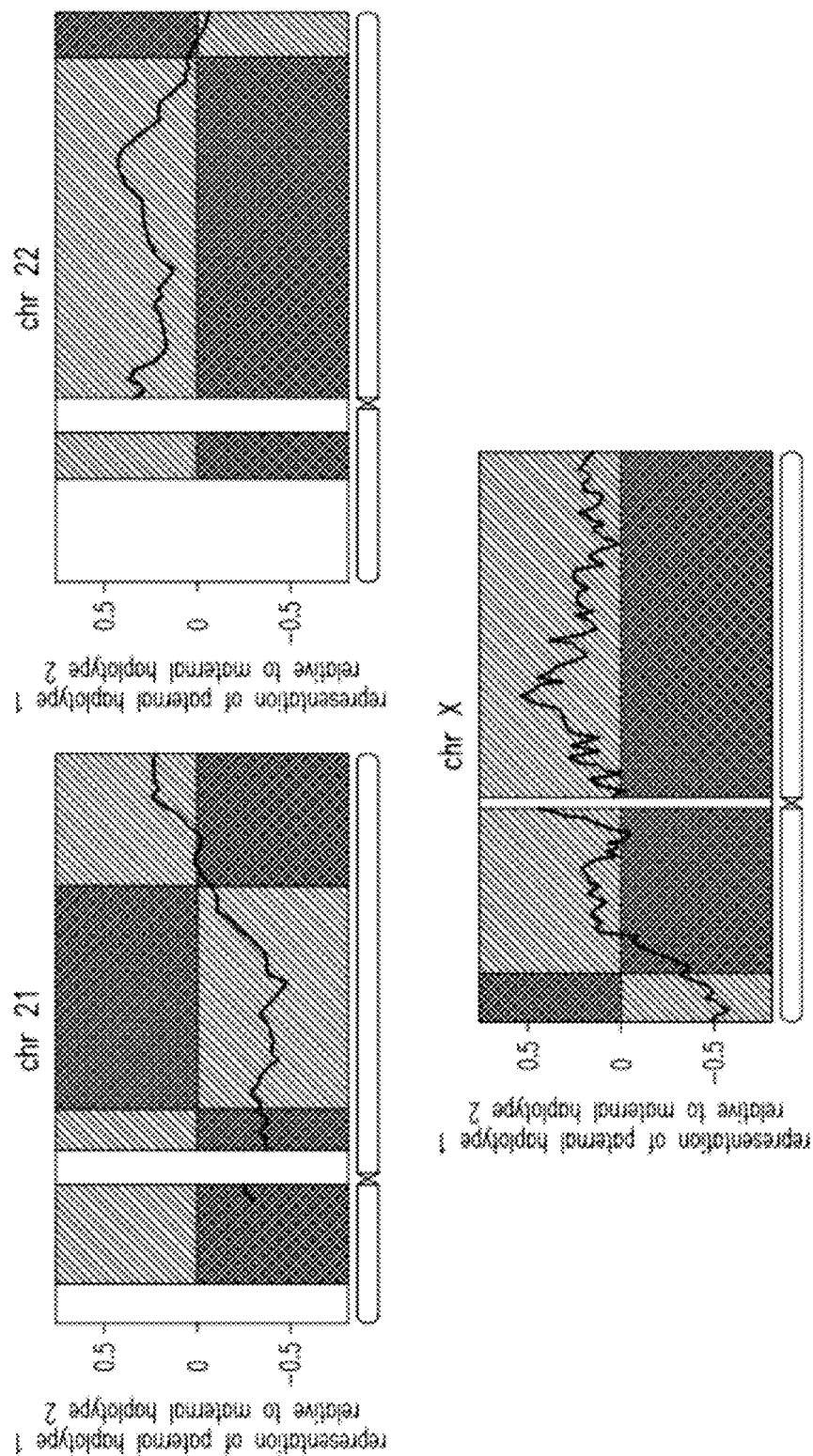
Figure 22B:
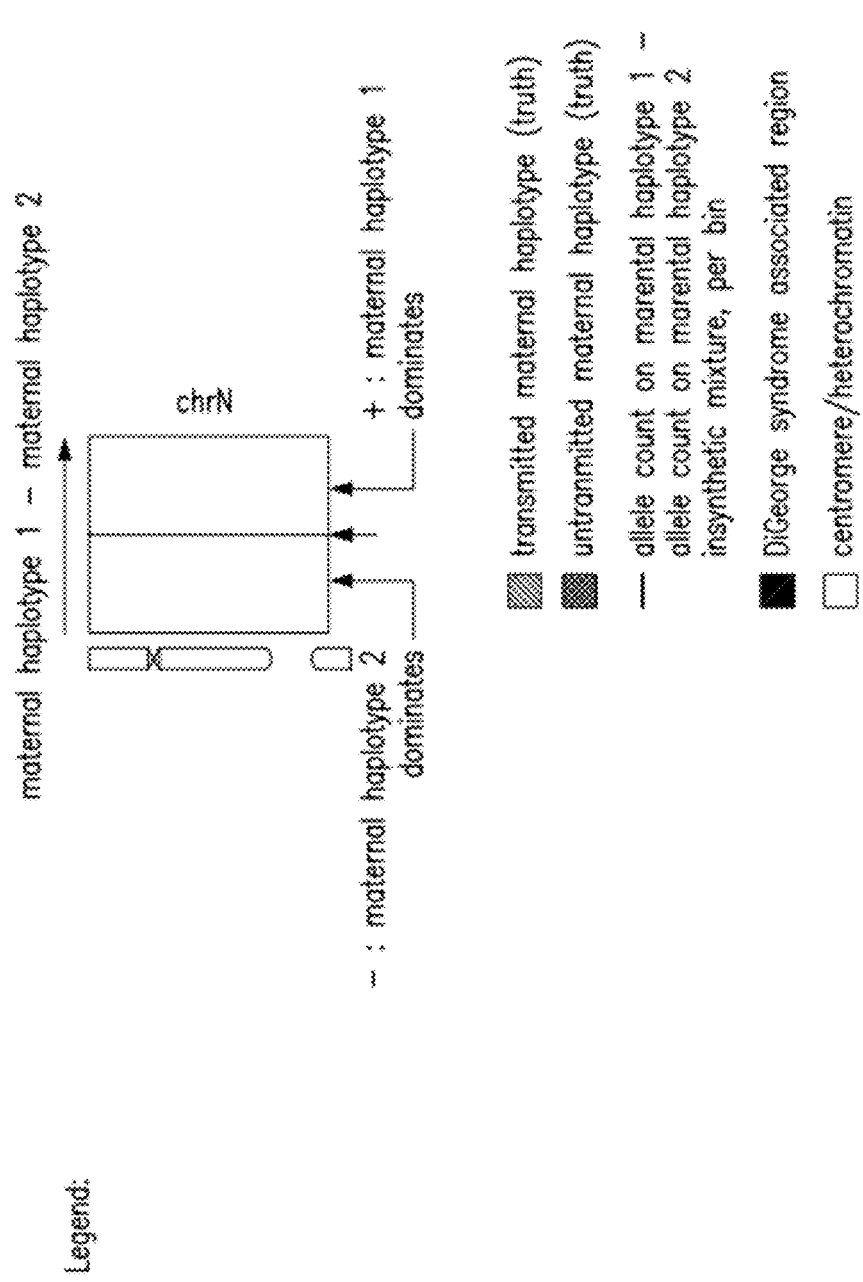
Figures 1, 22B:
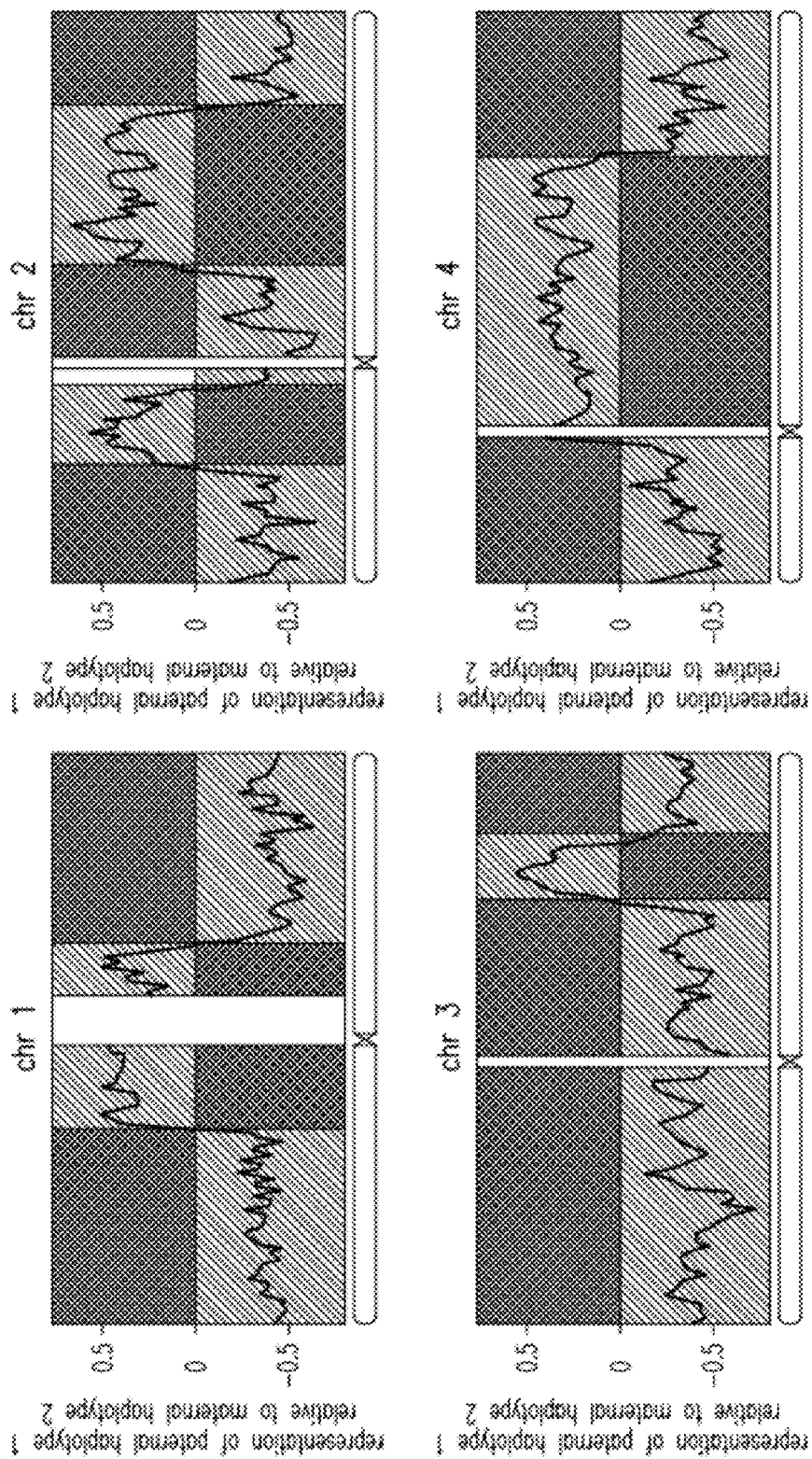
Figures 2, 22B:
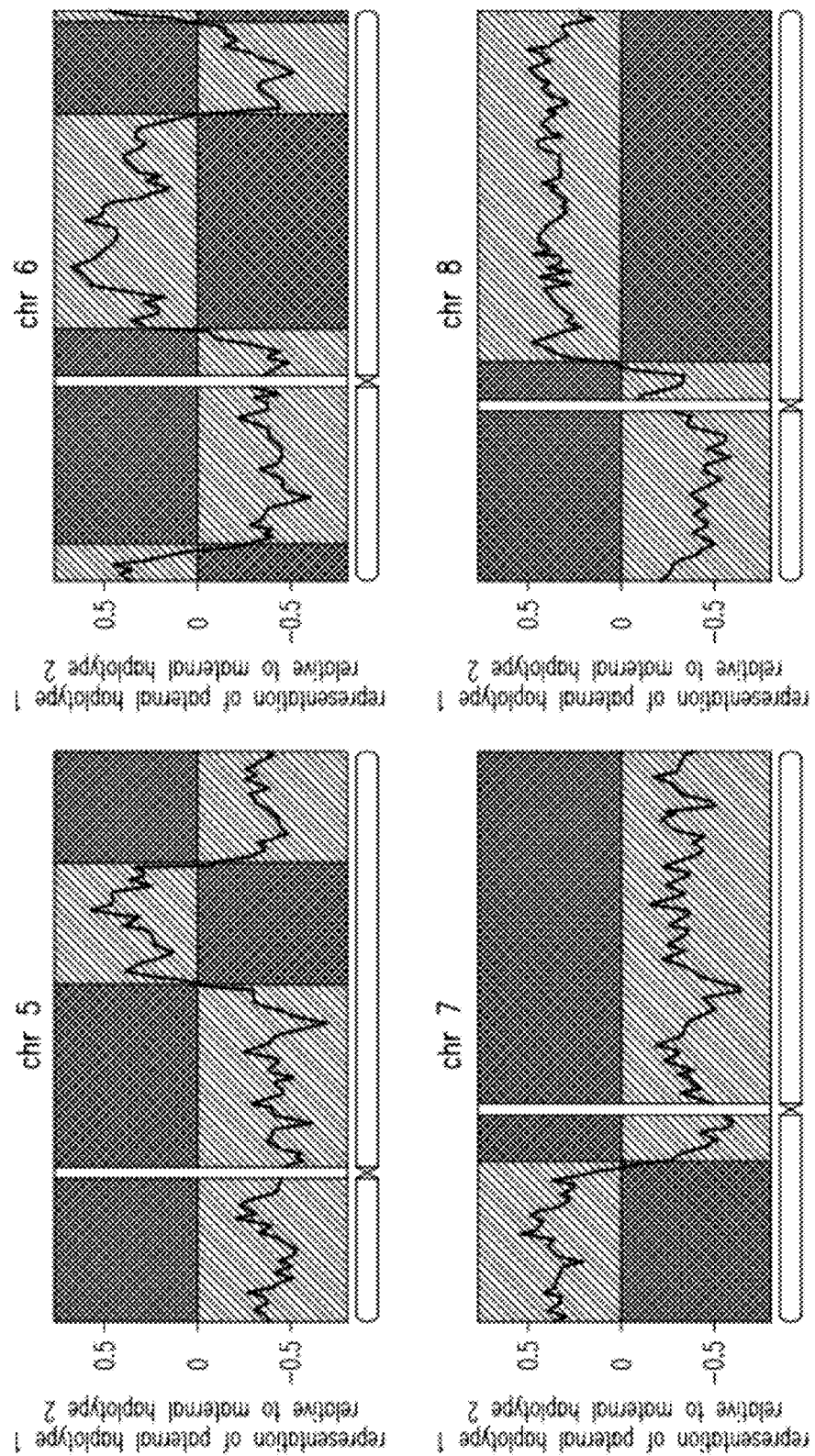
Figures 3, 22B:
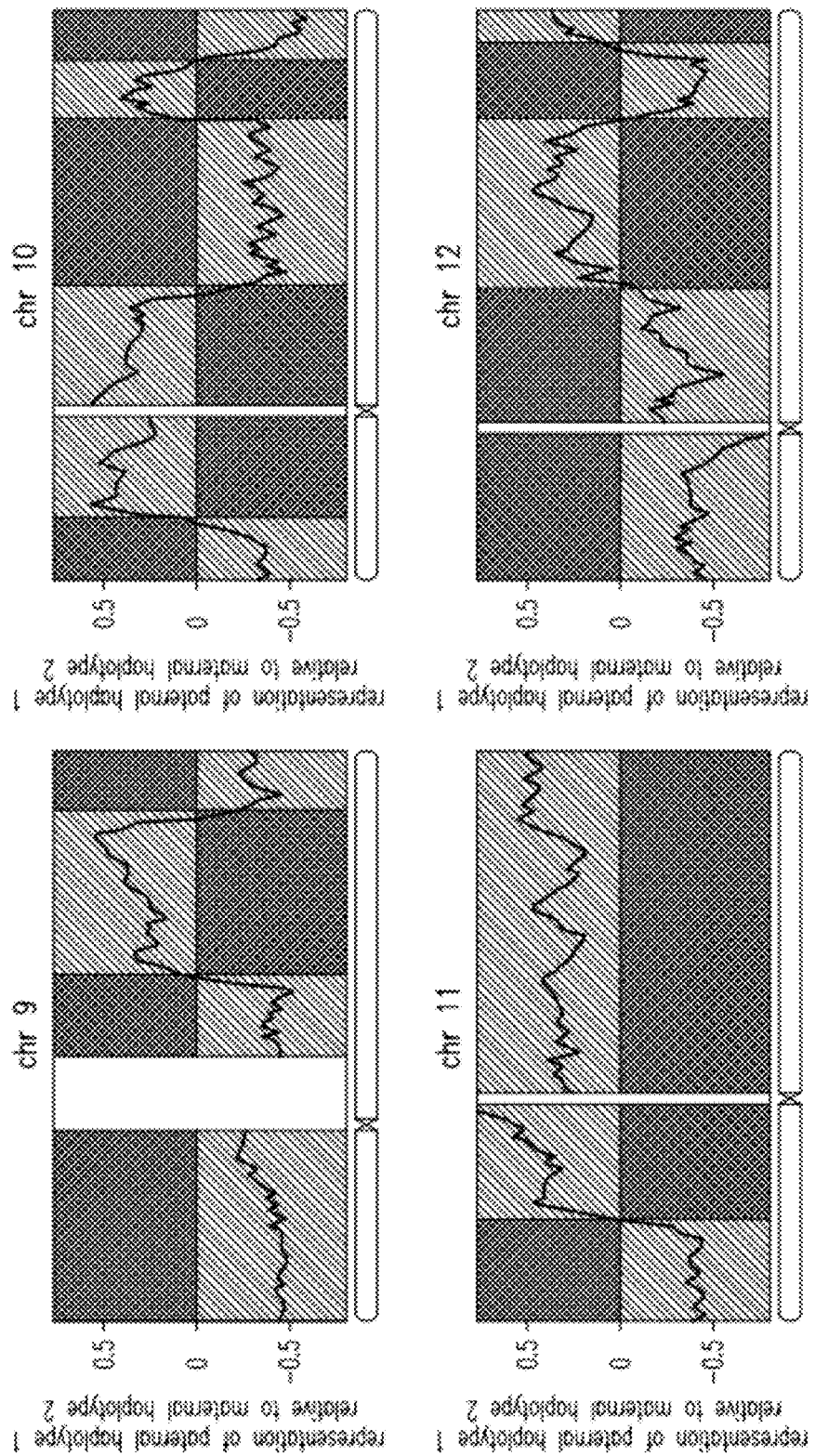
Figures 4, 22B:
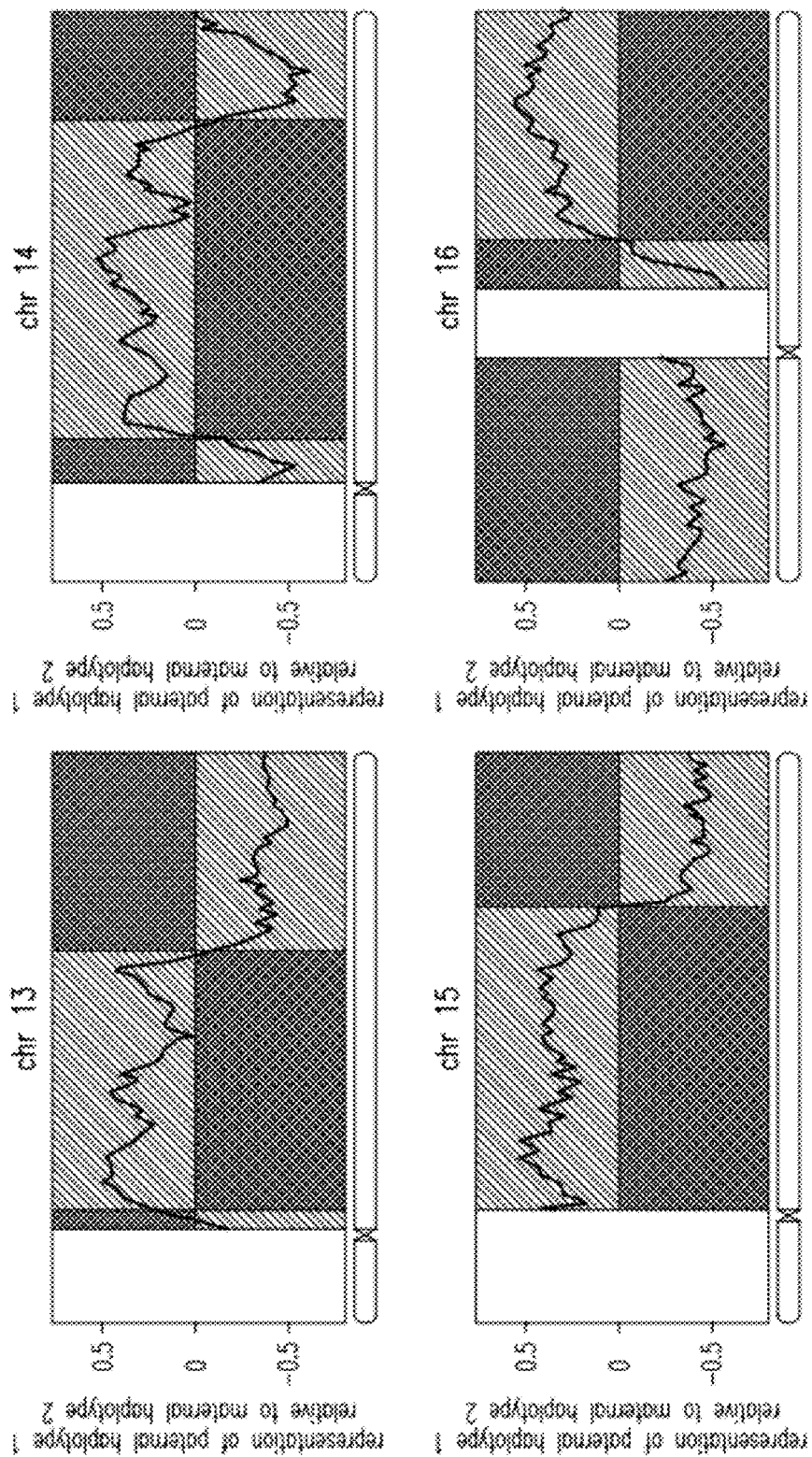
Figures 5, 22B:
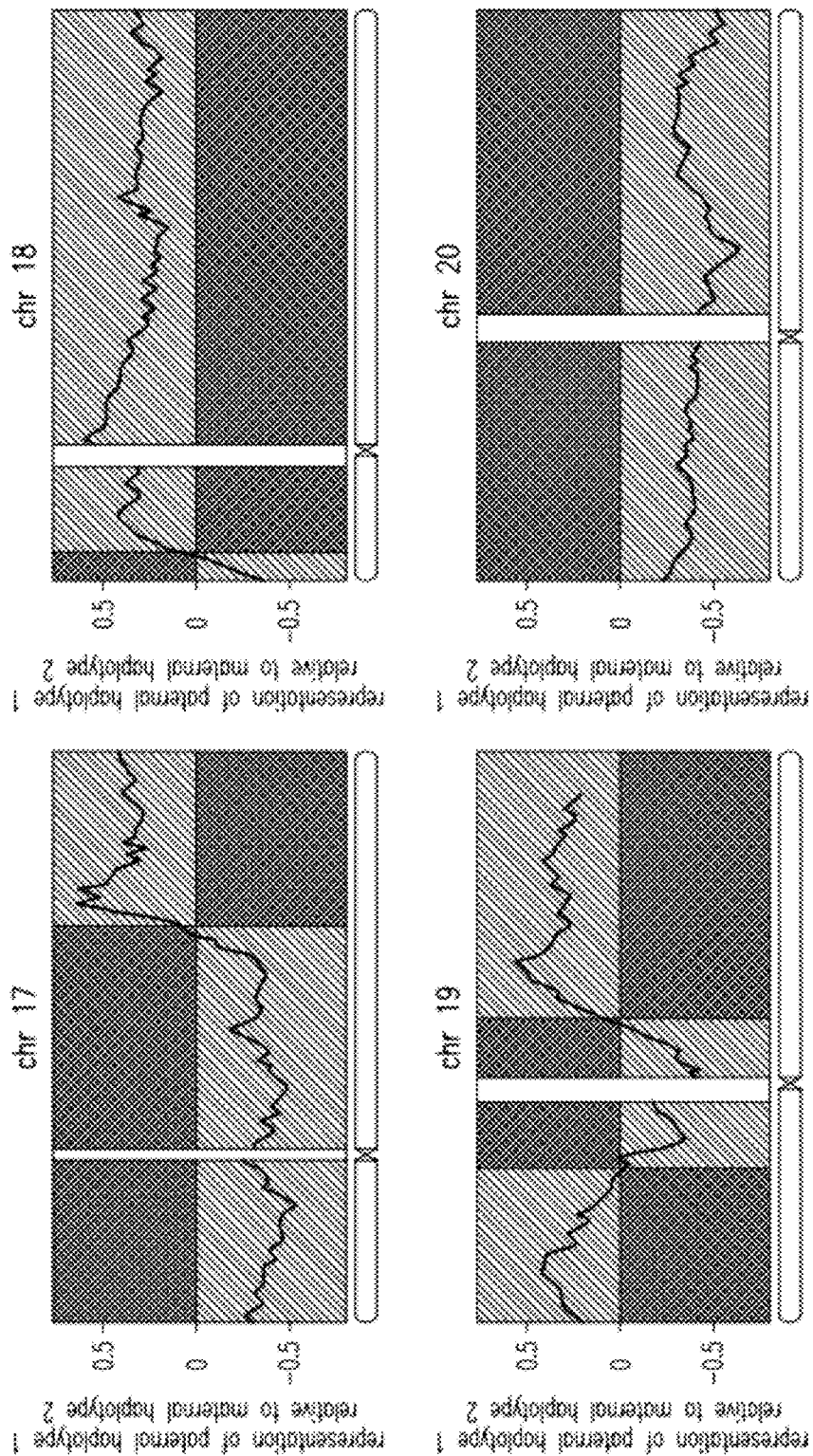
Figures 6, 22B:
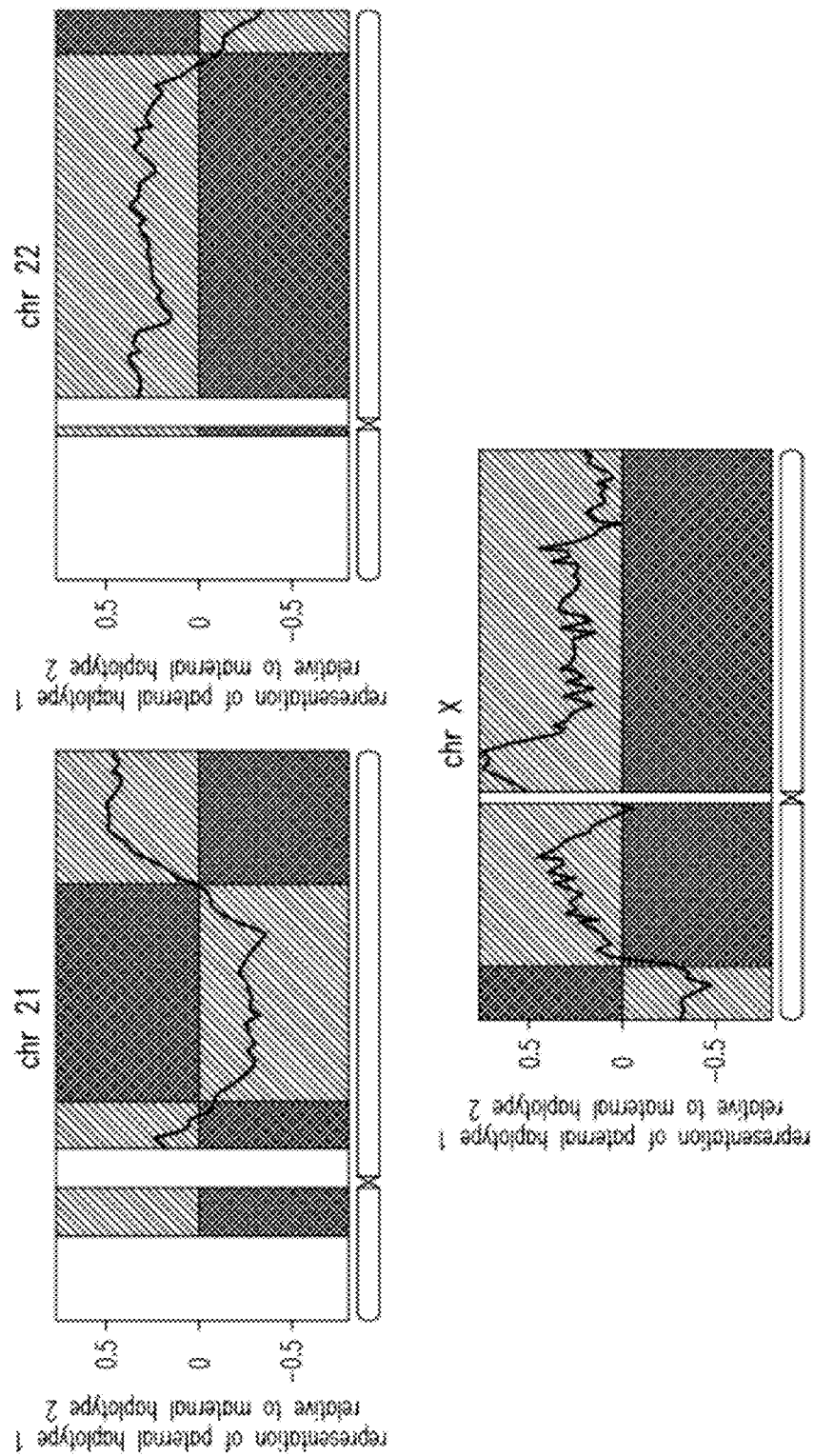
Figure 22C:
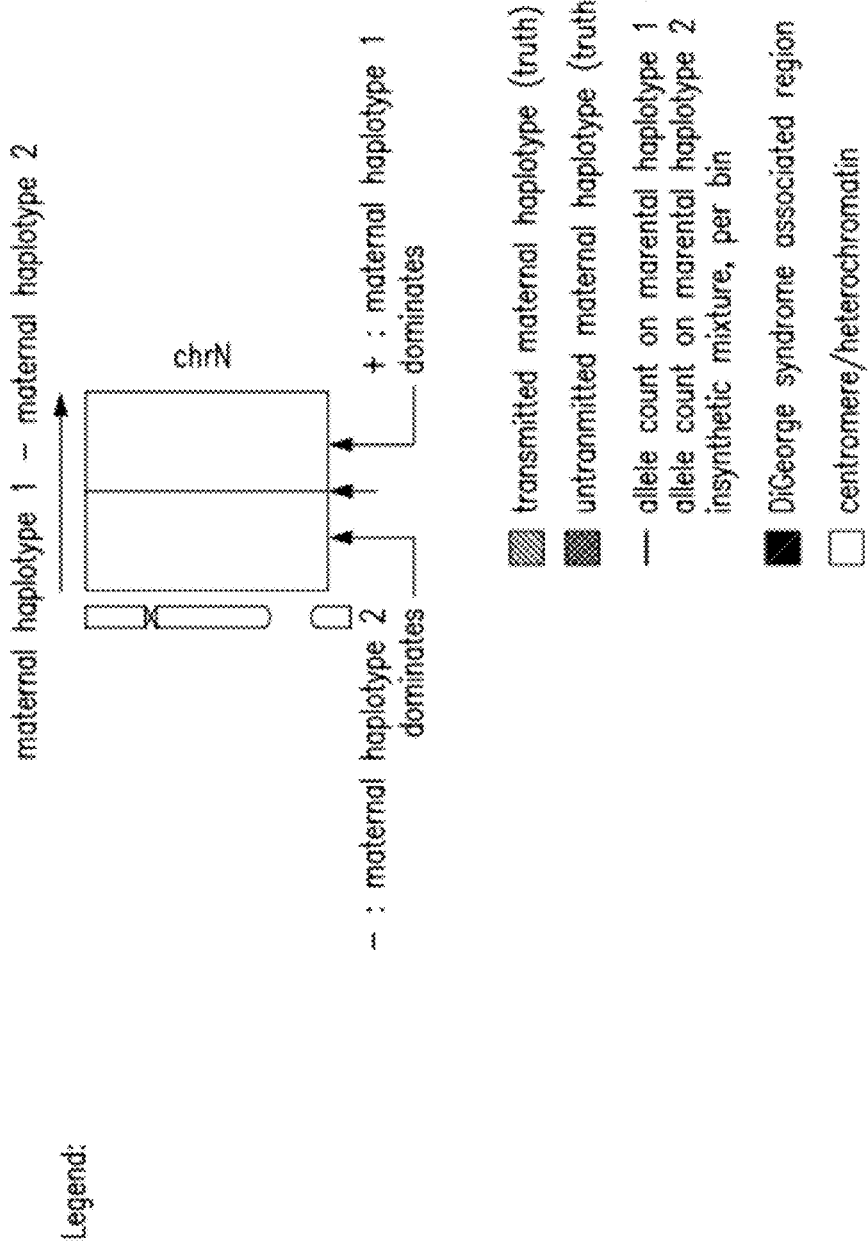
Figures 2, 22C:
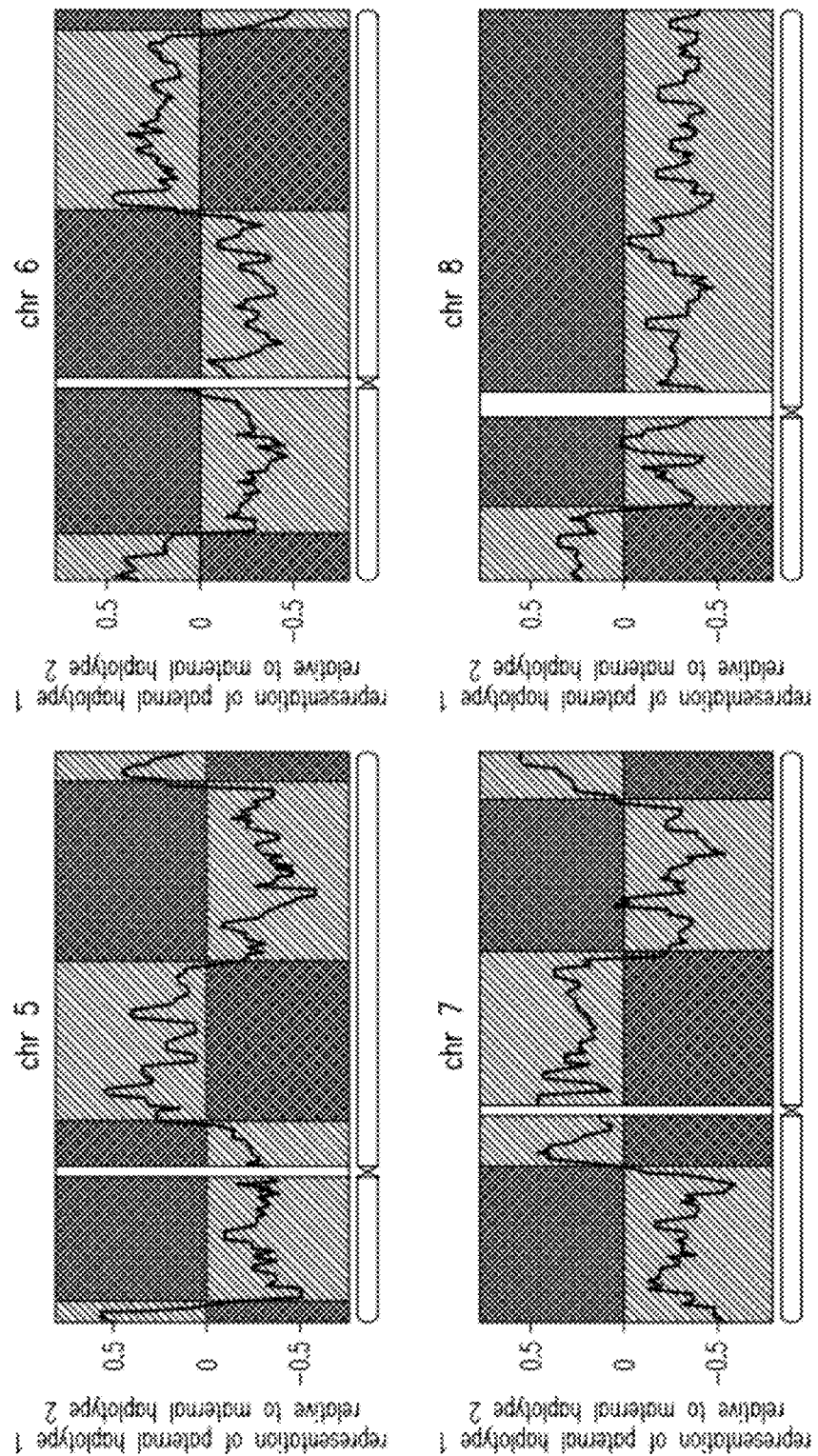
Figures 3, 22C:
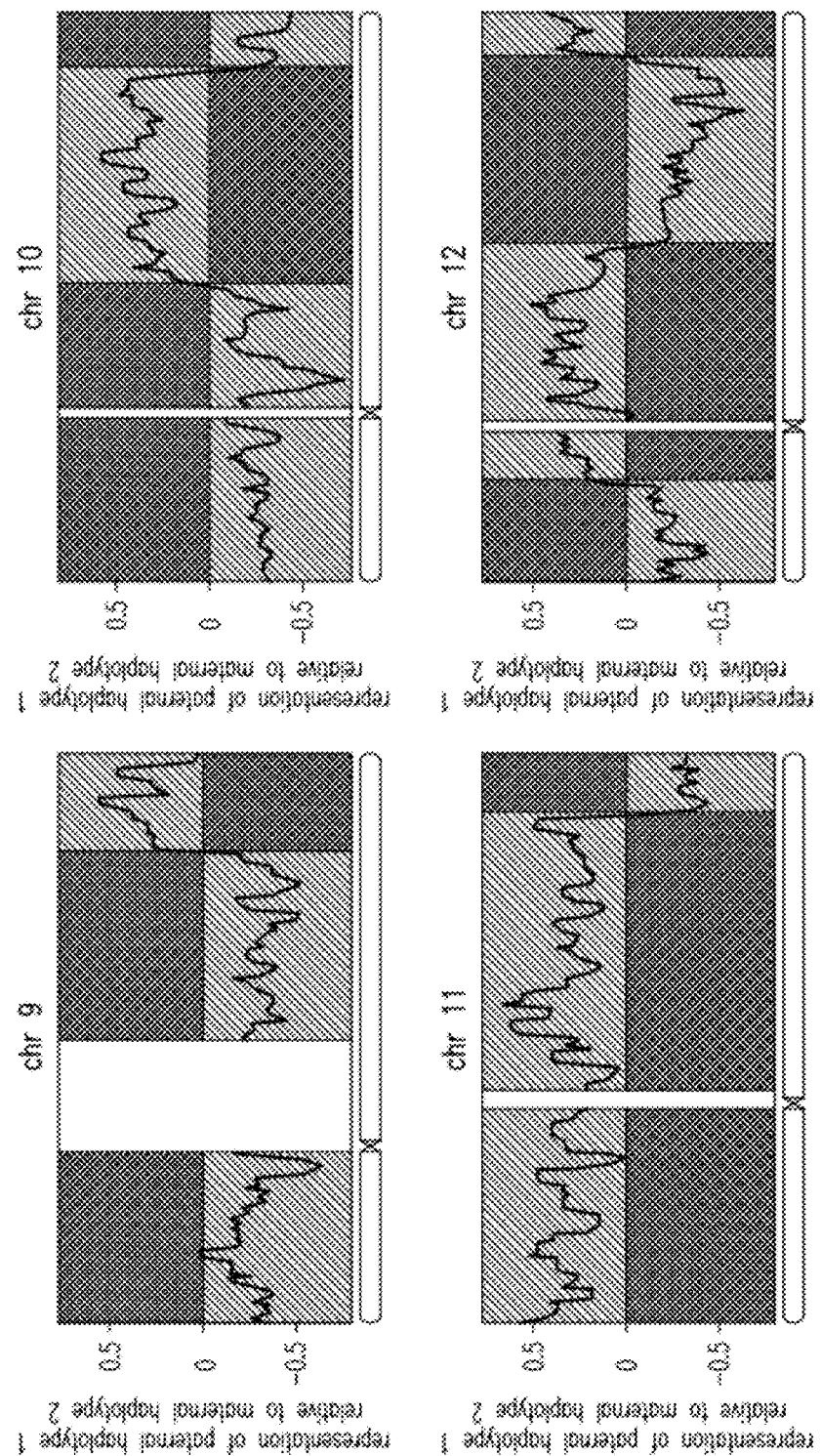
Figures 4, 22C:
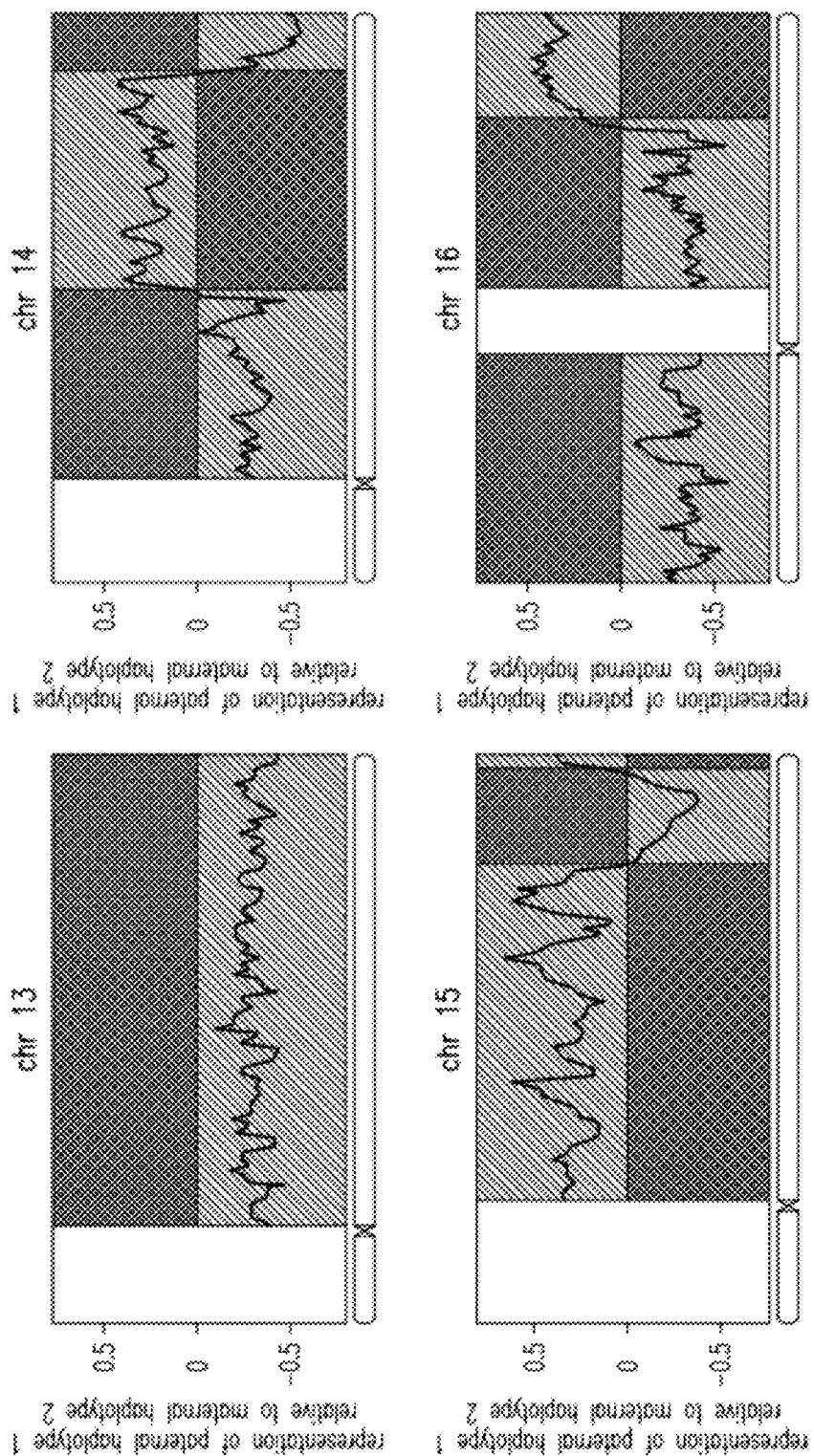
Figures 5, 22C:
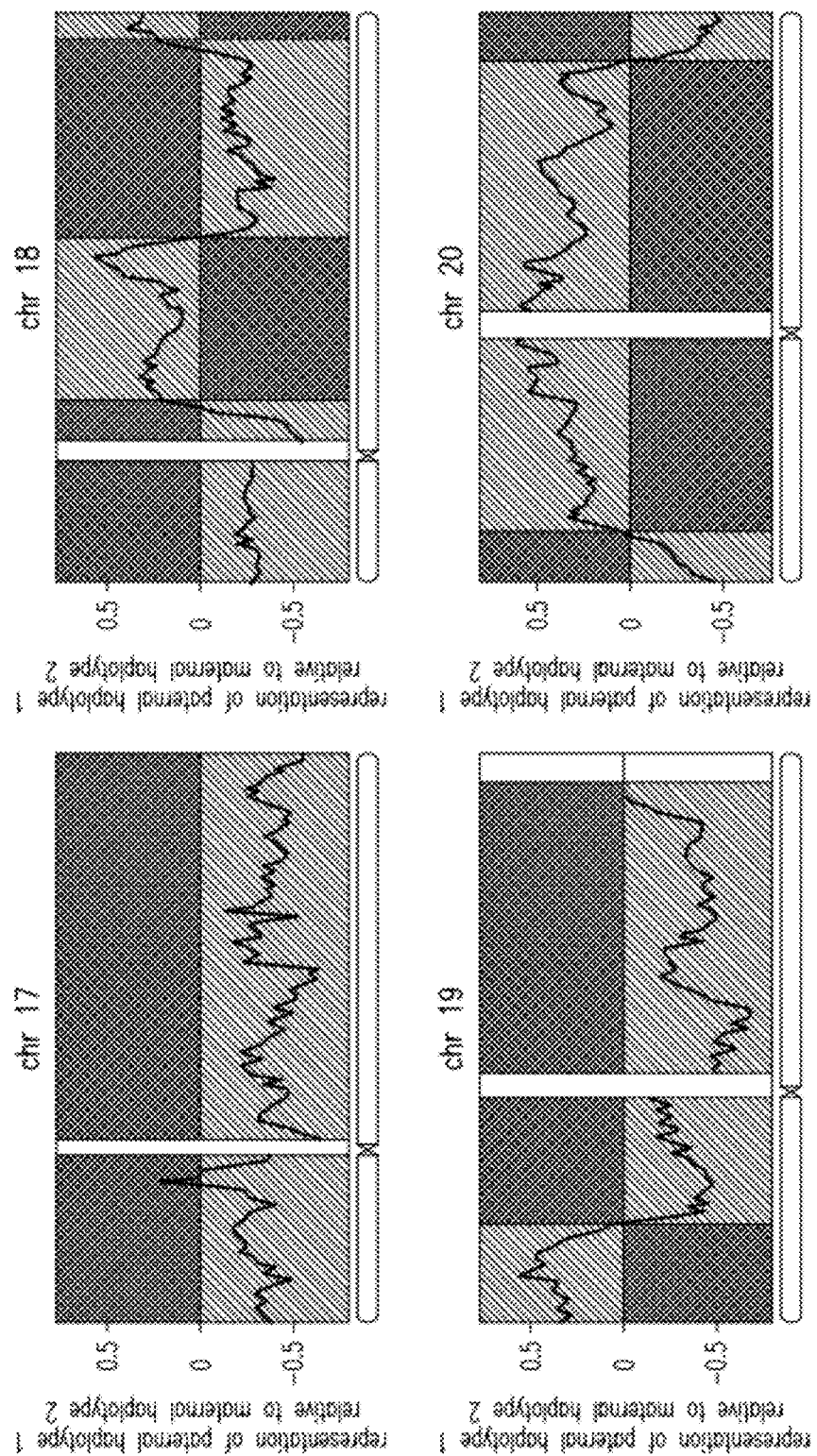
Figures 6, 22C:
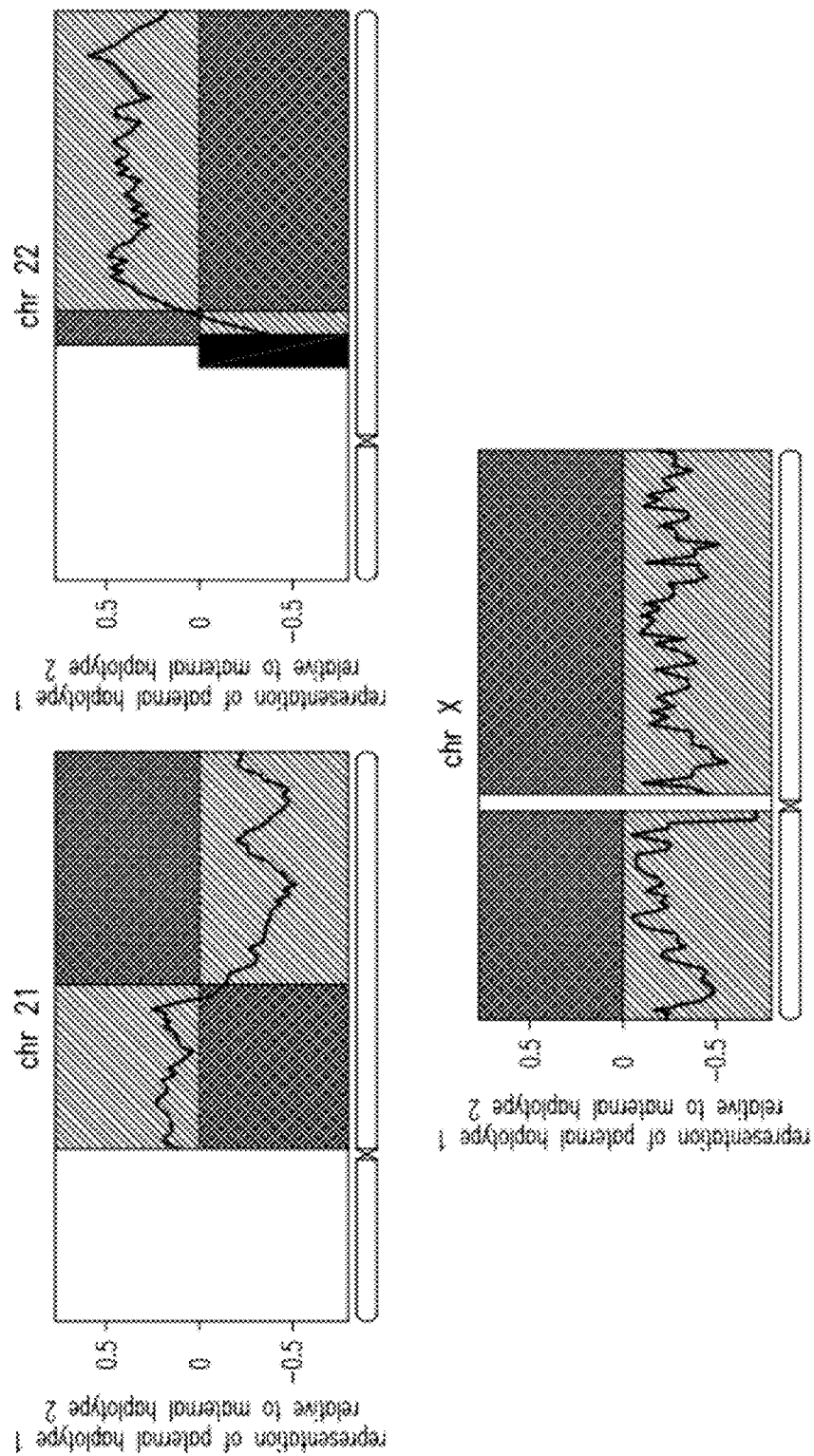
Figure 22D:
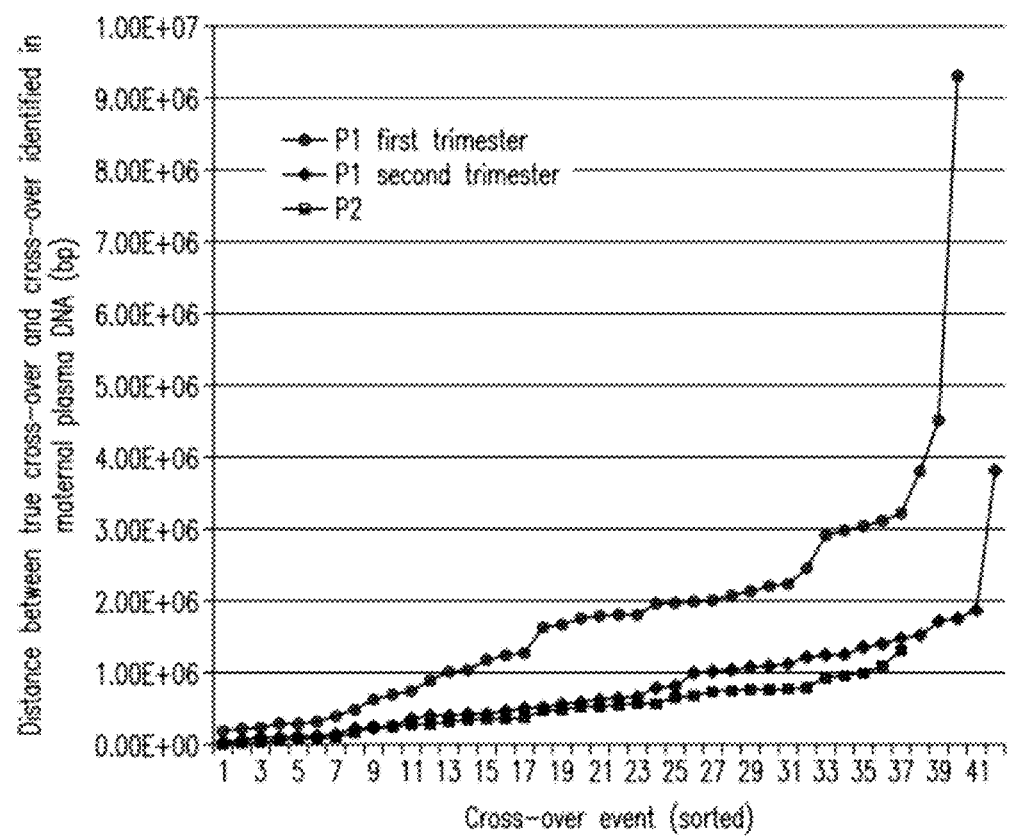

FIG. 22A-C. Determining the inheritance of maternal haplotypes by the fetus in maternal plasma DNA. FIG. 22A is a legend for FIG. 22A-1 to A-6. FIG. 22A-1 to A-6. Patient 1, first trimester plasma. Bin size is 15 Mb and 20 Mb for autosomes and chromosome X respectively. FIG. 22B is a legend for FIG. 22B-1 to B-6. FIG. 22B-1 to B-6. Patient 1, second trimester plasma. Bin size is 7.5 Mb and 10 Mb for autosomes and chromosome X respectively. FIG. 22C is a legend for FIG. 22C-1 to C-6. FIG. 22C-1 to C-6. Patient 2. Bin size is 3.5 Mb and 5 Mb for autosomes and chromosome X respectively. The black region near the centromere on chromosome 22 denotes the deleted region associated with DiGeorge syndrome on one of the maternal haplotypes. FIG. 22D. The distance between each measured cross-over on the maternal chromosomes and the respective true cross-over. The cross-over events are sorted by the distance. Two events were missed in P1's first trimester library.

Figure 23A:
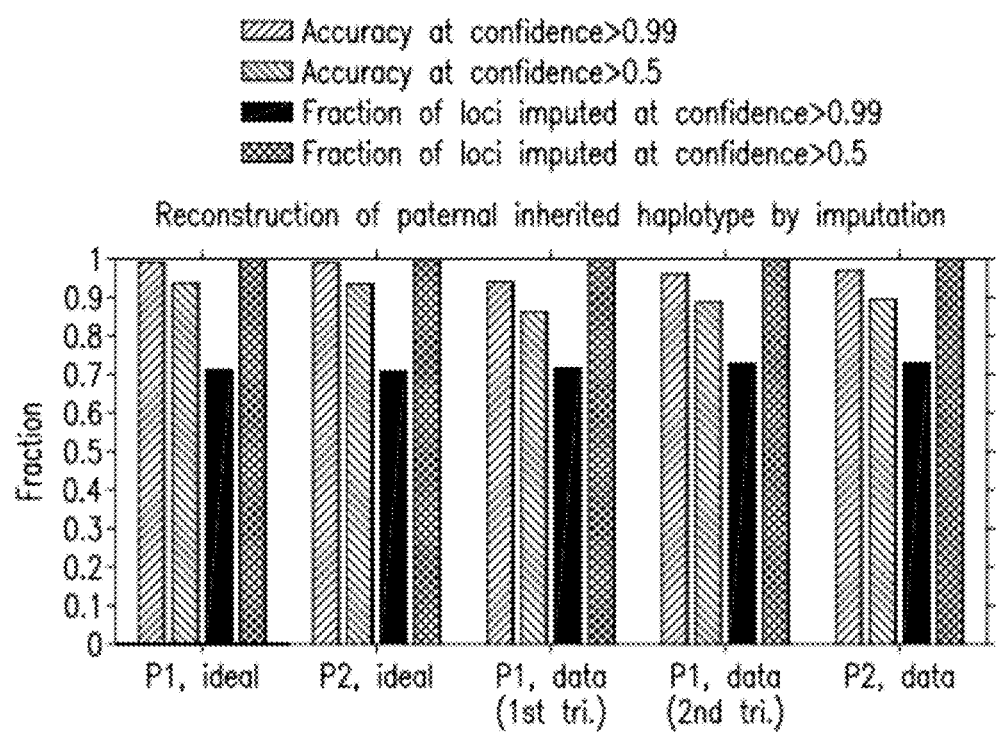
Figure 23B:
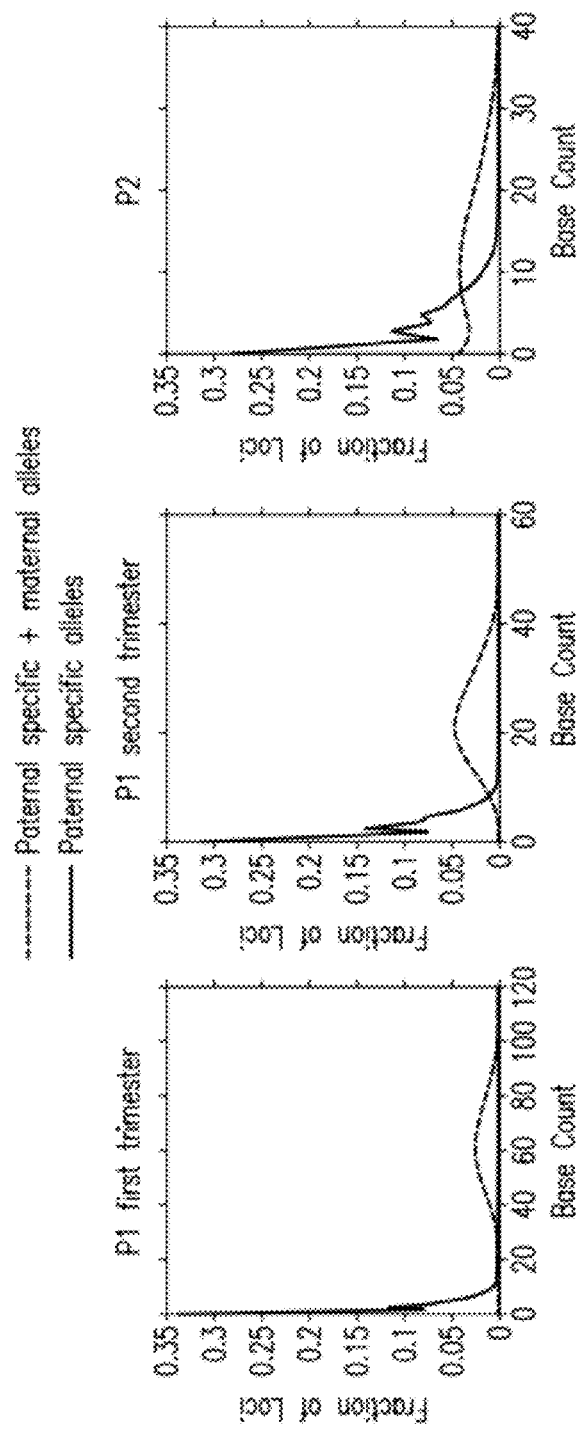

FIG. 23A-B. Reconstruction of the paternally inherited chromosomes based on paternal specific alleles detected in maternal plasma. FIG. 23A. Fraction of paternal specific alleles detected at different sequencing depth. FIG. 23B. Distribution of per base coverage at locations at which mother is homozygous. Solid curve line: Paternal specific alleles, broken curve line: paternal specific alleles + maternal alleles.

Figure 24:
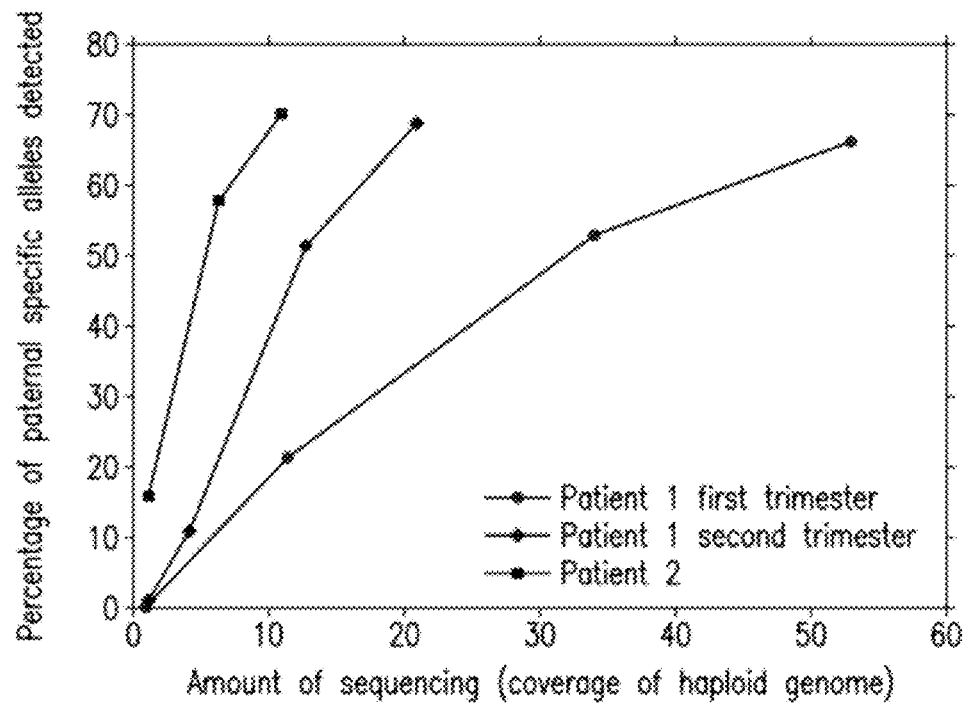

FIG. 24. Direct deterministic phasing (DDP) of maternal genome. Whole-genome haplotyping was achieved using 3 and 4 single cells for Patient 1 (P1) and Patient 2 (P2) respectively.

DETAILED DESCRIPTION OF THE INVENTION

As discussed in the Background section, haplotypes are difficult to measure because it requires the separate analysis of each of the two homologous copies of a region in the genome. While physical separation of two DNA strands carrying almost identical homologous regions is challenging, single-molecule analysis is well-suited for this application. By diluting a mixture containing multiple homologous copies of a region to single-molecule density and performing genetic analysis on individual molecules, one can measure haplotypes. This is the concept behind several published molecular haplotyping techniques (Zhang et al., 2006; Mitra et al., 2003; Ding & Cantor, 2003; Michalatos Beloin et al., 1996; Ruano et al., 1990; Xiao et al., 2009), but they cannot provide whole-genome haplotypes because the analyses were performed on DNA that is fragmented during DNA extraction and/or they can only measure a few loci on one molecule. The strategy presented here solves these problems by globally amplifying single, intact chromosome molecules from a single cell, such that the high-throughput genetic analyses of the amplified materials provides genome-wide haplotypes of an individual.

Noninvasive measurement of fetal genotypes that are heterozygous in the fetus and homozygous in the mother is trivial, since one only needs to detect the presence of an allele that is not present in the mother. Noninvasive measurement of fetal genotypes that are heterozygous in the mother is much more challenging but has important application, especially for the diagnosis of autosomal recessive diseases. In such situation where both the mother and father are carriers of a disease associated locus, it is of interest to determine if the fetus has inherited both copies of the recessive allele. Like the detection of aneuploidy, determining fetal genotypes in such situations has traditionally been difficult because of the maternal background DNA in maternal plasma. (Wheeler et al., 2008; Bentley et al., 2008; Ahn et al., 2009; Kim et al, 2009; Wang et al., 2008; Pushkarev, et al., 2009; Schuster et al., 2010).

The same approach of single molecule counting for noninvasive detection of fetal aneuploidy can be applied to develop assays for detecting autosomal recessive diseases in the fetus. One simply counts the number of each alleles of the bi-allelic SNP of interest and determines if the counts of two alleles are in balance. If one allele is over-represented compared to the other, then the fetus is homozygous for the over-represented allele. If the counts of the two alleles are similar, the fetus is heterozygous. A drawback to this method is that there is only one copy of the target allele per genome equivalent, a large number of counts of the alleles is needed for confident measurement, and there is limited amount of DNA per volume of plasma. However, since each individual human inherits large haplotype blocks from each of his/her parents, and each of the parental haplotype is defined by large set of specific alleles, the inventors recognized that digitally counting the haplotype specific markers enables one to determine which allele at a locus is inherited by the fetus without encountering problems with sample limitation.

The following definitions are used herein:

By "allele" is meant one of two or more forms of a gene. Diploid organisms such as humans contain two copies of each chromosome, and thus carry one allele on each.

By "homozygous" is meant that an organism contains two of the same alleles at a particular locus.

By "heterozygous" is meant that an organism contains two different alleles at a particular locus.

By "haplotype" is meant a combination of alleles at multiple loci along a single chromosome. A haplotype can be based upon a set of single-nucleotide polymorphisms (SNPs) on a single chromosome.

By "haplotype" block is meant a group of alleles that are inherited together.

Haplotypes refer to the combinations of alleles at multiple loci along a single chro-mosome. They arise because of the diploid nature of our genomes. Knowledge of the complete haplotypes of individuals is important in personalized medicine, as a number of studies have demonstrated the links of specific haplotypes to resistance or susceptibility to diseases. A well-known example is the association of human leukocyte antigens (HLA) haplotypes with autoimmune diseases (de Bakker et al., 2006; Stewart et al, 2004) and clinical outcomes in transplantations (Petersdorf et al., 2007). Haplotypes within the apolipoprotein gene cluster may influence plasma triglyceride concentrations and the risk toward atherosclerosis (Groenendijk et al., 2001). Some research suggests that a specific β-globin locus haplotype is associated with better prognosis of sickle cell disease (Nagel et al., 1991), while other studies have linked haplotypes in matrix metalloproteinase gene cluster to cancer development (Sun et al., 2006). Haplotypes are also important in pharmacogenomics, an example being the association of β-2 adrenergic receptor to responses to drug treatment of asthma (Drysdale et al., 2000). Deterministic haplotyping greatly increases the power of genome-wide association studies in finding candi-date genes associated with common but complex traits. It also contributes to the understanding of population genetics and histori-cal human migrations and the study of cis-acting regulation in gene expression.

By "imputation" is meant the ability to unambiguously identify all polymorphic sites in a chromosomal region based on the fact that the appearance together of certain SNPs in a haplotype block is statistically associated.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The present invention recognizes that given the sequenced diploid genomes of the parents (sequence of each of the homologous copies of a chromosome), the fetal genome can be worked out by determining which parental haplotypes are inherited. The availability of haplotype information from the parents drastically reduces the input plasma DNA requirement. Instead of counting the alleles at a particular SNP locus, the allele counts of all SNPs within a haplotype block can contribute to the determination of which parental haplotype is inherited. Since the number of cross-over events is limited in meiosis, the number of breaks in the original parental chromosomes is small and there is a large number of informative SNPs that can be measured for each parental haplotype. This approach also provides information regarding inheritance of copy number variants.

Briefly, the present invention is directed to a method and device for the non-invasive determination of parental haplotypes inherited by a fetus, and may be used to determine the fetal genome, or portions thereof, non-invasively. The method can be performed using a combination of paternal and maternal information, or can utilize solely maternal haplotype information. To perform the method, one obtains maternal tissue containing both maternal and fetal genetic material. Preferably, the maternal tissue is maternal peripheral blood or blood plasma. The term "plasma" may include plasma or serum. In order to distinguish random variation from fetal results, a large number of reactions are run, and statistical methods are applied to the results.

The discrete samples are in reaction samples where the target sequences can be analyzed. The reaction samples may be, for example, wells in a microtiter plate, aqueous phases in an emulsion, areas in an array surface, or reaction chambers in a microfluidic device. The reaction samples may be used for PCR analysis of the discrete samples. The discrete samples are contacted with a plurality of PCR primers, including at least one (or one forward and one reverse) primer directed specifically to a maternal control sequence, expected to be the same in both mother and fetus. PCR primers are also directed specifically to a fetal sequence, i.e., one which may be present in both mother and fetus, but is amplified or altered in the fetus. PCR amplification will allow detection of these two different sequences. The PCR method may be (but is not necessarily) quantitative. Quantitative real time PCR, which includes hybridizing target sequences with a nucleic acid having a fluorescent label, may be used. A fluorescent probe hybridizing to the target sequence may also be used. A number of "digital PCR" protocols are known for this purpose, as well as bead-based or emulsion PCR. While florescent probes are readily available and may be used to provide sensitive results, e.g., in FRET combinations, other labeling techniques may be used.

The number of discrete samples is chosen according to the results desired. In one aspect, it is preferred that a high degree of statistical significance is obtained, and any method of digital counting may be used, including but not limited to PCR, sequencing and hybridization. The results to be obtained should be statistically significant for purposes of the analysis conducted, e.g. initial screening, primary diagnosis, etc. A commonly used measure of statistical significance when a highly significant result is desired is p<0.01, i.e., a 99% confidence interval based on a chi-square or t-test. In some embodiments, other statistical methods can be used. For example, a cut-off value might be determined using SPRT. Fan and Quake (2010b) demonstrate that the sensitivity of detection of fetal abnormalities is limited only by counting statistics.

Any genetically transmissible disease may be detected according to the present method, including known alterations in one or more of the genes: CFTR, Factor VIII (F8 gene), beta globin, hemachromatosis, G6PD, neurofibromatosis, GAPDH, beta amyloid, and pyruvate kinase. The sequences and common mutations (e.g., single nucleotide polymorphisms or SNPs) of these genes are known. Other genetic abnormalities may be detected, such as those involving a sequence which is deleted in a human chromosome, is moved in a translocation or inversion, or is duplicated in a chromosome duplication, wherein said sequence is characterized in a known genetic disorder in the fetal genetic material not present in the maternal genetic material. For example chromosome trisomies may include partial, mosaic, ring, 18, 14, 13, 8, 6, 4 etc. A listing of known abnormalities may be found in the OMIM Morbid map, http://www.ncbi.nlm.nih.gov/Omimigetmorbid.cgi.

The present invention comprises a method for analyzing a maternal sample, e.g., from peripheral blood. It is not invasive into the fetal space, as is amniocentesis or chorionic villi sampling. In the preferred method, fetal DNA which is present in the maternal plasma is used.

In certain aspects, the present invention may comprise a computer programmed to analyze sequence data obtained from a mixture of maternal and fetal chromosomal DNA. Each autosome (chr. 1-22) is computationally segmented into contiguous, non-overlapping windows. (A sliding window could also be used). Each window is of sufficient length to contain a significant counts of alleles that define each of the parental haplotype (and the count is dependent on sequencing depth and number of markers within the window) and not still have a number of windows per chromosome. Typically, a window will be between a few hundred kb and a few Mb.

In yet more detail, the present invention is described by the following items which represent preferred embodiments thereof.

1. A method of non-invasively determining parental haplotypes which are inherited by a fetus, comprising:
   a. obtaining a maternal sample from a female pregnant woman with at least one fetus, wherein said sample contains DNA from both the pregnant female and the fetus;
   b. determining a paternally inherited haplotype by the steps of:
      i. determining a set of single nucleotide polymorphisms (SNPs) in the DNA of the fetus's father;
      ii. determining a set of SNPs in the DNA of the fetus's mother;
      iii. determining all SNPs that are heterozygous in the father and homozygous in the mother to identify at various loci alleles present in the father and absent in the mother, thereby defining each of the father's haplotypes; and
      iv. counting a number of representative alleles on each paternal haplotype to determine a representation of the two haplotypes;
      v. comparing the representation of the two haplotypes to obtain a relative representation;
      vi. determining an over-representation $\epsilon$ of one of the two haplotypes; and
      vii. correlating said over-representation $\epsilon$ with a paternally inherited haplotype; and
   c. determining a maternally inherited haplotype by the steps of:
      i. determining all SNPs that are heterozygous in the fetus's mother; and
      ii. identifying alleles present in the mother but absent in the paternally inherited haplotype at each SNP locus to define the mother's haplotypes;
      iii. counting a number of representative alleles on each maternal haplotype to determine a representation of the two haplotypes;
      iv. comparing the representation of the two haplotypes to obtain a relative representation;
      v. determining an over-representations of one of the two haplotypes; and
      vi. correlating said over-representations with a maternally inherited haplotype;

2. The method of Item 1, wherein the relative representation of haplotypes is measured by digitally counting markers, wherein the markers are alleles that define each of the parental haplotypes.

3. The method of Item 1, wherein sums of the count of markers specific to each of two maternal haplotypes per fixed distance are compared to determine which maternal haplotype is over-represented.

4. The method of Item 1, wherein sums of the count of markers specific to each of two paternal haplotypes per fixed distance are compared to determine which paternal haplotype is over-represented.

5. The method of Item 2, wherein the digital counting is performed by measuring numbers of counts of single DNA molecules.

6. The method of Item 5, wherein the measuring is by sequencing, digital polymerase chain reaction (PCR) or hybridization (or any method that enables the reading of the allelic identity at a specific locus on single DNA molecules).

7. The method of Item 1, wherein a portion of the fetal genome is determined.

8. The method of Item 7, wherein the entire fetal genome is determined.

9. A method of estimating fetal DNA fraction by measuring the relative representation of the parental haplotypes of Item 1.

10. A method of non-invasively determining maternal haplotypes which are inherited by a fetus, comprising:
    a. obtaining a maternal sample from a female pregnant with at least one fetus, wherein said sample contains DNA from both the pregnant female and the fetus;
    b. counting markers in said sample that define each of two maternal haplotypes to determine a representation of the two haplotypes;
    c. comparing the representation of the two haplotypes to obtain a relative representation;
    d. determining an over-representation $\epsilon$ of one of the two haplotypes; and
    e. correlating said over-representation $\epsilon$ with a transmitted maternal haplotype.

11. The method of Item 10, wherein the relative representation of haplotypes is measured by digitally counting markers, wherein the markers are alleles that define each of the maternal haplotypes.

12. The method of Item 11, wherein sums of the count of markers specific to each of two maternal haplotypes per fixed distance are compared to determine which maternal haplotype is over-represented.

13. The method of Item 11, wherein the digital counting is performed by measuring numbers of counts of single DNA molecules carrying specific markers.
14. The method of Item 13, wherein the measuring is by sequencing, digital polymerase chain reaction (PCR) or hybridization (or any method that enables the reading of the allelic identity at a specific locus on single DNA molecules).
15. The method of Item 10, wherein a portion of the fetal genome is determined
16. The method of Item 15, wherein the entire fetal genome is determined.
17. The method of Item 10, further comprising non-invasively reconstructing the paternally inherited haplotypes.
18. The method of Item 17, wherein the reconstruction of the paternally inherited haplotypes is achieved by haplotype imputations using paternal-specific alleles detected in the sample.
19. A method of determining an appropriate set of markers that define a maternal haplotype, comprising determining alleles that are present at polymorphic loci in a first maternal haplotype but not at corresponding loci on a second maternal haplotype.
20. The method of Item 19, wherein the alleles that are present at polymorphic loci in the first maternal haplotype but not at corresponding loci on the second maternal haplotype are also not at corresponding loci on either paternal haplotype.
21. A method of determining an appropriate set of markers that define a paternal haplotype, comprising determining alleles that are present at polymorphic loci in a first paternal haplotype but not at corresponding loci on a second paternal haplotype.
22. The method of Item 21, wherein the alleles that are present at polymorphic loci in the first paternal haplotype but not at corresponding loci on the second paternal haplotype are also not at corresponding loci on either maternal haplotype.
23. The method of Item 21, wherein the number of markers in the set can be increased by haplotype imputation.
24. The method of Item 18 or 23, wherein the haplotype imputation comprises statistically inferring allelic identities at any unmeasured loci by comparing observed alleles on the haplotype to be imputed with a database of previously documented haplotypes of which allelic identities are known at both measured and unmeasured loci.
25. The method of Item 23, wherein the database is from a normal population.
26. The method of Item 23, wherein the database is from a population of carriers with a particular disease that is genetically transmissible.
27. A method of determining a minimum amount of digital sampling to achieve a desired confidence level as to which parental haplotypes are over-represented, comprising:
a. estimating a fraction of fetal DNA present in the sample; and
b. estimating density of available markers.
28. A method of estimating fetal DNA fraction comprising measuring relative representation of fetal haplotypes.
29. The method of Item 19 or 21, wherein determining a set of markers that define a haplotype of an individual can be obtained by:
a. comparing alleles at polymorphic loci across related family members; or
b. analyzing alleles at polymorphic loci on single DNA molecules or single chromosome molecules.
30. A microfluidic device for performing the method of Item 27, comprising:
a. a chromosome partitioning region;
b. an amplification region; and
c. a product retrieval region.
31. The microfluidic device of Item 30, further comprising:
a. a cell sorting region;
b. a chromosome release region;
32. The device of Item 31, wherein in the cell-sorting region, a single metaphase cell is identified and captured from a cell suspension, and lysed to form a chromosome suspension.
33. The device of Item 31, wherein in the chromosome partitioning region, the chromosome suspension is randomly separated into a plurality of partitions of a channel.
34. The device of Item 30, wherein in the amplification region, isolated chromosomes are individually amplified by multiple strand displacement amplification.
35. A computer program for controlling the microfluidic device of Item 30.

The following examples are provided to aid the understanding of the present invention, the true scope of which is set forth in the appended claims. It is understood that modifications can be made in the procedures set forth without departing from the spirit of the invention.

EXAMPLES

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Example 1

Figure 1A:
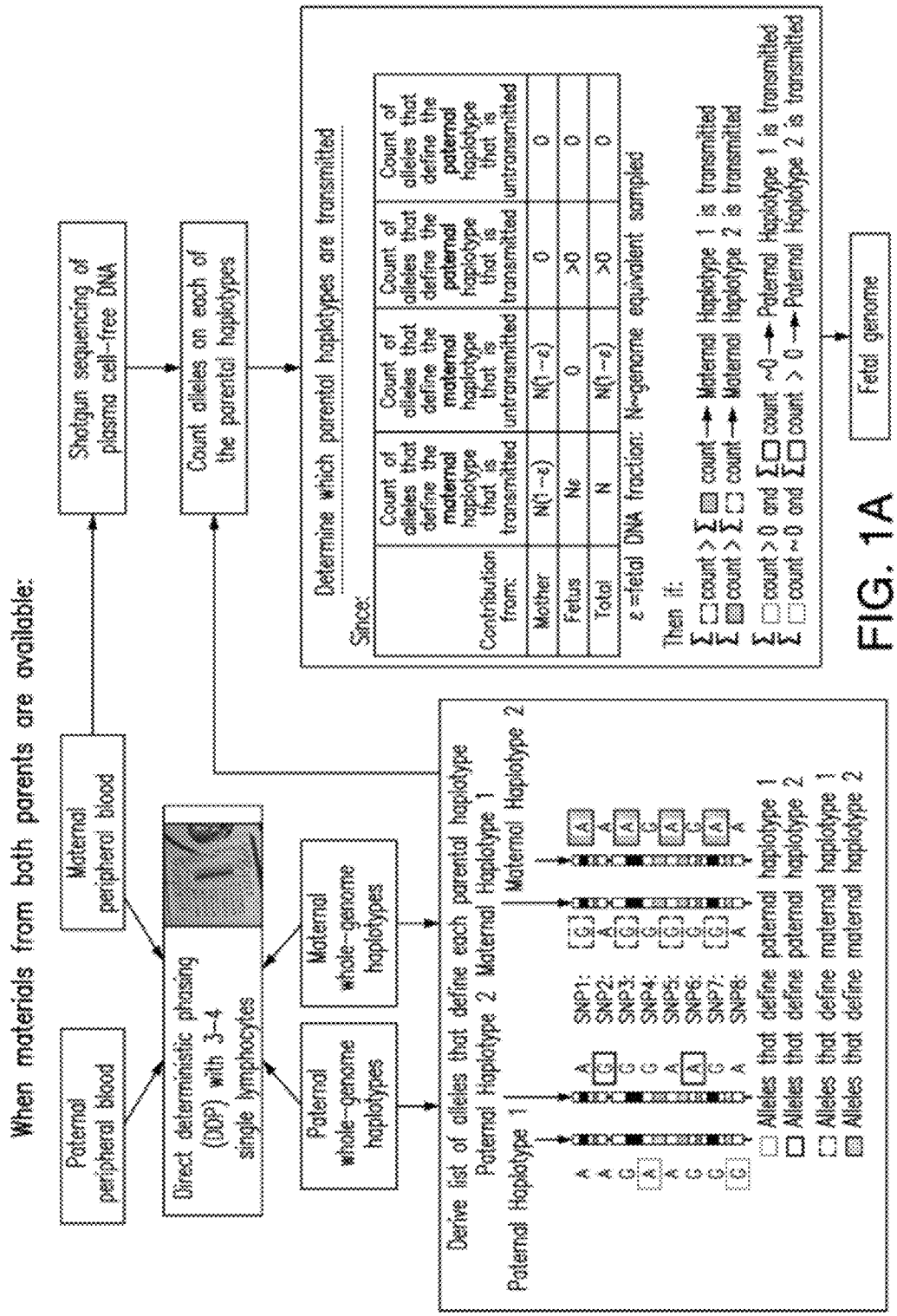
FIG. 1A-B. Outline of the strategy for determining the fetal genome noninvasively.
Figure 1B:
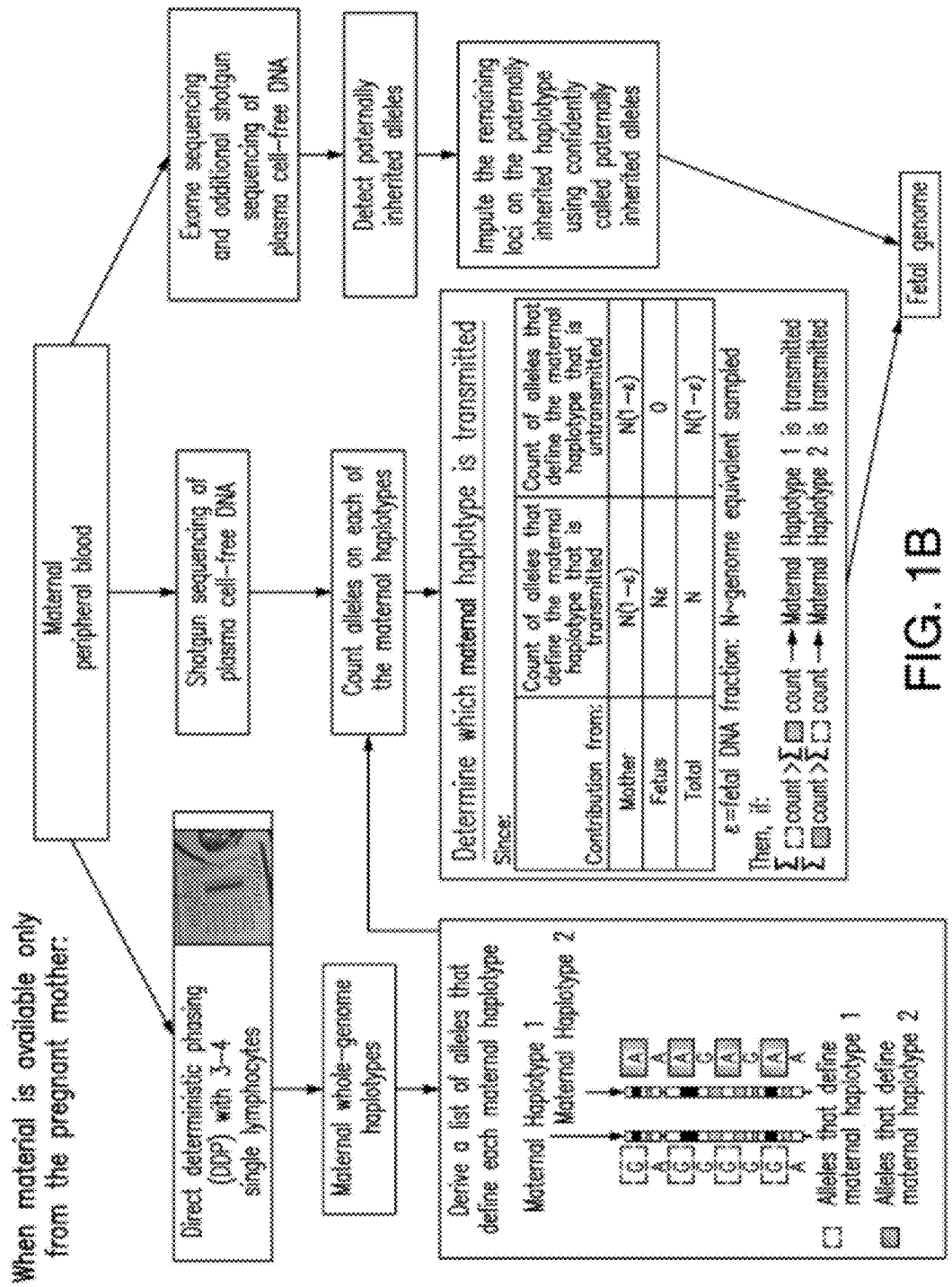
Figure 2:
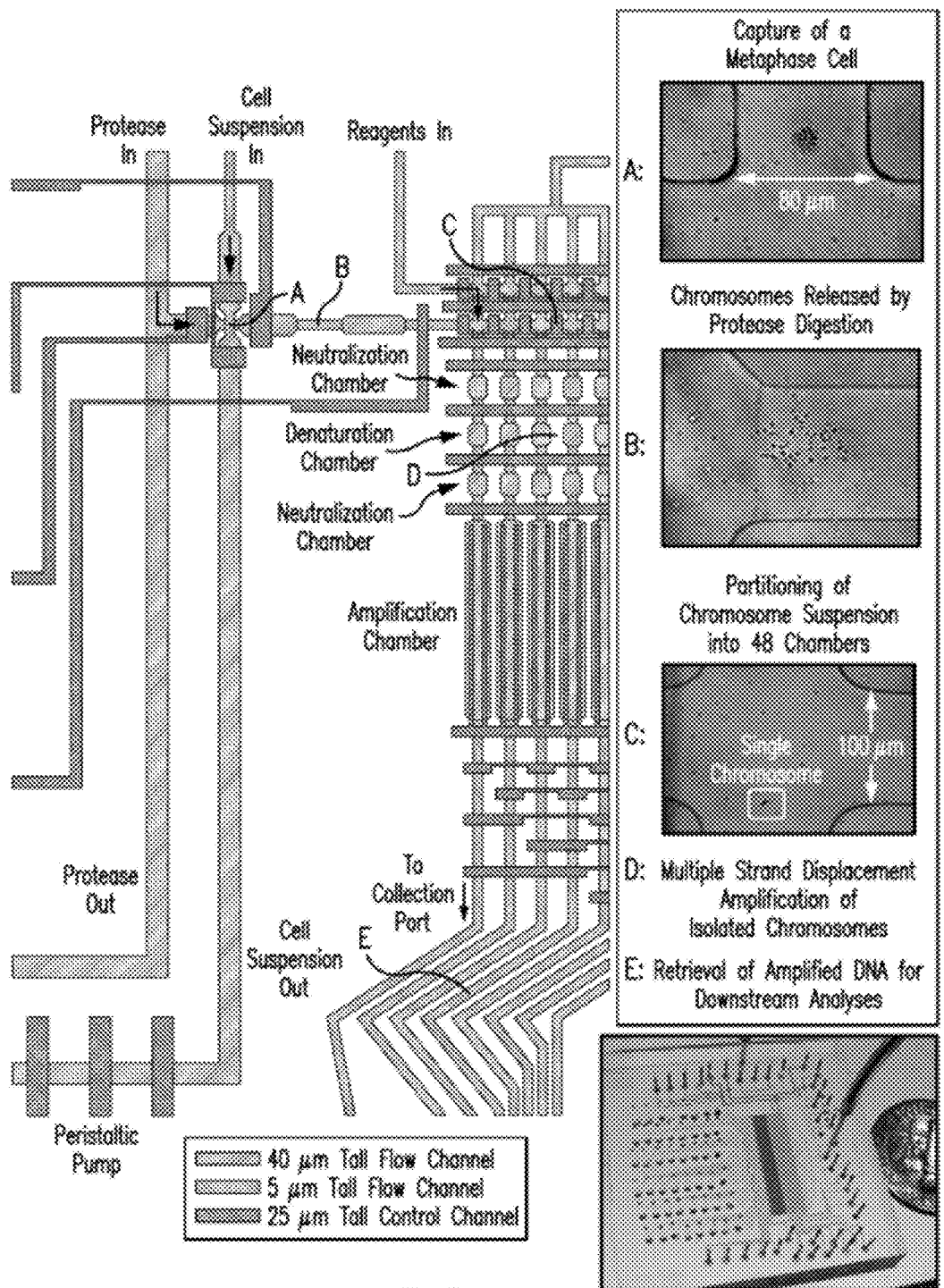
FIG. 2. Microfluidic device designed for the amplification of metaphase chromosomes from a single cell to achieve direct deterministic phasing (DDP). A single metaphase cell is recognized microscopically and captured in region A. Protease (pepsin at low pH) is introduced to generate chromosome suspension in region B. Chromosome suspension is partitioned into 48 units (region C). Content in each partition is individually amplified (region D). Specifically, chromosomes at low pH are first neutralized and treated with trypsin to digest chromosomal proteins. Chromosomes are denatured with alkali and subsequently neutralized for multiple strand displacement amplification to take place. As reagents are introduced sequentially into each air-filled chamber, enabled by the gas permeability of device's material, chromosomes are pushed into one chamber after the next and finally arrive in the amplification chamber. Amplified materials are retrieved at the collection ports (region E). In the overview image of the device, control channels are filled with green dye. Flow channels in the cell-sorting region and amplification region are filled with red and blue dyes, respectively.
Figure 3A:
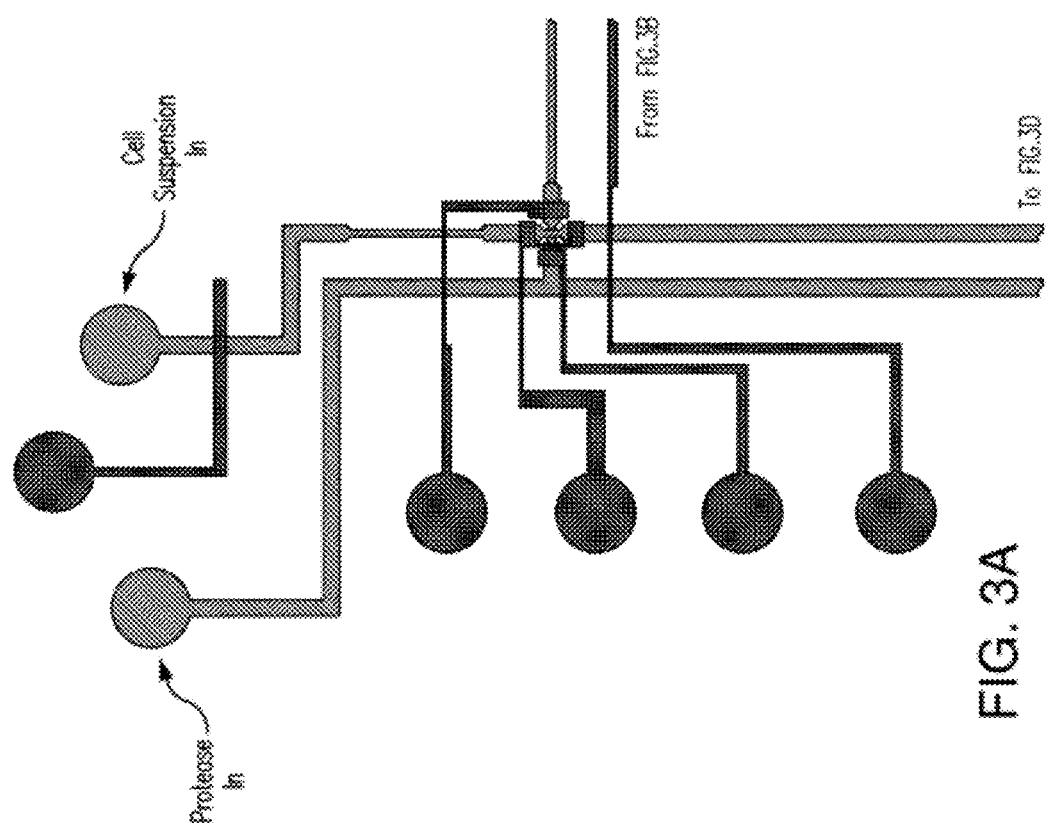
FIG. 3A-F. Overview of the microfluidic device used for whole-genome haplotyping.
Figure 3F:
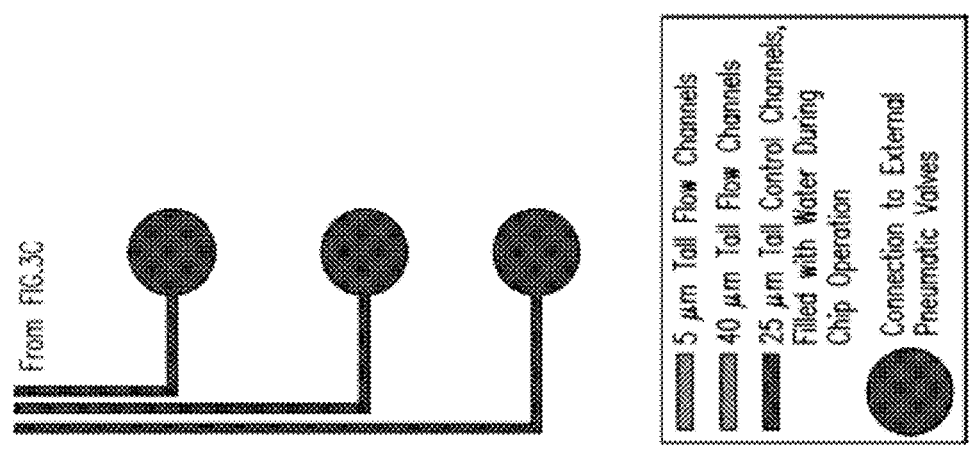
Figure 4A:
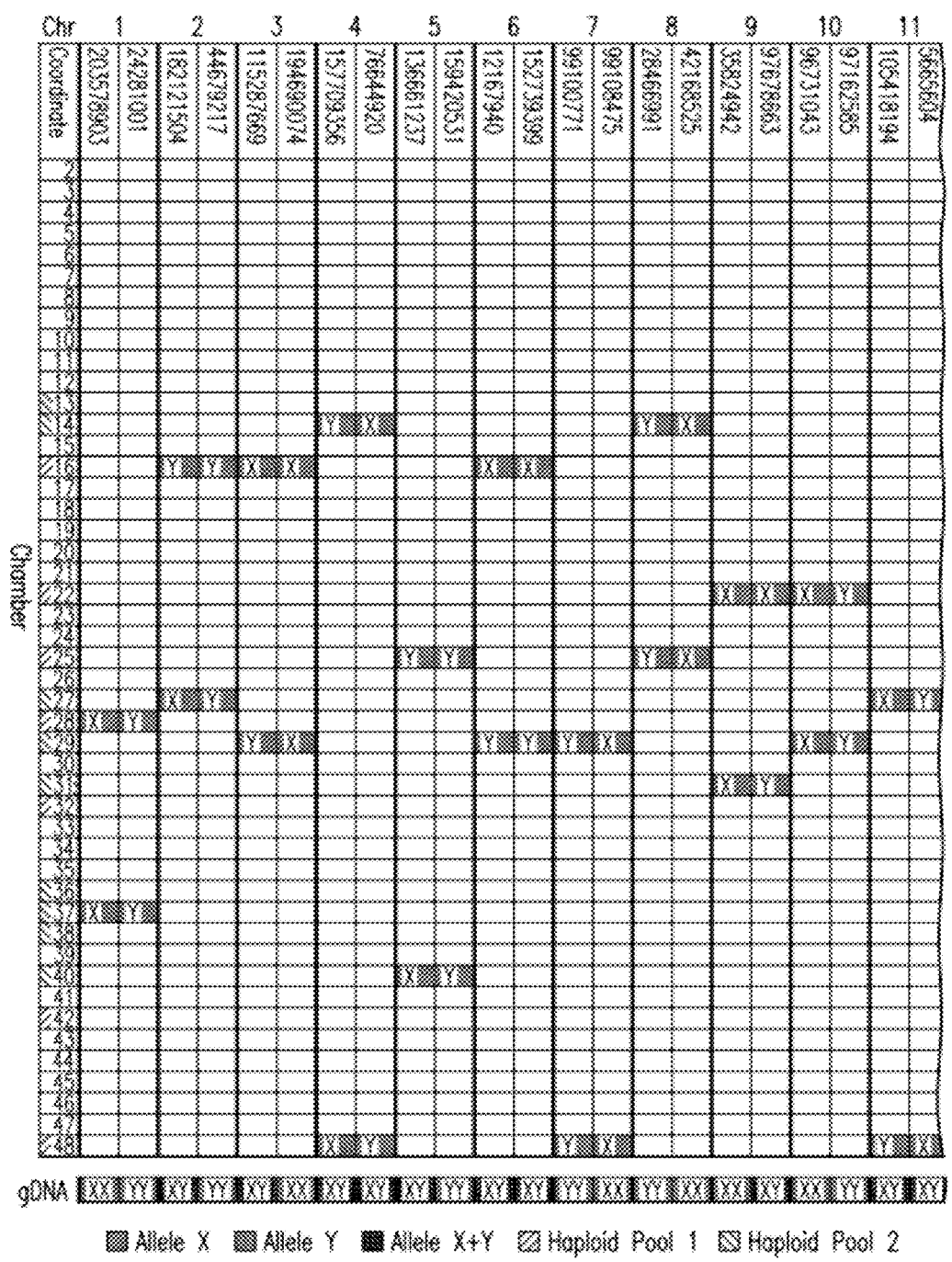
FIG. 4A-B. Determination of the identity of chromosomal origin of amplification products in microfluidic device using 46-loci PCR. This table represents results from an experiment using a single metaphase cell of P0's cultured whole blood. A row represents the content inside a chamber on the microfluidic device, and a column represents a locus, with specified chromosome and coordinate (NCBI Build 36.1). Each locus, except those on chromosomes 17 and 20, were found in two chambers. The two alleles of a SNP are highlighted in red and green. Heterozygous loci are labeled in blue. Chamber numbers labeled yellow were pooled together and genotyped on one whole-genome genotyping array, and chamber numbers labeled orange were pooled together and genotyped on another array. Genomic DNA extracted from cultured whole blood was also tested with the same 46-loci PCR.

To address the shortcomings of the prior art, the inventors have developed an approach termed "Direct Deterministic Phasing" (DDP) in which the intact chromosomes from a single cell are dispersed and amplified on a microfluidic device (FIGS. 2, 3). FIGS. 2 and 3 presents the overview of the microfluidic device for separation and amplification of chromosomes within a single cell. Three masks, one carrying the patterns of the 5 m flow layer, one carrying the patterns of the 40 pm flow layer, and one carrying the patterns of the 25 pm control layer, were printed on transparencies with 40,000 dpi resolution (Fineline Imaging). The two masks carrying flow layers were scaled up by 1.5% to accommodate shrinkage of the thick PDMS layer when it was peeled off from the mold. The flow mold was created with positive photoresist, while the control mold was created with negative photoresist. The protocols in this section were provided by the Stanford Microfluidics Foundry.

The microfluidic device has five regions (FIG. 2). It consists of a cell-sorting region, where a single metaphase cell is identified microscopically and captured from a cell suspension; a chromosome release region, where metaphase chromosomes are released by protease digestion of the cytoplasm; a chromosome partitioning region, where the chromosome suspension is randomly separated into 48 partitions of a long narrow channel; an amplification region, where isolated chromosomes are individually amplified by multiple strand displacement amplification; and a product retrieval region, where amplified products are individually collected.

The microfluidic device was made of polydimethylsiloxane (PDMS) and was fabricated using multi-layer soft lithography (Unger et al., 2000; Thorsen et al., 2002; Melin & Quake, 20070. The two-layered device had rectangular 25 pm tall control channels at the bottom and rounded flow channels at the top. The device was bonded to a glass slide coated with a thin layer of PDMS. In the cell-sorting region of the device, flow channels were 40 μm high and 200 μm wide. In the amplification region of the device, flow channels were 5 μm and 100 μm wide and reaction chambers were 40 μm tall. A 'push-up' membrane valve was formed at locations where a control channel crossed over with a flow channel and was actuated when the control channel was pressurized at 20 to 25 psi and pushed against the flow channel above. The area of each valve was 200 μm×200 μm for the 40 μm flow channels, and 100 μm×100 μm for the 5 μm flow channels. Membrane valves were controlled by external pneumatic solenoid valves that were driven by custom electronics connected to the USB port of a computer. A Matlab program was written to interface with the valves. Fluid flow within the cell sorting region was controlled by a set of peristaltic pump on chip. In the amplification region, reagents were introduced sequentially by dead-end filling, which was possible due to the gas permeability of PDMS. The amount of reagent introduced was determined by the volume of each reaction chamber. Detailed protocols of the fabrication of the device follow.

Preparation of Device

The flow mold contains rounded features of two heights. The first layer with features of 5 μm was fabricated with SPR220-7 photoresist. The second layer with features of 40 μm was fabricated with AZ50 photoresist:
1. Treat wafer with HDMS (hexamethyldisilazane) for 5 min.
2. Spin coat 5PR220-7: 500 rpm for 5 s, 3200 rpm for 30 s.
3. Soft bake: 115° C. for 90 s.
4. Expose to UV for 65 s.
5. Develop mask by soaking in MF-319 for 3 to 5 minutes. Rinse with water.
6. Hard bake: increase temperature from 25° C. to 190° C. with a ramping rate of 10° C. per hour for 15 hours.
7. Treat wafer with HMDS for 5 min.
8. Spin coat AZ50: 500 rpm for 10 s, 1100 rpm for 30 s.
9. Soft bake at 115° C. for 4 min, 65° C. for 1 min. Set hot plate to AutoOFF and cool to room temperature.
10. Expose wafer to UV in 2 cycles of 30 s.
11. Develop mask in AZ developer. Rinse with water.
12. Hard bake: increase temperature from 25° C. to 190° C. with a ramping rate of 10° C./hour for 15 hour.

The control mold contains rectangular features of 25 μM and was fabricated with SU2025 photoresist:
1. Spin coat SU2025 photoresist: 500 rpm for 5 s, 2700 rpm for 60 s.
2. Soft bake: 65° C. for 2 min, 95° C. for 5 min, 65° C. for 2 min.
3. Expose to UV for 20 s.
4. Post bake: 65° C. for 2 min, 95° C. for 5 min, 65° C. for 2 min.
5. Develop mask in SU8 developer for 1-2 minutes, rinse with isopropanol.
6. Hard bake: increase temperature from 65° C. to 150° C. with a ramping rate of 120° C. Bake for 2 hours.

The microfluidic devices were fabricated with PDMS (polydimethylsiloxane):
1. Thick layer: Prepare 50 g of RTV PDMS by mixing together Part A and Part B at a 5:1 ratio in a hybrid mixer for 1 min, followed by 2 min of degassing. Pour mixture onto the flow mold and degas in a vacuum chamber for 30 min or until bubbles disappear. Bake at 80° C. for 1 hr.
2. Thin layer: prepare 21 g of RTV PDMS by mixing together Part A and Part B at a 20:1 ratio in a hybrid mixer for 1 min, followed by 2 min of degassing. Spin mixture onto the control mold with a spin speed of 1500 rpm for 60 s and a ramp time of 15 s. Bake at 80° C. for 40 min.
3. Cut and peel off the thick layer from the flow mold. Punch holes on the thick layer and align it to the control mold coated with PDMS. Bake together for 1.5 hr.
4. Coat blank glass slides by spinning RTV PDMS (20:1 Part A: Part B) at 2000 rpm directly onto the glass slide and bake at 80° C. for 40 min.
5. Peel off the thick and thin layers from the control mold. Punch holes and place on the glass slide. Bake at 80° C. overnight.

Cell Culture

Two types of cells were tested on the device: lymphoblastoid cell lines used in the International HapMap Project and lymphocytes from whole blood of a donor.

EBV-transformed lymphoblastoid cell lines (Coriell Cell Repositories) were cultured in RPMI 1640, supplemented with 15% fetal bovine serum. To enrich the population of mitotic cells, each culture was treated with 2 mM thymidine (Sigma) for 24 hours at 37° C. Followed by multiple washings in PBS, cells were cultured in normal medium for 3 hours and treated with 200 ng/ml nocodazole (Sigma) for 2 hours at 37° C. to arrest cells at metaphase.

Whole blood (~250 microliter) obtained from a fingerprick was treated with sodium heparin and cultured in PB-Max medium (Invitrogen) for 4 days. The culture was treated with 50 ng/ml colcemid (Invitrogen) for 6 hours. The culture was layered on top of Accuspin System-Histopaque-1077 (Sigma) and centrifuged for 8 min at 2500 rpm. Nucleated cells at the interface was removed and washed once with Hank's Buffered Salt Solution (HBSS).

Metaphase arrested cells incubated with 75 mM KCl at room temperature for 10 to 15 minutes. Acetic acid was added to the cell suspension at a final concentration of 2% to fix the cells. After fixation on ice for 30 minutes, cells were washed twice with PBS-1% BSA-1 mM EDTA and once with PBS-1% BSA-1 mM EDTA-1% Triton, and finally suspended in 75 mM KCl-1 mM EDTA-1% Triton X-100. Cells were treated with 0.2 mg/ml RNaseA (Qiagen) prior to loading onto the microfluidic device.

Protocols for Extraction of DNA from Cell-Free Plasma

Blood Processing
1. Collect 20 ml of peripheral blood in EDTA Vacutainer.
2. Centrifuge tubes at 1600 g for 10 min at 4° C.
3. Aliquot 850 ul of plasma into 1.5 ml polypropylene tubes, with care not to disturb the buffy coat.
4. Centrifuge tubes at 16000 g for 10 min at 4° C. to remove residual cells.
5. Carefully remove supernatant (~800 μl) and place in new 1.5 ml polypropylene tubes.
6. Perform centrifugation as soon as blood is collected. Aliquots of cell-free plasma can be stored at −80° C. until further processing.
7. In this study, DNA was extracted from plasma using two commercial kits with slight modifications from manufacturers' protocols.

Extraction of Cell-free DNA Using QIAamp DNA Micro Kit (Qiagen)

The following protocol contains modifications to the 'Small Volume of Blood Protocol' in the manufacturer's manual.
1. Set temperature of heating block to 56° C.
2. Equilibrate samples, buffer AE or water to room temperature.
3. Add appropriate amount of carrier RNA into buffer AL (10 μg of carrier RNA per ml of buffer AL). For instance, 7 ml of buffer AL requires 700 of carrier RNA.
4. Pipet 40 μl Proteinase K into bottom of 1.5 ml microcentrifuge tube.
5. Add 400 μl plasma to a microcentrifuge tube (2 separate tubes for a total of 800 μl plasma).
6. Add 400 μl of buffer AL to sample. Mix by pulse-vortexing for 15 s.
7. Incubate at 56° C. for 10 min.
8. Briefly centrifuge 1.5 ml microcentrifuge tube to remove drops from the inside of the lid.
9. Add 200 μl ethanol (96-100%) to sample. Mix by vortexing for 15 s. Incubate at room temperature for 3 min. Briefly centrifuge.
10. Apply sample to MinElute spin column in a 2 ml collection tube. Centrifuge at 6000 g for 1 min (depending on volume of column, it may be needed to apply sample to column repeatedly). Place spin column in clean 2 ml collection tube.
11. Add 500 μl Buffer AW1 to column. Centrifuge at 6000 g for 1 min. Place spin column in a clean 2 ml collection tube.
12. Add 500 μl Buffer AW2. Centrifuge at 6000 g for 1 min.
13. Place spin column in a new 2 ml collection tube and centrifuge 20000 g for 3 min (Buffer AW2 may affect downstream applications)
14. Flip spin for 20000 g for 3 min.
15. Prewarm buffer AE at 56° C.
16. Place spin column in a clean 1.5 ml microcentrifuge tube. Add 500 μl Buffer AE.
17. Incubate at room temperature for 5 min. Centrifuge at 6000 g for 1 min.

A.3 Extraction of Cell-free DNA Using Nucleospin Plasma F Kit (Macherey-Nagel)

The only deviation from the manufacturer's instructions is the omission of the final open-lid drying step.

Cell Sorting, Chromosome Release, and Multiple Strand Displacement Amplification Prior to the loading of cell suspension, the cell-sorting channel of the device was treated with Pluronic F127 (0.2% in PBS). Cell suspension was introduced into the device using an on-chip peristaltic pump and an off-chip pressure source. Metaphase cells could be distinguished from interphase cells microscopically by morphological differences. Once a single metaphase cell was recognized at the capture chamber, surrounding valves were actuated to isolate it from the remaining cell suspension. Pepsin solution (0.01% in 75 mM KCl, 1% Triton X-100, 2% acetic acid) was introduced to digest the cytoplasm and release the chromosomes. The chromosome suspension was pushed into a long narrow channel and partitioned into forty-eight 180 picoliter compartments by actuating a series of valves along the channel. Trypsin (0.25%) in 150 mM Tris-HCl (pH 8.0) (1.2 nanoliter) was introduced to neutralize the solution and to digest chromosomal proteins. Ten minutes later, denaturation buffer (Qiagen's Repli-G Midi kit's buffer DLB supplemented with 0.8% Tween-20) (1.4 nanoliter) was introduced. The device was placed on a flat-topped thermal cycler set at 40° C. for 10 minutes. This was followed by the introduction of neutralization solution (Repli-G kit's stop solution) (1.4 nanoliter) and incubation at room temperature for 10 minutes. A mixture of reaction buffer (Qiagen's Repli-G Midi Kit), phi29 polymerase (Qiagen's Repli-G Midi Kit), 1× protease inhibitor cocktail (Roche) and 0.5% Tween-20 (16 nanoliter) was fed in. The total volume per reaction was 20 nanoliter and the device was placed on the flat-topped thermal cycler set at 32° C. for about 16 hours. Amplification products from each chamber was retrieved from its corresponding outlet by flushing the chamber with TE buffer (pH 8.0) supplemented with 0.2% Tween-20. About 5 μl of products were collected in from each chamber. Products were incubated at 65° C. for 3 min to inactivate the phi29 enzyme.

Initial Genotyping with 46-loci Taqman PCR

For each single cell experiment, the chromosomal origins of the contents of each microfluidic chamber were established by a 46-loci Taqman genotyping PCR on the 48.48 Dynamic Array (Fluidigm), a microfluidic device that allows 48 assays to be performed on 48 samples simultaneously. The assays used are listed in FIG. 18. Pre-amplification was performed on 1.25 μl of retrieved products from each chamber, according to manufacturer's protocol, prior to being assayed on the Dynamic Array.

Since cells are arrested at the early stage of metaphase, the chromosomes have duplicated but sister chromatids are still bound together at the centromere. Each metaphase cell therefore has 46 separable chromosomes and no more than two chambers should contain templates for a given PCR genotyping assay. As expected, for assays that yielded PCR signals in two chambers, the alleles for both chambers matched that of the genomic DNA if the individual was homozygous for the tested locus, and the alleles of the two chambers were different if the individual was heterozygous for the tested locus (FIG. 4).

Because the chromosomes were randomly dispersed into chambers, there would be occasions that both homologous copies of a chromosome co-located in the same chamber (for instance, chromosomes 17 and 20 in FIG. 4). This probability can be made arbitrarily small by increasing the number of chambers, and in practice three to four single cell experiments were performed to ensure that homologous copies of each chromosome are separated in at least one single cell experiment.

Whole-genome Phasing Using Genotyping Arrays

DNA products retrieved from the microfluidic device were amplified a second time in 10 μl volume using the Repli-G Midi Kit's protocol for amplifying purified genomic DNA. Products from multiple chambers were pooled together into two mixtures such that each mixture contained one of the homologous copies of each chromosome. Each mixture, containing roughly one haploid genome of a cell, was genotyped on Illumina's HumanOmni1-Quad BeadChip Array or HumanOmni1S BeadChip Array. Genomic DNA was also genotyped on the same types of arrays.

For each chromosome homolog, the allelic identity of a SNP was determined from the consensus among the biological replicates. If equal number of both alleles were observed at the site, no consensus was drawn. The error of a single genotyping measurement was estimated by counting the number of inconsistent allele call at sites typed more than once. For SNPs of which only one of the alleles was observed, the identity of the other allele was determined using the genotypes of genomic DNA. The combination of the consensus alleles from the two homologs at each SNP site should in principle agree with the genotype call of the genomic DNA control. SNPs that did not follow this rule (~0.3% to 0.4%) were eliminated from downstream analyses.

Whole-genome Haplotyping of Members in a CEU Family Trio

Whole-genome Haplotypes of Three CEU Individuals

Figure 5A:
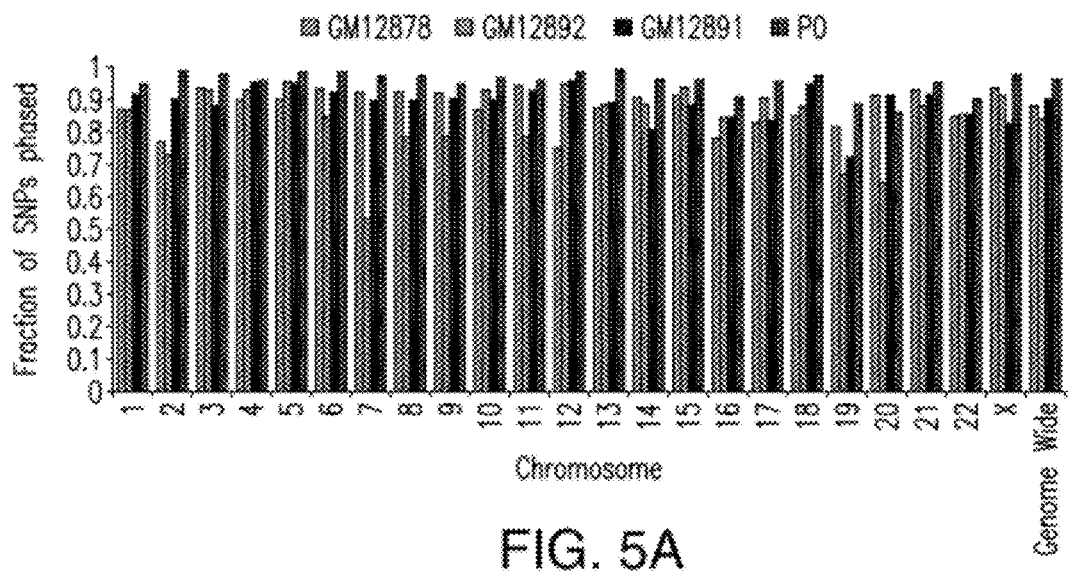
FIG. 5A-B. Statistics of whole-genome haplotyping.
Figure 5B:
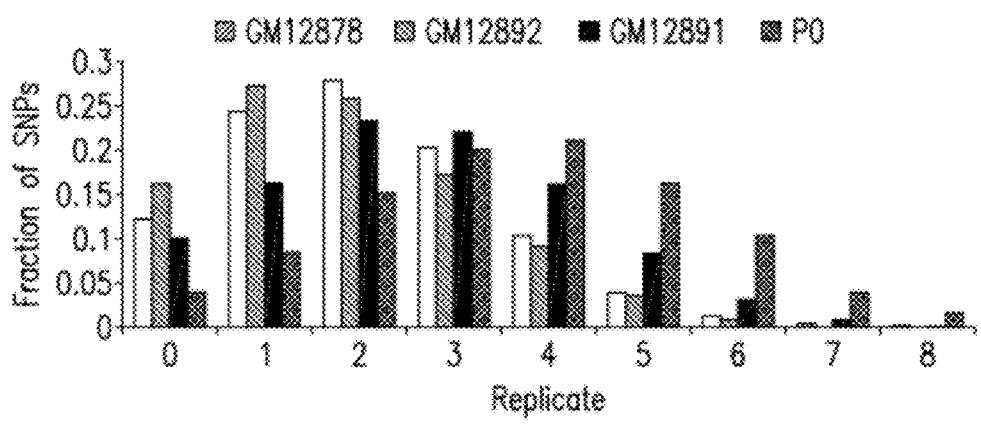

Initial experiments were performed on three lymphoblastoid cell lines, GM12891, GM12892, and GM12878, representing a father-mother-daughter trio in the CEU (Caucasian of European descent in Utah) 1463 family. These cell lines have been extensively genotyped in the HapMap project. Experiments were performed on three to four single metaphase cells from each individual. Each homologous chromosomehad on average ~2 to 3 biological replicates and each SNP was phased on average 2 to 3 times (FIG. 5A). Phases were established for ~87.9%, ~89.9%, and ~433.8% of ~970,000 refSNPs present on the array for GM12878, GM12891, and GM12892, respectively (FIG. 5B). By counting the number of inconsistent allele calls among biological replicates of each chromosome homolog, the error originating from amplification and genotyping for a single phase measurement was estimated to be 0.2% to 0.4%. The actual phasing error per SNP was much smaller because the final phases of most SNPs were determined by the consensus among replicates and can be made as small as desired by increasing the number of replicates.

Figure 6:
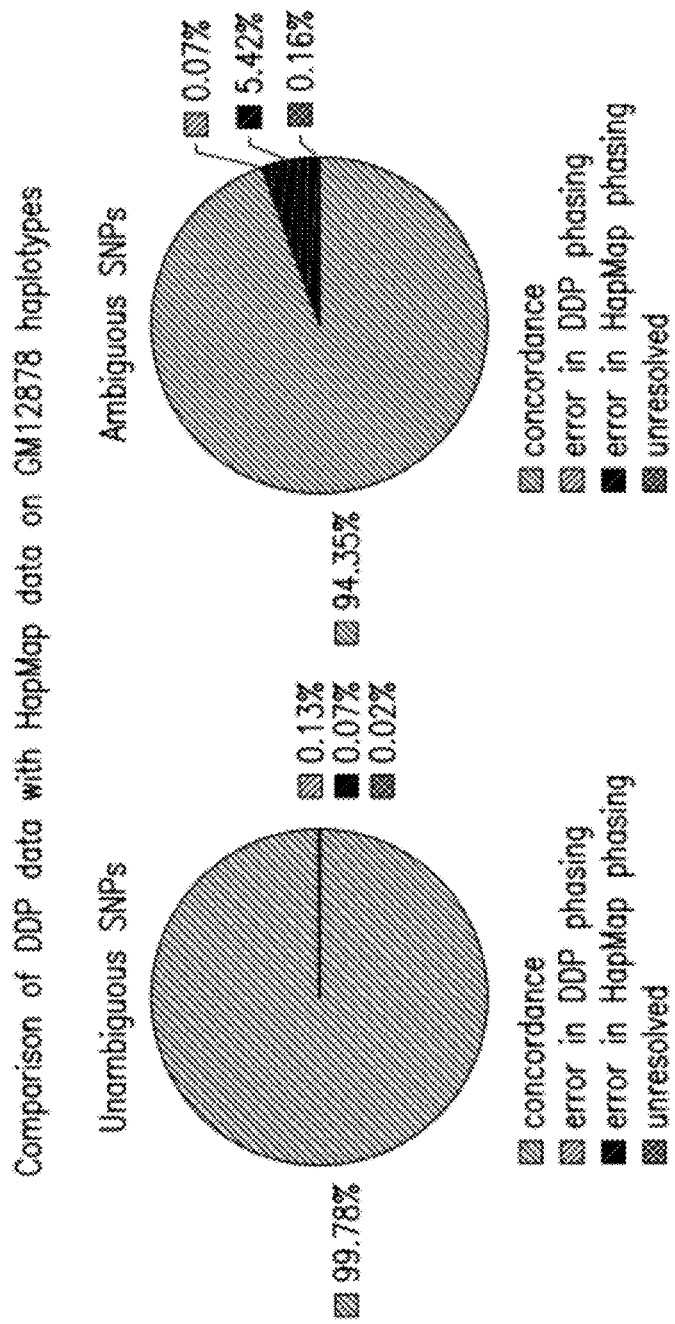
FIG. 6. Comparison of experimentally determined phases of ~160,000 heterozygous SNPs of GM12878 (child of the trio) and those determined by phase III of the HapMap project. Unambiguous SNPs refer to those that are homozygous for at least one parent and are deterministically phased using family data in HapMap. This comparison shows the accuracy of DDP. Ambiguous SNPs refer to those that are heterozygous for all members of the trio and statistical phasing is used in HapMap. This comparison suggests the importance of experimental phasing even when family data is available.

Comparison of Direct Deterministic Phasing and Statistical Inference of Haplotypes In the HapMap project, haplotypes in the CEU population were obtained by studying the genotypes of family trios. About 80% of the heterozygous SNPs of the child can be unambiguously phased given that one parent is homozygous for the SNP. The remaining ~20% of heterozygous SNPs in the child are ambiguous and require statistical phasing because both parents are heterozygous. The phases of the child (GM12878) determined by DDP was compared against the computational phasing data using the program Impute++ available from Phase III of the HapMap project, excluding SNPs with A/T and G/C alleles. Comparison of DDP and HapMap data on unambiguous SNPs provides an estimate of the accuracy of DDP. The concordance rate between the two data sets was 99.8%. The small number of inconsistencies arose from either error in DDP genotyping or error in genotyping in HapMap data (FIG. 6). When considering ambiguous SNPs alone, the incongruence rate between the two data sets was 5.7%. The majority of these inconsistencies (96.0%) came from incorrect statistical phasing in the HapMap project, since the phases of these ambiguous SNPs in the child could confirmed by the experimentally determined phases of the two parents (FIG. 6). These data agree with previous evaluations of the accuracies of statistical phasing in CEU trios (International HapMap Consortium, 2005; Marchini et al., 2006) and highlights the need of direct experimental phasing even when family data is available.

Direct Observation of Recombination in a Family Trio

Figure 7A:
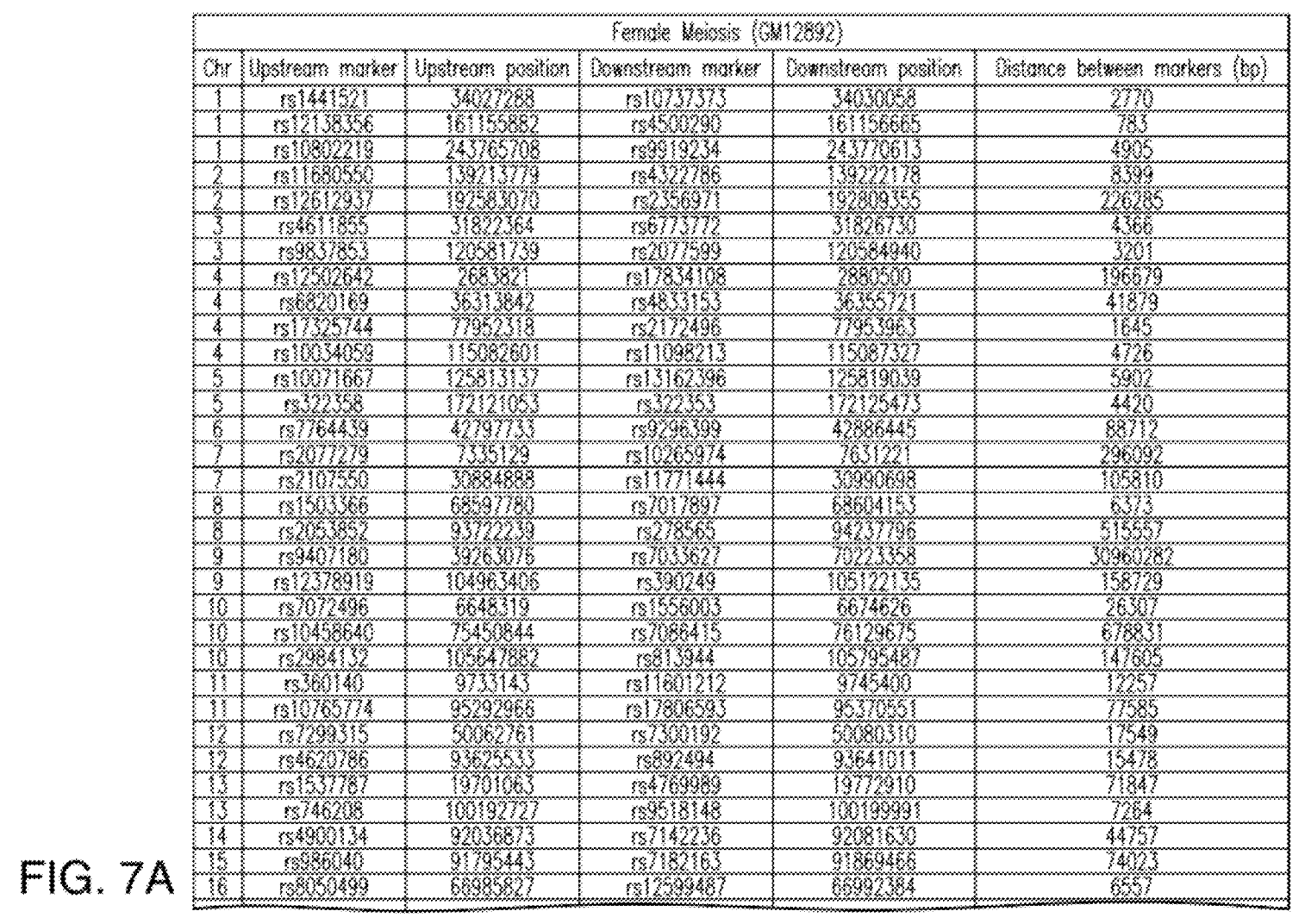
Figure 7B:
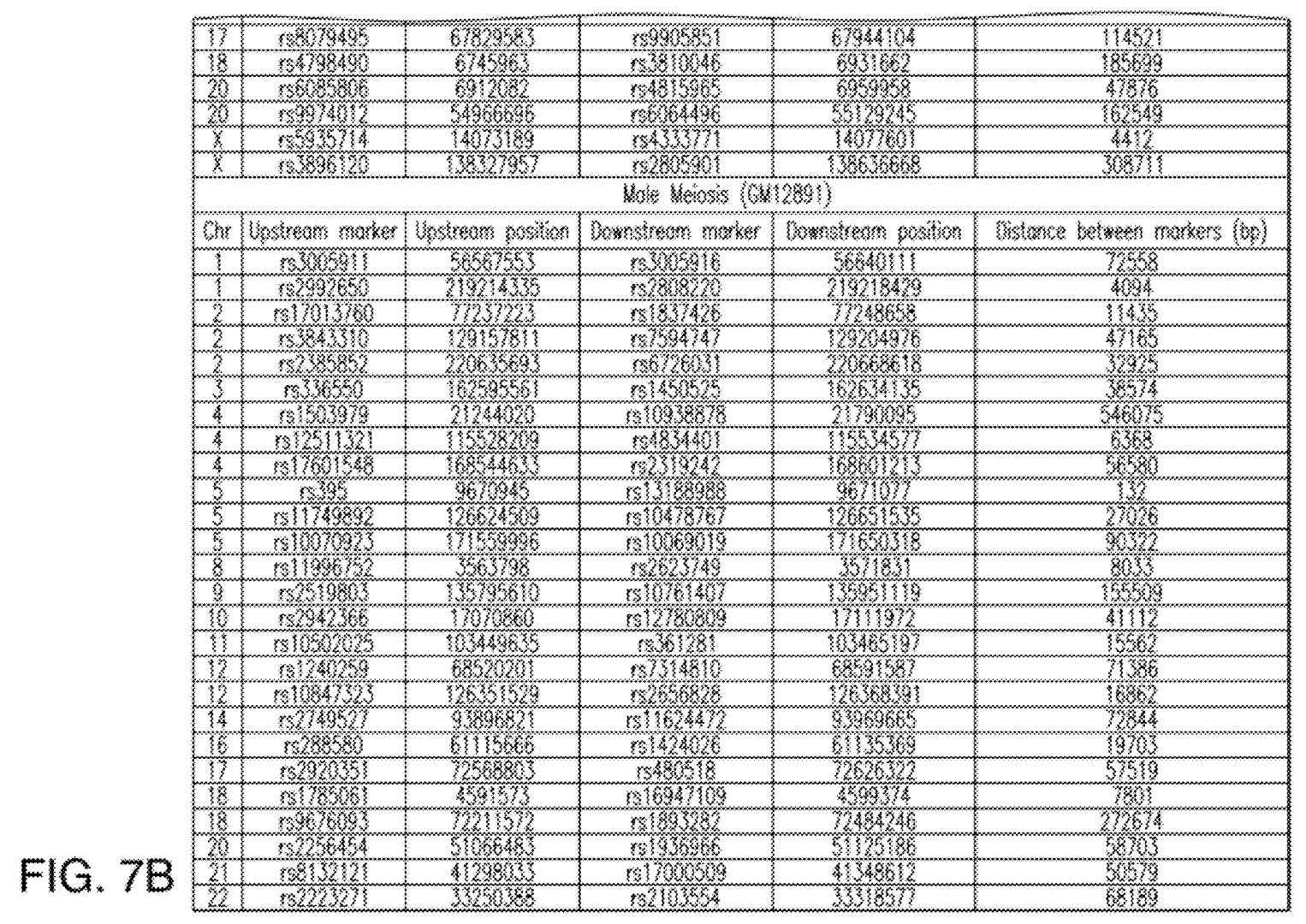
Figure 9:
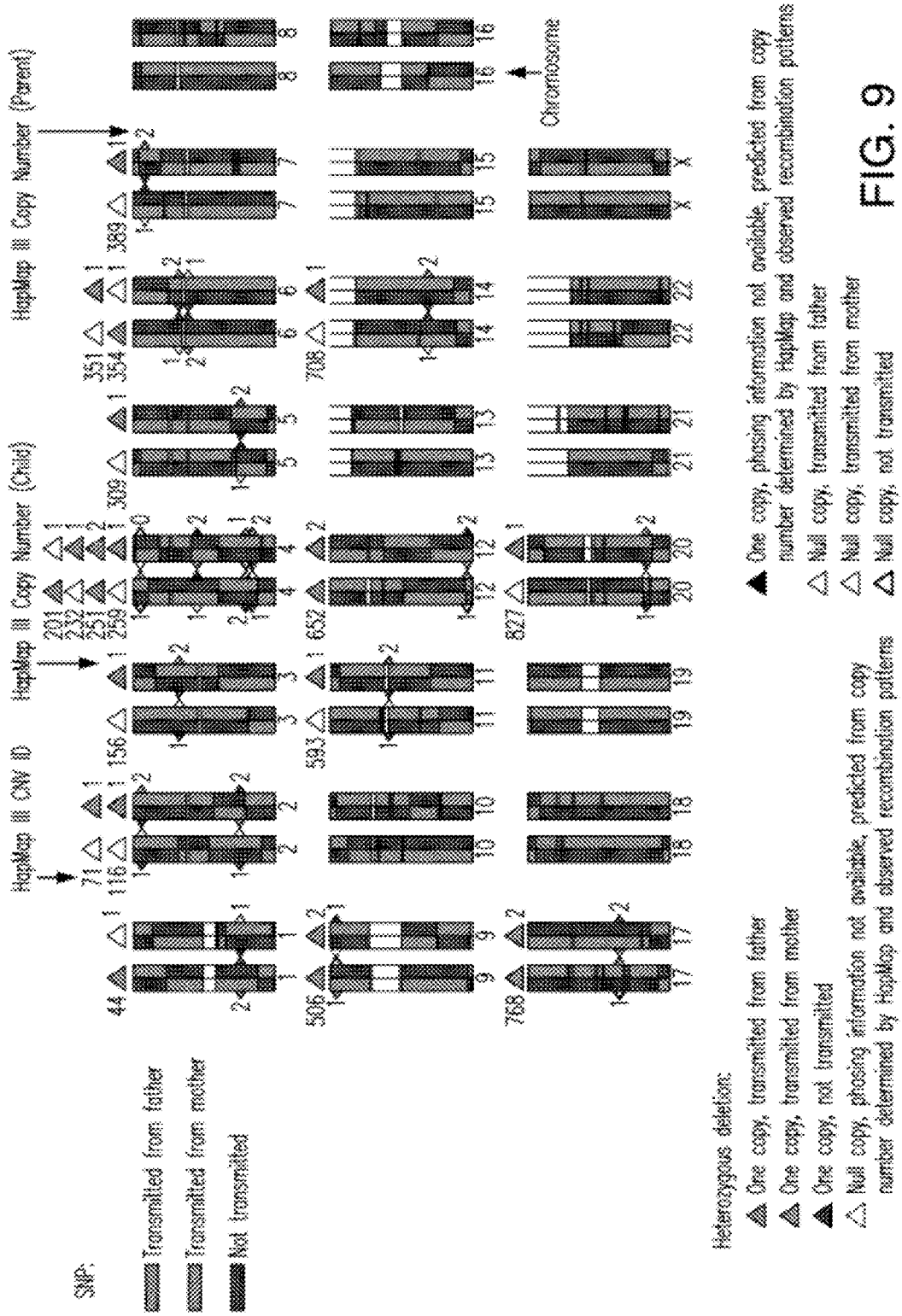
FIG. 9. Direct observation of recombination events and deterministic phasing of heterozygous deletions in the family trio. Each allele with DDP data available for the child and the parent is represented by a hatched horizontal line. The alleles transmitted to the child from the father are labeled in left-hatching. The alleles transmitted to the child from the mother are labeled in right-hatching. Untransmitted alleles are labeled in crosshatching. Centromeres and regions of heterochromatin are not assayed by genotyping arrays and are thus in white. Heterozygous deletions in the parents are represented as triangles along each homologous chromosome. A solid triangle represents one copy and a hollow triangle represents a null copy. The phases of deletions are determined for each parent independently. The triangles are color coded according to the state of transmittance as determined by the location of the deletion relative to spots of recombination. The phases of the deletions in the child are determined independent of the parents and are shown on top of the parental chromosomes. The integers on the left are the IDs of each region given by HapMap phase III. The numbers on the right are the copy number of a region of in the child as determined by HapMap. Chromosomes are plotted with the same length.

The availability of parental haplotypes allowed us to directly measure the products of recombination events that led to an individuals unique genome, which could previously only be inferred using three-generation families (Broman et al., 1998) or two-generation families with large sibships (Kong et al., 2002). Each homologous chromosome of the child was aligned to the pair of chromosomes of the parent of which the chromosome was inherited from. FIG. 9 illustrates the cross-over events resulting from the paternal and maternal meioses. A total of 26 and 38 events were detected in the male meiosis and female meiosis, respectively, with a median resolution of ~43-44 kb (FIG. 7). This resolution was limited only by the density of the markers. The number of detected recombination events matched those in previous reports and supports the notion that the number of recombination events in females is generally higher than that in males (Broman et al., 1998; Frazer et al., 2007). In addition to the switch-over of large blocks of homologous chromosomes as a result of recombination, switch-overs at single sites were observed, constituting ~0.4% of the total number of SNPs in each parent-child comparison; these are presumably products of gene conversion or cell-culture induced mutations, as well as DDP error.

Phasing of Heterozygous Deletions

Figure 8A:
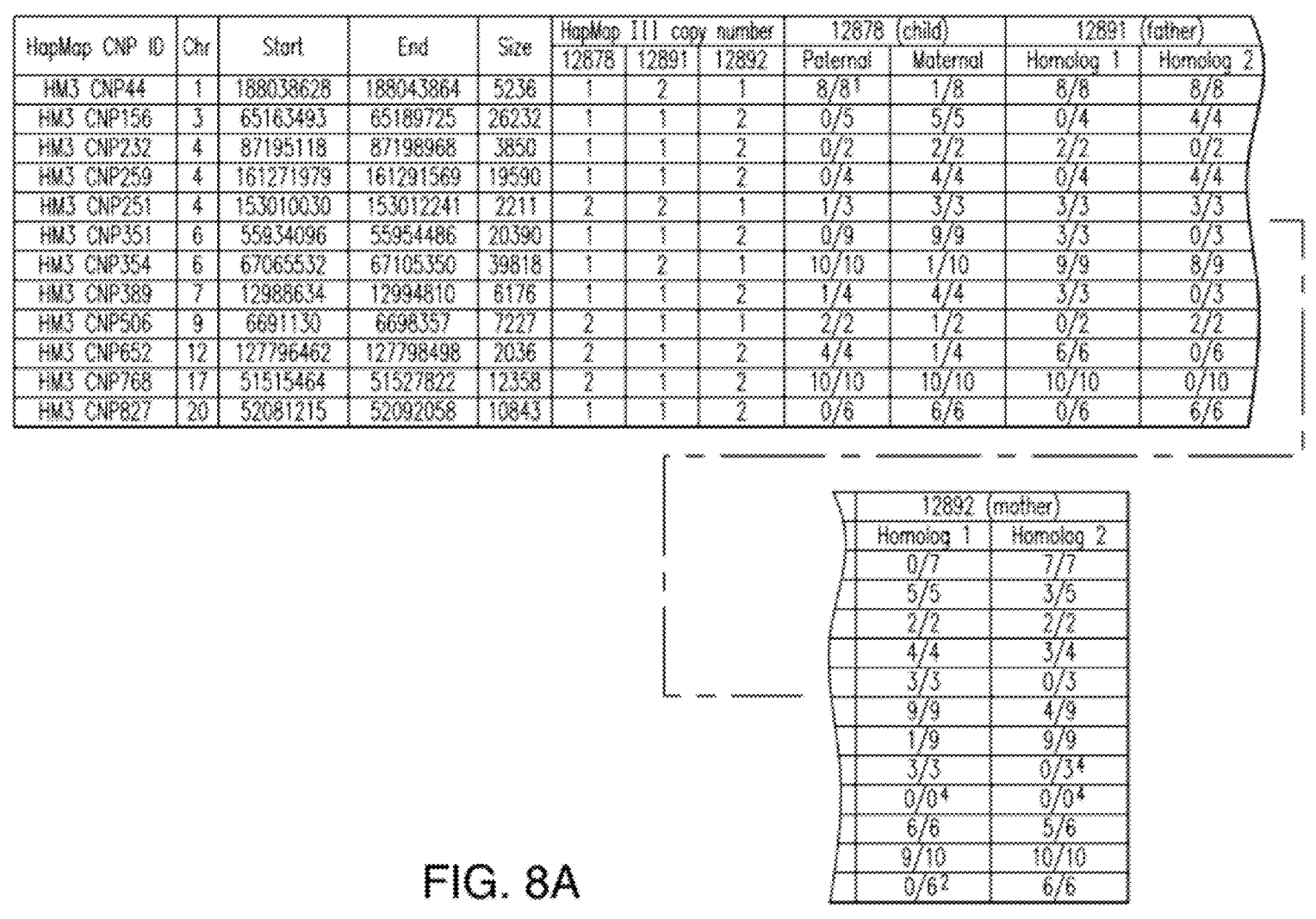

While CNVs can be statistically phased using methods similar to the statistical phasing of SNPs (Su et al., 2010; McCarroll et al., 2008; Conrad et al., 2010), direct experimental phasing of structural variation such as copy number polymorphisms over long ranges has largely been unexplored (Su et al., 2010). As a proof of principle, heterozygous deletions, as determined by phase III of the HapMap Project and accessible by genotyping arrays, of the three individuals in the family trio, were experimentally phased. This type of variation was chosen because they represent the simplest form of copy number variation, following homozygous deletion. The assumption was that one of the chromosome homolog should give no calls for SNP markers or no PCR amplification within a region of heterozygous deletions. Using this rule, 12 and 6 heterozygous deletions present within the family trio were phased using genotyping array data (FIG. 8A) and real-time PCR (FIG. 8B), respectively. The details of the PCR assays can be found in (FIG. 19). All of the phased heterozygous deletions within the trio agreed with the inheritance pattern (FIG. 9).

Whole-genome Haplotyping of a European Individual

Whole-genome Haplotyping Using Genotyping Arrays

Having validated the DDP approach on well characterized HapMap samples, it was applied to determine the haplotypes of an individual, labeled P0, whose genome has been sequenced (Pushkarev et al., 2009) and clinically annotated (Ashley et al., 2010). Since only a few cells are required for DDP, a blood sample collected from a finger-prick was sufficient for the experiments. Whereas some of the early microfluidic devices used for experiments with the family trio contained defects leading to the failure to retrieve products from some chambers, refinement in device fabrication yielded fully functional devices and thus improved the number of SNPs phased per single cell experiment for P0. The average number of pairs of autosomal chromosomes separated per single cell of P0 was 17.5.

Figure 10:
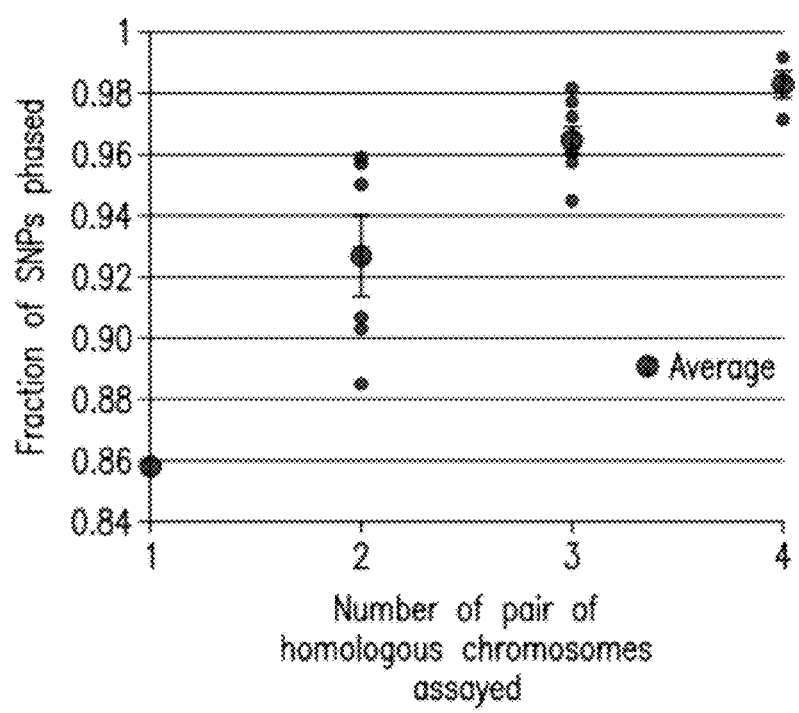
FIG. 10. Fraction of SNPs phased as a function of the number of pair of homologous chromosome assayed. This is based on the results from four single cell experiments of P0. Each point represents the coverage of an autosome. The error bars represent standard error of the mean.
Figure 11:
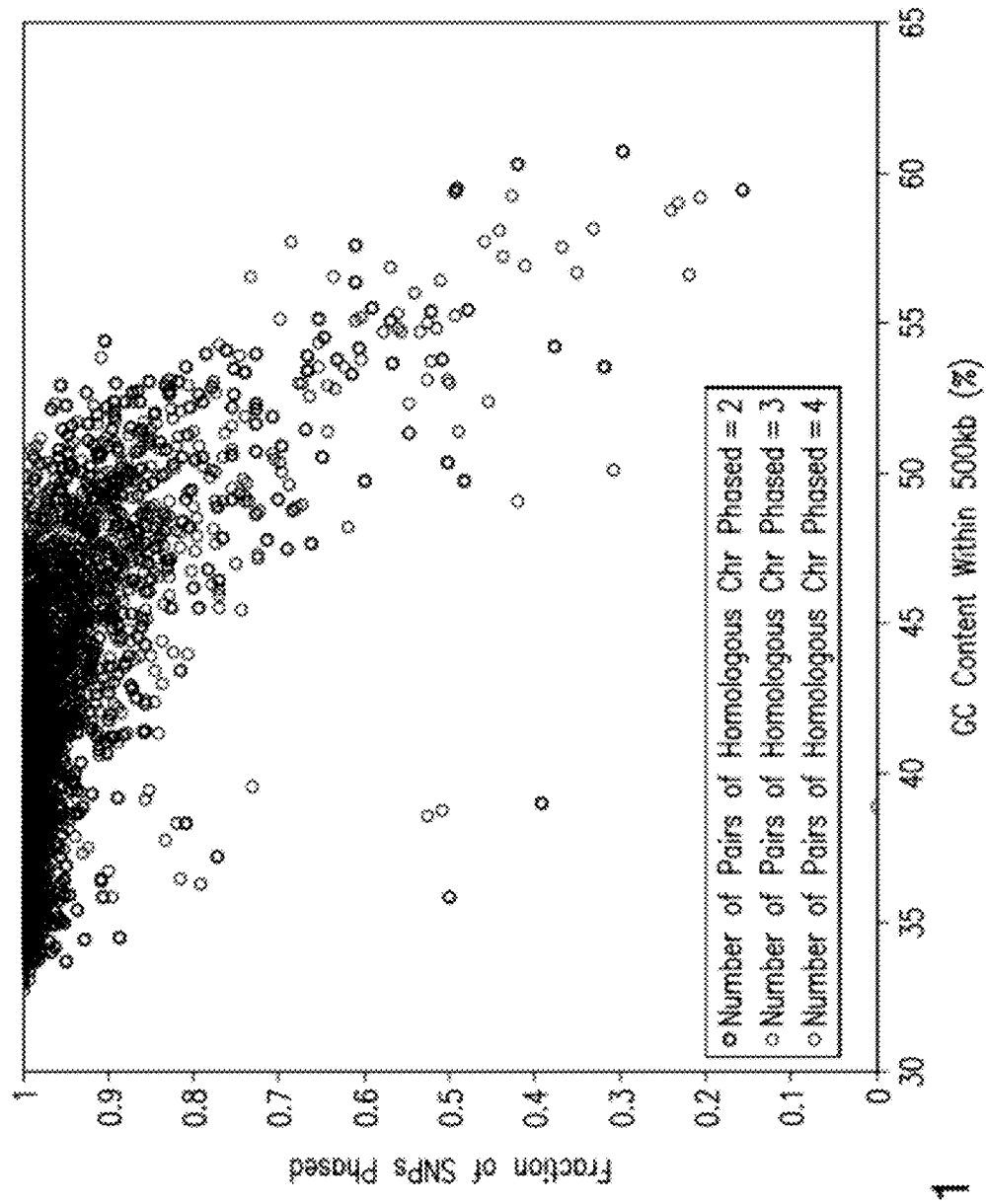
FIG. 11. SNPs in regions with relatively higher GC content are less accessible by genotyping arrays, potentially resulted from phi29's reduced amplification efficiency in regions with higher GC content. Plotted here is the fraction of SNPs phased by genotyping arrays (based on the ability of the arrays to type the alleles in amplified materials) as a function of GC content of regions where SNPs are located. Shown here are data from whole-genome haplotyping of P0 using Illumina's Omni1S arrays. Fraction of SNPs successfully phased within each 500 kb bin was measured and plotted against the GC content of the bin. The 22 autosomes are separated into 3 groups and given three labels, depending on how many pairs of homologous copies were assayed (out of the four single cells experimented).

Pools of haploid DNA derived from each of four single cells were assayed on the HumanOmni1-Quad array and HumanOmni1S array. The two different arrays complement each other. About 96.1% of the ~1.2 million SNPs present on the HumanOmni1S array were covered using four single cells (FIG. 5B). An additional ~861,000 SNPs were phased using materials from 3 single cells and the HumanOmni1Quad array (About 89.0% of autosomal refSNPs present on the array). For homologous chromosomes that were separated in all four single cell replicates (i.e., 4 biological replicates of each homologous copy), up to 99.2% of all SNPs assayed on a chromosome were phased (FIG. 10). We noticed that the SNPs that were not phased tended to cluster together and closer inspection revealed that they were usually located in regions with higher GC content (FIG. 11). Stronger molecular associations between DNA strands at regions with higher GC content might have led to more difficult amplification and such phenomena associated with phi29 has been previously reported (Bredel et al., 2005).

Phasing of Chromosome 6 Using High-throughput Sequencing

Phasing of SNPs was also achieved by direct sequencing. Amplified materials from three single copies of P0's chromosome 6 were sequenced lightly. Three chambers containing amplified materials from a single copy of chromosome were selected from the four single cell experiments of P0 for paired-end sequencing on Illumina's Genome Analyzer II. Two chambers contained materials from chromosome 6 only, while the third chamber contained materials from a homolog of chromosomes 6, 16, and 18. Second-round amplified materials from these chambers were fragmented through a 30-minute 37° C. incubation with 4/11 dsDNA Fragmentase (NEB) in a 20 μl reaction. Fragmented DNA was end-repaired, tailed with a single A base, and ligated with adaptors. A 12-cycle PCR was carried out and PCR products with sizes between 300-500 bp were selected using gel extraction. Sequencing libraries were quantified with digital PCR (Hillier et al., 2008). Each library was sequenced on two lanes on the flow cell. Thirty-six base pairs were sequenced on each end.

Image analysis, base calling, and alignment were performed using Illumina's GA Pipeline version 1.5.1. The first 32 bases on each read were aligned to the human genome (hg18). SNP calling was carried out using Illumina's CASAVA version 1.6.0. Positions covered at least three times according to the "sort.count" intermediate files were used in downstream analyses. A list of heterozygous SNPs was obtained from the sequenced genome of P0. The phases of heterozygous SNPs were determined either from the direct observation of both alleles in the different homologs, or by inferring the identity of the unobserved allele if only allele was detected.

Figure 12:
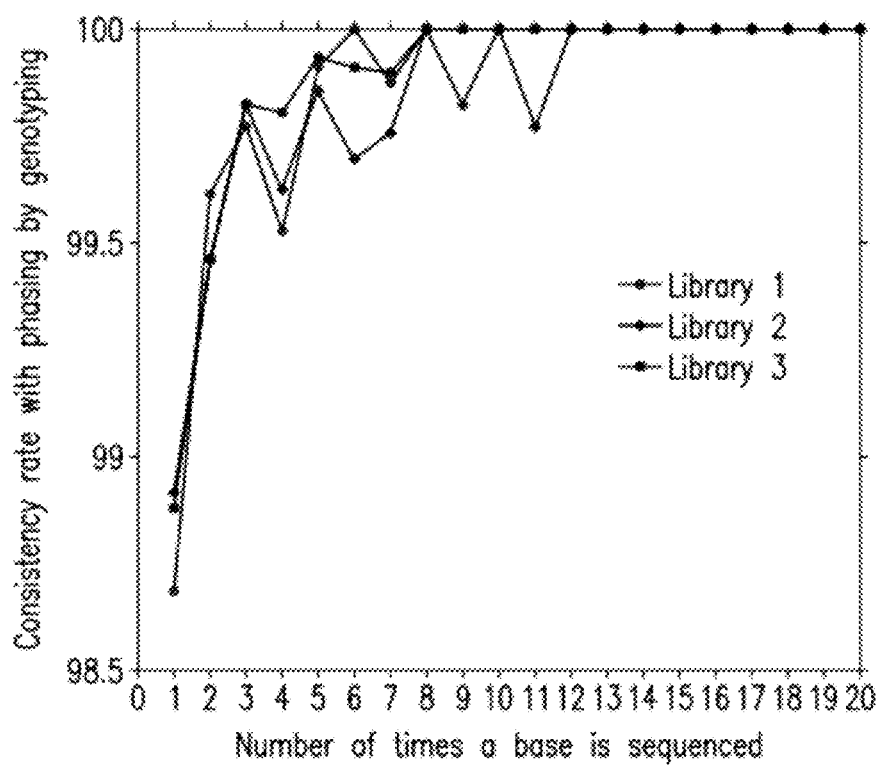
FIG. 12. Concordance of phasing by sequencing and phasing by genotyping arrays as a function of sequencing coverage. Three different copies of chromosome 6 of P0 were sequenced. Only SNPs that were phased more than twice with genotyping arrays were compared.
Figure 14A:
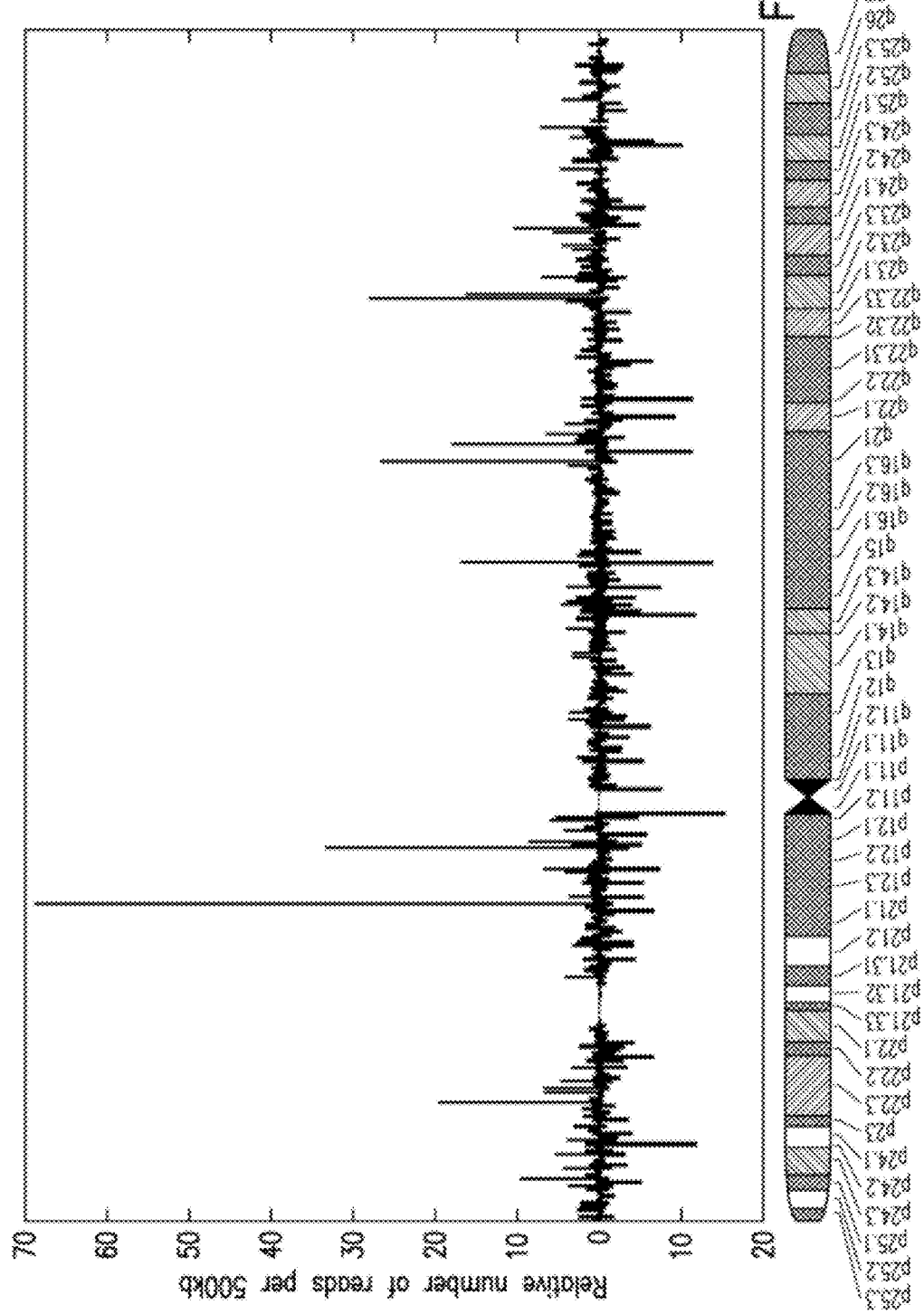
FIG. 14A-C: Number of reads per 500 kb relative to the sample median. Each plot shows a pair-wise comparison. Sequences within the centromeric and the polymorphic MHC regions could not properly align.
Figure 14B:
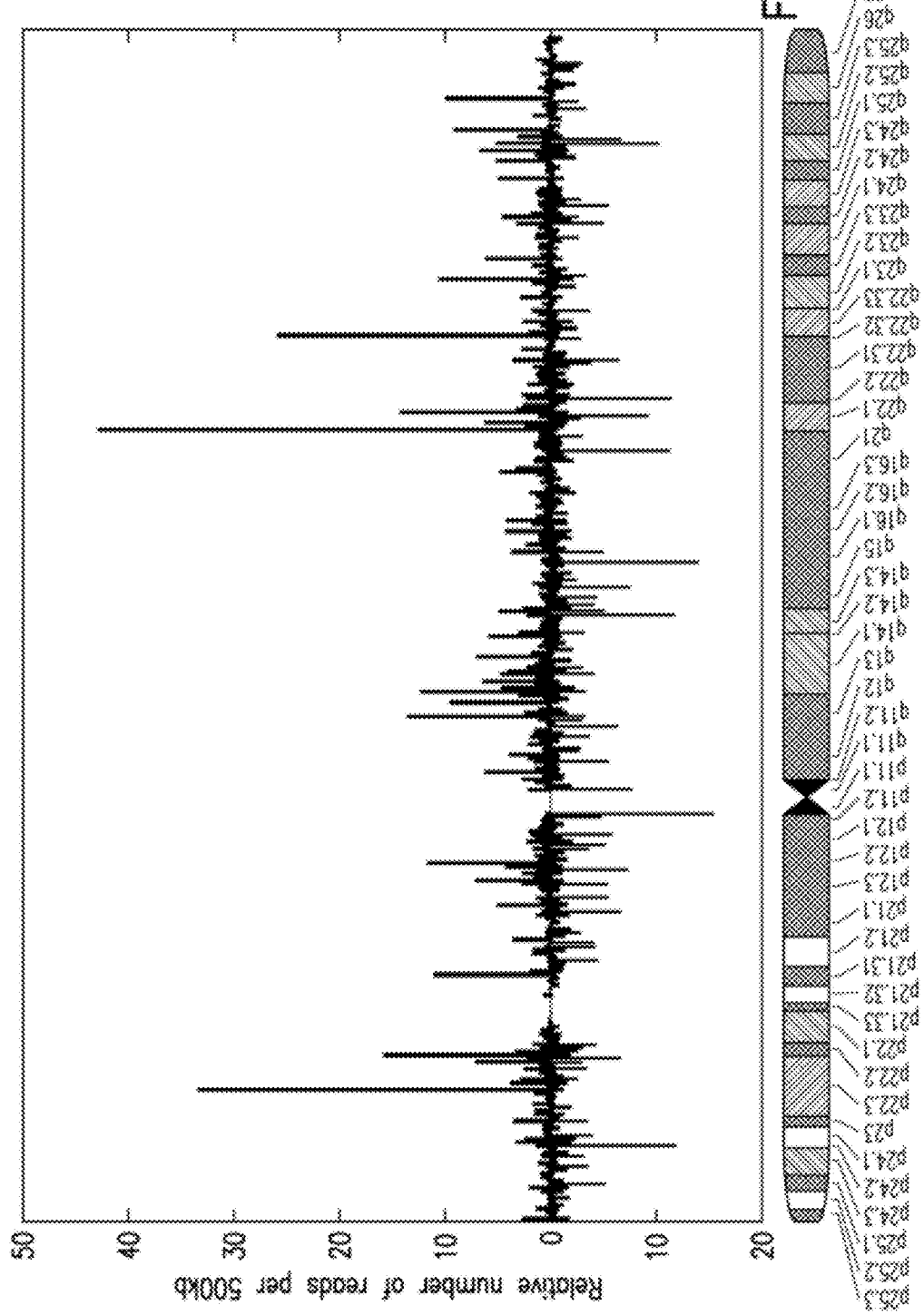
Figure 14C:
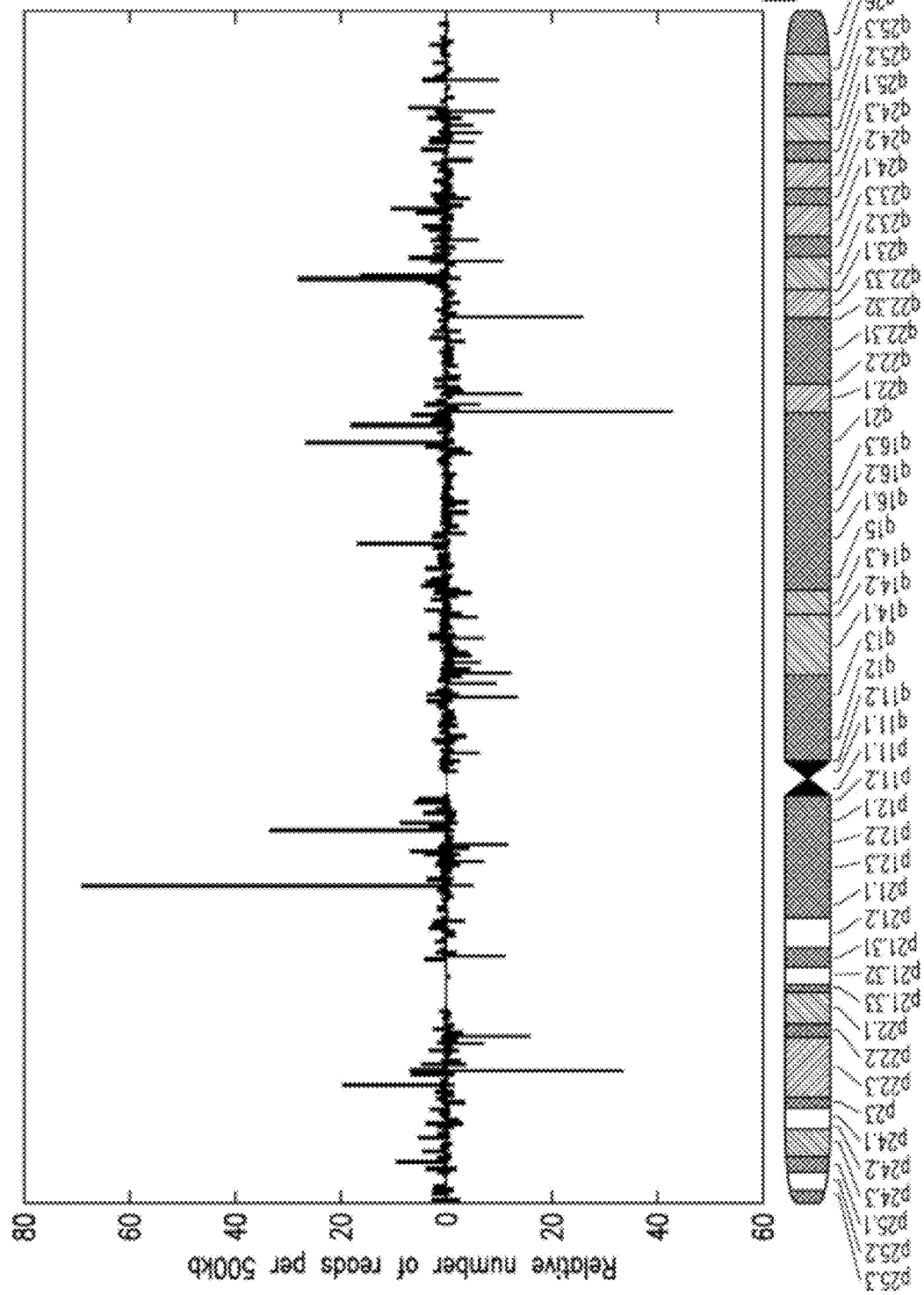
Figure 14D:
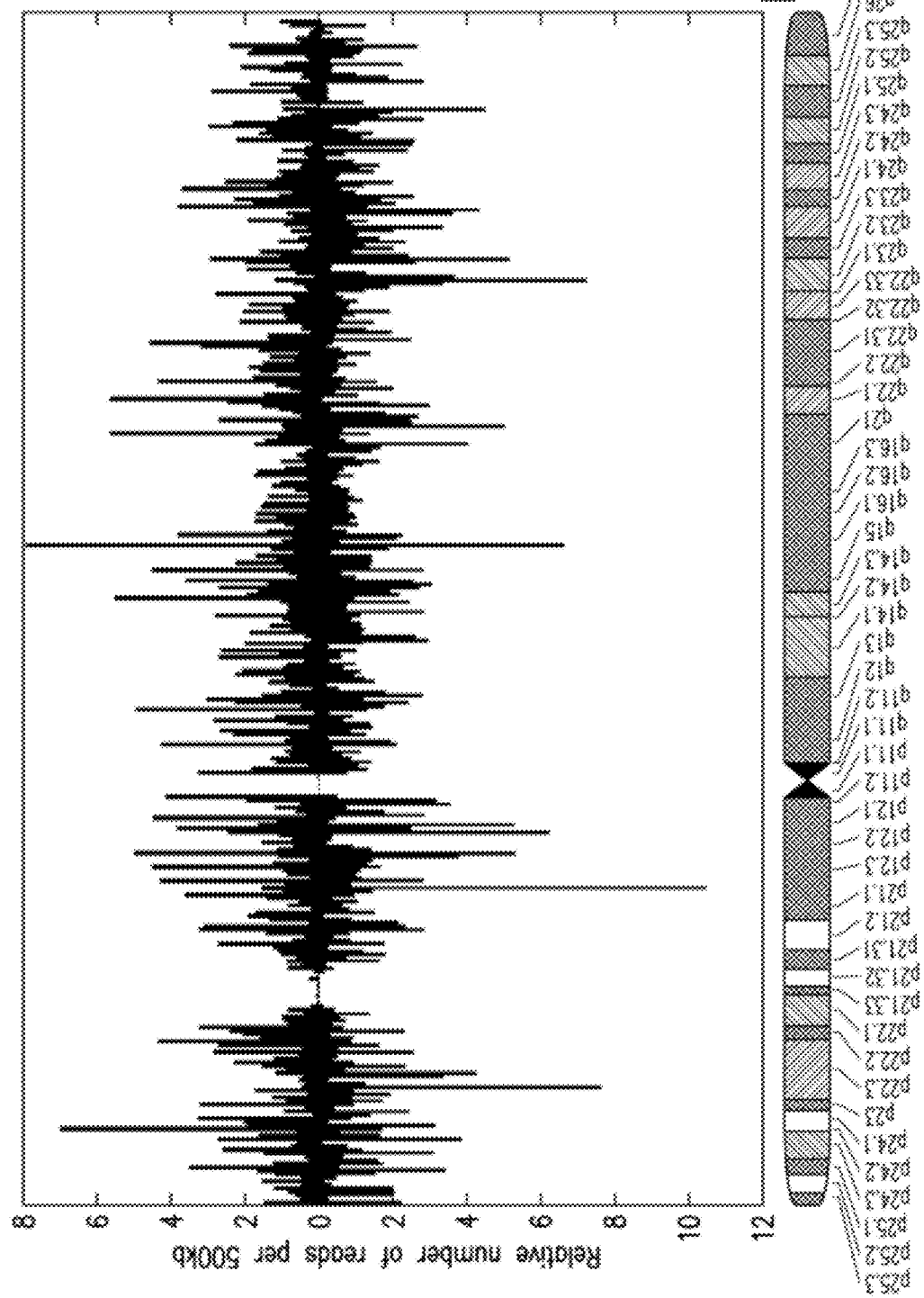
FIG. 14D-F: Same as above, except that redundant reads, potentially resulting from PCR during sequencing library preparation, were removed.
Figure 14E:
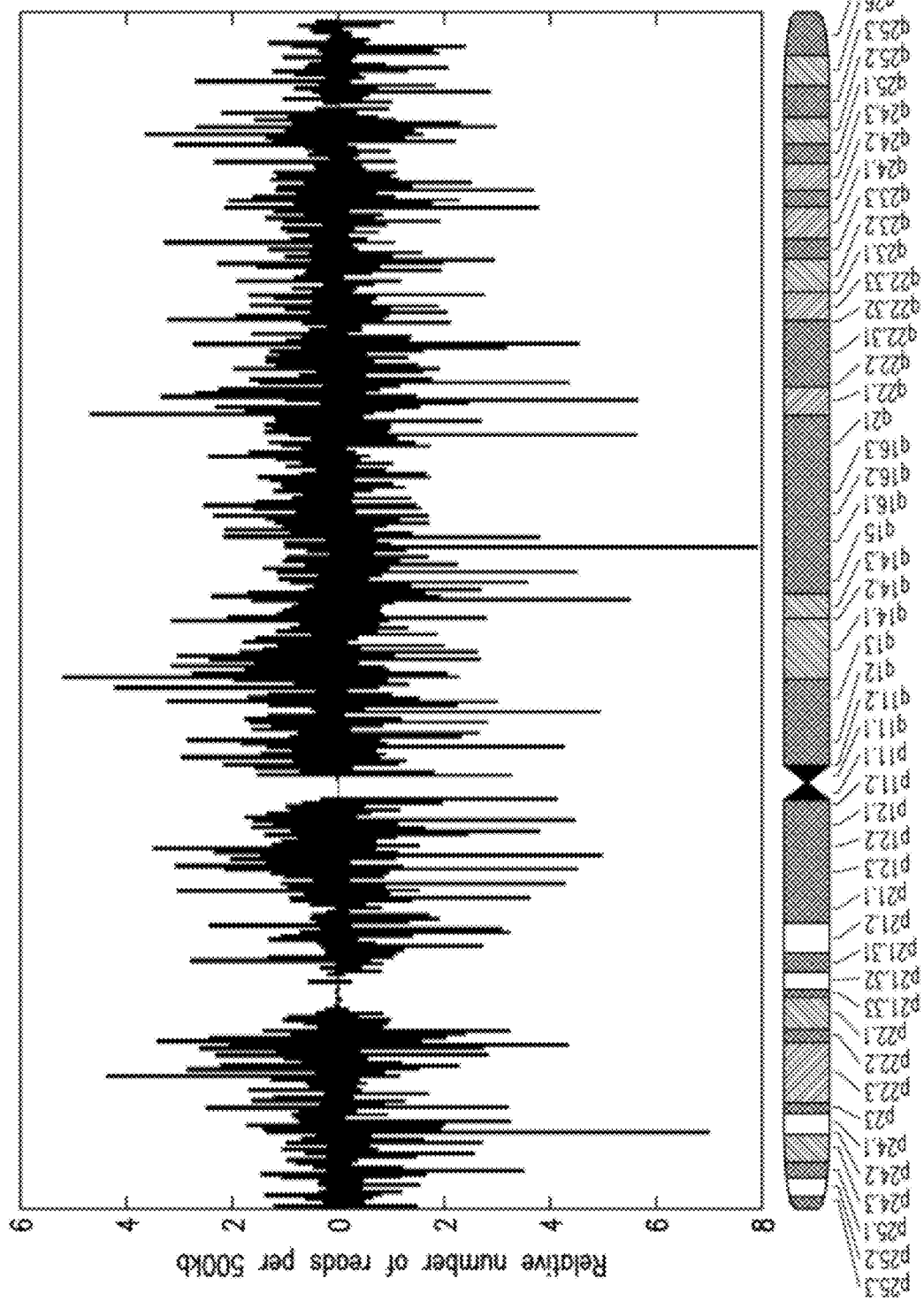
Figure 14F:
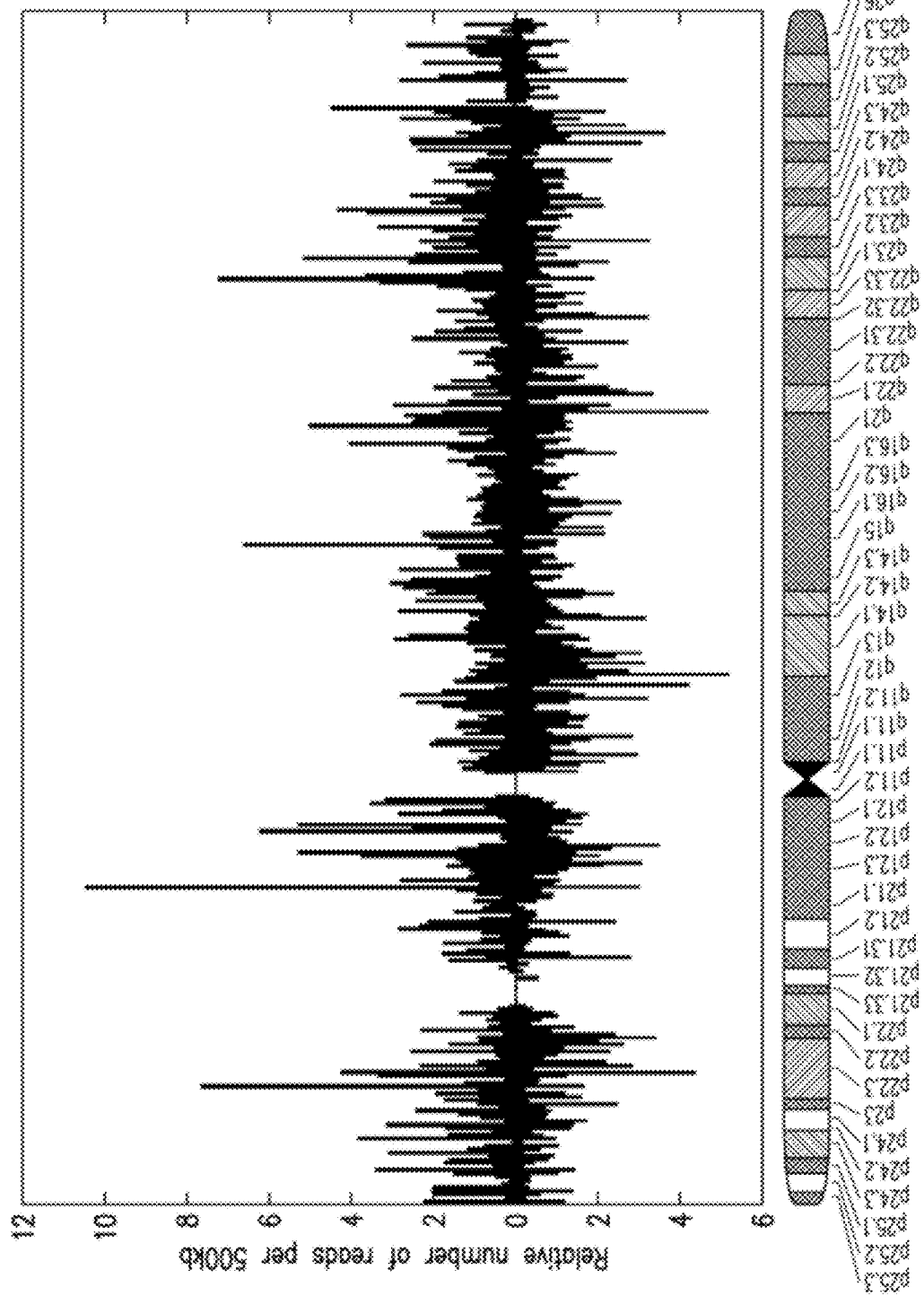
Figure 14G:
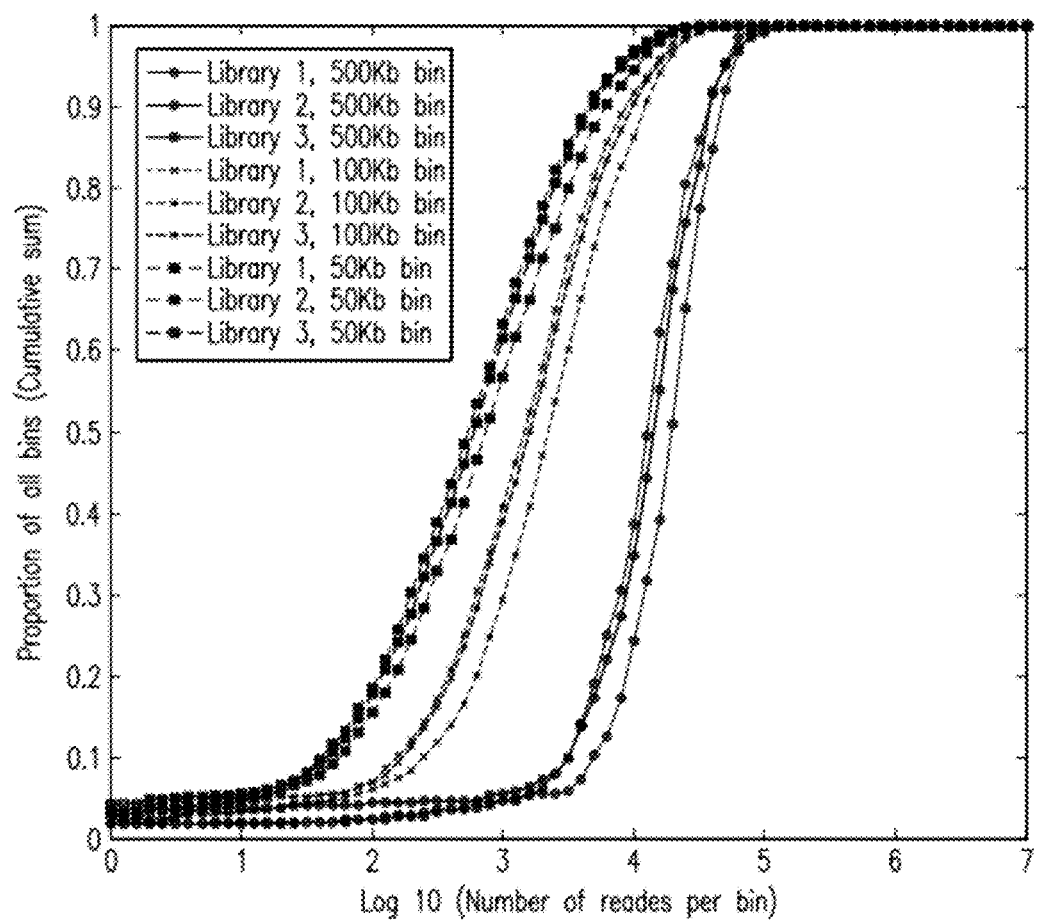
FIG. 14G: Cumulative distribution of the number of reads per bin, with bin size ranging from 50 kb to 500 kb.

About 46,000 heterozygous SNPs on chromosome 6 determined by previous genome sequencing were phased, including several of the medically relevant rare variants that were identified in the clinical annotation of the genome (Ashley et al., 2010). For alleles called by three or more fold coverage, the concordance rate of phasing by sequencing and phasing by genotyping arrays was 99.8% (FIG. 12). This indicates that allele calling with haploid materials can be achieved accurately with relatively low coverage, an advantage over conventional genotyping by sequencing which requires much higher fold coverage to guarantee accuracy of heterozygous SNPs.

The amplification of minute amount of materials using the polymerase phi29 has been known to cause amplification bias and formation of non-specific products that would undermine sequencing performance. The inventors previously demonstrated improved performance of whole-genome amplification of single bacterium by reducing amplification volumes by ~1000 fold using microfluidic devices similar to the one in this study (Marcy et al., 2007a; Marcy et al., 2007b). The present sequencing experiments show that non-specific products constituted a very small amount. For the two libraries that contained chromosome 6 materials only, the majority of the reads (~78%) aligned to chromosome 6 and only ~6% of reads did not give any hits against the human genome (FIG. 13). These experiments also provide a characterization of the amplification bias for human chromosome sized single molecule templates (FIGS. 13, 14). A large proportion of the sequenced reads were present more than once, and some reads were over-abundant. This was likely results of PCR during library preparation and cluster generation and not from phi29 amplification, as the long phi29 amplified products were enzymatically fragmented randomly before library preparation. In addition, the median insert size was less than 100 bp, while electrophoretic analyses of the libraries indicated the bulk of the sample was longer than 200 bp, suggesting that the shorter inserts that were redundant as a result of PCR during library preparation was enriched severely during cluster generation. Even with the removal of redundant reads, the distribution of reads across the chromosome was non-uniform, but the distribution of reads over most (~80-90%) of the chromosome in all sequenced copies was within 1.5 to 2 orders of magnitude (FIG. 14).

Comparison of Experimental Phasing and Statistical Phasing

Since haplotypes have been difficult to obtain experimentally, statistical inference of haplotypes has been widely used, especially in genome-wide association studies involving unrelated individuals. Yet very limited number of studies has been conducted to evaluate the accuracy of these computational approaches due to the lack of experimental data.

The experimentally obtained haplotypes of P0 offer a source of data to assess the performance of computational phasing. To compare statistical phasing methods with direct physical haplotyping in the absence of family information, the program PHASE (version 2.1) (Stephens et al., 2001; Stephens et al., 2003; Stephens et al., 2005), which is considered to have higher accuracy compared to other inference software (Stephens et al. 2005; International HapMap Consortium, 2005), was used to infer haplotypes in P0. Four regions on each autosomal chromosome (except chromosomes 4, 20, 21), each having 100 bi-allelic SNPs that were heterozygous in P0, were randomly chosen. Only SNPs with both alleles directly haplotyped and with perfect concordance with genotype determined by whole genome sequencing were selected. Each region covered a range of ~0.7 to ~3.3 Mb (average 2 Mb), with an average SNP to SNP distance of ~20 kb. The 176 phased CEU haplotypes in phase III of the Hap-Map project were used as known haplotypes for the inference. For each region, the reconstruction was run three times with the same default settings but different random seeds.

Figure 15A:
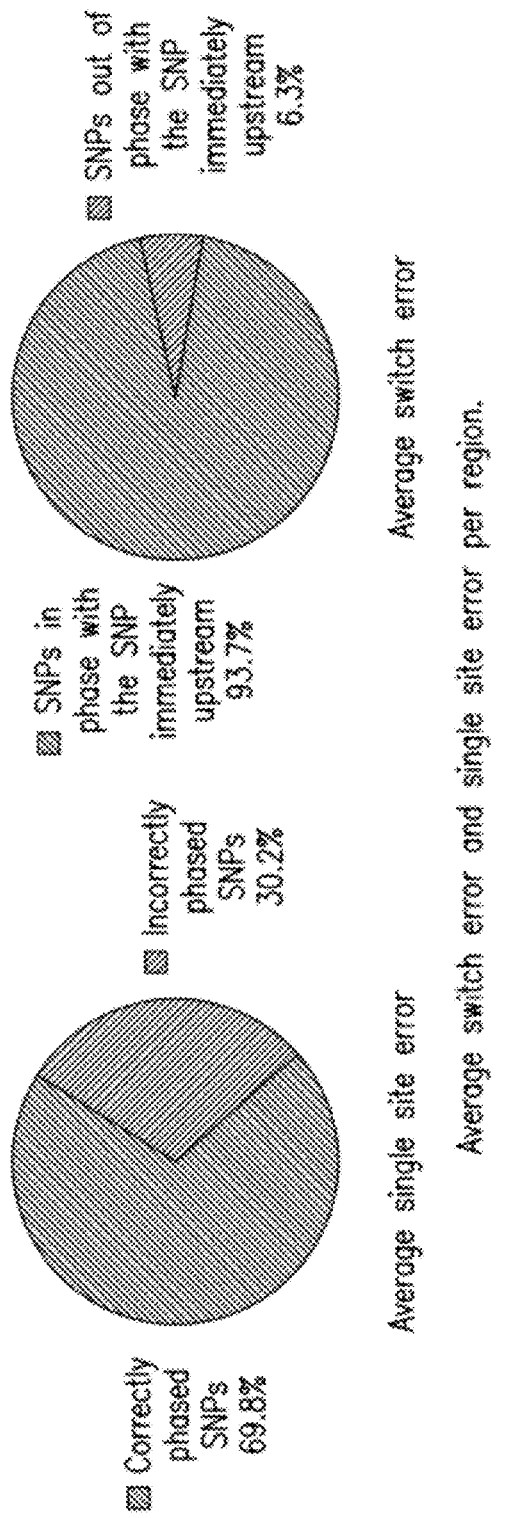
FIG. 15A-B. Comparison of experimentally determined phases of P0 and those determined by PHASE. Seventy-six regions on the autosomal chromosomes were randomly selected and statistically phased three times. Each region carried 100 heterozygous SNPs and spanned an average of ~2 Mb. Switch error rate was calculated as the proportion of heterozygous SNPs with different phases relative to the SNP immediately upstream. Single site error rate was calculated as the proportion of heterozygous SNPs with incorrect phase. A SNP was considered correctly phased if it had the dominant phase. For each region, the average values from the three runs were reported. The deterministic phases measured by DDP are taken as the ground truth.
Figure 15B:
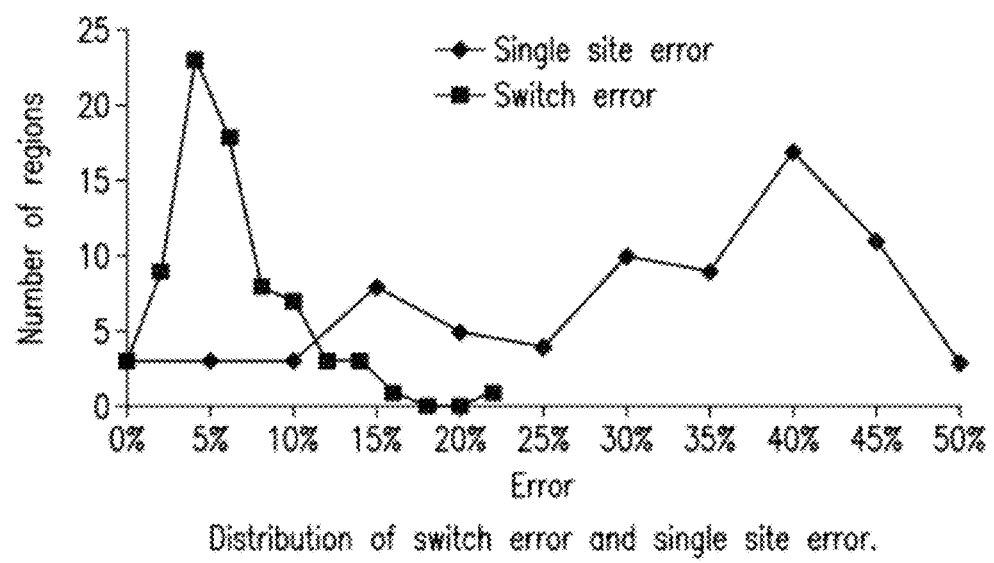
Figure 17A:
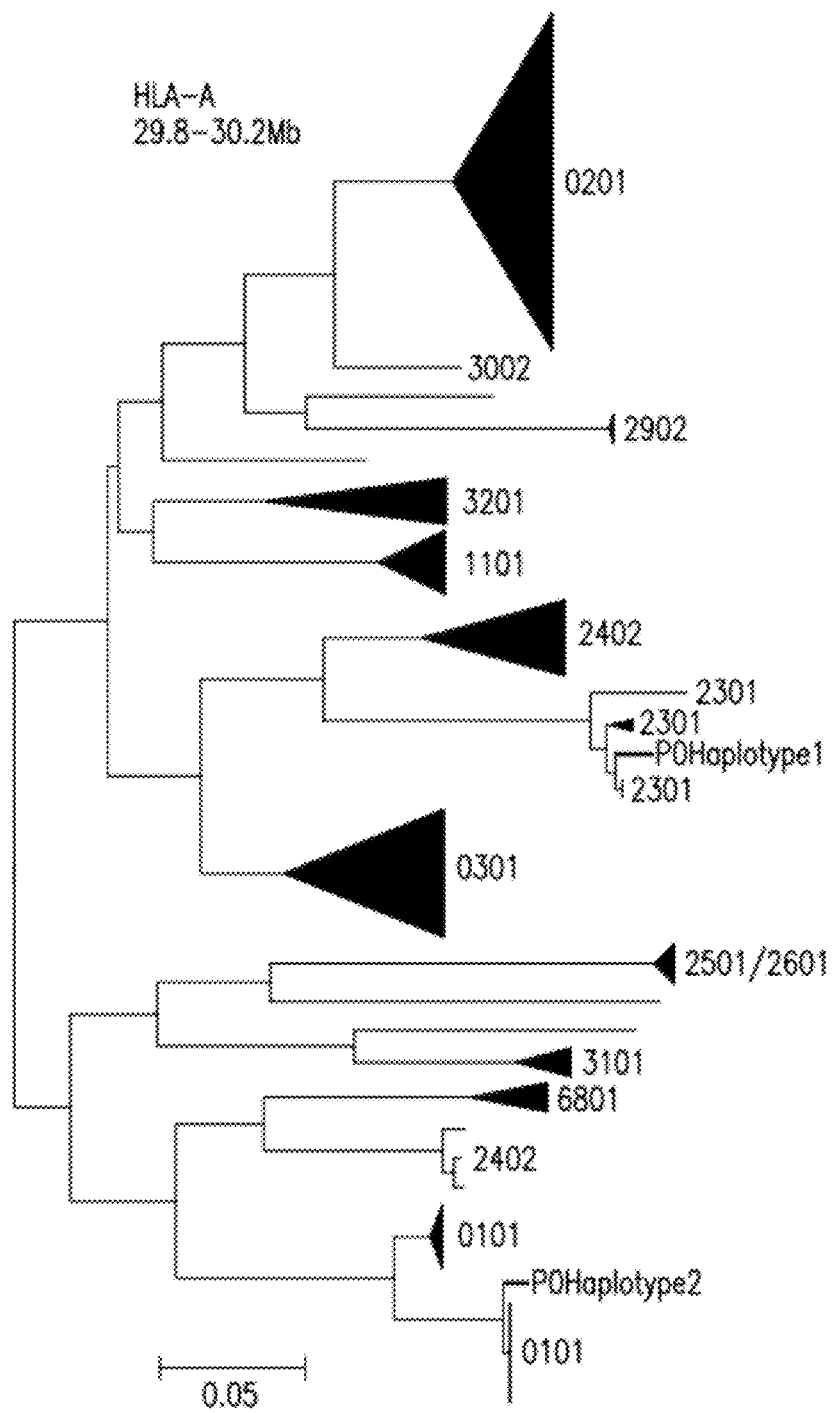
Figure 17B:
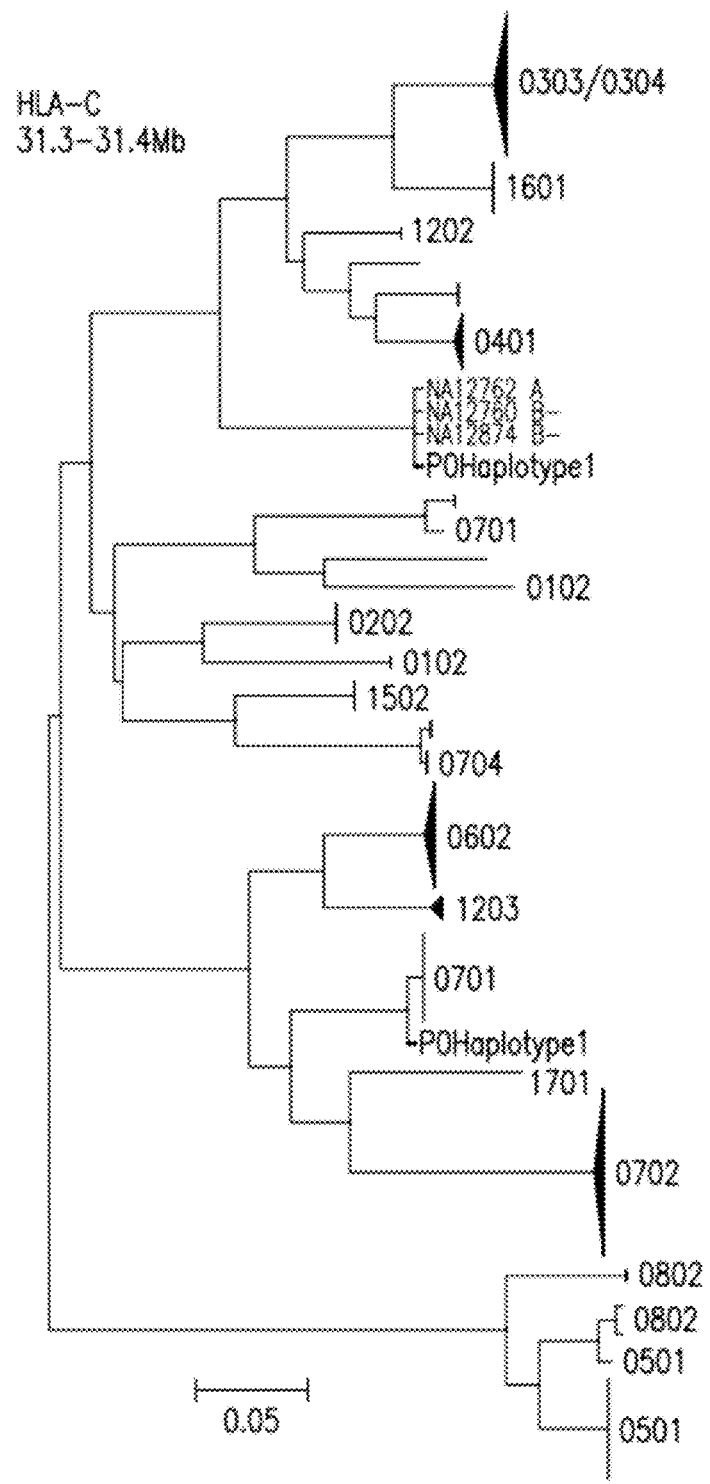
Figure 17C:
Figure 17D:
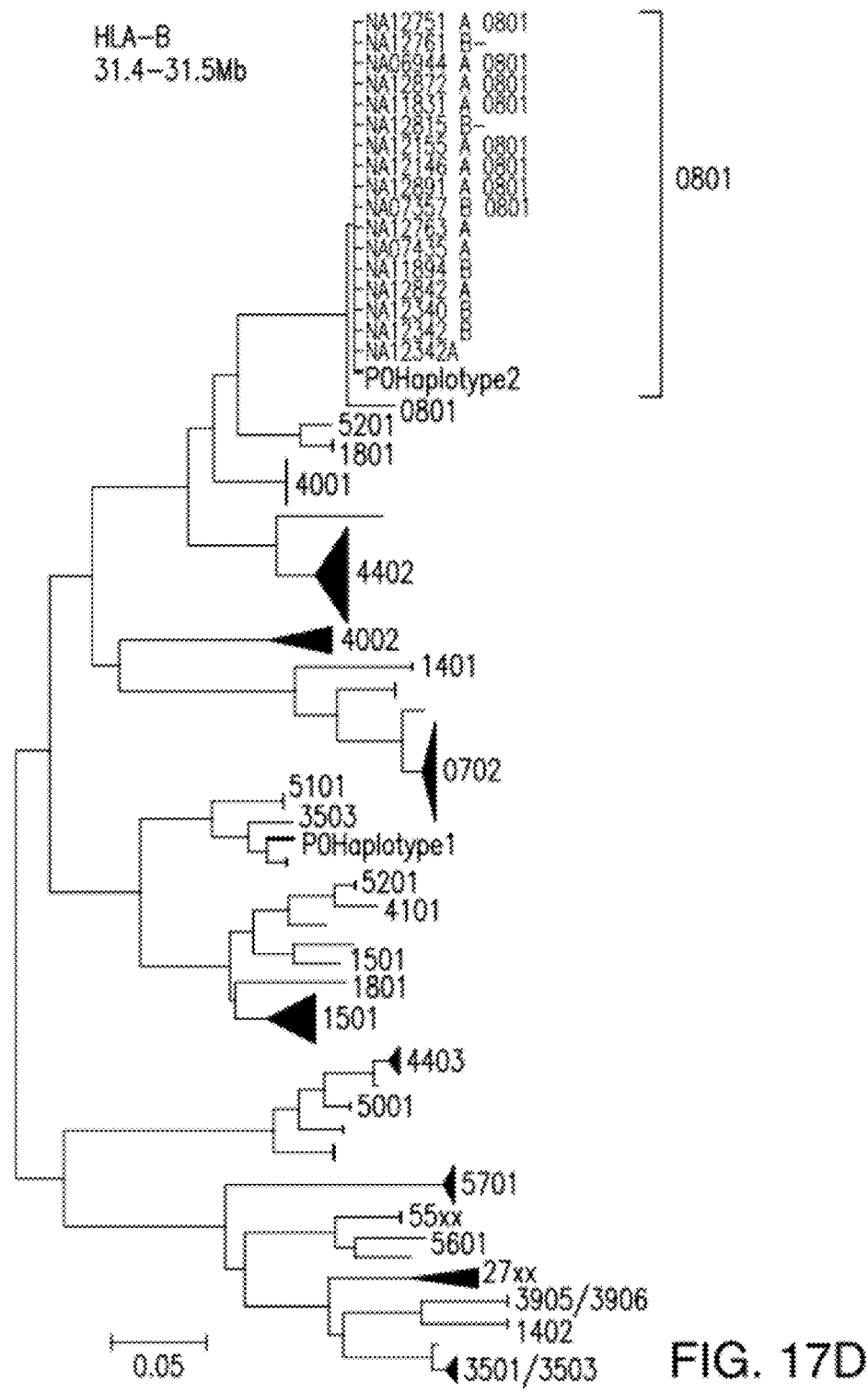
Figure 17E:
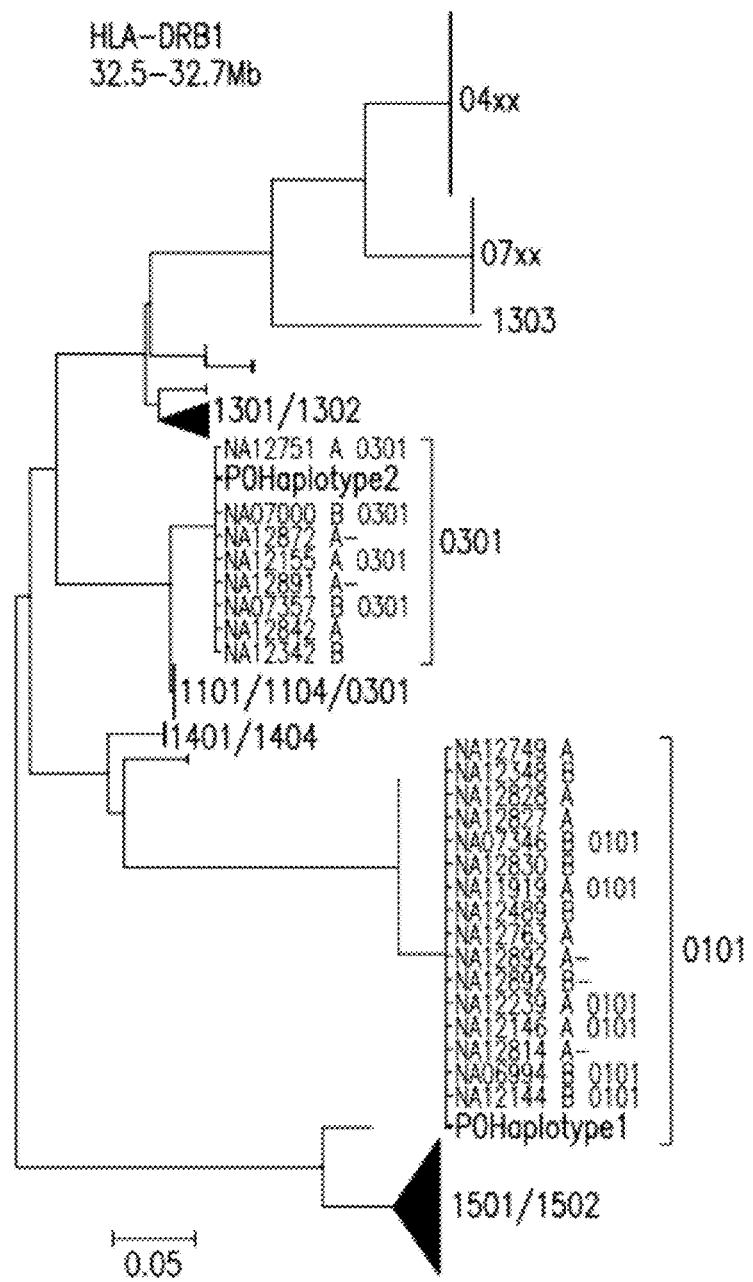
Figure 17F:
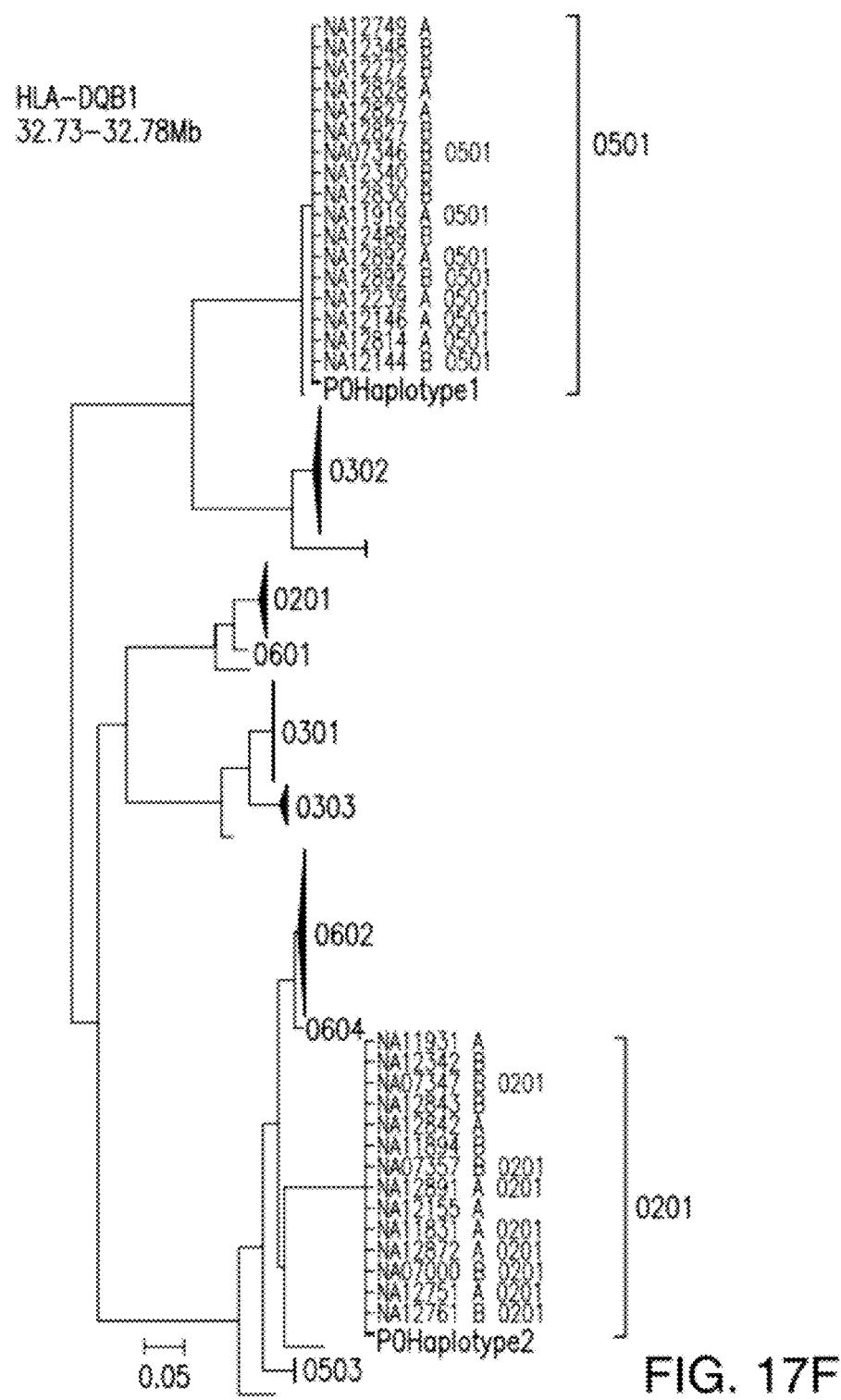

Alignment of statistically determined haplotypes and haplotypes determined by DDP an average of 6.3 block switches per region, calculated as the proportion of heterozygous SNPs with different phases relative to the SNP immediately upstream, per region. The average block size was ~260 kb. If one consider a SNP having the dominant phase to be correctly phased, an average of 30.2% of heterozygous SNPs were incorrectly phased (FIG. 15). These results agreed with two previous studies that compared statistical haplotype inference with real phases obtained from somatic cell hybrids and complete hydatidform moles, and illustrate the importance of direct experimental phasing especially over long ranges and when family data is not available (Kukita et al., 2005; Andres et al., 2007).

Phasing of Heterozygous Deletions

All 8 heterozygous deletions that had been detected by genome sequencing of P0 and previously validated by digital PCR (Pushkarev et al., 2009) were phased (FIG. 9), using data from genotyping arrays and real-time PCR. For real-time PCR, the assays were the same as those used in the study of Pushkarev et. Al, 2009. Results from all three platforms among all three single cells were consistent.

Direct Determination of the HLA Haplotypes

An important application of DDP is the determination of the HLA haplotypes within an individual. The HLA loci are highly polymorphic and are distributed over 4 Mb on chromosome 6. The ability to haplotype the HLA genes within the region is clinically important since this region is associated with autoimmune and infectious diseases (Shiina et al., 2009) and the compatibility of HLA haplotypes between donor and recipient can influence the clinical outcomes of transplantation (Petersdorf et al., 2007). Yet molecular techniques to measure HLA haplotypes in individuals are still limited (Guo et al., 2006).

To determine the HLA haplotypes, the HLA allele at each locus has to first be determined. This is usually achieved by costly direct sequencing. Here, a simpler approach was used to determine the allele at each HLA locus by taking advantage of the experimentally determined SNP haplotypes of P0 and the availability of SNP haplotypes (from phase III of the HapMap Project) and HLA typing data (from the study of de Bakker et. Al. (de Bakker et al., 2006) at http://www.inflammgen.org) of a panel of CEU individuals. Specifically, a total of 176 phased CEU haplotypes together with experimentally phased haplotypes of P0, were used to construct neighbor-joining trees at each of the six classical HLA loci on chromosome 6. The coordinate boundaries of which haplotyped SNPs were used for each locus are presented in FIG. 17. The number of SNPs used for HLA-A, HLA-B, HLA-C, HLA-DRB-, HLA-DQA, and HLA-DQB were 420, 139, 89, 59, 14, and 34, respectively. Allele sharing distances was computed for each pair of haplotypes as $$\frac{1}{n}\sum_{i=1}^{n} d_i,$$

where n is the number of loci and $d_i$ equals 0 for matched alleles and 1 for unmatched alleles at the ith SNP locus. Trees were constructed using MEGA 4.1 (Tamura et al., 2007). Since similar HLA alleles carry similar SNP haplotypes that cluster together on a tree, the allelic identity of each homologous chromosome of P0 at each HLA locus could be determined by the allelic identities of its nearest neighbors in the tree (FIG. 17).

The combination of the alleles at each HLA locus determined by phylogenetic analyses agreed with direct HLA typing of genomic DNA. Combining the results form all loci yielded the two HLA haplotypes of P0 (FIG. 17). One of the HLA haplotypes is the 8.1 ancestral haplotype, which is one of the most frequently observed haplotypes in Caucasians and is associated with elevated risks of immunopathological diseases.

A few technical improvements in the DDP approach benefit high-throughput experimentation.

Firstly, the identification and capture of a single mitotic cell in a suspension is currently a manual process that requires a skillful operator. This step can be potentially automated by labeling cells with fluorescently tagged mitotic specific antibodies (such as anti-phosphohistone-H3) and by incorporating computer vision.

Secondly, metaphase chromosomes tend to stick together and form clumps after enzymatic digestion of cytoplasm, leading to the presence of multiple chromosomes in a chamber. Although homologous copies of most chromosomes in a cell are usually separated in the current setting, the ideal case would be to separate each and every chromosome in a cell, which would benefit the identification of chromosomal rearrangements and the phasing of copy number variants and repeats that can potentially be present on different non-identical chromosomes. In the current protocol, RNases were used to remove excess cytoplasmic RNA that might contribute to the stickiness of chromosomes but additional improvements in the chromosome separation chemistry would be desirable.

Thirdly, amplification of minute amount of materials using the polymerase phi29 has been known to cause formation of non-specific products and amplification bias (Lasken 2007). The presence of non-specific products is not relevant when SNP arrays are used for phase determination, but is undesirable when the materials are to be sequenced, resulting in a reduction of throughput of useful information. By reducing amplification volume from 50 microliter of a bench-top reaction to 20 nanoliter of a microfluidic chamber, very little non-specific products in the amplified materials was detected, as revealed by the sequencing results of chromosome 6 (FIG. 13). Amplification bias, on the other hand, remains present (FIG. 14), and increases the required sequencing depth in order to obtain coverage of the entire chromosome. Since amplification bias appeared to be mostly random (FIG. 14), a potential solution is to pool amplified products from multiple copies of the same chromosome homolog from multiple single-cell experiments.

Lastly, the amplified materials from each microfluidic chamber can potentially be barcoded. Molecular barcoding are short DNA tags and has been commonly used in high-throughput multiplex sequencing. Barcoding amplified materials from each chamber can reduce the number of collection outlets from the current design of one outlet per chamber to one outlet per device. Because collection outlets are macro features, the reduction in the number of outlets enables more micro features to be incorporated per chip area. Thus, potentially more single cells can be processed on a device and thus the throughput would be improved.

Single Cell Aneuploidy Detection

The microfluidic device is also capable of determining the karyotype of a single cell and detecting chromosomal rearrangements within a single cell, since the chromosomes remain intact during separation and the number of each chromosome can be digitally read out from the counts of chambers containing amplified materials derived from each particular chromosome. In the experiments described above, in most cases, two chambers displayed positive signals for each autosome-specific marker, and one chamber displayed signal for each of the sex chromosomes in males. The present approach has important applications in areas where studying the genomes of single cells is beneficial. Examples include pre-implantation genetic diagnosis, noninvasive prenatal diagnosis involving rare circulating fetal cells in maternal blood, and cancer research relating to the study of heterogeneous cell population in tumors and rare circulating tumor cells.

Towards Complete Personal Genome Sequencing

To properly study a human genome, the conventional approach of sequencing the diploid genome as a mixture should be supplemented or replaced by techniques that can examine each of the haploids separately. This is especially important for short-read sequencing technologies since assembling short reads is challenging computationally. To date, all studies describing personal genomes sequenced using these technologies relied heavily on the reference human genome for mapping short reads and focused mostly on the identification of novel SNPs and copy number variants (Wheeler et al., 2008; Bentley et al., 2008; Ahn et al., 2009; Kim et al., 2009; Wang et al., 2008; Pushkarev et al., 2009; Schuster et al., 2010). Not only did those personal genomes suffer from imperfections such as gaps, miscalled bases, and difficulties in determining large-scaled structural variation, they failed to address unique haploid structure of homologous chromosomes. Only a handful of studies included statistical haplotype construction from short read sequencing data in their analyses (Wang et al., 2008).

Whereas the bulk of the experiments described here focused on direct deterministic phasing of ~1 million variants accessible by genotyping arrays, DDP can be utilized to phase all variants in the genome. Direct deterministic phasing of tagSNPs present on the genotyping arrays inherently provides phasing information for common variants that are in strong linkage disequilibrium with the tagSNPs. For rare variants, the most straightforward approach is to sequence the amplified materials from separated chromosomes. This can yield phasing information for all genomic variants, including the rare and private ones, which are absent on standard genotyping arrays. The approach should enable complete sequencing and assembly of each of the individual chromosomes in a normal or diseased genome, including the direct phasing of all kinds of copy number variants (in addition to heterozygous deletions shown in the above experiments) and the detection of chromosomal rearrangements and structural variants.

The present haplotyping technique is not limited to human genomes. The study of the genomes of all other organisms should benefit from this approach as well.

Conclusion

Conventional experimental methods of studying the human genome have been limited by the inability to independently study each of the homologous copies of the chromosomes. These haplotypes are important features of the genome but in general cannot be easily determined. Described above is the development of a microfluidic device that is capable of separating and amplifying homologous copies of each chromosome within a single human metaphase cell. SNP array analysis and direct sequencing of amplified materials originating from single copies of chromosomes within single cells enabled completely deterministic whole-genome personal haplotyping. Several practical applications of this approach were demonstrated, including direct observation of recombination events in a family trio, deterministic phasing of structural variation in individuals, and the direct measurement of the HLA haplotypes of an individual.

The present work bridges the gap between traditional cytogenetics and modern molecular techniques. The former allows one to visually inspect individual chromosomes in a single cell under a microscope but has limited resolution, while the later enable us to examine single DNA bases but does not efficiently permit the study of individual cells and chromosomes. It allows for the complete sequencing of the two haploid genomes of an individual, which would become essential in the era of personalized genomics and medicine. It also answers important questions in biology, such as gene regulation and inter-individual variability. The technique of physically separating chromosomes on a microfluidic device can be extended to the study of the epigenetic differences between the homologous chromosomes within an individual.

Example 2

The inventors demonstrate here a practical technique that enables the determination of a fetal genome noninvasively from maternal blood. The strategy relies on the knowledge of genome-wide chromosome length haplotypes of the parents obtained using a recently reported microfluidic device, and makes use of high-throughput sequencing as a molecular counting tool to determine which of the parental haplotypes are over-represented in maternal plasma DNA due to the contribution from the fetal genome. Except at regions where recombination of parental chromosomes have occurred, the fetal genome can be unambiguously deciphered from maternal plasma with shallow sequencing when haplotype information of both parents is known, and additional sequencing effort allows the fetal genome to be determined substantially when only maternal information is available. The ability to determine the fetal genome from maternal plasma facilitates the diagnosis of all inherited genetic diseases.

Introduction

It has been known for several decades that fetal genetic materials exist in maternal blood. The presence of these materials, either in the form of intact fetal cells or cell-free fetal DNA, has enabled the development of a number of noninvasive prenatal diagnostic techniques. However, the diagnosis of fetal genetic diseases using fetal materials from maternal blood is not trivial because fetal materials only constitute a small amount relative to the maternal counterpart.

The inventors have demonstrated that fetal aneuploidy can be measured noninvasively by shotgun sequencing cell-free DNA in maternal plasma. The technique was based on counting the number of sequence tags originating from each chromosome in maternal plasma to determine if any chromosome is over- or under-represented as a consequence of a pregnant mother carrying an aneuploid fetus. This technique has since been verified by multiple groups and various scale.

Recently, the inventors proposed using molecular counting to analyze the entire fetal genome noninvasively from maternal plasma. While aneuploidy detection relies on counting relative representation each of the 23 (female) or 24 (male) chromosomes, the determination of the fetal genome proposed relies on counting the relative representation of parental chromosomes (i.e., the four different parental haplotypes of the same chromosome). In this work, the use of a recently developed microfluidic device, which enables the determination of whole-genome parental haplotypes, was combined with shotgun sequencing of maternal plasma DNA, to show for the first time that the fetal genome could be deciphered practically from maternal plasma. Even when paternal information is not available, the inventors were able to determine the fetal genome substantially. The ability to determine the fetal genome from maternal plasma would subsequently facilitate the diagnosis of all inherited genetic diseases.

Methods

Sequencing of a Mixture Containing DNA from a HapMap Duo

Genomic DNA extracted from the cell lines GM12892 (mother) and GM12878 (daughter) were mixed with a mass ratio of 7:3 (i.e., daughter's contribution to the mixture ($\epsilon$) was 30%). The mixture was fragmented by sonication to a size range <300 bp. DNA fragments were end-polished, A-tailed, and ligated with the full-length adaptor for Illumina sequencing. The final PCR step in the library preparation workflow was omitted (Kozarewa et al., 2009). The library was quantified by digital PCR before loading on to the flow cell (White et al., 2009). The library was shotgun sequenced on one lane of the flow cell on a GAII. Image analysis and base calling were performed using Illumina's data analysis pipeline 1.6. The reads were aligned to the human genome (hg18) using the algorithm ELAND in the Illumina's data analysis pipeline. A list of allele calls at each base position along each chromosome was obtained using Illumina's CASAVA software (version 1.6). Only alleles called with quality scores >30 were used.

Whole-genome Haplotyping of Patient Subjects

The subject was recruited to the study under approval of the Internal Review Board of Stanford University. Postpartum maternal whole blood was collected into sodium heparin coated Vacutainer. Postpartum blood was used in this study because blood samples collected during pregnancy were not cyropreserved as required for culture. One milliliter of whole blood was cultured with PB Max Karyotyping medium for 4 days. Direct deterministic phasing (DDP) was performed on 3 to 4 single cells.

Whole-genome Genotyping of the Study Subjects and their Infants

Genomic DNA was extracted from 200 μl of postpartum maternal blood and 200 μl cord blood using QIAamp Blood Mini Kit (Qiagen), and subjected to genome-wide genotyping on Illumina's Omni1-Quad genotyping array.

Whole-genome Shotgun Sequencing of Maternal Plasma

Maternal blood was collected into EDTA coated Vacutainers. Blood was centrifuged at 1600 g for 10 min at 4° C., and the plasma was centrifuged again at 16000 g for 10 min at 4° C. to remove residual cells. Cell-free DNA was extracted from plasma using QIAamp Blood Mini Kit (Qiagen). DNA was extracted from 1 to 2 ml of plasma, and subsequently converted into Illumina sequencing libraries. Sequencing was performed on the GAII and the HiSeq instruments (Table 3). Sequences were aligned to the human genome (hg19) using CASVA version 1.7.0. Only alleles called with quality scores >30 were used. In addition, only alleles that match previously reported variants in dbSNP were used for analyses.

Imputation of Untyped Loci of the Maternal Genomes

Imputation was performed using Impute v1 (Marchini, J. 2006), using the—haploid option. For the mock sample, untyped loci of the mother and father were imputed using the 1000 Genome Project pilot phase data of the CEU population, based on the ~800,000 markers phased by DDP. For the clinical samples, imputation was performed using August 2010 data from the 1000 Genome Project of the CEU population. For maternal genomes, imputation was based on the ~1 million markers phased by DDP. For paternal haplotypes, imputation was based on non-maternal alleles observed in shotgun sequencing data. Imputation was performed in 5 Mb segments along each chromosome.

Digital PCR Confirmation of Fetal Inheritance of DiGeorge Associated Deletion

The inheritance of the maternal haplotype carrying the deletion on chromosome 22q11.1 by the fetus of Patient 2 was independently confirmed by digital PCR performed on cord blood genomic DNA. The number of single molecule amplification of an amplicon within the deletion region was compared to that of an amplicon on chromosome 1. A ratio of ~0.5 indicated that the maternal deletion was inherited.

Determining Locations of Recombination

The true recombination events on the maternally inherited sets of chromosomes were determined by comparing the genotype of the fetus and to the allele on each of the two maternal haplotypes at locations where the fetus is homozygous and the mother is heterozygous. In maternal plasma, a cross-over event between the two maternal haplotypes giving rise to the maternally inherited chromosome in the fetus was called if in plasma DNA if two criteria were met: 1. A continuous increase or decrease in the relative representation of haplotype 1 over haplotype 2 (i.e., the expression $N_{p1}/n_{p1} - N_{p2}/n_{p2}$ and the variables were explained in the main text), accompanied by a sign change, as one scanned in the direction from the p arm to the q arm of a chromosome. 2. The sign of the expression remained the same for the majority of the sliding bins 5 Mb downstream, based on the fact of cross-overs are rarely close to each other (positive interference).

Estimating Fetal DNA Fraction from Maternal Plasma Sequencing

Fetal DNA fraction was estimated in two ways: 1. From the over-representation of one of the maternal haplotypes. 2. From the presence of paternally inherited haplotype. Precisely, fetal DNA fraction ($\epsilon$) was estimated as $2x/(2-x)$, where x is the median absolute value of the expression ($N_{p1}/n_{p1} - N_{p2}/n_{p2}$) for all bins evaluated on either the maternal haplotypes or the paternal haplotypes, divided by the average marker density of the two maternal haplotypes.

Results and Discussion

Principle for Noninvasive Determination of the Fetal Genome from Maternal Plasma In maternal plasma, the maternal genome and fetal genome are mixed together in the form of short, cell-free DNA. Since the fetal genome is a combination of the four parental chromosomes, or haplotypes, as a result of random assortment and recombination during meiosis, for each genomic region, three haplotypes exist in maternal plasma: the maternal haplotype that is transmitted to the fetus, the maternal haplotype that is not transmitted, and the paternal haplotype that is transmitted. If the relative copy number of the untransmitted maternal haplotype is 1-$\epsilon$, the relative copy number of the transmitted maternal haplotype is 1 and that of the transmitted paternal haplotype is $\epsilon$, where $\epsilon$ is the fetal DNA fraction (FIG. 1). Therefore, the transmitted parental haplotypes are over-represented compared to the untransmitted ones. By measuring the relative amount of parental haplotypes, one can deduce the fetal genome.

The four parental haplotypes are differentiated by the alleles specific to each of them, termed 'markers', and the representation of these parental haplotypes in maternal plasma is determined by counting the number of these markers.

The markers that define each of the paternal haplotypes are the alleles that are present in one paternal haplotype but not in the other paternal haplotype nor the two maternal haplotypes. The inheritance of paternal haplotypes is determined by counting the markers specific to each of the paternal haplotypes; only the alleles on the transmitted paternal haplotypes would be present in maternal plasma (FIG. 1).

The inventors developed a microfluidic device that is capable of separating and amplifying homologous copies of each chromosome within a single human metaphase cell. SNP array analysis of amplified materials obtained from single cells enabled them to achieve completely deterministic whole-genome personal haplotypes of four individuals, including members of a CEU trio and an unrelated European individual of up to ~96% of all assayed SNPs at ~99.8% accuracy. Strictly speaking, the markers that define each maternal haplotype are the alleles that are present in one maternal haplotype but not in the other maternal haplotype nor the two paternal haplotypes. However, since it is rare that two unrelated persons share the same long-range haplotype, that is, a haplotype much longer than the usual length of haplotype blocks observed in the population (~100 kb), the presence of alleles contributed by the transmitted paternal haplotype at these loci would not interfere with the measurement of representation of maternal haplotypes as long as the haplotype being considered is sufficiently long and thus the inventors choose to use all the maternal heterozygous loci to define the two maternal haplotypes (FIG. 1). This choice substantially increases the number of maternal markers that can be used and therefore maximizes the available information given a genome equivalent of DNA sampled.

The inheritance of maternal haplotypes is determined by counting the markers that define each of the maternal haplotypes and by comparing the representation of the two haplotypes; the transmitted maternal haplotype would be over-represented by an amount of $\epsilon$. Such over-representation, however small, would be revealed provided that the counting depth is sufficient. Given two distributions of Poisson random variables, one with mean of N, and the other with mean of N(1-$\epsilon$), where N is the cumulative sum of the count of markers of all usable markers on the transmitted maternal haplotype, the sampling requirement of N to differentiate the two distributions can be estimated from the following expression, using the normal approximation of the Poisson distribution for large values of N:

$$\frac{N - N(1-\varepsilon)}{\sqrt{N(1-\varepsilon) + N}} = \frac{N\varepsilon}{\sqrt{N(1-\varepsilon) + N}} \geq z_\alpha$$

where $z_\alpha$ is the z-score associated with the confidence level of $\alpha$. Thus, $$N \geq \frac{z_\alpha^2 (2-\varepsilon)}{\varepsilon^2}$$

Table 2 present the estimated requirement of N for different values of fetal DNA fraction ($\varepsilon$) and level of confidence ($\alpha$). For molecular counting using shotgun sequencing, the required genome coverage is proportional to the ratio of N and the number of usable markers within each haplotype (n). Given that the number of cross-over events is limited in a meiosis and the number of breaks in the original parental chromosomes is small, if each of the parental chromosomes is fully phased, a large number of usable markers per haplotype is available and thus shallow sequencing would be sufficient to determine the fetal genome from maternal plasma.

TABLE 2

Estimated sampling requirement (N) for noninvasively determining the inheritance of maternal haplotypes. N refers to the cumulative sum of the allele count of all usable markers on the transmitted maternal haplotype.

| Fetal fraction | $z_\alpha$ (95%) | $z_\alpha$ (99%) | $z_\alpha$ (99.9%) |
|---|---|---|---|
| 0.01 | 76448 | 132462 | 215400 |
| 0.02 | 19016 | 32949 | 53579 |
| 0.03 | 8409 | 14570 | 23693 |
| 0.05 | 2996 | 5192 | 8443 |
| 0.1 | 730 | 1265 | 2057 |
| 0.15 | 316 | 547 | 890 |
| 0.2 | 173 | 300 | 487 |
| 0.25 | 108 | 186 | 303 |
| 0.3 | 73 | 126 | 204 |
| 0.35 | 52 | 90 | 146 |
| 0.4 | 38 | 67 | 108 |
| 0.45 | 29 | 51 | 83 |
| 0.5 | 23 | 40 | 65 |

Proof of Principle Experiment: Mixture of HapMap Duo (Mother and Child)

The inventors first simulated maternal plasma DNA by preparing a mixture of genomic DNA extracted from the cell lines GM12892 (mother) and GM12878 (daughter), with a mass ratio of 7:3 (i.e., daughter's contribution to the mixture ($\varepsilon$) was 30%). The mixture was sequenced on Illumina platform and yielded 0.25× coverage of the haploid genome. These two cell lines were used because the chromosomes of the three members of this family trio were fully phased by a whole-genome haplotyping method developed recently, termed 'direct deterministic phasing (DDP)' (Fan et al., 2011) that involves amplification of dispersed metaphase chromosomes from a single cell on a microfluidic device.

Since the haplotypes were phased from one end of the chromosome with high density of loci, the inventors could confidently impute many untyped loci on each of the parental chromosomes based on these loci using data from the 1000 Genome Project. The accuracy of imputation was high (>98%) based on leave-one-out validation carried out internally of the imputation program. Imputation increased the number of loci that could be used for haplotype counting by several folds and therefore lowered the sequencing requirement for counting.

The inheritance of maternal haplotypes by the child was determined by the over-representation of one maternal haplotype over the other. Each chromosome was divided into 10 Mb bins, with sliding step of 100 kb. The bin size was chosen such that the total number of count of markers within the bin was at least that required to overcome counting noise (Table 2, FIG. 20). Because the density of markers for chromosome X haplotyped (i.e., present on the Illumina array) was only half of that on the autosomes, the bin size was increased accordingly (Table 3). For each bin, the relative haplotype representation was calculated using the expression ($N_{p1}/n_{p1} - N_{p2}/n_{p2}$), where $N_{p1}$ is the number of occurrences of markers defining 'maternal haplotype 1' within the bin counted by sequencing, $n_{p1}$ is the total number of usable markers that define 'maternal haplotype 1' within the bin, $N_{p2}$ is the number of occurrences of markers defining 'maternal haplotype 2' within the bin counted by sequencing, $n_{p2}$ is the total number of usable markers that define 'maternal haplotype 2' within the bin. The fraction of child's DNA ($\varepsilon$) could be estimated from the amount of over-representation of the transmitted maternal haplotype relative to the averaged representation of the two maternal haplotypes, and was estimated to be ~0.29, which was consistent throughout the genome and agreed with the mass ratio of the genomic DNA of the two individuals in the mixture. The over-represented maternal haplotypes could be unambiguously identified (FIG. 21a, black line) and agree with the true inheritance (FIG. 21a, shaded background). All but one cross-over events on the maternal chromosomes were identified. The cross-over event that was missed was located very close to the heterochromatin region on the q-arm of maternal chromosome 13 and the resultant measurable size of the haplotype block was only a few megabases in length. The median distance between each identified cross-over from the true cross-over was ~770 kb (FIG. 21c).

TABLE 3

Details of samples and experimental statistics.

| Sample | Mock sample: Synthetic mixture of Mother (HapMap NA1289) and Daughter (HapMap NA12878) | Patient 1, first trimester | Patient 1, second trimester | Patient 2 |
|---|---|---|---|---|
| Number of maternal cells haplotyped | 3 (from reference x) | 3 | 3 | 4 |

TABLE 3-continued

Details of samples and experimental statistics.

| Sample | Mock sample: Synthetic mixture of Mother (HapMap NA1289) and Daughter (HapMap NA12878) | Patient 1, first trimester | Patient 1, second trimester | Patient 2 |
|---|---|---|---|---|
| Percent of maternal SNPs haplotyped | (from reference x) | 96% | 96% | 92% |
| Fetal karyotype | 46XX | 46XX | 46XX | 46XX |
| Gestational age when plasma was drawn | — | 9$^{th}$ wk | 23$^{rd}$ wk | ?? |
| Sequencing platform | GAII (36 bp) | GAII (76 bp), HiSeq (100 bp) | GAII (76 bp), HiSeq (100 bp) | HiSeq (51 bp) |
| Initial number of sequenced bases for determining inheritance of maternal haplotypes | 0.72 Gb | 32.7 Gb | 11.9 Gb | 3.7 Gb |
| Final number of sequenced bases for reconstructing paternally inherited haplotypes | (no additional sequencing) | 151 Gb | 59.7 Gb | 30.8 Gb |
| Fetal DNA fraction | ~0.29 | ~0.05 | ~0.18 | ~0.43 |
| Size of bin for measuring relative representation of maternal haplotypes (autosomes) | 20 Mb (without imputed SNPs); 10 Mb (with imputed SNPs) | 15 Mb | 7.5 Mb | 3.5 Mb |
| Size of bin for measuring relative representation of maternal haplotypes (chromosome X) | 10 Mb | 20 Mb | 10 Mb | 5 Mb |

The inheritance of the paternal haplotypes was determined by measuring the presence of markers for one paternal haplotype and the absence of markers for the other paternal haplotype. There were occasions in which markers within short distance from both parental haplotypes were present, possibly due to sequencing error or imputation error. To remove this noise, the paternal chromosomes were divided into 10 Mb bins with a step size of 100 kb. The representation of one paternal haplotype over the other paternal haplotype in each bin, as defined by $N_{p1}/n_{p1} - N_{p2}/n_{p2}$, was calculated, where $N_{p1}$ is the number of occurrences of markers defining 'paternal haplotype 1' within the bin counted by sequencing, $n_{p2}$ is the number of usable markers that define 'paternal haplotype 1' within the bin, $N_{p2}$ is the number of occurrences of markers defining 'paternal haplotype 2' within the bin counted by sequencing, $n_{p2}$ is the number of usable markers that define 'paternal haplotype 2' within the bin. The paternal haplotypes that were transmitted were unambiguously identified (FIG. 21*b*, black line) and agree with the true inheritance (FIG. 21*b*, shaded background). The resolution of crossover events depended on the density of the markers detected by sequencing, and the median resolution was ~400 kb. (FIG. 21*c*).

Overall, ~99.6% of the paternal inheritance and ~98.2% of maternal inheritance of the child's genome could be correctly deduced in this mixture.

Application to Clinical Samples

The inventors validated the technique by applying it to samples collected from two pregnancies. The mothers were referred to as 'Patient 1 (P1)' and 'Patient 2 (P2)'. P1 carried a female fetus with normal karyotype, while P2 was an individual with DiGeorge syndrome and postnatal observations of the female infant revealed cardiac defects typically associated with DiGeorge syndrome. Direct deterministic phasing (DDP) was performed on 3 or 4 maternal metaphase cells obtained by culturing maternal whole blood (Table 3). About 92% to 96% of the ~1 million SNPs present on the Omni1Quad BeadChip array (Illumina) were phased (FIG. 24). In addition, genomic DNA of cord blood collected at delivery was also genotyped on the same array to serve as the true reference for fetal genotypes.

Cell-free DNA was extracted from plasma collected during the first trimester (9$^{th}$ week of gestation) and second trimester (23$^{rd}$ week of gestation) from P1, and during the third trimester of P2. The cell-free DNA samples were initially shotgun sequenced on the Illumina platform, yielding a total of ~33.1 Gb (equivalent to ~11.6 fold coverage of the accessible fraction of the haploid human genome), ~11.5 Gb (~4.0 fold coverage), and ~3.7 Gb (~1.3 fold coverage) for the libraries of P1's first trimester, P1's second trimester, and P2 respectively (Table 3).

To determine the fetal inheritance of maternal haplotypes, the inventors compared the representation of the two copies of maternal chromosomes in 15 Mb (Patient 1, first trimester), 7.5 Mb (Patient 1, second trimester), or 3.5 Mb (Patient 2) bins, with sliding steps of 100 kb, based on the ~1 million markers phased with the Illumina array. The choice of the bin size was dictated by the minimum sampling requirement as predicted in Table 1, given the fetal DNA fraction (FIG. 20, Table 3). For all 3 plasma samples, the over-represented maternal haplotypes could be unambiguously identified (FIG. 22, black line).

The true inheritance of maternal haplotypes was determined by aligning the homozygous SNPs of the fetus by cord blood genotyping against the two maternal haplotypes defined by the phased maternal heterozygous SNPs (FIG. 22, shaded background, pink: transmitted, gray: untransmitted). There were 42 and 37 true cross-over events within the maternally inherited chromosomes transmitted to the fetuses of P1 and P2 respectively. All cross-overs were identified in P1's second trimester and P2's samples, while 2 cross-overs were missed in P1's first trimester sample. Both of these events were close to the heterochromatin (chr13 and chr21) resulting in switches of small blocks that contain few markers available for counting. The identified cross-over events were within ~1.8 Mb, ~630 kb, and ~470 kb (median) of the true cross-overs for P1's first trimester, P1's second trimester, and P2 samples, respectively (FIG. 22d). The resolution of the identification of cross-over events was dependent on the choice of bin size, which ultimately depended on fetal DNA fraction and sequencing depth. Taken into account for the uncertainty surrounding regions of cross-overs and cross-overs that were missed, about 97.4%, 98.9%, and 99.4% of all maternal inheritance can be correctly deduced in the P1's first trimester, P1's second trimester, and P2's samples, respectively.

Patient 2 is an individual with DiGeorge syndrome. Whole-genome haplotyping identified a ~2.85 Mb deletion on 22q11.1 that is associated with the syndrome on one of the chromosomes (denoted as 'maternal haplotype 2' in FIG. 22c), independently verified by PCR. Haplotype counting in maternal plasma indicated an over-representation of 'maternal haplotype 2' of the region immediately adjacent to that deletion, suggesting fetal inheritance of the DiGeorge syndrome associated deletion (FIG. 22c, deletion was indicated in black). Such result was confirmed by digital PCR of cord blood DNA.

At the initial sequencing depth that was sufficient for determining inheritance of maternal haplotypes, non-maternal alleles (i.e., bases that were different from the maternal alleles at locations where maternal genotypes were homozygous) were identified every one out of ~4-8 kb (depending on samples). If paternal haplotypes were known for these cases of pregnancies, the inherited paternal haplotype could be determined following the same approach illustrated for the mock sample using these non-maternal alleles as markers for the two paternal haplotypes, thereby revealing the entire fetal genome noninvasively. The rest of the loci on the paternally inherited chromosomes can be reconstructed by haplotype imputation based on paternal specific alleles detected in maternal plasma. This yields information of the paternally inherited half of the fetal genome, even without prior knowledge of paternity. Imputation accuracy is determined in part by the density of markers, and the number of identified non-maternal alleles was dependent on sequencing depth and fetal DNA fraction. It was estimated that if all the paternal specific alleles were correctly identified in maternal plasma (1 such allele every ~1 kbp), imputation would determine the allelic identity at ~70% of the loci along the entire paternally inherited chromosome with at least >99% accuracy (FIG. 23A). To prove the principle, the inventors performed additional sequencing of the plasma DNA libraries to a depth that was predicted to cover all paternal specific alleles at least once (namely ~52.7×, ~20.8×, ~10.7× haploid genome coverage for P1's first and second trimester samples, and P2's sample respectively), and the percentage of paternal alleles in maternal plasma roughly agreed with the estimated fetal DNA fraction (Table 2) (FIGS. 23B and C). At such sequencing depth, the inventors were able to detect ~66-70% of all the paternal specific alleles. Using those markers, the inventors imputed ~70% of the paternally inherited haplotypes with ~94-97% accuracy (FIG. 23A). The lower than ideal accuracy was due the fact that some paternally inherited alleles were not detected, and false detection of paternal alleles as a result of sequencing and/or amplification errors—approximately 5% of the non-maternal alleles were not actual paternal alleles.

Discussion

As illustrated by these experiments with a mixture of maternal and child's DNA, as well as three clinical samples, the knowledge of chromosome length haplotypes of the two parents coupled to shotgun sequencing of maternal plasma cell-free DNA could reveal the entire fetal genome noninvasively with little ambiguity. The present method made use of a microfluidic technique that the inventors recently developed that enabled whole-genome, chromosome-length haplotypes to be obtained simply from a few single blood cells. Therefore, parental haplotypes could be determined without the need of information from other family members, which is especially important for diagnosis of fetuses of couples without prior pregnancies. Because the amount of sequencing required to determine relative representation of parental haplotypes in maternal plasma decreases with increasing number of available markers specific to each haplotype, the knowledge of the chromosome-length haplotypes of the parents enabled us to determine fetal inheritance of parental haplotypes using shallow depth of sequencing even when fetal DNA percentage is much lower (~11× for ~5% fetal DNA) with no ambiguity over the entire genome, except near regions of cross-overs and telomeres, given that information from both parents are available.

The inventors showed that even without paternal information, inheritance of maternal haplotypes could be determined unambiguously with shallow sequencing. The knowledge of fetal inheritance of maternal haplotypes alone is already valuable for diagnosis of various types of genetic diseases, namely those involving maternal transmission. These include all X-linked disorders, including Fragile X syndrome. in which the copy of maternal chromosome X carrying a defective locus is transmitted to a male fetus, as well as diseases caused by maternal deletions, such as the special case of DiGeorge syndrome illustrated above. In addition, half of the cases of autosomal recessive disorders can be excluded. In the cases when autosomal recessive disorders cannot be ruled out, that is, the disease-associated haplotype of the mother is transmitted as determined from haplotype counting in maternal plasma, the final diagnosis may be achieved by the identification of any paternal specific alleles that are linked to the disease-associated alleles or the alternative normal allele, either using additional sequencing of plasma DNA demonstrated in this study, or more targeted approaches such as PCR and/or exome sequencing. While the current study utilized haplotype databases of the normal population for imputing linked loci on the paternally inherited haplotype, the application of such technique for diagnosis of rarer genetic diseases requires knowledge of long-range haplotypes associated with these diseases, and building databases of disease associated haplotypes would be extremely valuable.

The method described here offers a gateway to the comprehensive noninvasive prenatal diagnosis of genetically inherited diseases. With the advances in genomic technologies, there is no practical barrier to having the entire fetal genome determined noninvasively, which is useful in prenatal diagnosis.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference. While this invention has been particularly shown and described with references to preferred embodiments thereof, it will be understood by those skilled in the art that various changes in form and details may be made therein without departing from the scope of the invention encompassed by the appended claims.

References

ACOG Practice Bulletin. Invasive prenatal testing for aneuploidy. Obstet Gynecol, No. 88, 110: 1459-1467 (2007).

Ahn, S. M. et al. The first Korean genome sequence and analysis: full genome sequencing for a socio-ethnic group. Genome Res 19, 1622-1629 (2009).

Alberry, M. et al. Free fetal DNA in maternal plasma in anembryonic pregnancies: confirmation that the origin is the trophoblast. Prenat Diagn. 27:415-418 (2007).

Alfirevic, Z. and J. P. Neilson. Antenatal screening for Down's syndrome. Bmj 329: 811-812. [0136]5 (2004).

Amicucci, P. et al. Prenatal diagnosis of myotonic dystrophy using fetal DNA obtained from maternal plasma. Clin Chem. 46:301-302 (2000).

Andres, A. M. et al. Understainding the accuracy of statistical haplotype inference with sequence data of known phase. Genet Epidemiol 31, 659-671 (2007).

Annas, G. J. Ethical aspects of non-invasive prenatal diagnosis: medical, market, or regulatory model? Early Hum Dev. 47:S5-S11 (1996).

Ashley, E. A. et al. Clinical assessment incorporating a personal genome. Lancet 375, 1525-1535, doi:S0140-6736 (10)60452-7 [pii] 10.1016/S0140-6736(10)60452-7 (2010).

Bentley, D. R. et al. Accurate whole human genome sequencing using reversible terminator chemistry. Nature 456, 53-59, doi:nature07517 [pii] 10.1038/nature07517 (2008).

Bianchi, D. W. Prenatal diagnosis by analysis of fetal cells in maternal blood. J. Pediatr. 127:847-856 (1995).

Bianchi, D. W., et al. Isolation of fetal DNA from nucleated erythrocytes in maternal blood. Proc Natl Acad Sci USA, 87: 3279-3283 (1990).

Bianchi, D. W., et al. Fetal gender and aneuploidy detection using fetal cells in maternal blood: analysis of NIFTY I data. National Institute of Child Health and Development Fetal Cell Isolation Study. Prenat Diagn, 22: 609-615 (2002).

Bianchi, D. W., et al. PCR quantitation of fetal cells in maternal blood in normal and aneuploid pregnancies. Am J Hum Genet, 61: 822-829 (1997).

Birch, L. et al. Accurate and robust quantification of circulating fetal and total DNA in maternal plasma from 5 to 41 weeks of gestation. Clin Chem. 51:312-320 (2005).

Bischoff, F. Z. et al. Cell-free fetal DNA and intact etal cells in maternal blood circulation: implications for first and second trimester nno-invasive prenatal diagnosis. Hum Reprod Update, 8:493-500 (2002).

Bischoff, F. Z. et al. Noninvasive determination of fetal RhD status using fetal DNA in maternal serum and PCR. J Soc Gynecol Investig. 6:64-69 (1999).

Bredel, M., et al. Amplification of whole tumor genomes and gene-by-gene mapping of genomic aberrations from limited sources of fresh-frozen and paraffin-embedded DNA. J Mol Diagn 7, 171-182, doi:7/2/171 [pii] (2005).

Broman, K. W., et al. Comprehensive human genetic maps: individual and sex-specific variation in recombination. Am J Hum Genet. 63, 861-869, doi:50002-9297(07)61389-5 [pii] 10.1086/302011 (1998).

Burgtorf, C. et al. Clone-based systematic haplotyping (CSH): a procedure for physical haplotyping of whole genomes. Genome Res 13:2717-2724 (2003).

Bustamante-Aragones, A. et al. Prenatal diagnosis of Huntington disease in maternal plasma: direct and indirect study. Eur J. Neurol. 15:1338-1344 (2008).

Chan, K. C. et al. Hypermethylated RASSF1A in maternal plasma: a universal fetal DNA marker that improves the reliability of noninvasive prenatal diagnosis. Clin Chem. 52:2211-2218 (2006).

Chan, K C, et al. Size distributions of maternal and fetal DNA in maternal plasma. Clin Chem, 50: 88-92 (2004).

Cheung, M. C., et al. Prenatal diagnosis of sickle cell anaemia and thalassaemia by analysis of fetal cells in maternal blood. Nat Genet, 14: 264-268 (1996).

Chim, S. S. et al. Detection of the placental epigenetic signature of the maspin gene in maternal plasma. P Natl Acad Sci USA. 102:14753-14758 (2005).

Chiu, R. W. et al. Non-invasive prenatal assessment of trisomy 21 by multiplexed maternal plasma DNA sequencing: large scale validity study. BMJ. 342: c7401 (2011).

Chiu, R. W. et al. Noninvasive prenatal diagnosis of fetal chromosomal aneuploidy by massively parallel genomic sequencing of DNA in maternal plasma. Proc Natl. Acad Sci USA 105(51), 20458-20463 (2008).

Chiu, R. W. et al. Noninvasive prenatal exclusion of congenital adrenal hyperplasia by maternal plasma analysis: a feasibility study. Clin Chem. 48:778-780 (2002a).

Chiu, R. W. et al. Prenatal exclusion of beta thalassaemia major by examination of maternal plasma. Lancet 360: 998-1000 (2002b).

Conrad, D. F. et al. Origins and functional impact of copy number variation in the human genome. Nature 464, 704-712, doi:nature08516 [pii] 10.1038/nature08516 (2010).

Consortium, T. I. H. A haplotype map of the human genome. Nature 437, 1299-1320 (2005).

Cooper, G. and R. Hausman. The cell: a molecular approach (Sinauer Associates, Inc, Sunderland), p. 168 (2007).

Costa, J. M. et al. First-trimester fetal sex determination in maternal serum using real-time PCR. Prenat Diagn. 21:1070-1074 (2001).

Cunningham, F., et al. Williams Obstetrics (McGraw-Hill Professional, New York), p. 942 (2002).

de Bakker, P. I. et al. A high-resolution HLA and SNP haplotype map for disease association studies in the extended human MHC. Nat Genet. 38, 1166-1172, doi:ng1885 [pii] 10.1038/ng1885 (2006).

Deng, Y. H. et al. Non-invasive prenatal diagnosis of trisomy 21 by reverse transcriptase multiplex ligation-dependent probe amplification. Clin Chem Lab Med. 49:641-646 (2011).

Dhallan, R., et al. A non-invasive test for prenatal diagnosis based on fetal DNA present in maternal blood: a preliminary study. Lancet, 369: 474-481 (2007).

Ding, C. and C. R. Cantor. Direct molecular haplotyping of long-range genomic DNA with M1-PCR. Proc Nall Acad Sci USA 100, 7449-7453 (2003).

Ding, C. et al. MS analysis of single-nucleotide differences in circulating nucleic acids: Application to noninvasive prenatal diagnosis. Proc Natl Acad Sci USA 101, 10762-10767 (2004).

Dohm, J. C. et al. Substantial biases in ultra-short read data sets from high-throughput DNA sequencing. Nucleic Acids Res (2008).

Douglas, J. A. et al. Experimentally-derived haplotypes substantially increase the efficiency of linkage disequilibrium studies. Nature genetics 28, 361-364, doi:10.1038/ng582 ng582 [pii] (2001).

Drysdale, C. M. et al. Complex promoter and coding region beta 2-adrenergic receptor haplotypes alter receptor expression and predict in vivo responsiveness. Proc Natl Acad Sci USA 97, 10483-10488, doi:97/19/10483 [pii] (2000).

Durbin, R. M. et al. A map of human genome variation from population-scale sequencing. Nature 467, 1061-1073, doi: nature09534 [pii] 10.1038/nature09534 (2010).

Ehrich, M., et al. Noninvasive detection of fetal trisomy 21 by sequencing of DNA in maternal blood: a study in a clinical setting. Am J Obstet. Gynecol. 204:e201-e211 (2011).

Faas, B. H. et al. Detection of fetal RHD-specific sequences in maternal plasma. Lancet. 352:1196 (1998).

Fan, C. and Stephen Quake. In Principle Method for Noninvasive Determination of the Fetal Genome. Available from Nature Precedings [http://dx.doi.org/10.1038/npre.2010.5373.1] (2010a).

Fan, H. C. and S. R. Quake. Detection of aneuploidy with digital polymerase chain reaction. Anal Chem. 79:7576-7579 (2007a).

Fan, H. C. and S. R. Quake. Sensitivity of noninvasive prenatal detection of fetal aneuploidy from maternal plasma using shotgun sequencing is limited only by counting statistics. PLoS One.5:e10439 (2010b).

Fan, H. C., Ph.D. Thesis, Molecular counting:from noninvasive prenatal diagnostics to whole-genome haplotyping. Stanford University (November 2010) [http://purl.stanford.edu/cw095xw9265].

Fan, H. C., et al. Analysis of the size distributions of fetal and maternal cell-free DNA by paired-end sequencing. Clin Chem. 56(8):1279-86 (2010c).

Fan, H. C., et al. Deciphering the fetal genome noninvasively from maternal blood. Manuscript in preparation.

Fan, H. C., et al. Microfluidic digital PCR enables rapid prenatal diagnosis of fetal aneuploidy. Am J Obstet. Gynecol., 200(5):543.e1-7 (2009).

Fan, H. C. et al. Noninvasive diagnosis of fetal aneuploidy by shotgun sequencing DNA from maternal blood. Proc Nall Acad Sci USA 105, 16266-16271 (2008).

Fan, H. C. and S. R. Quake. Detection of aneuploidy with digital polymerase chain reaction. Anal Chem, 79: 7576-7579 (2007b).

Fan, H. C. and S. R. Quake. Sensitivity of Noninvasive prenatal detection of fetal aneuploidy from maternal plasma using shotgun sequencing is limited only by counting statistics. PLoS One 5(5): e10439 (March 2010).

Fan, H. C. et al. Whole-genome molecular haplotyping from single cells. Nat Biotechnol 29(1):51-57 (2011).

Farina, A. et al. Fetal DNA in maternal plasma as a screening variable for preeclampsia. A preliminary nonparametric analysis of detection rate in low-risk nonsymptomatic patients. Prenat Diagn. 24:83-86 (2004).

Farina, A. et al. Quantitative distribution of a panel of circulating mRNA in preeclampsia versus controls. Prenat Diagn. 26:1115-1120 (2006).

Frazer, K. A. et al. A second generation human haplotype map of over 3.1 million SNPs. Nature 449, 851-861 (2007).

Fucharoen, G. et al. Prenatal detection of fetal hemoglobin E gene from maternal plasma. Prenat Diagn. 23:393-396 (2003).

Geifman-Holtzman, O. et al. Diagnostic accuracy of noninvasive fetal Rh genotyping from maternal blood—a meta—analysis. Am J Obstet. Gynecol. 195:1163-1173 (2006).

Ghanta, S. et al. Non-invasive prenatal detection of trisomy 21 using tandem single nucleotide polymorphisms. PLoS One. 5:e13184 (2010).

Giacona, M. B, et al. Cell-free DNA in human blood plasma: length measurements in patients with pancreatic cancer and healthy controls. Pancreas, 17: 89-97 (1998).

Gonzalez-Gonzalez, M. C. et al. Huntington disease-unaffected fetus diagnosed from maternal plasma using QF-PCR. Prenat Diagn. 23:232-234 (2003a).

Gonzalez-Gonzalez, M. C. et al. Huntington disease prenatal diagnosis by maternal semiquantitative fluorescent-PCR. Neurology. 60:1214-1215 (2003b).

Gonzalez-Gonzalez, M. C. et al. Prenatal detection of a cystic fibrosis mutatin in fetal DNA from maternal plasma. Prenat Diagn. 22:946-948 (2002).

Groenendijk, M., et al. The apoAI-CIII-MV gene cluster. Atherosclerosis 157, 1-11, doi:50021915001005391 [pii] (2001).

Grundevikk and Rosen. Molecular Diagnosis of Aneuploidies, [http://www.molbiotech.chalmers.se/research/mk/mbtk/Molecular%20diagnostics%20of%20aneuploidies%20-%20rapport.pdf]

Guo, Z. et al. Long-range multilocus haplotype phasing of the MHC. Proc Natl Acad Sci USA 103, 6964-6969, doi:0602286103 [ph] 10.1073/pnas.0602286103 (2006).

Hamada H, et al. Fetal nucleated cells in maternal peripheral blood: frequency and relationship to gestational age. Hum Genet, 91: 427-432 (1993).

Harris, T. D., et al. Single-molecule DNA sequencing of a viral genome. Science, 320: 106-109 (2008).

Hartl, D. L. Essential Genetics: A Genomics Perspective, Jones & Bartlett Publishers (2009).

Hassold, T. et al. Human aneuploidy: incidence, origin, and etiology. Environ Mol. Mutagen. 28:167-175 (1996).

Heckerling P. S. et al. A cost-effectiveness analysis of amniocentesis and chorionic villus sampling for prenatal genetic testing. Med. Care. 32:863-880 (1994).

Herzenberg, L. A., et al. Fetal cells in the blood of pregnant women: detection and enrichment by fluorescence-activated cell sorting. Proc Natl Acad Sci USA, 76: 1453-1455 (1979).

Hillier, L. W., et al. Whole-genome sequencing and variant discovery in C. elegans. Nat Methods, 5: 183-188 (2008).

Honda, H. et al. Fetal gender determination in early pregnancy through qualitative and quantitative analysis of fetal DNA in maternal serum. Hum. Genet. 110:75-79 (2002).

Howie, B. N. et al. A flexible and accurate genotype imputation method for the next generation of genome-wide association studies. PLoS Genet. 5, e1000529 (2009).

Hromadnikova, et al. Quantitative analysis of DNA levels in maternal plasma in normal and Down Syndrome pregnancies. BMC Pregnancy and Childbirth 2(4): 1-5 (2002).

Hromadnikova, I. et al. Replicate real-time PCR testing of DNA in maternal plasma increases the sensitivity of noninvasive fetal sex determination. Prenat Diagn. 23:235-238 (2003).

Hyett, J. A. et al. Reduction in diagnostic and therapeutic interventions by non-invasive determination of fetal sex in early pregnancy. Prenat Diagn. 25:1111-1116 (2005).

International Blood Group Reference Laboratory. Overview of IBCRL reference and diagnostic services. Available at:

http://ibgrl.blood.co.uk/ReferenceServices/RfeServ-frames.htm. Accessed May 6, 2011.

Jahr, S., et al. DNA fragments in the blood plasma of cancer patients: quantitations and evidence for their origin from apoptotic and necrotic cells. Cancer Res, 61: 1659-1665 (2001).

Jorgez, C. J. and F. Z. Bischoff. Improving enrichment of circulating fetal DNA for genetic testing: size fractionation followed by whole gene amplification. Fetal Diagn Ther. 25:314-319 (2009).

Khosrotehrani, K. and D. W. Bianchi. Fetal cell microchimerism: helpful or harmful to the parous woman? Curr Opin Obstet Gynecol, 15: 195-199 (2003).

Kim, J. I. et al. A highly annotated whole-genome sequence of a Korean individual. Nature 460, 1011-1015, doi:nature08211 [pii] 10.1038/nature08211 (2009).

Kong, A. et al. A high-resolution recombination map of the human genome. Nat Genet. 31, 241-247 (2002).

Kozarewa, I. et al. Amplification-free Illumina sequencing-library preparation facilitates improved mapping and assembly of (G+C)-biased genomes. Nat Methods 6, 291-295 (2009).

Kukita, Y. et al. Genome-wide definitive haplotypes determined using a collection of complete hydatidiform moles. Genome Res 15, 1511-1518, doi:15/11/1511 [ph] 10.1101/gr.4371105 (2005).

Lander, E. S., et al. Initial sequencing and analysis of the human genome. Nature, 409: 860-921 (2001).

Lazaros, L. et al. Non-invasive prenatal detection of paternal origin hb lepore in a male fetus at the $7^{th}$ week of gestation. Fetal Diagn Ther. 21:506-509 (2006).

Lee, W. et al. A high-resolution atlas of nucleosome occupancy in yeast. Nat Genet, 39: 1235-1244 (2007).

Leung, T. N. et al. Maternal plasma fetal DNA as a marker for preterm labour. Lancet. 352:1904-1905 (1998).

Levy, S. et al. The diploid genome sequence of an individual human. PLoS Biol 5, e254, doi:07-PLBI-RA-1258 [pH] 10.1371/journal.pbio.0050254 (2007).

Liao, G. J. et al. Targeted massively parallel sequencing of maternal plasma DNA permits efficient and unbiased detection of fetal alleles. Clin Chem. 57:92-101 (2011).

Li, et al. Detection of Paternally Inherited Fetal Point Mutations for .beta.-Thalassemia Using Size Fractionated Cell-Free DNA in Maternal Plasma. J. Amer. Med. Assoc. 293: 843-849 (Feb. 16, 2005).

Li, Y., et al. Improved prenatal detcction of a fetal point mutation for achondroplasia by the use of size-fractionated circulatory DNA in maternal plasma-case report. Prenat Diagn. 24:896-898 (2004a).

Li, Y. et al. Non-invasive prenatal detection of achondroplasia in size-fractionated cell-free DNA by MALDI-TOF MS assay. Prenat Diagn. 27: 11-17 (2007).

Li, Y. et al. Size fractionation of cell-free DNA in maternal plasma improves the detection of a paternally inherited beta-thalassemia point mutation by MALDITOF mass spectrometry. Fetal Diagn Ther. 25:246-249 (2009).

Li, Y., et al. Size separation of circulatory DNA in maternal plasma permits ready detection of fetal DNA polymorphisms. Clin Chem, 50: 1002-1011 (2004b).

Lo. Fetal DNA in Maternal Plasma: Biology and Diagnostic Applications. Clin. Chem. 46:1903-1906 (2000).

Lo, Y. M. and R. W. Chiu. Prenatal diagnosis: progress through plasma nucleic acids. Nat Rev Genet, 8: 71-77 (2007).

Lo, Y. M, et al. Digital PCR for the molecular detection of fetal chromosomal aneuploidy. Proc Natl Acad Sci USA, 104: 13116-13121 (2007a).

Lo, Y. M. et al. Increased fetal DNA concentrations in the plasma of pregnant women carrying fetuses with trisomy 21. Clin Chem, 45: 1747-1751 (1999a).

Lo, Y. M. et al. Maternal plasm DNA sequencing reveals the genome-wide genetic and mutational profile of the fetus. Sci. Transl. Med. 2:61ra91; doi:10.1126/scitranslmed.3001720 (2010).

Lo, Y. M. et al. Plasma placental RNA allelic ratio permits noninvasive prenatal chromosomal aneuploidy detection. Nat Med, 13: 218-223 (2007b).

Lo, Y. M. et al. Presence of fetal DNA in maternal plasma and serum. Lancet 350, 485-487 (1997), Lo, Y. M. et al. Quantitative abnormalities of fetal DNA in maternal serum in preeclampsia. Clin Chem. 45:184-188 (1999b).

Lo, Y. M. et al. Quantitative analysis of fetal DNA in maternal plasma and serum: implications for noninvasive prenatal diagnosis. Am J Hum Genet. 62, 768-775 (1998).

Lo, Y. M. et al. Quantitative analysis of the bidirectional fetomaternal transfer of nucleated cells and plasma DNA. Clin. Chem. 46:1301-1309 (2000).

Lo, Y. M. et al. Rapid clearance of fetal DNA from maternal plasma. Am J Hum Genet, 64: 218-224 (1999c).

Lun, F. M. et al. Noninvasive prenatal diagnosis of a case of Down syndrome due to Robertsonian translocation by massively parallel sequencing of maternal plasma DNA. Clin Chem. 57 (2011).

Lun, F. M., et al. Noninvasive prenatal diagnosis of monogenic diseases by digital size selection and relative mutation dosage on DNA in maternal plasma. P Natl Acad Sci USA. 105:19920-19925 (2008).

Ma, K. et al. Should free fetal DNA testing replace anenatal anti-D administration for prevention of Rhesus alloimmuniation? Am J Obstet. Gynecol. 204(S1):A139 (2011).

Ma, L. et al. Direct determination of molecular haplotypes by chromosome microdissection. Nat Methods 7, 299-301, doi:nmeth.1443 [pii] 10.1038/nmeth.1443 (2010).

Maiers, M. et al. High-resolution HLA alleles and haplotypes in the United States population. Hum Immunol 68, 779-788, doi:S0198-8859(07)00094-8 [pil] 10.1016/j.humimm.2007.04.005 (2007).

Malone F. D., et al. First-trimester or second-trimester screening, or both, for Down's syndrome. N Engl J Med, 353: 2001-2011 (2005).

Marchini, J. et al. A comparison of phasing algorithms for trios and unrelated individuals. Am J Hum Genet. 78, 437-450, doi:S0002-9297(07)62383-0 [pii] 10.1086/500808 (2006).

Marcy, Y. et al. Dissecting biological "dark matter" with single-cell genetic analysis of rare and uncultivated TM7 microbes from the human mouth. ProcNall Acad Sci USA 104, 11889-11894, doi:0704662104 [pii] 10.1073/pnas.0704662104 (2007a).

Marcy, Y. et al. Nanoline reactors improve multiple displacement amplification of genomes from single cells. PLoS Genet. 3, 1702-1708 (2007b).

Maron, J. L. et al. Gene expression analysis in pregnant women and their infants identifies unique fetal biomarkers that circulate in maternal blood. J Clin Invest. 117:3007-3019 (2007).

McCarroll, S. A. et al. Integrated detection and population-genetic analysis of SNPs and copy number variation. Nat Genet. 40, 1166-1174, doi:ng.238 [pii] 10.1038/ng.238 (2008).

Michalatos-Beloin, S. et al. Molecular haplotyping of genetic markers 10 kb apart by allele-specific long-range PCR. Nucleic Acids Res 24, 4841-4843, doi:160250 [pii] (1996).

Mitra, R. D. et al. Digital genotyping and haplotyping with polymerase colonies. Proc Natl Acad Sci USA 100, 5926-5931 (2003).

Nagel, R. L. et al. The Senegal DNA haplotype is associated with the amelioration of anemia in African-American sickle cell anemia patients. Blood 77, 1371-1375 (1991).

Nelson, J. L. Your cells are my cells. Sci Am, 298: 64-71 (2008). News Focus "An Earlier Look at Baby's Genes. Science 309:1476 (Sep. 2, 2005).

Ng, E. K. et al. The concentration of circulating corticotropin-releasing hormone mRNA in maternal plasma is increased in preeclampsia. Clin Chem. 49:727-731 (2003).

Nicolaides, K. et al. Comparison of chorionic villus sampling and amniocentesis for fetal karyotyping at 10-13 weeks' gestation. Lancet. 344:435-439 (1994).

Norbury, G. and C. J. Norbury. Non-invasive prenatal diagnosis of single gene disorders: how close are we? Seminin Fetal Neonatal Med. 13:76-83 (2008).

Nygren, A. O. et al. Quantification of fetal DNA by use of methylation-based DNA discrimination. Clin Chem. 56:1627-1635 (2010).

Old, R. W. et al. Candidate epigenetic biomarkers for non-invasive prenatal diagnosis of Down syndrome. Reprod Biomed Online 15:227-235 (2007).

Oudejans, C. B. et al. Detection of chromosome 21-encoded mRNA of placental origin in maternal plasma. Clin Chem. 49:1445-1449 (2003).

Ozsolak, F. et al. High-throughput mapping of the chromatin structure of human promoters. Nat Biotechnol, 25: 244-248 (2007).

Petersdorf, E. W. et al. MHC haplotype matching for unrelated hematopoietic cell transplantation. PLoS Med 4, e8, doi:06-PLME-RA-0442R3 [pii] 10.1371/journal.pmed.0040008 (2007).

Poon, et al. Differential DNA Methylation between Fetus and Mother as a Strategy for Detecting Fetal DNA in Maternal Plasma. Clin. Chem. 48(1): 35-41 (2002).

Poon, L. L. et al. Presence of fetal RNA in maternal plasma. Clin Chem 46, 1832-1834 (2000).

Price, P. et al. The genetic basis for the association of the 8.1 ancestral haplotype (A1, B8, DR3) with multiple immunopathological diseases. Immunol Rev 167, 257-274 (1999).

Purwosunu, Y. et al. Cell-free mRNA concentrations of CRH, PLAC1, and selectin-P are increased in the plasma of pregnant women with preeclampsia. Prenat Diagn. 27:772-777 (2007).

Pushkarev, D. et al. S. R. Single-molecule sequencing of an individual human genome. Nat Biotechnol 27, 847-852 (2009).

Quake, S. R. and H. C. Fan. Non-invasive fetal genetic screening by digital analysis. USA Provisional Patent Application No. 60/764,420. 20. Mardis E R (2008) Next-Generation DNA Sequencing Methods. Annu Rev Genomics Hum Genet, 9: 387-402 (2006).

Rijnders, R. J. et al. Cell-free fetal DNA is not present in plasma of nonpregnant mothers. Clin Chem, 50: 679-681; author reply 681 (2004).

Ruano, G. et al. Haplotype of multiple polymorphisms resolved by enzymatic amplification of single DNA molecules. Proc Natl Acad SciUSA 87, 6296-6300 (1990).

Saito, H. et al. Prenatal DNA diagnosis of a single-gene disorder from maternal plasma. Lancet, 356:1170 (2000).

Samura, O. et al. Cell-free fetal DNA in maternal circulation after amniocentesis. Clin Chem, 49: 1193-1195 (2003).

Santacroce, R. et al. Identification of fetal gender in maternal blood is a helpful tool in the prenatal diagnosis of haemophilia. Haemophilia 12:417-422 (2006).

Sayres, L. C. et al. Cell-free fetal nucleic acid testing: a review of the technology and its applications. CME Review Article, 66:431-442 (2011).

Schones, D. E., et al. Dynamic regulation of nucleosome positioning in the human genome. Cell, 132: 887-898 (2008).

Schuster, S. C. et al. Complete Khoisan and Bantu genomes from southern Africa. Nature 463:943-947 (2010).

Segal, E., et al. A genomic code for nucleosome positioning. Nature, 442: 772-778 (2006).

Sekizawa, A., et al. Accuracy of fetal gender determination by analysis of DNA in maternal plasma. Clin Chem. 47:1856-1858 (2001).

Sekizawa, A. et al. Cell-free fetal DNA in the plasma of pregnant women with severe fetal growth restriction. Am J Obstet. Gynecol. 188:480-484 (2003a).

Sekizawa, A. et al. Cell-free fetal DNA is increased in plasma of women with hyperemesis gravidarum. Clin Chem. 47:2164-2165 (2004a).

Sekizawa, A., et al. Evaluation of bidirectional transfer of plasma DNA trhough placenta. Human Genet., 113:307-310 (2003b).

Sekizawa, A. et al. Increased cell-free fetal DNA in plasma of two women with invasive placenta. Clin Chem. 48:353-354 (2002).

Sekizawa, A. et al. Proteinuria and hypertension are independent factors affecting fetal DNA values: a retrospective analysis of affected and unaffected patients. Clin Chem. 50:221-224 (2004b).

Sherman, S. et al. Fragile X syndrome: diagnostic and carrier testing. Genet Med 7:584-587 (2005).

Shiina, T. et al. The HLA genomic loci map: expression, interaction, diversity and disease. J Hum Genet. 54, 15-39, doi:jhg20085 [pii] 10.1038/jhg.2008.5 (2009).

Simpson, J. L. and S. Elias. Isolating fetal cells in maternal circulation for prenatal diagnosis. Prenat Diagn. 14:1229-1242 (1994).

Smid, M. et al. No evidence of fetal DNA persistence in maternal plasma after pregnancy. Hum Genet, 112: 617-618 (2003).

Sohda, S. et al. The proportion of fetal nucleated red blood cells in maternal blood: estimation by FACS analysis. Prenat Diagn, 17: 743-752 (1997).

Steele, C. D. et al. Prenatal diagnsis using fetal cells isolated from maternal peripheral blood: a review. Clin. Obstet. Gynecol., 39:801-813 (1996).

Stephens, M. and P. Donnelly. A comparison of bayesian methods for haplotype reconstruction from population genotype data. Am J Hum Genet. 73, 1162-1169, doi: 50002-9297(07)61978-8 [pii] 10.1086/379378 (2003).

Stephens, M. and P. Scheet. Accounting for decay of linkage disequilibrium in haplotype inference and missing-data imputation. Am J Hum Genet. 76, 449-462, doi:S0002-9297(07)63341-2 [pii] 10.1086/428594 (2005).

Stephens, M. et al. A new statistical method for haplotype reconstruction from population data. Am J Hum Genet. 68, 978-989, doi:50002-9297(07)61424-4 [pu] 10.1086/319501 (2001).

Stewart, C. A. et al. Complete MHC haplotype sequencing for common disease gene mapping. Genome Res 14, 1176-1187, doi:10.1101/gr.2188104 2188104 [pH] (2004).

Su, S. Y. et al. Inferring combined NCV/SNP haplotypes from genotype data. Bioinformatics 26:1437-1445 (2010).

Sun, T. et al. Haplotypes in matrix metalloproteinase gene cluster on chromosome 11 q22 contribute to the risk of lung cancer development and progression. Clin Cancer Res 12, 7009-7017, doi:12/23/7009 [pii] 10.1158/1078-0432.CCR-06-0464 (2006).

Tamura, K. et al. MEGA4: Molecular Evolutionary Genetics Analysis (MEGA) software version 4.0. Mol Biol Evol 24, 1596-1599, doi:msm092 [pii] 10.1093/molbev/msm092 (2007).

Tong, Y. K. et al. Noninvasive prenatal detection of fetal trisomy 18 by epigenetic allelic ratio analysis in maternal plasma: Theoretical and empirical considerations. Clin Chem, 52: 2194-2202 (2006).

Tsui, N. B. et al. Noninvasive prenatal diagnosis of hemophilia by microfluidics digital PCR analysis of maternal plasma DNA. Blood. 117:3684-3691 (2001).

Tsui, N. B. et al. Systematic micro-array based identification of placental mRNA in maternal plasma: towards non-invasive prenatal gene expression profiling. J Med. Genet. 41:461-467 (2004).

Tufan, et al. Analysis of Cell-Free Fetal DNA from Maternal Plasma and Serum Using a Conventional Multiplex PCR: Factors Influencing Success. Turk. J. Med. Sci. 35: 85-92 (2005).

Venter, et al. The sequence of the human genome. Science (5507):1304-51 (2001).

Wagner, J. et al. Non-invasive prenatal paternity testing from maternal blood. Int J Legal Med. 123:75-79 (2009).

Wald, N. J. et al. A new approach to antenatal screening for Fragile X syndrome. Prenat. Diagn. 23:345-351 (2003).

Walknowska, J. et al. Practical and theoretical implications of fetal-maternal lymphocyte transfer. Lancet 1:1119-1122 (1969).

Wang, J. et al. The diploid genome sequence of an Asian individual. Nature 456:60-65 (2008).

Wapner, R. et al. First-trimester screening for trisomies 21 and 18. N Engl J Med, 349: 1405-1413 (2003).

Wataganara, T. et al. Placental volume, as measured by 3-dimensional sonography and levels of maternal plasma cell-free fetal DNA. Am J. Obstet Gynecol, 193:496-500 (2005).

Wheeler, D. A. et al. The complete genome of an individual by massively parallel DNA sequencing. Nature 452, 872-876 (2008).

White, R. A., III, et al. Digital PCR provides sensitive and absolute calibration for high throughput sequencing. BMC Genomics 10, 116 (2009).

Woolley, A. T. et al. Direct haplotyping of kilobase-size DNA using carbon nanotube probes. Nat Biotechnol 18, 760-763 (2000).

Wright, C. Cell-free fetal nucleic acids for noninvasive prenatal diagnosis: report of the UK expert working group. Cambridge, England: PHG Foundation (2009).

Xiao, M. Et al. Direct determination of molecular haplotypes from single DNA molecules. Nat Methods 6, 199-201 (2009).

Xie, Y., et al. Etiology of infections in the wounded victims of Wenchuan Earthquake. 89(6):366-70. Chinese (2009).

Xu, X., et al. The genomic sequence of the Chinese hamster ovary (CHO)-K1 cell line. Nat. Biotechnol. 29(8):735-41 (2011).

Yuan, G. C. et al. Genome-scale identification of nucleosome positions in S. cerevisiae. Science, 309: 626-630 (2005).

Zhang, K. et al. Long-range polony haplotyping of individual human chromosome molecules. Nat Genet. 38, 382-387 (2006).

Zhong, X. Y. et al. Elevation of both maternal and fetal extracellular circulating deoxyribonucleic acid concentrations in the plasma of pregnant women with preeclampsia. Am J Obstet. Gynecol. 184:414-419 (2001a).

Zhong, X. Y. et al. Risk free simultaneous prenatal identification of fetal Rhesus D status and sex by multiplex real-time PCR using cell free fetal DNA in maternal plasma. Swiss Med. Wkly. 131:70-74 (2001b).

Zhong, X.Y. et al. The levels of circulatory cell free fetal DNA in maternal plasma are elevated prior to the onset of preeclampsia. Hypertens Pregnancy. 21:77-83 (2002).

Zimmermann, B. et al. Novel real-time quantitative PCR test for trisomy 21. Clin Chem. 48:362-363 (2002).

U.S. Patent Application No. 20040137470
U.S. Pat. No. 6,440,705
U.S. Pat. No. 7,888,017
U.S. Pat. No. 8,008,018
U.S. Patent Publication No. 2007/0202525
U.S. Patent Publication No. 2009/0029377
U.S. Patent Publication No. 2009/0053719
U.S. Patent Publication No. 2009/0087847
U.S. Patent Publication No. 2010/0112575

The invention claimed is:

1. A method of non-invasively determining parental haplotypes which are inherited by a fetus, comprising:
   a. obtaining a maternal sample from a female pregnant with at least one fetus, wherein said sample contains DNA from both the pregnant female and the fetus;
   b. determining a paternally inherited haplotype by the steps of:
      i. simultaneously isolating all of the chromosomes from a single metaphase cell of the fetus's father by partitioning said chromosomes into a plurality of channels of a microfluidic device and analyzing each of said chromosomes to determine a set of paternal single nucleotide polymorphisms (SNPs);
      ii. simultaneously isolating all of the chromosomes from a single metaphase cell of the fetus's mother by partitioning said chromosomes into a plurality of channels of a microfluidic device and analyzing each of said chromosomes to determine a set of maternal single nucleotide polymorphisms (SNPs);
      iii. determining all SNPs that are heterozygous in the father and homozygous in the mother to identify at various loci alleles present in the father and absent in the mother, thereby defining each of the father's haplotypes; and
      iv. counting a number of representative alleles on each paternal haplotype to determine a representation of the two paternal haplotypes in the maternal sample containing DNA from the pregnant female and the fetus;
      v. comparing the representation of the two paternal haplotypes to obtain a relative representation in the maternal sample containing DNA from the pregnant female and the fetus;
      vi. determining an over-representation $\epsilon$ of one of the two paternal haplotypes in the maternal sample containing DNA from the pregnant female and the fetus; and
      vii. correlating said over-representation $\epsilon$ with a paternally inherited haplotype; and
   c. determining a maternally inherited haplotype by the steps of:
      i. determining all SNPs that are heterozygous in the fetus's mother; and
      ii. identifying alleles present in the mother but absent in the paternally inherited haplotype at each SNP locus to define the mother's haplotypes;
      iii. counting a number of representative alleles on each maternal haplotype to determine a representation of the two maternal haplotypes;
      iv. comparing the representation of the two maternal haplotypes to obtain a relative representation;
      v. determining an over-representation $\epsilon$ of one of the two maternal haplotypes in the maternal sample containing DNA from the pregnant female and the fetus; and
      vi. correlating said over-representation $\epsilon$ with a maternally inherited haplotype.

2. The method of claim 1, wherein the relative representation of haplotypes is measured by digitally counting markers, wherein the markers are alleles that define each of the parental haplotypes.

3. The method of claim 2, wherein sums of the count of markers specific to each of two maternal haplotypes within a haplotype block are compared to determine which maternal haplotype is over-represented.

4. The method of claim 2, wherein sums of the count of markers specific to each of two paternal haplotypes within a haplotype block are compared to determine which paternal haplotype is over-represented.

5. The method of claim 2, wherein the digital counting is performed by measuring numbers of counts of single DNA molecules.

6. The method of claim 5, wherein the measuring is by sequencing, digital polymerase chain reaction (PCR) or hybridization.

7. The method of claim 1, wherein a portion of the fetal genome is determined.

8. The method of claim 7, wherein the entire fetal genome is determined.

9. A method of estimating the fraction of fetal DNA present in a maternal sample containing DNA from a pregnant female and a fetus by measuring the relative representation of the parental haplotypes according to claim 1.

10. A method of non-invasively determining maternal haplotypes which are inherited by a fetus, comprising:
   a. obtaining a maternal sample from a female pregnant with at least one fetus, wherein said sample contains DNA from both the pregnant female and the fetus;
   b. counting markers in said sample that define each of two maternal haplotypes to determine a representation of the two haplotypes, comprising selecting markers that define two maternal haplotypes by simultaneously isolating all of the chromosomes from a single metaphase cell of the fetus's mother by partitioning said chromosomes into a plurality of channels of a microfluidic device;
   c. comparing the representation of the two maternal haplotypes in the maternal sample containing DNA from the pregnant female and the fetus to obtain a relative representation;
   d. determining an over-representation $\epsilon$ of one of the two haplotypes in the maternal sample containing DNA from the pregnant female and the fetus; and
   e. correlating said over-representation $\epsilon$ with an inherited maternal haplotype.

11. The method of claim 10, wherein the relative representation of haplotypes is measured by digitally counting markers, wherein the markers are alleles that define each of the maternal haplotypes.

12. The method of claim 11, wherein sums of the count of markers specific to each of two maternal haplotypes within a haplotype block are compared to determine which maternal haplotype is over-represented.

13. The method of claim 11, wherein the digital counting is performed by measuring numbers of counts of single DNA molecules carrying specific markers.

14. The method of claim 13, wherein the measuring is by sequencing, digital polymerase chain reaction (PCR) or hybridization.

15. The method of claim 10, wherein a portion of the fetal genome is determined.

16. The method of claim 15, wherein the entire fetal genome is determined.

17. The method of claim 10, further comprising non-invasively reconstructing the paternally inherited haplotypes.

18. The method of claim 17, wherein the reconstruction of the paternally inherited haplotypes is achieved by haplotype imputations using paternal-specific alleles detected in the sample.

* * * * *

SEQUENCE LISTING

```
<160> NUMBER OF SEQ ID NOS: 24

<210> SEQ ID NO 1
<211> LENGTH: 18
<212> TYPE: DNA
<213> ORGANISM: Artificial Sequence
<220> FEATURE:
<223> OTHER INFORMATION: HM3 CNP71 forward primer

<400> SEQUENCE: 1
aaggcttcct tagctcct                                                    18

<210> SEQ ID NO 2
<211> LENGTH: 20
<212> TYPE: DNA
<213> ORGANISM: Artificial Sequence
<220> FEATURE:
<223> OTHER INFORMATION: HM3 CNP116 forward primer

<400> SEQUENCE: 2
```
gcctcagttt caggcattat                                           20

<210> SEQ ID NO 3
<211> LENGTH: 20
<212> TYPE: DNA
<213> ORGANISM: Artificial Sequence
<220> FEATURE:
<223> OTHER INFORMATION: HM3 CNP201 forward primer

<400> SEQUENCE: 3
tccactgacc agatacatgc                                           20

<210> SEQ ID NO 4
<211> LENGTH: 20
<212> TYPE: DNA
<213> ORGANISM: Artificial Sequence
<220> FEATURE:
<223> OTHER INFORMATION: HM3 CNP309 forward primer

<400> SEQUENCE: 4
attcataata gccggagtgg                                           20

<210> SEQ ID NO 5
<211> LENGTH: 20
<212> TYPE: DNA
<213> ORGANISM: Artificial Sequence
<220> FEATURE:
<223> OTHER INFORMATION: HM3 CNP371 forward primer

<400> SEQUENCE: 5
ctgaatggct gtgtatggaa                                           20

<210> SEQ ID NO 6
<211> LENGTH: 20
<212> TYPE: DNA
<213> ORGANISM: Artificial Sequence
<220> FEATURE:
<223> OTHER INFORMATION: HM3 CNP593 forward primer

<400> SEQUENCE: 6
taaaatggag cgatgactga                                           20

<210> SEQ ID NO 7
<211> LENGTH: 20
<212> TYPE: DNA
<213> ORGANISM: Artificial Sequence
<220> FEATURE:
<223> OTHER INFORMATION: HM3 CNP708 forward primer

<400> SEQUENCE: 7
ctgtggttgt gagtcctgag                                           20

<210> SEQ ID NO 8
<211> LENGTH: 20
<212> TYPE: DNA
<213> ORGANISM: Artificial Sequence
<220> FEATURE:
<223> OTHER INFORMATION: HM3 CNP71 reverse primer

<400> SEQUENCE: 8
tgaaagaaac tcatggctca                                           20

<210> SEQ ID NO 9
<211> LENGTH: 20
<212> TYPE: DNA
<213> ORGANISM: Artificial Sequence

```
<220> FEATURE:
<223> OTHER INFORMATION: HM3 CNP116 reverse primer

<400> SEQUENCE: 9
ctgctgcctc atagaagtga                                               20

<210> SEQ ID NO 10
<211> LENGTH: 20
<212> TYPE: DNA
<213> ORGANISM: Artificial Sequence
<220> FEATURE:
<223> OTHER INFORMATION: HM3 CNP201 reverse primer

<400> SEQUENCE: 10
accatcagac caagacatcc                                               20

<210> SEQ ID NO 11
<211> LENGTH: 20
<212> TYPE: DNA
<213> ORGANISM: Artificial Sequence
<220> FEATURE:
<223> OTHER INFORMATION: HM3 CNP309 reverse primer

<400> SEQUENCE: 11
aggcctattt cattgtttgg                                               20

<210> SEQ ID NO 12
<211> LENGTH: 20
<212> TYPE: DNA
<213> ORGANISM: Artificial Sequence
<220> FEATURE:
<223> OTHER INFORMATION: HM3 CNP371 reverse primer

<400> SEQUENCE: 12
aattcaacct gcagaagcat                                               20

<210> SEQ ID NO 13
<211> LENGTH: 20
<212> TYPE: DNA
<213> ORGANISM: Artificial Sequence
<220> FEATURE:
<223> OTHER INFORMATION: HM3 CNP593 reverse primer

<400> SEQUENCE: 13
gtcccaactc tgaagtttgc                                               20

<210> SEQ ID NO 14
<211> LENGTH: 20
<212> TYPE: DNA
<213> ORGANISM: Artificial Sequence
<220> FEATURE:
<223> OTHER INFORMATION: HM3 CNP708 reverse primer

<400> SEQUENCE: 14
tgttacggtt ctgaagagca                                               20

<210> SEQ ID NO 15
<211> LENGTH: 26
<212> TYPE: DNA
<213> ORGANISM: Artificial Sequence
<220> FEATURE:
<223> OTHER INFORMATION: HM3 CNP71 probe

<400> SEQUENCE: 15
ttgctttctg atagtttctt ggcctg                                        26
```

```
<210> SEQ ID NO 16
<211> LENGTH: 24
<212> TYPE: DNA
<213> ORGANISM: Artificial Sequence
<220> FEATURE:
<223> OTHER INFORMATION: HM3 CNP116 probe

<400> SEQUENCE: 16 ccaccccta ccttctcttt ctgc                                            24

<210> SEQ ID NO 17
<211> LENGTH: 21
<212> TYPE: DNA
<213> ORGANISM: Artificial Sequence
<220> FEATURE:
<223> OTHER INFORMATION: HM3 CNP201 probe

<400> SEQUENCE: 17
tccgtggtta taggccatgc c                                              21

<210> SEQ ID NO 18
<211> LENGTH: 27
<212> TYPE: DNA
<213> ORGANISM: Artificial Sequence
<220> FEATURE:
<223> OTHER INFORMATION: HM3 CNP309 probe

<400> SEQUENCE: 18
aatccaaatg tctattcaac cagtgca                                        27

<210> SEQ ID NO 19
<211> LENGTH: 24
<212> TYPE: DNA
<213> ORGANISM: Artificial Sequence
<220> FEATURE:
<223> OTHER INFORMATION: HM3 CNP371 probe

<400> SEQUENCE: 19
tccccatgtc ctatgtctgc aatt                                           24

<210> SEQ ID NO 20
<211> LENGTH: 27
<212> TYPE: DNA
<213> ORGANISM: Artificial Sequence
<220> FEATURE:
<223> OTHER INFORMATION: HM3 CNP593 probe

<400> SEQUENCE: 20
tcaagaagtg tcctactttg cctgaga                                        27

<210> SEQ ID NO 21
<211> LENGTH: 20
<212> TYPE: DNA
<213> ORGANISM: Artificial Sequence
<220> FEATURE:
<223> OTHER INFORMATION: HM3 CNP708 probe

<400> SEQUENCE: 21
tccactctgc tggggaggct                                                20

<210> SEQ ID NO 22
<211> LENGTH: 20
<212> TYPE: DNA
<213> ORGANISM: Artificial Sequence
<220> FEATURE:
<223> OTHER INFORMATION: SRY Forward Primer
```

```
<400> SEQUENCE: 22
cgcttaacat agcagaagga                                          20

<210> SEQ ID NO 23
<211> LENGTH: 20
<212> TYPE: DNA
<213> ORGANISM: Artificial Sequence
<220> FEATURE:
<223> OTHER INFORMATION: SRY Reverse Primer

<400> SEQUENCE: 23
agtttcgaac tctggcacct                                          20

<210> SEQ ID NO 24
<211> LENGTH: 25
<212> TYPE: DNA
<213> ORGANISM: Artificial Sequence
<220> FEATURE:
<223> OTHER INFORMATION: SRY Probe

<400> SEQUENCE: 24
tgtcgcactc tccttgtttt tgaca                                    25
```